US008658794B2

(12) United States Patent
de Man et al.

(10) Patent No.: US 8,658,794 B2
(45) Date of Patent: Feb. 25, 2014

(54) 8-METHYL-1-PHENYL-IMIDAZOL[1,5-A]PYRAZINE COMPOUNDS AS LCK INHIBITORS AND USES THEREOF

(75) Inventors: Adrianus Petrus Antonius de Man, Hurwenen (NL); Johannes Bernardus Maria Rewinkel, Berghem (NL); Christiaan Gerardus Johannes Maria Jans, Cuijk (NL); Hans Cornelis Andreas Raaijmakers, Eindhoven (NL); Jacobus Cornelis Henricus Maria Wijkmans, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 13/577,417

(22) PCT Filed: Feb. 3, 2011

(86) PCT No.: PCT/EP2011/051584
§ 371 (c)(1),
(2), (4) Date: Aug. 6, 2012

(87) PCT Pub. No.: WO2011/095556
PCT Pub. Date: Aug. 11, 2011

(65) Prior Publication Data
US 2012/0309966 A1    Dec. 6, 2012

Related U.S. Application Data

(60) Provisional application No. 61/302,255, filed on Feb. 8, 2010.

(30) Foreign Application Priority Data

Feb. 8, 2010    (EP) .................................... 10152862

(51) Int. Cl.
C07D 495/00    (2006.01)
(52) U.S. Cl.
USPC ........... 544/350; 544/117; 544/359; 546/118; 546/199; 548/335.1; 548/469; 548/518; 548/950; 549/50; 549/356; 549/510

(58) Field of Classification Search
USPC .................. 544/117, 350, 359; 546/118, 199; 548/335.1, 469, 518, 950; 549/50, 356, 549/510
See application file for complete search history.

(56) References Cited

FOREIGN PATENT DOCUMENTS

| WO | WO01/19828 | 3/2001 |
|---|---|---|
| WO | WO2005/037836 | 4/2005 |
| WO | WO 2011/095556 | * 8/2011 |

OTHER PUBLICATIONS

Jordan, V. C. Nature Reviews: Drug Discovery, 2, 2003, 205.*
Borhani D W et al: "A-420983: a potent, orally active inhibitor of lck with efficacy in a model of transplant rejection", Bioorganic & Medicinal Chemistry Letters, Pergamon, Elsevier Science, vol. 14, No. 10, May 17, 2004, pp. 2613-2616.

* cited by examiner

*Primary Examiner* — Douglas M Willis
(74) *Attorney, Agent, or Firm* — Maria V. Marucci

(57) ABSTRACT

The present invention provides 8-methyl-1-phenyl-imidazo [1,5-a]pyrazine derivatives according to formula I or pharmaceutically acceptable salts thereof. The compounds of the current invention show inhibitory activity against Lck and can be used for the treatment of Lck-mediated diseases or Lck-mediated conditions such as inflammatory disorders.

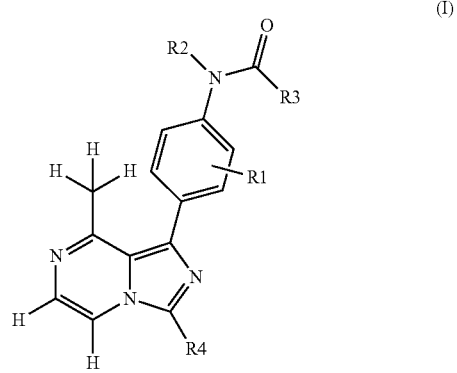

12 Claims, No Drawings

8-METHYL-1-PHENYL-IMIDAZOL[1,5-A]PYRAZINE COMPOUNDS AS LCK INHIBITORS AND USES THEREOF

BACKGROUND OF THE INVENTION

Non-receptor tyrosine kinases are intracellular enzymes which, in the presence of ATP phosphorylate proteins at tyrosine residues. These enzymes are key regulators of cellular signal transduction, leading to the activation, proliferation and differentiation of cells. The Src family of non-receptor tyrosine kinases comprises eight members: Src, Yes, Fyn, Lck, Lyn, Hck, Blk and Fgr, of which the first three kinases are ubiquitously expressed and the latter five kinases are primarily found in the haematopoietic system (Benatie et al. Current medical chemistry, 2008, 15, 1154-1165; Bogon et al. Oncogene 2004. 23, 7918-7927; Parsons et al. Oncogene, 2004. 23, 7906-7909). Members of the Src family display a conserved domain organization, which contains a myristoylated N-terminal domain, a unique region, a Src-homology 2 (SH2) domain, a SH3 domain, a tyrosine kinase domain and a C-terminal negative regulatory domain.

The Scr family members expressed in the haematopoietic system play an important role in the regulation of cells of the immune system and enhanced activity of these kinases has been implicated in a variety of malignant and non-malignant proliferative disorders. A particular Src family kinase of interest is the lymphocyte specific kinase (Lck) p56, which is primarily expressed in T lymphocytes and NK T cells. Lck, a proximal tyrosine kinase, is crucial for the initiation of signal transduction via the T cell receptor (TCR), which activates T lymphocytes. Upon antigen recognition, via MHC-TCR/peptide interaction, Lck is recruited to the TCR complex via the CD4/8 co-receptor, where it phosphorylates specific tyrosine residues in the immotyrosine-based activation motifs (ITAMs) located within the TCR ζchain. This phosphorylation event is crucial for the recruitment of the Syk-family kinase ZAP70 via SH2 interaction. Sequential phosphorylation of ZAP70 by Lck activates downstream signal transduction, leading to the activation and recruitment of other kinase family members and enzymes, resulting $Ca^{2+}$ release leading towards full activation of the T cell (Palacios et al. Oncogene, 2004; 23, 7990-8000; Iwashima et al. 1994; 263, 1136-1139; Weiss A et al. 1994; 76, 263-274). Inhibition of Lck kinase activity will arrest TCR-mediated activation of ZAP70 and downstream mobilization of $Ca^{2+}$ release, thereby inhibiting antigen-dependent activation of T lymphocytes.

Lck kinase inhibitors are useful for the treatment of chronic T cell disorders like multiple sclerosis and rheumatoid arthritis, as well as acute inflammatory disorders in which T cells play a prominent role including transplant rejection, atopic dermatitis and delayed type hypersensitivity (DTH). There clearly is a need for low molecular weight inhibitors of Lck for the treatment of chronic T cell disorders.

In WO2001019829 the use of pyrazolopyrimidine derivatives is directed to a method for the inhibition of, among others, Lck. The pyrazolopyrimidine derivatives of said patent application which is inserted by reference allow many different substituents as can be deduced from the definitions for substituents G, R2 and R3 in said pyrazolopyrimidine derivatives which are listed in WO2001019829. U.S. Pat. No. 7,459,554 describes imidazopyrazines tyrosine kinase inhibitors, including Lck. Also in this series of compounds, a very large variety of substituents is allowed as follows from the definitions for $R^1$ and $Q^1$ and their substituents as indicated in columns 10 to 15 of U.S. Pat. No. 7,459,554. Compounds according to WO2001019829 or U.S. Pat. No. 7,459,554 have an optionally substituted 8-amino substituent (NHR3 or $NH_2$, respectively) (numbering according to Formula I). Furthermore, a large flexibility in the type and size of substituents is allowed.

Crystal structures of three Src family members: Src, Hck and Lck have enabled a detailed view of how the Src family of kinases is regulated, and the way in which small molecule inhibitors can inactivate these enzymes [Williams et al., JBC, 284, 284-291 (2009)]

Binding studies of Lck and ligands like 4-amino-1-cyclohexyl-3-phenyl-pyrazolo[3,4-d]pyrimidines reveal the 4-amino group (the 4-position in this compound is comparable with the 8-position in Formula I) making a key H-bond donor contact to the backbone C=O of Glu317 whilst the N5 pyrimidine nitrogen contacts the backbone NH of Met319 [Barbani et al., Bioorg. Med. Chem. Lett. 14, 2004 2613; Abbott et al., Bioorg. Med. Chem. Lett. 17, 1167-1171 (2007)]. All these studies reveal the presence of such an H-bond to the backbone C=O of Glu317. A similar binding has been mode has been observed for ATP-analogues and imidazo[1,5a]pyrazines (Strucuture 7(6) p651 (1999)) (EMBOj 27(14) 1985-1994 (2008)).

Binding studies of Lck and ligands like 4-amino-1-cyclohexyl-3-phenyl-pyrazolo[3,4-d]pyrimidines further reveal that the 3-phenyl group and its substituents (corresponding with R3 in Formula 1) extends into the hydrophobic pocket of Lck and that the 1-cyclohexyl group and its substituents (corresponding with R4 in Formula 1) extends into the solvent exposed region of the Lck binding pocket [Barbani et al., Bioorg. Med. Chem. Lett. 14, 2004 2613; Abbott et al., Bioorg. Med. Chem. Lett. 17, 1167-1171 (2007)].

We have found a series of compounds that lack the H-bond donor capacity to make an H-bond contact with the backbone C=O of Glu 317 and are surprisingly effective inhibitors of Lck.

SUMMARY OF THE INVENTION

The present invention provides 8-methyl-1-phenyl-imidazol[1,5-a]pyrazine compounds. More specifically, the present invention provides 8-methyl-1-phenyl-imidazol[1,5-a]pyrazine compounds according to formula I or pharmaceutically acceptable salts thereof.

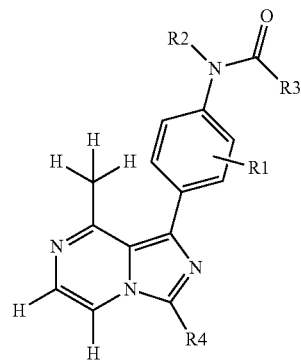

Formula I

In this formula the substituents are defined as

R1 is one or two groups independently selected from hydrogen, hydroxy, (1-6C)alkoxy, (1-6C)alkyl, halogen or cyano;

R2 is H or (1-6C)alkyl;

R3 is a group capable of extending into the hydrophobic pocket of the Lck binding pocket;

R4 is a group extending into the solvent exposed region of the Lck binding pocket and optionally is capable of interacting via an H-bond with the sidechain of Asp326 of the Lck binding pocket.

The present invention also relates to pharmaceutical compositions comprising compounds having Formula I and to the use of said compounds for the manufacture of medicaments for the treatment of chronic T cell disorders as well as acute inflammatory disorders in which T cells play a prominent role.

DETAILED DESCRIPTION OF THE INVENTION

The present invention provides 8-methyl-1-phenyl-imidazol[1,5-a]pyrazine derivatives.

More specifically, the present invention provides 8-methyl-1-phenyl-imidazol[1,5-a]pyrazine derivatives according to formula I or pharmaceutically acceptable salts thereof.

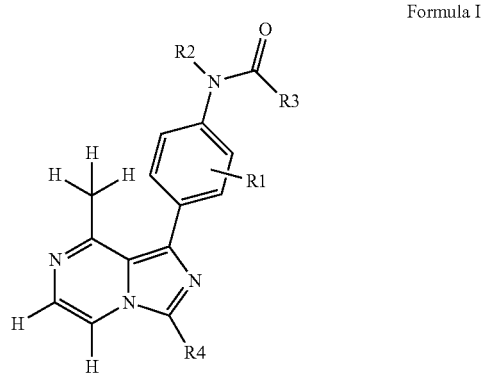

Formula I

In this formula the substituents are defined as

R1 is one or two groups independently selected from hydrogen, hydroxy, (1-6C)alkoxy, (1-6C)alkyl, halogen or cyano;
R2 is H or (1-6C)alkyl;
R3 is a group capable of extending into the hydrophobic pocket of the Lck binding pocket;
R4 is a group extending into the solvent exposed region of the Lck binding pocket and optionally is capable of interacting via a H-bond with the sidechain of Asp326 of the Lck binding pocket.

The compounds of the current invention show inhibitory activity against Lck and can be used for the treatment of Lck-mediated disease or Lck-mediated condition like the treatment of chronic T cell disorders and acute inflammatory disorders in which T cells play a prominent role. These diseases or conditions include allergies, leukemia, inflammatory bowel disease, rheumatoid arthritis, glomerulonephritis, lung fibrosis, psoriasis, hypersensitivity reactions of the skin, atherosclerosis, restenosis, allergic asthma, multiple sclerosis, type 1 diabetes, multiple sclerosis, rheumatoid arthritis, atopic dermatitis, delayed type hypersensitivity (DTH), acute rejection of transplanted organs as well as Graft versus Host Disease (GvHD). Lck inhibitors can be used for treatment of the indications mentioned hereinbefore.

The term heterocyclyl means a heterocyclic substituent consisting of one or more C and at least one atom chosen from N, O, or S, within a ring structure of 3, 4, 5, 6, 7 atoms. Combinations with O and S in one ring are excluded. Preferred heteroatoms are N or O. More preferred heteroatom is N. Preferred number of heteroatoms is 1 or 2. Preferred number of atoms in the ring structure is 5 or 6. A heterocyclyl is saturated, partially unsaturated, unsaturated or aromatic. Preferably the heterocyclyl is saturated. Examples of a heterocyclyl groups include, but are not limited to aziridine, azirine, dioxirane, azetidine, oxetane, thietane, dioxetane, dithietane, dithiete, tetrahydropyrrole, azolidine, pyrrolidine, dihydropyrrole, pyrroline, pyrrole tetrahydrofuran, dihydrofuran, pyrazine, tetrahydrothiophene, dihydrothiophene, arsole, azoles, thiazoles, isothiazoles, dithiolanes, imidazolidine, pyrazole, imidazole, oxazolidine, oxazole, isoxazole, thiazolidine, thiazole, isothiazole, dioxolane, dithiazoles, triazole, tetrazole, piperidine, pyridine, tetrahydropyran, pyran, thiane, thiine, piperazine, diazines, oxazine, thiazine, dithiane, dioxane, dioxin, triazine, trioxane, tetrazine, azepine, thiepin, diazepine, and morpholine. Preferred heterocyclyl groups are imidazole, triazole, pyrazine, pyrrolidine, piperazine, morpholine, azetidine, pyran, and piperidine. The heterocyclyl can be attached via one of the C atoms or via one of the hetero atoms. N-attached heterocyclyl means the heterocyclyl contains at least one N in the ring structure and is attached via one of these N atoms.

The terms as used herein refer to the following:

(1-2C)alkyl is an alkyl group having 1-2 carbon atoms, being methyl or ethyl.

(1-3C)alkyl is a branched or unbranched alkyl group having 1-3 carbon atoms, being methyl, ethyl, propyl or isopropyl.

(1-4C)alkyl is a branched or unbranched alkyl group having 1-4 carbon atoms, being methyl, ethyl, propyl, isopropyl, butyl, isobutyl, sec-butyl and tert-butyl. (1-3C)alkyl groups being preferred.

(1-5C)alkyl is a branched or unbranched alkyl group having 1-5 carbon atoms, for example methyl, ethyl, propyl, isopropyl, butyl, isobutyl, sec-butyl, tert-butyl, pentyl and isopentyl. (1-4C)alkyl groups being preferred.

(1-6C)alkyl is a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being the most preferred.

(2-3C)alkyl is a branched or unbranched alkyl group having 2-3 carbon atoms, for example ethyl, propyl, isopropyl.

(2-4C)alkyl is a branched or unbranched alkyl group having 2-4 carbon atoms, for example ethyl, propyl, isopropyl, butyl and tert-butyl.

(2-5C)alkyl is a branched or unbranched alkyl group having 2-5 carbon atoms, for example, ethyl, propyl, isopropyl, butyl, tert-butyl and n-pentyl. (2-4C)alkyl are preferred.

(2-6C)alkyl is a branched or unbranched alkyl group having 2-6 carbon atoms, for example ethyl, propyl, isopropyl, butyl, tert-butyl, n-pentyl and n-hexyl. (2-5C)alkyl groups are preferred, (2-4C)alkyl being the most preferred.

(1-2C)alkoxy is an alkoxy group having 1-2 carbon atoms, the alkyl moiety having the same meaning as previously defined.

(1-3C)alkoxy is an alkoxy group having 1-3 carbon atoms, the alkyl moiety having the same meaning as previously defined. (1-2C)alkoxy groups are preferred.

(1-4C)alkoxy is an alkoxy group having 1-4 carbon atoms, the alkyl moiety having the same meaning as previously defined. (1-3C)alkoxy groups are preferred, (1-2C)alkoxy groups being most preferred.

(1-5C)alkoxy is an alkoxy group having 1-5 carbon atoms, the alkyl moiety having the same meaning as previously defined. (1-4C)alkoxy groups are preferred, (1-3C)alkoxy groups being most preferred.

(1-6C)alkoxy is an alkoxy group having 1-6 carbon atoms, the alkyl moiety having the same meaning as previously defined. (1-5C)alkoxy groups are preferred, (1-4C)alkoxy groups being most preferred.

(2-4C)alkoxy is an alkoxy group having 2-4 carbon atoms, the alkyl moiety being ethyl, propyl, isopropyl, butyl, isobutyl, sec-butyl and tert-butyl.

(1-6C)alkoxy is an alkoxy group having 1-6 carbon atoms, the alkyl moiety having the same meaning as previously defined. (1-4C)alkoxy groups are preferred.

(3-6C)cycloalkyl is a cycloalkyl group having 3-6 carbon atoms, such as cyclopropyl, ethylcyclopropyl, cyclopropylmethyl, cyclobutyl, methylcyclobutyl, cyclopentyl and cyclohexyl.

(3-7C)cycloalkyl is a cycloalkyl group having 3-7 carbon atoms, such as cyclopropyl, ethylcyclopropyl, cyclopropylmethyl, cyclobutyl, methylcyclobutyl, cyclopentyl, cyclohexyl and cycloheptyl. (3-6C)cycloalkyl groups are preferred.

(3-6C)cycloalkoxy is a cycloalkyl group having 3-6 carbon atoms, with the same meaning as previously defined, attached via a ring carbon atom to an exocyclic oxygen atom.

(3-7C)cycloalkoxy is a cycloalkyl group having 3-7 carbon atoms, with the same meaning as previously defined, attached via a ring carbon atom to an exocyclic oxygen atom.

(1-6C)alkoxy(1-4C)alkyl is an alkoxyalkyl group, the alkoxy group of which contains 1-6 carbon atoms with the same meaning as previously defined, which is attached to an alkyl group containing 1-4 carbon atoms with the same meaning as previously defined.

(1-6C)alkoxy(2-6C)alkyl is an alkoxyalkyl group, the alkoxy group of which contains 1-6 carbon atoms with the same meaning as previously defined, which is attached to an alkyl group containing 2-6 carbon atoms with the same meaning as previously defined.

(1-6C)alkoxy-(3-6C)cycloalkyl is an alkoxycycloalkyl group, the alkoxy group of which contains 1-6 carbon atoms with the same meaning as previously defined, which is attached to an cycloalkyl group containing 3-6 carbon atoms with the same meaning as previously defined.

(1-4C)alkylcarbonyl is a alkylcarbonyl group, the alkyl group of which contains 1-4 carbon atoms with the same meaning as previously defined.

(1-2C)alkoxycarbonyl is an alkoxycarbonyl group, the alkoxy group of which contains 1-2 carbon atoms with the same meaning as previously defined.

(1-4C)alkoxycarbonyl is an alkoxycarbonyl group, the alkoxy group of which contains 1-4 carbon atoms with the same meaning as previously defined. (1-2C)alkoxycarbonyl groups are preferred.

(1-6C)alkoxycarbonyl is an alkoxycarbonyl group, the alkoxy group of which contains 1-6 carbon atoms with the same meaning as previously defined. (1-4C)alkoxycarbonyl groups are preferred. (1-2C)alkoxycarbonyl groups are most preferred.

(2-4C)alkoxycarbonyl is an alkoxycarbonyl group, the alkoxy group of which contains 2-4 carbon atoms with the same meaning as previously defined.

(1-4C)alkoxycarbonyl is an alkoxycarbonyl group, the alkoxy group of which contains 1-4 carbon atoms with the same meaning as previously defined. (1-2C)alkoxycarbonyl groups are preferred.

amino(1-4C)alkyl is an aminoalkyl group, the amino group of which is attached to an alkyl group containing 1-4 carbon atoms with the same meaning as previously defined.

amino(2-4C)alkoxy is an aminoalkoxy group, the amino group of which is attached to an alkoxy group containing 2-4 carbon atoms with the same meaning as previously defined.

amino(2-4C)alkoxycarbonyl is an aminoalkoxycarbonyl group, the amino group of which is attached to an (2-4C) alkoxycarbonyl group with the same meaning as previously defined.

aminocarbonyl(1-4C)alkyl is an aminocarbonylalkyl group, the aminocarbonyl of which is attached to an alkyl group containing 1-4 carbon atoms with the same meaning as previously defined.

aminocarbonyl(1-6C)alkoxy is an aminocarbonylalkoxy group, the aminocarbonyl of which is attached to an alkoxy group containing 1-6 carbon atoms with the same meaning as previously defined.

(1-4C)alkylcarbonyloxy is an alkylcarbonyloxy group, the alkyl group of which contains 1-4 carbon atoms with the same meaning as previously defined.

(1-3C)alkoxy(2-4C)alkoxy is an alkoxyalkoxy group, the (1-3C)alkoxy moiety of which contains 1-3 carbon atoms with the same meaning as previously defined, which is attached to an alkoxy group having 2-4 carbon atoms with the same meaning as previously defined.

[(1-4C)alkyl]amino is an alkylamino group, the alkyl group of which contains 1-4 carbon atoms with the same meaning as previously defined.

[(1-6C)alkyl]amino is an alkylamino group, the alkyl group of which contains 1-6 carbon atoms with the same meaning as previously defined.

(1-4C)alkylaminocarbonyloxy is an alkylaminocarbonyloxy group, the alkyl group of which contains 1-4 carbon atoms with the same meaning as previously defined which is attached to an aminocarbonyloxy group.

[(1-6C)alkoxy(2-6C)alkyl]aminocarbonyl(1-4C)alkyl is an [alkoxyalkyl]aminocarbonylalkyl group, the amino group of which is substituted with an (1-6C)alkoxy(2-6C)alkyl group as previously defined. The aminocarbonyl group is attached to an alkyl group which contains 1-4 carbon atoms, with the same meaning as previously defined.

(1-6C)alkoxycarbonylamino is an alkoxycarbonylamino group, the alkoxy group of which contains 1-6 carbon atoms with the same meaning as previously defined.

(1-6C)alkylaminocarbonylamino is an alkylaminocarbonylamino group, the alkyl group of which contains 1-6 carbon atoms with the same meaning as previously defined.

(1-6C)alkylcarbonylamino is an alkylcarbonylamino group, the alkyl group of which contains 1-6 carbon atoms with the same meaning as previously defined.

(3-6C)cycloalkoxy(1-4C)alkyl is an cycloalkoxyalkyl group, the cycloalkoxy group of which contains 3-6 carbon atoms with the same meaning as previously defined, which is attached to an alkyl group containing 1-4 carbon atoms with the same meaning as previously defined.

(3-6C)cycloalkyl(1-3C)alkyl is a cycloalkylalkyl group, the cycloalkyl group of which contains 3-6 carbon atoms with the same meaning as previously defined, which is attached to an alkyl group containing 1-3 carbon atoms with the same meaning as previously defined.

(3-6C)cycloalkylaminocarbonyloxy is a cycloalkylaminocarbonyloxy group, the cycloalkyl group of which contains 3-6 carbon atoms with the same meaning as previously defined, which is attached to an aminocarbonyloxy group.

cyclyl-N is N-attached heterocyclyl with the same meaning as previously defined.

(cyclyl-N)(1-4C)alkyl is an heterocyclylalkyl group, the heterocyclyl group of which contains at least one N in the ring structure and is attached via one of these N atoms to the alkyl group containing 1-4 carbon atoms with the same meaning as previously defined.

(cyclyl-N)-(2-4C)alkoxy is a alkoxy group which contains 2-4 carbon atoms with the same meaning as previously defined, substituted with a cyclyl-N group with the same meaning as previously defined.

(cyclyl-N)carbonyl is a cyclyl-N group attached to a carbonyl group said cyclyl-N has the same meaning as previously defined.

(cyclyl-N)carbonyl(1-6C)alkoxy is a alkoxy group containing 1-6 carbon atoms as previously defined, substituted with a (cyclyl-N)carbonyl group as previously defined.

(cyclyl-N)carbonylamino is a carbonylamino group, the carbonyl of which is substituted with a cyclyl-N group as previously defined.

(1-4C)alkylamino is an amino group, monosubstituted with an alkyl group containing 1-4 carbon atoms and having the same meaning as previously defined.

(di)[(1-4C)alkyl]amino is an amino group, disubstituted with alkyl group(s), each independently containing 1-4 carbon atoms and having the same meaning as previously defined.

(1-6C)alkylamino is an amino group, monosubstituted with an alkyl group containing 1-6 carbon atoms and having the same meaning as previously defined.

(di)[(1-6C)alkyl]amino is an amino group, disubstituted with alkyl group(s), each independently containing 1-6 carbon atoms and having the same meaning as previously defined.

(di)[(1-6C)alkyl]amino(1-4C)alkyl is a (di)[(1-6C)alkyl]amino group, as previously defined, and which is connected to an alkyl group containing 1-4 carbon atoms as previously defined.

(di)[(1-6C)alkyl]amino(2-4C)alkoxy is a (di)alkylaminoalkoxy group, the (di)alkylamino group of which is as previously defined, and which is connected to an alkoxy group having 2-4 carbon atoms with the same meaning as previously defined.

(di)[(1-6C)alkyl]aminocarbonyl is a (di)alkylaminocarbonyl group, the (di)alkylamino group of which is as previously defined.

(di)[(1-6C)alkyl]aminocarbonyl(1-4C)alkyl is a (di)alkylaminocarbonyl group, the (di)alkylamino group of which is as previously defined, and is connected via the amino group to a carbonyl group which is connected to an alkyl group containing 1-4 carbon atoms as previously defined.

(di)[(1-6C)alkyl]aminocarbonyl(1-6C)alkoxy is a (di)alkylaminocarbonylalkoxy group, the (di)alkylamino group of which is as previously defined, and is connected via the amino group to a carbonyl group which is connected to an alkoxy group containing 1-6 carbon atoms as previously defined.

[(1-6C)alkoxy(2-6C)alkyl]amino is an alkoxyalkylamino group, the amino group of which is substituted with an alkoxyalkyl group, and the alkoxy group of which containing 1-6 carbon atoms having the same meaning as previously defined and the alkyl group of which containing 2-6 carbon atoms having the same meaning as previously defined,

[(1-6C)alkoxy(2-6C)alkyl]aminocarbonyl is an alkoxyalkylaminocarbonlyl group, the alkoxyalkylamino group of which is as previously defined.

[(1-6C)alkoxy(2-6C)alkyl]amino(1-4C)alkyl is an alkoxyalkylaminoalkyl group, the alkoxyalkylamino group of which is as previously defined, is connected via the amino group to an alkyl group containing 1-4 carbon atoms having the same meaning as previously defined.

[(1-6C)alkoxy(2-6C)alkyl]amino(2-4C)alkoxy is an alkoxyalkylaminoalkoxy group, the alkoxyalkylamino group of which is as previously defined, is connected via the amino group to an alkoxy group containing 2-4 carbon atoms having the same meaning as previously defined.

[(1-6C)alkoxycarbonyl(1-6C)alkyl]amino is an amino group substituted with an (1-6C)alkoxycarbonyl(1-6C)alkyl group, the (1-6C)alkoxycarbonyl group of which is as previously defined, is attached to an (1-6C)alkyl group as previously defined.

[(1-6C)alkyl][(1-6C)alkoxy(2-6C)alkyl]amino is an amino group substituted with an alkyl group having 1-6 carbon atoms which is as previously defined and with an alkoxyalkyl group the alkoxy group of which contains 1-6 carbon atoms with the same meaning as previously defined, which is attached to an alkyl group having 2-6 carbon atoms with the same meaning as previously defined.

[(1-6C)alkyl][(1-6C)alkoxy(2-6C)alkyl]aminocarbonyl is an [(1-6C)alkyl][(1-6C)alkoxy(2-6C)alkyl]amino group, as previously defined connected via the amino group to a carbonyl group.

[(1-6C)alkyl][(1-6C)alkoxy(2-6C)alkyl]amino(1-4C)alkyl is an [(1-6C)alkyl][(1-6C)alkoxy(2-6C)alkyl]amino group as previously defined, connected via the amino group to a alkyl group which contains 1-4 carbon atoms as previously defined.

[(1-6C)alkyl][(1-6C)alkoxy(2-6C)alkyl]amino(2-4C)alkoxy is an [(1-6C)alkyl][(1-6C)alkoxy(2-6C)alkyl]amino group as previously defined, connected via the amino group to a alkoxy group which contains 2-4 carbon atoms as previously defined.

[(1-6C)alkyl][(1-6C)alkylcarbonyl]amino(1-4C)alkyl is an amino group substituted with an alkyl group having 1-6 carbon atoms which is as previously defined and with an alkylcarbonyl group the alkyl group of which contains 1-6 carbon atoms with the same meaning as previously defined, connected via the amino group to an alkyl group which contains 1-4 carbon atoms as previously defined.

[(1-4C)alkyl][(1-4C)alkylcarbonyl]amino(1-4C)alkyl is an amino group substituted with an alkyl group having 1-4 carbon atoms which is as previously defined and with an alkylcarbonyl group the alkyl group of which contains 1-4 carbon atoms with the same meaning as previously defined; connected via the amino group to an alkyl group which contains 1-4 carbon atoms as previously defined.

[(1-4C)alkylcarbonyl]amino(1-4C)alkyl is an amino group substituted with an alkylcarbonyl group the alkyl group of which contains 1-4 carbon atoms with the same meaning as previously defined, connected via the amino group to an alkyl group which contains 1-4 carbon atoms as previously defined.

[(1-4C)alkoxycarbonyl]amino(1-4C)alkyl is an amino group substituted with an alkoxycarbonyl group the alkyl group of which contains 1-4 carbon atoms with the same meaning as previously defined, connected via the amino group to an alkyl group which contains 1-4 carbon atoms as previously defined.

[(1-4C)alkyl][(1-4C)alkoxycarbonyl]amino(1-4C)alkyl is an amino group substituted with an alkyl group having 1-4 carbon atoms which is as previously defined and with an alkoxycarbonyl group the alkyl group of which contains 1-4 carbon atoms with the same meaning as previously defined, connected via the amino group to an alkyl group which contains 1-4 carbon atoms as previously defined.

[(1-6C)alkyl][(1-6C)alkylcarbonyl]amino(1-6C)alkoxy is an amino group substituted with an alkyl group having 1-6 carbon atoms which is as previously defined and with an alkylcarbonyl group the alkyl group of which contains 1-6 carbon atoms with the same meaning as previously defined, connected via the amino group to an alkoxy group which contains 1-6 carbon atoms as previously defined.

[(1-6C)alkyl][(3-6C)cycloalkylcarbonyl]amino(1-6C)alkoxy is an amino group substituted with an alkyl group having 1-6 carbon atoms which is as previously defined and with an cycloalkylcarbonyl group having 3-6 carbon atoms with the same meaning as previously defined, connected via the amino group to an alkoxy group which contains 1-6 carbon atoms as previously defined.

[(1-6C)alkyl][hydroxy(1-6C)alkyl]aminocarbonyl(1-4C)alkyl is an amino group substituted with an alkyl group having 1-6 carbon atoms which is as previously defined and with an hydroxyalkyl group the alkyl group of which contains 1-6 carbon atoms with the same meaning as previously defined, connected via the amino group to an carbonyl group which is connected to an alkyl group which contains 1-4 carbon atoms as previously defined.

[(1-6C)alkyl][hydroxy(2-6C)alkyl]amino is an amino group substituted with an alkyl group having 1-6 carbon atoms which is as previously defined and with an hydroxyalkyl group the alkyl group of which contains 2-6 carbon atoms with the same meaning as previously defined.

[(1-6C)alkyl][hydroxy(2-6C)alkyl]amino(1-4C)alkyl is an [(1-6C)alkyl][hydroxy(2-6C)alkyl]amino group as previously defined, connected via the amino group to an alkyl group which contains 1-4 carbon atoms as previously defined.

[(1-6C)alkyl][hydroxy(2-6C)alkyl]aminocarbonyl is an [(1-6C)alkyl][hydroxy(2-6C)alkyl]amino group as previously defined connected via the amino group to an carbonyl group.

[(1-6C)alkyl][hydroxy(2-6C)alkyl]amino(2-4C)alkoxy is an [(1-6C)alkyl][hydroxy(2-6C)alkyl]amino group as previously defined, connected via the amino group to an alkoxy group the alkyl moiety of which having 2-4 carbon atoms as previously defined.

[(1-6C)alkyl]amino(1-4C)alkyl is an alkylaminoalkyl group, the alkyl group of the alkylamino group contains 1-6 carbon atoms with the same meaning as previously defined, connected via the amino group to an alkyl group which contains 1-4 carbon atoms with the same meaning as previously defined.

[(1-6C)alkyl]amino(2-4C)alkoxy is an alkylaminoalkoxy group, the alkyl group of which contains 1-6 carbon atoms with the same meaning as previously defined, connected via the amino group to an alkoxy group which contains 2-4 carbon atoms with the same meaning as previously defined.

[(1-6C)alkyl]amino(2-4C)alkoxycarbonyl is an [(1-6C)alkyl]amino(2-4C)alkoxy group as previously defined, connected via the oxygen of the alkoxy group to a carbonyl group.

[(1-6C)alkyl]aminocarbonyl is an alkylaminocarbonyl group, the alkyl group of which contains 1-6 carbon atoms with the same meaning as previously defined, connected via the amino group to an carbonyl group.

[(1-6C)alkyl]aminocarbonyl(1-4C)alkyl is an [(1-6C)alkyl]aminocarbonyl group as previously defined, connected via the carbonyl group to an alkyl group which contains 1-4 carbon atoms with the same meaning as previously defined.

[(1-6C)alkyl]aminocarbonyl(1-6C)alkoxy is an [(1-6C)alkyl]aminocarbonyl group as previously defined, connected via the carbonyl group to an alkoxy group which contains 1-6 carbon atoms as previously defined.

[(1-6C)alkylcarbonyl][(1-6C)alkoxy(2-6C)alkyl]amino is an amino group substituted with an alkylcarbonyl group the alkyl group of which contains 1-6 carbon atoms which is as previously defined and with an alkoxyalkyl group the alkoxy group of which contains 1-6 carbon atoms as previously defined, the alkyl group of which contains 2-6 carbon atoms with the same meaning as previously defined.

[(1-6C)alkylcarbonyl]amino(1-4C)alkyl is an amino group substituted with an alkylcarbonyl group the alkyl group of which having 1-6 carbon atoms which is as previously defined, connected via the amino group to an alkyl group which contains 1-4 carbon atoms as previously defined.

[(1-6C)alkylcarbonyl]amino(1-6C)alkoxy is an amino group substituted with an alkylcarbonyl group the alkyl group of which having 1-6 carbon atoms which is as previously defined, connected via the amino group to an alkoxy group which contains 1-6 carbon atoms as previously defined.

[(3-6C)cycloalkylcarbonyl]amino(1-6C)alkoxy is an amino group substituted with an cycloalkylcarbonyl group the cycloalkyl group of which having 3-6 carbon atoms which is as previously defined, connected via the amino group to an alkoxy group which contains 1-6 carbon atoms as previously defined.

[hydroxy(1-6C)alkyl]aminocarbonyl(1-4C)alkyl is an amino group substituted with an hydroxyalkyl group the alkyl group of which having 1-6 carbon atoms which is as previously defined, connected via the amino group to a carbonyl group which is connected to an alkyl group which contains 1-4 carbon atoms as previously defined.

[hydroxy(1-6C)alkyl]aminocarbonyl(1-6C)alkoxy is an amino group substituted with an hydroxyalkyl group the alkyl group of which having 1-6 carbon atoms which is as previously defined, connected via the amino group to a carbonyl group which is connected to an alkoxy group which contains 1-6 carbon atoms as previously defined.

[hydroxy(2-6C)alkyl]amino is an amino group substituted with an hydroxyalkyl group the alkyl group of which having 2-6 carbon atoms which is as previously defined.

[hydroxy(2-6C)alkyl]amino(1-4C)alkyl is an hydroxyalkylaminoalkyl group the [hydroxy(2-6C)alkyl]amino group of which is as previously defined, is connected via the amino group to an alkyl group which contains 1-4 carbon atoms as previously defined.

[hydroxy(2-6C)alkyl]aminocarbonyl is a hydroxyalkylaminocarbonyl group the [hydroxy(2-6C)alkyl]amino group of which is as previously defined, is connected via the amino group to a carbonyl group.

[hydroxy(2-6C)alkyl]amino(2-4C)alkoxy is a hydroxyalkylaminoalkoxy group, the [hydroxy(2-6C)alkyl]amino of which is as previously defined, is connected via the amino group to an alkoxy group which contains 2-4 carbon atoms as previously defined.

5 or 6 membered heterocyclyl is a heterocyclyl as previously defined with a ring structure of 5 or 6 atoms.

(di)[(1-6C)alkyl]amino(1-4C)alkyl is a dialkylamino group, the alkyl groups of which each contain(s) 1-6 carbon atoms with the same meaning as previously defined, connected via the amino group to an alkyl group which contains 1-4 carbon atoms with the same meaning as previously defined.

halogen is fluorine, chlorine, bromine or iodine. Fluorine is preferred.

The term "heteroaryl" as used herein refers to heterocyclic, and polyheterocyclic aromatic moieties having 5-14 ring atoms of which 1-5 heteroatoms. Heteroaryl groups are optionally substituted. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like. Preferred heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinoiinyl, benzotriazolyl, benzothiazolyl, benzooxazolyl, benzimidazolyl, isoquinolinyl, indolyl, isoindolyl, acridinyl, or benzoisoxazolyl.

Heteroaryl groups further include a group in which a heteroaromatic ring is fused to one or more heteroaromatic or hetero-nonaromatic rings where the radical or point of attachment is on the heteroaromatic ring. Examples include tetrahydroquinoline, tetrahydroisoquinoline, indole and pyrido[3,4-d]pyrimidinyl, imidazo[1,2-a]pyrimidyl, imidazo[1,2-a]pyrazinyl, imidazo[1,2-a]pyiridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, thieno[2,3-b]pyrrole, pyrrolo[2,3-d]pyrimidyl, triazolopyrimidyl, pyridopyranyl. Preferred are bicyclic heteroaromatic ring systems with 6-9 C atoms and 1-3 hetero atoms independently selected from N, S, or O, in which a heteroaromatic ring is fused to one or more aromatic or nonaromatic rings where the radical or point of attachment is on the heteroaromatic ring. More preferred are bicyclic heteroaromatic ring systems with 6-8 C atoms and 1 or 2 heteroatoms independently selected from N or S. Most preferred are indole and thieno[2,3-b]pyrrole ring systems. The term "heteroaryl" also refers to rings that are optionally substituted. The term "heteroaryl" may be used interchangeably with the term "heteroaryl ring" or the term "heteroaromatic".

hydroxy(1-4C)alkyl is an hydroxyalkyl group, the alkyl group of which having 1-4 carbon atoms as previously defined.

hydroxy(1-6C)alkoxy is an hydroxyalkoxy group, the alkoxy group of which having 1-6 carbon atoms as previously defined.

R621-(2-4C)alkoxy is an alkoxy group containing 2-4 carbon atoms as previously defined, substituted with an R621 group as defined.

R732-carbonyl is R732 connected via a carbonyl group in which R732 is as defined.

R733-carbonyl is R733 connected via a carbonyl group in which R733 is as defined.

R735-carbonyl is R735 connected via a carbonyl group in which R735 is as defined.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound' or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt is well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, the treatment of chronic T cell disorders and acute inflammatory disorders in which T cells play a prominent role. These diseases or conditions include allergies, leukemia, inflammatory bowel disease, rheumatoid arthritis, glomerulonephritis, lung fibrosis, psoriasis, hypersensitivity reactions of the skin, atherosclerosis, restenosis, allergic asthma, multiple sclerosis, type 1 diabetes, multiple sclerosis, rheumatoid arthritis, atopic dermatitis, delayed type hypersensitivity (DTH), acute rejection of transplanted organs as well as Graft versus Host Disease (GvHD). Lck inhibitors can be used for treatment of the indications mentioned herein before.

In one aspect the invention relates to a compound according to formula 1 wherein R3 is (R31)(R32)CH—O; or R3 is (3-7C)cycloalkoxy which is optionally substituted with one or more fluoro or hydroxyl; or R3 is heteroaryl, which is optionally substituted with one or more groups from R34, R35, R36, halogen, hydroxyl or cyano;

R31 is H or (1-5C)alkyl optionally substituted with one or more fluoro, hydroxyl or (1-6C)alkoxy;

R32 is (1-5C)alkyl optionally substituted with one or more fluoro;

R34 is (1-6C)alkyl optionally substituted with one or more fluoro;

R35 is (1-6C)alkoxy optionally substituted with one or more fluoro;

R36 is hydrogen or (1-6C)alkyl optionally substituted with one or more hydroxyl or halogen, fluoro being the preferred substituent;

R4 is $$\begin{array}{c}\xi\\\xi\end{array}-Y\begin{array}{c}(CH_2)n\\\diagdown\\(CH_2)m\end{array}X \quad \text{or} \quad \begin{array}{c}\xi\\\xi\end{array}\begin{array}{c}(CH_2)r\\\diagdown\\(CH_2)m\end{array}\begin{array}{c}Z\\\diagup\\N-R9\end{array}$$

or
R4 is (1-4C)alkyl, optionally substituted independently by one or more substituents from R8, fluoro, hydroxyl;
wherein
m is 1, 2 or 3;
n is 1, 2 or 3;
r is 1 or 2;
Y is CR5 or N;
X is O, CHR6, C(R66)(R67), NR7, C=O;
Z is O or
Z forms with R9 a 5 or 6 membered heterocyclyl optionally substituted by R91;
R5 is H or (1-6C)alkyl optionally substituted with one or more fluoro;
R6 is R61, R62, R63, R65, H, hydroxy, fluoro;
R7 is R71, R72, R73, R74, H;
R8 is heteroaryl, optionally substituted with one or more groups from (1-4C)alkyl, hydroxy, (1-6C)alkoxy, amino, (di)[(1-4C)alkyl]amino, [(1-4C)alkyl]amino, halogen;
R9 is H or (1-6C)alkyl optionally substituted with one or more fluoro;
R61 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl. All of the alkyl groups in R61 are optionally substituted with one or more fluoro.
R62 is (1-6C)alkoxy, hydroxy(1-6C)alkoxy, (1-3C)alkoxy(2-4C)alkoxy, R621-(2-4C)alkoxy, (1-4C)alkylcarbonyloxy, (1-4C)alkylaminocarbonyloxy, (3-6C)cycloalkylaminocarbonyloxy. All of the alkyl groups in R62 are optionally substituted with one or more fluoro.
R63 is amino, [(1-6C)alkyl]amino, (di)[(1-6C)alkyl]amino, [hydroxy(2-6C)alkyl]amino, [(1-6C)alkyl][hydroxy(2-6C)alkyl]amino, (1-6C)alkoxycarbonylamino, (1-6C)alkylaminocarbonylamino, [(1-6C)alkoxy(2-6C)alkyl]amino, [(1-6C)alkyl][(1-6C)alkoxy(2-6C)alkyl]amino, (1-6C)alkylcarbonylamino, [(1-6C)alkylcarbonyl][(1-6C)alkoxy(2-6C)alkyl]amino. All of the alkyl groups in R63 are optionally substituted with one or more fluoro,
R65 is N-attached heterocyclyl which is optionally substituted with one or more oxo, fluoro or one or more R651;
R66 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl. All of the alkyl groups in R66 are optionally substituted with one or more fluoro.
R67 is hydroxy, (1-4C)alkoxy or fluoro;
R71 is (1-6C)alkyl, (3-6C)cycloalkyl, (3-6C)cycloalkyl(1-3C)alkyl. All of the alkyl groups in R71 are optionally substituted with one or more fluoro.
R72 is (1-4C)alkyl, which is substituted with one group selected from R721, R722, R724 and R725;
R73 is R732-carbonyl, R733-carbonyl, or R735-carbonyl;
R74 is heterocyclyl which is optionally substituted with one or more groups independently selected from fluoro or R741;
R91 is (1-6C)alkyl optionally substituted with one or more fluoro;
R621 is amino, [(1-6C)alkyl]amino, (di)[(1-6C)alkyl]amino, any of the alkyl groups is optionally substituted with one or more fluoro or;
R621 is N-attached heterocyclyl, optionally substituted with one or more fluoro;
R651 is (1-4C)alkyl, (3-6C)cycloalkyl, (3-6C)cycloalkyl(1-3C)alkyl, (1-4C)alkylcarbonyl. All of the alkyl groups in R651 are optionally substituted with one or more groups independently selected from fluoro, hydroxyl.
R721 is (1-6C)alkoxy, (3-6C)cycloalkoxy, (1-6C)alkoxy-(3-6C)cycloalkyl, (1-3C)alkoxy(2-4C)alkoxy, amino(2-4C)alkoxy, [(1-6C)alkyl]amino(2-4C)alkoxy, (di)[(1-6C)alkyl]amino(2-4C)alkoxy, [hydroxy(2-6C)alkyl]amino(2-4C)alkoxy, [(1-6C)alkyl][hydroxy(2-6C)alkyl]amino(2-4C)alkoxy, [(1-6C)alkoxy(2-6C)alkyl]amino(2-4C)alkoxy, [(1-6C)alkyl][(1-6C)alkoxy(2-6C)alkyl]amino(2-4C)alkoxy, (cyclyl-N)-(2-4C)alkoxy, [(1-6C)alkylcarbonyl]amino(1-6C)alkoxy, [(1-6C)alkyl][(1-6C)alkylcarbonyl]amino(1-6C)alkoxy, [(3-6C)cycloalkylcarbonyl]amino(1-6C)alkoxy, [(1-6C)alkyl][(3-6C)cycloalkylcarbonyl]amino(1-6C)alkoxy, aminocarbonyl(1-6C)alkoxy, [(1-6C)alkyl]aminocarbonyl(1-6C)alkoxy, (di)[(1-6C)alkyl]aminocarbonyl(1-6C)alkoxy, [hydroxy(1-6C)alkyl]aminocarbonyl(1-6C)alkoxy, (cyclyl-N)carbonyl(1-6C)alkoxy. All of the alkyl groups in R721 are optionally substituted with one or more groups independently selected from fluoro, hydroxyl.
R722 is amino, [(1-6C)alkyl]amino, (di)[(1-6C)alkyl]amino, [hydroxy(2-6C)alkyl]amino, [(1-6C)alkyl][hydroxy(2-6C)alkyl]amino, [(1-6C)alkoxy(2-6C)alkyl]amino, [(1-6C)alkyl][(1-6C)alkoxy(2-6C)alkyl]amino, cyclyl-N. All of the alkyl groups in R722 are optionally substituted with one or more fluoro.
R724 is (1-6C)alkoxycarbonylamino, [(1-6C)alkoxycarbonyl(1-6C)alkyl]amino, (1-6C)alkylaminocarbonylamino, (cyclyl-N)carbonylamino;
R725 is aminocarbonyl, [(1-6C)alkyl]aminocarbonyl, (di)[(1-6C)alkyl]aminocarbonyl, [hydroxy(2-6C)alkyl]aminocarbonyl, [(1-6C)alkyl][hydroxy(2-6C)alkyl]aminocarbonyl, [(1-6C)alkoxy(2-6C)alkyl]aminocarbonyl, [(1-6C)alkyl][(1-6C)alkoxy(2-6C)alkyl]aminocarbonyl, (cyclyl-N)carbonyl, amino(2-4C)alkoxycarbonyl, [(1-6C)alkyl]amino(2-4C)alkoxycarbonyl. All of the alkyl groups in R725 are optionally substituted with one or more fluoro.
R732 is (1-4C)alkyl, amino(1-4C)alkyl, [(1-6C)alkyl]amino(1-4C)alkyl, (di)[(1-6C)alkyl]amino(1-4C)alkyl, [hydroxy(2-6C)alkyl]amino(1-4C)alkyl, [(1-6C)alkyl][hydroxy(2-6C)alkyl]amino(1-4C)alkyl, [(1-6C)alkoxy(2-6C)alkyl]amino(1-4C)alkyl, [(1-6C)alkyl][(1-6C)alkoxy(2-6C)alkyl]amino(1-4C)alkyl, (cyclyl-N)(1-4C)alkyl, [(1-6C)alkylcarbonyl]amino(1-4C)alkyl, [(1-6C)alkyl][(1-6C)alkylcarbonyl]amino(1-4C)alkyl, hydroxy(1-4C)alkyl, (1-6C)alkoxy(1-4C)alkyl, (3-6C)cycloalkoxy(1-4C)alkyl, aminocarbonyl(1-4C)alkyl, [(1-6C)alkyl]aminocarbonyl(1-4C)alkyl, (di)[(1-6C)alkyl]aminocarbonyl(1-4C)alkyl, [hydroxy(1-6C)alkyl]aminocarbonyl(1-4C)alkyl, [(1-6C)alkyl][hydroxy(1-6C)alkyl]aminocarbonyl(1-4C)alkyl, [(1-6C)alkoxy(2-6C)alkyl]aminocarbonyl(1-4C)alkyl. All of the alkyl groups in R732 are optionally substituted with one or more fluoro.
R733 is (1-6C)alkoxy;
R735 is amino, [(1-6C)alkyl]amino, (di)[(1-6C)alkyl]amino, cyclyl-N. All of the alkyl groups in R735 are optionally substituted with one or more fluoro.

R741 is (1-4C)alkyl, (3-6C)cycloalkyl, (3-6C)cycloalkyl(1-3C)alkyl, (1-6C)alkoxy, (1-4C)alkylcarbonyl. All of the alkyl groups in R741 are optionally substituted with one or more groups independently selected from fluoro or hydroxyl.

In another aspect the invention relates to a compound of formula I wherein R1 is one or two groups independently selected from hydrogen, hydroxyl, (1-6C)alkoxy or halogen.

In another aspect the invention relates to a compound according to formula I wherein R1 is one or two groups independently selected from hydrogen, hydroxyl, (1-3C) alkoxy or halogen. Preferably, the invention relates to a compound according to formula I wherein R1 is one or two groups independently selected from hydrogen, hydroxyl, methoxy or fluorine.

In another aspect the invention relates to a compound according to formula I wherein R2 is hydrogen or (1-3C)alkyl preferably, the invention relates to a compound according to formula I wherein R2 is hydrogen.

In yet another aspect the invention relates to a compound according to formula I wherein R3 is (R31)(R32)CH—O; R31 is H or (1-5C)alkyl optionally substituted with one or more hydroxy; R32 is (1-5C)alkyl optionally substituted with one or more fluoro. Preferably, R31 and R32 are independently (1-3C)alkyl and R31 is optionally substituted with hydroxyl.

In yet another aspect the invention relates to a compound according to formula I wherein R3 is (3-7C)cycloalkoxy which is optionally substituted with one or more substituents selected from a group consisting of fluoro and hydroxyl.

In yet another aspect the invention relates to a compound according to formula I wherein R3 is heteroaryl, which is optionally substituted with one or more groups selected from R34, R35, R36, halogen or hydroxyl. Preferably R3 is indole, indazole, azaindole, thienopyrole or pyrolopyridine. R34 is (1-6C)alkyl optionally substituted with one or more fluoro and R35 is (1-6C)alkoxy optionally substituted with one or more fluoro. Preferably R34 is (1-3C)alkyl, R34 being methyl being most preferred. Preferably R35 is (1-3C)alkoxy, R35 being methoxy being most preferred. R36 is hydrogen or (1-6C)alkyl optionally substituted with one or more fluoro. Preferably R36 is (1-3C)alkyl, more preferred R36 is methyl. Preferred halogen substituens of R3 are fluoro and chloro. Fluoro substituents being more preferred.

In another aspect the invention relates to a compound according to formula I wherein
R3 is

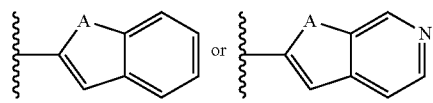

wherein
A is O or NR36, preferably A is NR36, and wherein each C is optionally substituted with one or more groups selected from R34, R35 and fluoro wherein
R34 is (1-6C)alkyl optionally substituted with one or more fluoro;
R35 is (1-6C)alkoxy optionally substituted with one or more fluoro;
R36 is hydrogen or (1-6C)alkyl optionally substituted with one or more fluoro.

In another aspect the invention relates to a compound according to formula I wherein R3 is

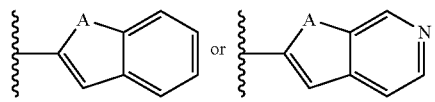

wherein
A is O or NR36, preferably A is NR36, and wherein each C is optionally substituted with one or more groups selected from R34, R35 and fluoro wherein
R34 is (1-6C)alkyl;
R35 is (1-6C)alkoxy;
R36 is hydrogen or (1-6C)alkyl, preferably R36 is (1-3C) alkyl, more preferred R36 is methyl.

In another aspect the invention relates to a compound according to formula I wherein
R3 is

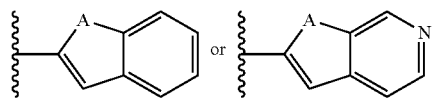

wherein
A is O or NR36, A is NR36 being preferred, and wherein each C is optionally substituted with one or more groups selected from R34, R35 and fluoro; R34 and R35 are preferred substituents wherein
R34 is (1-3C)alkyl, preferably R34 is methyl;
R35 is (1-3C)alkoxy, preferably R35 is methoxy;
R36 is (1-6C)alkyl, preferably R36 is (1-3C)alkyl, more preferred R36 is methyl.

In yet another aspect the invention relates to a compound according to formula I wherein
R3 is

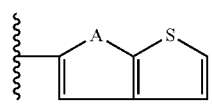

wherein
A is O or NR36, preferably A is NR36, and wherein each C is optionally substituted with one or more groups selected from R34, R35 and fluoro wherein
R34 is (1-6C)alkyl optionally substituted with one or more fluoro, preferably, R34 is (1-3C)alkyl optionally substituted with one or more fluoro, more preferably R34 is (1-3C)alkyl;
R35 is (1-6C)alkoxy optionally substituted with one or more fluoro. Preferably, R35 is (1-3C)alkoxy optionally substituted with one or more fluoro; more preferably R35 is (1-3C) alkoxy;
R36 is hydrogen or (1-6C)alkyl optionally substituted with hydroxyl or one or more fluoro, preferably R36 is hydrogen or (1-3C)alkyl optionally substituted with hydroxyl or one or more fluoro, more preferably R36 is hydrogen or (1-3C)alkyl, R36 is methyl being most preferred.

In another aspect the invention relates to a compound according to formula I wherein

R3=

[chemical structure: 5-membered ring labeled A and S]

wherein
A is O or NR36 and wherein each C is optionally substituted with one or more groups selected from R34 and R35; wherein R34 is (1-3C)alkyl preferably R34 is methyl; R35 is (1-3C)alkoxy, preferably R35 is methoxy; R36 is hydrogen or (1-6C)alkyl, preferably R36 is hydrogen or (1-3C)alkyl, more preferred R36 is hydrogen or methyl.

In yet another aspect the invention relates to a compound according to formula I wherein R4 is

[chemical structures showing two cyclic/linear substituent options with (CH2)n, (CH2)m, Y, X, Z, R9]

or
R4 is (1-4C)alkyl, optionally substituted independently by one or more substituents from R8, fluoro, hydroxy; wherein
m is 1, 2 or 3;
n is 1, 2 or 3;
r is 1 or 2;
Y is CR5 or N;
X is O, CHR6, C(R66)(R67), NR7, C=O;
Z is O or
Z forms with R9 a 5 or 6 membered heterocyclyl optionally substituted by R91;
R5 is H or (1-6C)alkyl optionally substituted with one or more fluoro;
R6 is R61, R62, R63, R65, H, hydroxy, fluoro;
R7 is R71, R72, R73, R74, H;
R8 is heteroaryl, optionally substituted with one or more groups from (1-4C)alkyl, hydroxy, (1-6C)alkoxy, amino, (di)[(1-4C)alkyl]amino, [(1-4C)alkyl]amino, halogen;
R9 is H or (1-6C)alkyl optionally substituted with one or more fluoro;
R61 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl[(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl, all of the alkyl groups in R61 are optionally substituted with one or more fluoro;
R62 is (1-6C)alkoxy, hydroxy(1-6C)alkoxy, (1-3C)alkoxy(2-4C)alkoxy, R621-(2-4C)alkoxy, (1-4C)alkylcarbonyloxy, (1-4C)alkylaminocarbonyloxy, (3-6C)cycloalkylaminocarbonylox, all of the alkyl groups in R62 are optionally substituted with one or more F;
R63 is amino, [(1-6C)alkyl]amino, (di)[(1-6C)alkyl]amino, [hydroxy(2-6C)alkyl]amino, [(1-6C)alkyl][hydroxy(2-6C)alkyl]amino, (1-6C)alkoxycarbonylamino, (1-6C)alkylaminocarbonylamino, [(1-6C)alkoxy(2-6C)alkyl]amino, [(1-6C)alkyl][(1-6C)alkoxy(2-6C)alkyl]amino, (1-6C)alkylcarbonylamino, [(1-6C)alkylcarbonyl][(1-6C)alkoxy(2-6C)alkyl]amino, all of the alkyl groups in R63 are optionally substituted with one or more fluoro;

R65 is N-attached heterocyclyl which is optionally substituted with one or more oxo, fluoro or one or more R651;
R66 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl, all of the alkyl groups in R66 are optionally substituted with one or more fluoro;
R67 is hydroxy, (1-4C)alkoxy or fluoro;
R71 is (1-6C)alkyl, (3-6C)cycloalkyl, (3-6C)cycloalkyl(1-3C)alkyl any of which is optionally substituted with one or more fluoro;
R72 is (1-4C)alkyl, which is substituted with R725;
R73 is R732carbonyl, R733carbonyl, or R735carbonyl;
R74 is heterocyclyl which is optionally substituted with one or more groups independently selected from fluoro or R741;
R91 is (1-6C)alkyl optionally substituted with one or more fluoro;
R621 is amino, [(1-6C)alkyl]amino, (di)[(1-6C)alkyl]amino, all of the alkyl groups in R621 are optionally substituted with one or more fluoro or;
R621 is N-attached heterocyclyl, optionally substituted with one or more fluoro;
R651 is (1-4C)alkyl, (3-6C)cycloalkyl, (3-6C)cycloalkyl(1-3C)alkyl, (1-4C)alkylcarbonyl all of the alkyl groups in R651 are optionally substituted with one or more groups independently selected from fluoro, hydroxyl;
R725 is aminocarbonyl, [(1-6C)alkyl]aminocarbonyl, (di)[(1-6C)alkyl]aminocarbonyl, [hydroxy(2-6C)alkyl]aminocarbonyl, [(1-6C)alkyl][hydroxy(2-6C)alkyl]aminocarbonyl, [(1-6C)alkoxy(2-6C)alkyl]aminocarbonyl, [(1-6C)alkyl][(1-6C)alkoxy(2-6C)alkyl]aminocarbonyl, (cyclyl-N)carbonyl, amino(2-4C)alkoxycarbonyl, [(1-6C)alkyl]amino(2-4C)alkoxycarbonyl, all of the alkyl groups in R725 are optionally substituted with one or more fluoro;
R732 is (1-4C)alkyl, amino(1-4C)alkyl, [(1-6C)alkyl]amino(1-4C)alkyl, (di)[(1-6C)alkyl]amino(1-4C)alkyl, [hydroxy(2-6C)alkyl]amino(1-4C)alkyl, [(1-6C)alkyl][hydroxy(2-6C)alkyl]amino(1-4C)alkyl, [(1-6C)alkoxy(2-6C)alkyl]amino(1-4C)alkyl, [(1-6C)alkyl][(1-6C)alkoxy(2-6C)alkyl]amino(1-4C)alkyl, (cyclyl-N)(1-4C)alkyl, [(1-6C)alkylcarbonyl]amino(1-4C)alkyl, [(1-6C)alkyl][(1-6C)alkylcarbonyl]amino(1-4C)alkyl, hydroxy(1-4C)alkyl, (1-6C)alkoxy(1-4C)alkyl, (3-6C)cycloalkoxy(1-4C)alkyl, aminocarbonyl(1-4C)alkyl, [(1-6C)alkyl]aminocarbonyl(1-4C)alkyl, (di)[(1-6C)alkyl]aminocarbonyl(1-4C)alkyl, [hydroxy(1-6C)alkyl]aminocarbonyl(1-4C)alkyl, [(1-6C)alkyl][hydroxy(1-6C)alkyl]aminocarbonyl(1-4C)alkyl, [(1-6C)alkoxy(2-6C)alkyl]aminocarbonyl(1-4C)alkyl, all of the alkyl groups in R732 are optionally substituted with one or more fluoro;
R733 is (1-6C)alkoxy;
R735 is amino, [(1-6C)alkyl]amino, (di)[(1-6C)alkyl]amino, cyclyl-N, all of the alkyl groups in R735 are optionally substituted with one or more fluoro;
R741 is (1-4C)alkyl, (3-6C)cycloalkyl, (3-6C)cycloalkyl(1-3C)alkyl, (1-6C)alkoxy, (1-4C)alkylcarbonyl all of the alkyl groups in R741 are optionally substituted with one or more fluoro or hydroxyl.

In yet another aspect the invention relates to a compound according to formula I wherein R4 is

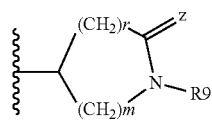

wherein
m is 1, 2 or 3, preferably, m is 1 or 2; r is 1 or 2; Z is O or Z forms with R9 a 5 or 6 membered heterocyclyl optionally substituted by R91, preferably Z forms with R9 a triazole ring optionally substituted with R91;
R9 is H or (1-6C)alkyl optionally substituted with one or more fluoro;
R91 is (1-6C)alkyl, preferably (1-3C)alkyl optionally substituted with one or more fluoro.

In another aspect the invention relates to a compound according to formula I wherein
R4 is

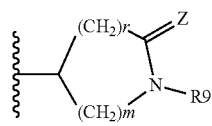

wherein
m is 1 or 2 and r is 1 or 2, preferably r is 1; Z is O and R9 is H or (1-6C)alkyl optionally substituted with one or more fluoro, preferably R9 is (1-3C)alkyl, R9 being methyl being preferred.

In yet another aspect the invention relates to a compound according to formula I wherein
R4 is

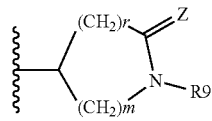

wherein m is 1 or 2, r is 1, Z is O, R9 is H or (1-3C)alkyl, R9 being methyl being preferred.

In yet another aspect the invention relates to a compound according to formula I wherein R4 is (1-4C)alkyl, optionally substituted independently with one or more substituents selected from R8, fluoro and hydroxyl wherein R8 is heteroaryl, optionally substituted independently with one or more substituents selected from (1-4C)alkyl, hydroxy, (1-6C)alkoxy, amino, (di)[(1-4C)alkyl]amino, [(1-4C)alkyl]amino and halogen.

In another aspect the invention relates to a compound according to formula I wherein R4 is (1-4C)alkyl, optionally substituted independently by one or more substituents from R8 or hydroxy. R8 is heteroaryl, preferably, R8 is imidazole.

In another aspect the invention relates to a compound according to formula I wherein R4=is

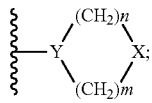

wherein
m is 1, 2 or 3;
n is 1, 2 or 3;

Y is CR5 or N;
X is O, CHR6, C(R66)(R67), NR7, C=O;
R5 is H or (1-6C)alkyl optionally substituted with one or more fluoro;
R6 is R61, R62, R63, R65, H, hydroxy, fluoro;
R7 is R71, R72, R73, R74, H;
R61 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl[(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl, all of the alkyl groups in R61 are optionally substituted with one or more fluoro;
R62 is (1-6C)alkoxy, hydroxy(1-6C)alkoxy, (1-3C)alkoxy(2-4C)alkoxy, R621-(2-4C)alkoxy, (1-4C)alkylcarbonyloxy, (1-4C)alkylaminocarbonyloxy, (3-6C)cycloalkylaminocarbonyloxy all of the alkyl groups in R62 are optionally substituted with one or more F;
R63 is amino, [(1-6C)alkyl]amino, (di)[(1-6C)alkyl]amino, [hydroxy(2-6C)alkyl]amino, [(1-6C)alkyl][hydroxy(2-6C)alkyl]amino, (1-6C)alkoxycarbonylamino, (1-6C)alkylaminocarbonylamino, [(1-6C)alkoxy(2-6C)alkyl]amino, [(1-6C)alkyl][(1-6C)alkoxy(2-6C)alkyl]amino, (1-6C)alkylcarbonylamino, [(1-6C)alkylcarbonyl][(1-6C)alkoxy(2-6C)alkyl]amino, all of the alkyl groups in R63 are optionally substituted with one or more fluoro;
R65 is N-attached heterocyclyl which is optionally substituted with one or more oxo, or fluoro or one or more R651;
R66 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl, all of the alkyl groups in R66 are optionally substituted with one or more fluoro;
R67 is hydroxy, (1-4C)alkoxy or fluoro;
R71 is (1-6C)alkyl, (3-6C)cycloalkyl, (3-6C)cycloalkyl(1-3C)alkyl all of the alkyl groups in R71 are optionally substituted with one or more fluoro;
R72 is (1-4C)alkyl, which is substituted with R725;
R73 is R732carbonyl, R733carbonyl, or R735carbonyl;
R74 is heterocyclyl which is optionally substituted with one or more groups independently selected from fluoro or R741;
R91 is (1-6C)alkyl optionally substituted with one or more fluoro;
R621 is amino, [(1-6C)alkyl]amino, (di)[(1-6C)alkyl]amino, any of the alkyl groups is optionally substituted with one or more fluoro or;
R621 is N-attached heterocyclyl, optionally substituted with one or more fluoro;
R651 is (1-4C)alkyl, (3-6C)cycloalkyl, (3-6C)cycloalkyl(1-3C)alkyl, (1-4C)alkylcarbonyl all of the alkyl groups in R651 are optionally substituted with one or more groups independently selected from fluoro or hydroxyl;
R725 is aminocarbonyl, [(1-6C)alkyl]aminocarbonyl, (di)[(1-6C)alkyl]aminocarbonyl, [hydroxy(2-6C)alkyl]aminocarbonyl, [(1-6C)alkyl][hydroxy(2-6C)alkyl]aminocarbonyl, [(1-6C)alkoxy(2-6C)alkyl]aminocarbonyl, [(1-6C)alkyl][(1-6C)alkoxy(2-6C)alkyl]aminocarbonyl, (cyclyl-N)carbonyl, amino(2-4C)alkoxycarbonyl, [(1-6C)alkyl]amino(2-4C)alkoxycarbonyl, all of the alkyl groups in R725 are optionally substituted with one or more fluoro;

R732 is (1-4C)alkyl, amino(1-4C)alkyl, [(1-6C)alkyl]amino(1-4C)alkyl, (di)[(1-6C)alkyl]amino(1-4C)alkyl, [hydroxy(2-6C)alkyl]amino(1-4C)alkyl, [(1-6C)alkyl][hydroxy(2-6C)alkyl]amino(1-4C)alkyl, [(1-6C)alkoxy(2-6C)alkyl]amino(1-4C)alkyl, [(1-6C)alkyl][(1-6C)alkoxy(2-6C)alkyl]amino(1-4C)alkyl, (cyclyl-N)(1-4C)alkyl, [(1-6C)alkylcarbonyl]amino(1-4C)alkyl, [(1-6C)alkyl][(1-6C)alkylcarbonyl]amino(1-4C)alkyl, hydroxy(1-4C)alkyl, (1-6C)alkoxy(1-4C)alkyl, (3-6C)cycloalkoxy(1-4C)alkyl, aminocarbonyl(1-4C)alkyl, [(1-6C)alkyl]aminocarbonyl(1-4C)alkyl, (di)[(1-6C)alkyl]aminocarbonyl(1-4C)alkyl, [hydroxy(1-6C)alkyl]aminocarbonyl(1-4C)alkyl, [(1-6C)alkyl][hydroxy(1-6C)alkyl]aminocarbonyl(1-4C)alkyl, [(1-6C)alkoxy(2-6C)alkyl]aminocarbonyl(1-4C)alkyl, all of the alkyl groups in R732 are optionally substituted with one or more fluoro;

R733 is (1-6C)alkoxy;

R735 is amino, [(1-6C)alkyl]amino, (di)[(1-6C)alkyl]amino, cyclyl-N, all of the alkyl groups in R651 are optionally substituted with one or more fluoro;

R741 is (1-4C)alkyl, (3-6C)cycloalkyl, (3-6C)cycloalkyl(1-3C)alkyl, (1-6C)alkoxy, (1-4C)alkylcarbonyl all of the alkyl groups in R741 are optionally substituted with one or more fluoro or hydroxyl.

In yet another aspect, the invention relates to a compound according to Formula I wherein
R4 is

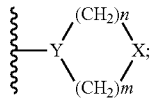

wherein
m is 1 or 2;
n is 1 or 2;
Y is CR5;
X is O, CHR6, C(R66)(R67), or NR7;
R5 is H or (1-6C)alkyl;
R6 is R61, R62, R63, R65, H, or hydroxy;
R7 is R72, R73, R71, R74 or H;
R61 is amino(1-4C)alkyl, [(1-6C)alkyl]amino(1-4C)alkyl, (di)[(1-6C)alkyl]amino(1-4C)alkyl[(1-4C)alkylcarbonyl]amino(1-4C)alkyl, or [(1-4C)alkoxycarbonyl]amino(1-4C)alkyl; preferably R61 is amino(1-3C)alkyl, [(1-3C)alkyl]amino(1-3C)alkyl, (di)[(1-3C)alkyl]amino(1-3C)alkyl, [(1-3C)alkylcarbonyl]amino(1-3C)alkyl, or [(1-3C)alkoxycarbonyl]amino(1-3C)alkyl;
R62 is (1-4C)alkylcarbonyloxy, (3-6C)cycloalkylaminocarbonyloxy;
R63 is amino, [(1-6C)alkyl]amino, (di)[(1-6C)alkyl]amino, [(1-6C)alkoxy(2-6C)alkyl]amino, [(1-6C)alkyl][(1-6C)alkoxy(2-6C)alkyl]amino, [(1-6C)alkylcarbonyl][(1-6C)alkoxy(2-6C)alkyl]amino, all of the alkyl groups in R63 are optionally substituted with one or more fluoro;
R65 is N-attached heterocyclyl which is optionally substituted with one or more oxo, fluoro or one or more R651, preferably R65 is azetidine, pyrrolidine, piperidine, piperazine or morpholine which is optionally substituted with one or more oxo, fluoro or one or more R651; more preferably R65 is piperazine which is optionally substituted with one or more oxo, fluoro or one or more R651.
R66 is [(1-6C)alkyl]amino(1-4C)alkyl;
R67 is hydroxyl;
R71 is (1-6C)alkyl;

R72 is (1-4C)alkyl, which is substituted with R725;
R73 is R732carbonyl, R733carbonyl, or R735carbonyl;
R74 is heterocyclyl which is optionally substituted with one or more groups independently selected from fluoro or R741
R651 is (1-4C)alkyl, (1-4C)alkylcarbonyl, preferably R651 is methyl of methylcarbonyl;
R725 is (di)[(1-6C)alkyl]aminocarbonyl;
R732 is (1-4C)alkyl, amino(1-4C)alkyl, (di)[(1-6C)alkyl]amino(1-4C)alkyl, [hydroxy(2-6C)alkyl]amino(1-4C)alkyl, hydroxy(1-4C)alkyl, (1-6C)alkoxy(1-4C)alkyl;
R733 is (1-6C)alkoxy;
R735 is amino;
R741 is (1-4C)alkylcarbonyl.

In another aspect, the invention relates to compounds according to Formula 1 wherein
R4 is

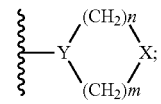

m is 1 or 2, m is 2 being preferred, n is 1 or 2; Y is CR5; X is CHR6 or NR7;
R5 is H or (1-6C)alkyl, R5 is H being preferred;
R6 is R63 or R65;
R7 is R71, R72, R73 or R74, H; R7 is R73 being preferred;
R63 is amino, [(1-6C)alkyl]amino, (di)[(1-6C)alkyl]amino, [(1-6C)alkoxy(2-6C)alkyl]amino, [(1-6C)alkyl][(1-6C)alkoxy(2-6C)alkyl]amino, or [(1-6C)alkylcarbonyl][(1-6C)alkoxy(2-6C)alkyl]amino, any of the alkyl groups of which is optionally substituted with one or more fluoro; preferably R63 is amino, [(1-3C)alkyl]amino, (di)[(1-3C)alkyl]amino, [(1-3C)alkoxy(2-3C)alkyl]amino, [(1-3C)alkyl][(1-3C)alkoxy(2-3C)alkyl]amino, [(1-3C)alkylcarbonyl][(1-3C)alkoxy(2-3C)alkyl]amino, all of the alkyl groups in R63 are optionally substituted with one or more fluoro.
R65 is azetidine, pyrrolidine, piperidine, piperazine or morpholine which is optionally substituted with one or more oxo, fluoro or one or more R651; preferably, R65 is piperazine which is optionally substituted with one or more oxo, fluoro or one or more R651;
R71 is (1-6C)alkyl; preferably R71 is (1-3C)alkyl, R71 being methyl being most preferred.
R72 is (1-4C)alkyl, which is substituted with R725; preferably R72 is methyl substituted with R725.
R73 is R732carbonyl, R733carbonyl, or R735carbonyl; preferably R73 is R732carbonyl.
R74 is heterocyclyl which is optionally substituted with one or more groups independently selected from fluoro or R741; preferably R74 is pyran or piperidin optionally substituted with R741;
R651 is (1-4C)alkyl, (1-4C)alkylcarbonyl, preferably R651 (1-3C)alkyl, (1-3C)alkylcarbonyl is more preferably, R651 is methyl or methyl-carbonyl.
R725 is (di)[(1-6C)alkyl]aminocarbonyl, preferably R725 is (di)[(1-3C)alkyl]aminocarbonyl, more preferably R725 is (di)[methyl]aminocarbonyl.
R732 is (1-4C)alkyl, amino(1-4C)alkyl, (di)[(1-6C)alkyl]amino(1-4C)alkyl, [hydroxy(2-6C)alkyl]amino(1-4C)alkyl, hydroxy(1-4C)alkyl, (1-6C)alkoxy(1-4C)alkyl; preferably R7321 is 1-3C)alkyl, amino(1-3C)alkyl, (di)[(1-3C)alkyl]amino(1-3C)alkyl, [hydroxy(2-3C)alkyl]amino(1-3C)alkyl, hydroxy(1-3C)alkyl, (1-3C)alkoxy(1-3C)alkyl;
R733 is (1-6C)alkoxy preferably R733 is (1-3C)alkoxy;

R735 is amino, [(1-6C)alkyl]amino, (di)[(1-6C)alkyl]amino,
R741 is (1-4C)alkylcarbonyl, preferably R741 is methylcarbonyl.

In yet another aspect the invention relates to a compound according to Formula I selected from the group consisting of
N-[2-Methoxy-4-[8-methyl-3-(tetrahydro-2H-pyran-4-yl)imidazo[1,5-a]pyrazine]phenyl]-1-methyl-1H-indole-2-carboxamide,
N-(4-(3-((Trans)-4-(4-acetylpiperazin-1-yl)cyclohexyl)-8-methylimidazo[1,5-a]pyrazin-1-yl)-2-methoxyphenyl)-4-methoxy-1-methyl-1H-indole-2-carboxamide,
(S)-pentan-2-yl 4-(3-(azetidin-1-yl)-8-methylimidazo[1,5-a]pyrazin-1-yl)-2-methoxyphenylcarbamate,
(S)-pentan-2-yl 4-(3-((R)-1-(2-(dimethylamino)acetyl)pyrrolidin-3-yl)-8-methylimidazo[1,5-a]pyrazin-1-yl)-2-methoxyphenylcarbamate,
(Trans)-4-O-(3-methoxy-4-(4-methoxy-1-methyl-1H-indole-2-carboxamido)phenyl)-8-methylimidazo[1,5-a]pyrazin-3-yl)cyclohexyl acetate,
N-(4-(3-((trans)-4-hydroxycyclohexyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide,
4-Methoxy-N-(2-methoxy-4-(8-methyl-3-((cis)-4-(4-methylpiperazin-1-yl)cyclohexyl)imidazo[1,5-a]pyrazin-1-yl)phenyl)-1-methyl-1H-indole-2-carboxamide,
N-(4-(3-((trans)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide,
N-(4-(3-((cis)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide,
(S)-Pentan-2-yl 2-methoxy-4-(3-((trans)-4-(2-methoxyethylamino)cyclohexyl)-8-methyl-imidazo[1,5-a]pyrazin-1-yl)phenylcarbamate,
N-(2-methoxy-4-(8-methyl-3-((trans)-4-morpholinocyclohexyl)imidazo[1,5-a]pyrazin-1-yl)phenyl)-1-methyl-1H-indole-2-carboxamide,
4-Methoxy-N-(2-methoxy-4-(8-methyl-3-(3-methyloxetan-3-yl)imidazo[1,5-a]pyrazin-1-yl)phenyl)-1-methyl-1H-indole-2-carboxamide,
N-(4-(3-(hydroxymethyl)-8-methylimidazo[1,5-a]pyrazin-1-yl)-2-methoxyphenyl)-4-methoxy-1-methyl-1H-indole-2-carboxamide,
N-(4-(3-((1H-imidazol-1-yl)methyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-(1-(tetrahydro-2H-pyran-4-yl)azetidin-3-yl)imidazo[1,5-a]pyrazin-1-yl)phenyl)-1-methyl-1H-indole-2-carboxamide,
4-Methoxy-N-(2-methoxy-4-(8-methyl-3-(piperidin-4-yl)imidazo[1,5-a]pyrazin-1-yl)phenyl)-1-methyl-1H-indole-2-carboxamide,
N-(4-(3-O-(2-(dimethylamino)-2-oxoethyl)pipendin-4-yl)-8-methylimidazo[1,5-a]pyrazin-1-yl)-2-methoxyphenyl)-1-methyl-1H-indole-2-carboxamide,
N-(4-(3-O-(2-(dimethylamino)acetyl)pipendin-4-yl)-8-methylimidazo[1,5-a]pyrazin-1-yl)-2-methoxyphenyl)-1-methyl-1H-indole-2-carboxamide,
N-(4-(3-(1-(2-Aminoacetyl)pipendin-4-yl)-8-methylimidazo[1,5-a]pyrazin-1-yl)-2-methoxyphenyl)-1-methyl-1H-indole-2-carboxamide,
N-(4-(3-(1-carbamoylpipendin-4-yl)-8-methylimidazo[1,5-a]pyrazin-1-yl)-2-methoxyphenyl)-4-methoxy-1-methyl-1H-indole-2-carboxamide,
Methyl 4-(1-(3-methoxy-4-(4-methoxy-1-methyl-1H-indole-2-carboxamido)phenyl)-8-methylimidazo[1,5-a]pyrazin-3-yl)piperidine-1-carboxylate,
N-(2-methoxy-4-(8-methyl-3-(4-methylpiperazin-1-yl)imidazo[1,5-a]pyrazin-1-yl)phenyl)-1-methyl-1H-indole-2-carboxamide,
N-(2-methoxy-4-(8-methyl-3-(morholin-4-yl)imidazo[1,5-a]pyrazin-1-yl)phenyl)-1-methyl-1H-indole-2-carboxamide,
Isopropyl 2-methoxy-4-(8-methyl-3-(4-morpholinopiperidin-1-yl)imidazo[1,5-a]pyrazin-1-yl)phenylcarbamate,
(S)-Pentan-2-yl 2-methoxy-4-(3-((trans)-4-((2-methoxyethyl)(methyl)amino)cyclohexyl)-8-methylimidazo[1,5-a]pyrazin-1-yl)phenylcarbamate,
N-(4-(3-((Trans)-4-(dimethylamino)cyclohexyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(3-((cis)-4-((2-methoxyethyl)(methyl)amino)cyclohexyl)-8-methylimidazo[1,5-a]pyrazin-1-yl)phenyl)-1-methyl-1H-indole-2-carboxamide, 4-Methoxy-N-(2-methoxy-4-(8-methyl-3-((cis)-4-morpholinocyclohexyl)imidazo[1,5-a]pyrazin-1-yl)phenyl)-1-methyl-1H-indole-2-carboxamide,
N-(4-(3-((Cis)-4-(dimethylamino)cyclohexyl)-8-methylimidazo[1,5-a]pyrazin-1-yl)-2-methoxyphenyl)-4-methoxy-1-methyl-1H-indole-2-carboxamide,
(S)-Pentan-2-yl 4-(3-((cis)-4-(4-acetylpiperazin-1-yl)cyclohexyl)-8-methylimidazo[1,5-a]pyrazin-1-yl)-2-methoxyphenylcarbamate,
(S)-Pentan-2-yl 4-(3-((cis)-4-(3,3-difluoroazetidin-1-yl)cyclohexyl)-8-methylimidazo[1,5-a]pyrazin-1-yl)-2-methoxyphenylcarbamate,
(S)-Pentan-2-yl 2-methoxy-4-(8-methyl-3-((1r,3r)-3-(4-methylpiperazin-1-yl)cyclobutyl)imidazo[1,5-a]pyrazin-1-yl)phenylcarbamate,
(S)-Pentan-2-yl 2-methoxy-4-(8-methyl-3-(3-(4-methylpiperazin-1-yl)cyclopentyl)imidazo[1,5-a]pyrazin-1-yl)phenylcarbamate,
(S)-Pentan-2-yl 2-methoxy-4-(3-((trans)-4-(N-(2-methoxyethyl)acetamido)cyclohexyl)-8-methylimidazo[1,5-a]pyrazin-1-yl)phenylcarbamate,
4-Methoxy-N-(2-methoxy-4-(8-methyl-3-(1-(tetrahydro-2H-pyran-4-yl)piperidin-4-yl)imidazo[1,5-a]pyrazin-1-yl)phenyl)-1-methyl-1H-indole-2-carboxamide,
(S)-Pentan-2-yl 4-(3-(4-acetylpiperazin-1-yl)-8-methylimidazo[1,5-a]pyrazin-1-yl)-2-methoxyphenylcarbamate,
N-(4-(3-(4-(1-Acetylpiperidin-4-yl)piperazin-1-yl)-8-methylimidazo[1,5-a]pyrazin-1-yl)-2-methoxyphenyl)-4-methoxy-1-methyl-1H-indole-2-carboxamide,
(S)-Pentan-2-yl 2-methoxy-4-(8-methyl-3-((trans)-4-(4-methylpiperazin-1-yl)cyclohexyl)imidazo[1,5-a]pyrazin-1-yl)phenylcarbamate,
N-(2-Methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide 2,2,2-trifluoroacetate,
N-(4-(3-((Trans)-4-(4-acetylpiperazin-1-yl)cyclohexyl)-8-methylimidazo[1,5-a]pyrazin-1-yl)-2-methoxyphenyl)-1-methyl-1H-indole-2-carboxamide,
(S)-Pentan-2-yl 4-(3-((trans)-4-(4-acetylpiperazin-1-yl)cyclohexyl)-8-methylimidazo[1,5-a]pyrazin-1-yl)-2-methoxyphenylcarbamate,
(R)—N-(4-(3-(1-(2-(Dimethylamino)acetyl)pyrrolidin-3-yl)-8-methylimidazo[1,5-a]pyrazin-1-yl)-2-methoxyphenyl)-4-methoxy-1-methyl-1H-indole-2-carboxamide, (S)-Pentan-2-yl 2-methoxy-4-(8-methyl-3-((cis)-4-(4-methylpiperazin-1-yl)cyclohexyl)imidazo[1,5-a]pyrazin-1-yl)phenylcarbamate,
N-(4-(3-(4-Acetylpiperazin-1-yl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-(4-(tetrahydro-2H-pyran-4-yl)piperazin-1-yl)imidazo[1,5-a]pyrazin-1-yl)phenyl)-1-methyl-1H-indole-2-carboxamide,
(R)-4-methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide,
(S)-4-Methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide,
4-Methoxy-N-(2-methoxy-4-(8-methyl-3-(3-(trifluoromethyl)-5,6-dihydro-[1,2,4]triazolo[4,3-a]pyrazin-7(8H)-yl)imidazo[1,5-a]pyrazin-1-yl)phenyl)-1-methyl-1H-indole-2-carboxamide,
4-Methoxy-N-(2-methoxy-4-(8-methyl-3-(1-methyl-2-oxopiperidin-4-yl)imidazo[1,5-a]pyrazin-1-yl)phenyl)-1-methyl-1H-indole-2-carboxamide,
N-(4-(3-((trans)-4-aminocyclohexyl)-8-methylimidazo[1,5-a]pyrazin-1-yl)-2-methoxyphenyl)-4-methoxy-1-methyl-1H-indole-2-carboxamide,
N-(4-(3-((trans)-4-(2,2-Difluoroethylamino)cyclohexyl)-8-methylimidazo[1,5-a]pyrazin-1-yl)-2-methoxyphenyl)-4-methoxy-1-methyl-1H-indole-2-carboxamide,
Isopropyl 4-(3-((trans)-4-(3,3-difluoroazetidin-1-yl)cyclohexyl)-8-methylimidazo[1,5-a]pyrazin-1-yl)-2-methoxyphenyl(methyl)carbamate,
5-Methoxy-N-(2-methoxy-4-(8-methyl-3-(tetrahydro-2H-pyran-4-yl)imidazo[1,5-a]pyrazin-1-yl)phenyl)-1H-pyrrolo[3,2-b]pyridine-2-carboxamide,
N-(2-Methoxy-4-(8-methyl-3-(1-methylpiperidin-4-yl)imidazo[1,5-a]pyrazin-1-yl)phenyl)-1-methyl-1H-indole-2-carboxamide,
(S)-4-Hydroxybutan-2-yl 2-methoxy-4-(8-methyl-3-(tetrahydro-2H-pyran-4-yl)imidazo[1,5-a]pyrazin-1-yl)phenylcarbamate,
4-Fluoro-N-(2-methoxy-4-(8-methyl-3-(1-methylpiperidin-4-yl)imidazo[1,5-a]pyrazin-1-yl)phenyl)-1-methyl-1H-indole-2-carboxamide,
N-(5-Fluoro-2-methoxy-4-(8-methyl-3-(tetrahydro-2H-pyran-4-yl)imidazo[1,5-a]pyrazin-1-yl)phenyl)-4-methoxy-1-methyl-1H-indole-2-carboxamide,
5-Hydroxypentan-2-yl 5-fluoro-2-methoxy-4-(8-methyl-3-(tetrahydro-2h-pyran-4-yl)imidazo[1,5-a]pyrazin-1-yl)phenylcarbamate,
(S)-sec-Butyl 2-methoxy-4-(8-methyl-3-((trans)-4-(4-methylpiperazin-1-yl)cyclohexyl)imidazo[1,5-a]pyrazin-1-yl)phenylcarbamate,
N-(4-(3-(1'-acetyl-1,4'-bipiperidin-4-yl)-8-methylimidazo[1,5-a]pyrazin-1-yl)-2-methoxyphenyl)-4-methoxy-1-methyl-1H-indole-2-carboxamide,
(S)-pentan-2-yl 2-methoxy-4-(3-((S)-1-(2-methoxyacetyl)pyrrolidin-3-yl)-8-methylimidazo[1,5-a]pyrazin-1-yl)phenylcarbamate,
(trans)-4-(1-(3-Methoxy-4-(4-methoxy-1-methyl-1H-indole-2-carboxamido)phenyl)-8-methylimidazo[1,5-a]pyrazin-3-yl)cyclohexyl cyclopentylcarbamate,
(R)—N-(4-(3-(1-(2-(dimethylamino)-2-oxoethyl)pyrrolidin-3-yl)-8-methylimidazo[1,5-a]pyrazin-1-yl)-2-methoxyphenyl)-4-methoxy-1-methyl-1H-indole-2-carboxamide,
(R)—N-(4-(3-(1-(2-hydroxyacetyl)pyrrolidin-3-yl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-((trans)-4-(piperazin-1-yl)cyclohexyl)imidazo[1,5-a]pyrazin-1-yl)phenyl)-1-methyl-1H-indole-2-carboxamide,
4-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrole-2-carboxamide,
N-(2-methoxy-4-(8-methyl-3-((trans)-4-(4-methylpiperazin-1-yl)cyclohexyl)imidazo[1,5-a]pyrazin-1-yl)phenyl)-6-methyl-6H-thieno[2,3-b]pyrrole-5-carboxamide,
N-(2-Methoxy-4-(8-methyl-3-((trans)-4-(4-methylpiperazin-1-yl)cyclohexyl)imidazo[1,5-a]pyrazin-1-yl)phenyl)-6H-thieno[2,3-b]pyrrole-5-carboxamide,
4-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indole-2-carboxamide,
4-Hydroxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide,
(S)-Pentan-2-yl 4-(3-((trans)-4-(aminomethyl)cyclohexyl)-8-methylimidazo[1,5-a]pyrazin-1-yl)-2-methoxyphenylcarbamate,
1-Methyl-N-(4-(8-methyl-3-((trans)-4-(4-methylpiperazin-1-yl)cyclohexyl)imidazo[1,5-a]pyrazin-1-yl)phenyl)-1H-indole-2-carboxamide,
N-(2-hydroxy-4-(8-methyl-3-((trans)-4-(4-methylpiperazin-1-yl)cyclohexyl)imidazo[1,5-a]pyrazin-1-yl)phenyl)-4-methoxy-1-methyl-1H-indole-2-carboxamide,
4-Methoxy-N-(2-methoxy-4-(8-methyl-3-((trans)-4-((methylamino)methyl)cyclohexyl)imidazo[1,5-a]pyrazin-1-yl)phenyl)-1-methyl-1H-indole-2-carboxamide,
N-(4-(3-((trans)-4-((dimethylamino)methyl)cyclohexyl)-8-methylimidazo[1,5-a]pyrazin-1-yl)-2-methoxyphenyl)-4-methoxy-1-methyl-1H-indole-2-carboxamide,
(S)-Pentan-2-yl 4-(3-((trans)-4-((dimethylamino)methyl)cyclohexyl)-8-methylimidazo[1,5-a]pyrazin-1-yl)-2-methoxyphenylcarbamate,
6-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indazole-3-carboxamide,
5-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-b]pyridine-2-carboxamide,
N-(4-(3-((trans)-4-(acetamidomethyl)cyclohexyl)-8-methylimidazo[1,5-a]pyrazin-1-yl)-2-methoxyphenyl)-4-methoxy-1-methyl-1H-indole-2-carboxamide,
(S)-pentan-2-yl 4-(3-((trans)-4-(acetamidomethyl)cyclohexyl)-8-methylimidazo[1,5-a]pyrazin-1-yl)-2-methoxyphenylcarbamate,
(S)-pentan-2-yl 4-(3-((trans)-4-(methoxycarbonylmethyl)cyclohexyl)-8-methylimidazo[1,5-a]pyrazin-1-yl)-2-methoxyphenylcarbamate,
4-Methoxy-N-(2-methoxy-4-(8-methyl-3-(4-oxocyclohexyl)imidazo[1,5-a]pyrazin-1-yl)phenyl)-1-methyl-1H-indole-2-carboxamide,
N-(4-(3-((trans)-4-hydroxy-4-((methylamino)methyl)cyclohexyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-(1-methyl-5-oxopyrrolidin-3-yl)imidazo[1,5-a]pyrazin-1-yl)phenyl)-1-methyl-1H-indole-2-carboxamide, 4-Methoxy-N-(2-methoxy-4-(8-methyl-3-((trans)-4-(4-methyl-3-oxopiperazin-1-yl)cyclohexyl)imidazo[1,5-a]pyrazin-1-yl)phenyl)-1-methyl-1H-indole-2-carboxamide, 5-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-c]pyridine-2-carboxamide, In yet another aspect the invention relates to a compound according to Formula 1 selected from the group consisting of 4-methoxy-N-(2-methoxy-4-(8-methyl-3-((trans)-4-morpholinocyclohexyl)imidazo[1,5-a]pyrazin-1-yl)phenyl)-1-methyl-1H-indole-2-carboxamide, S)-pentan-2-yl 2-methoxy-4-(8-methyl-3-(tetrahydro-2H-pyran-4-yl)imidazo[1,5-a]pyrazin-1-yl)phenylcarbamate, (S)-pentan-2-yl 2-methoxy-4-(8-methyl-3-((trans)-4-morpholinocyclohexyl)imidazo[1,5-a]pyrazin-1-yl)phenylcarbamate, (S)-pentan-2-yl 4-(3-(1-(2-(dimethylamino)acetyl)piperidin-4-yl)-8-methylimidazo[1,5-a]pyrazin-1-yl)-2-methoxyphenylcarbamate, (S)-pentan-2-yl 4-(3-(1-(2-(dimethylamino)-2-oxoethyl)piperidin-4-yl)-8-methylimidazo[1,5-a]pyrazin-1-yl)-2-methoxyphenylcarbamate, (S)-pentan-2-yl 2-methoxy-4-(8-methyl-3-morpholinoimidazo[1,5-a]pyrazin-1-yl)phenylcarbamate, isopropyl 2-methoxy-4-(8-methyl-3-((trans)-4-(4-methylpiperazin-1-yl)cyclohexyl)imidazo[1,5-a]pyrazin-1-yl)phenylcarbamate, 4-fluoro-N-(2-methoxy-4-(8-methyl-3-(tetrahydro-2H-pyran-4-yl)imidazo[1,5-a]pyrazin-1-yl)phenyl)-1-methyl-1H-indole-2-carboxamide, tert-butyl 2-methoxy-4-(8-methyl-3-((trans)-4-(4-methylpiperazin-1-yl)cyclohexyl)imidazo[1,5-a]pyrazin-1-yl)phenylcarbamate, N-(4-(3-(1-(2-(dimethylamino)-2-oxoethyl)piperidin-4-yl)-8-methylimidazo[1,5-a]pyrazin-1-yl)-2-methoxyphenyl)-4-methoxy-1-methyl-1H-indole-2-carboxamide, N-(4-(3-(azetidin-1-yl)-8-methylimidazo[1,5-a]pyrazin-1-yl)-2-methoxyphenyl)-1-methyl-1H-indole-2-carboxamide, 5-hydroxypentan-2-yl 2-methoxy-4-(8-methyl-3-((trans)-4-(4-methylpiperazin-1-yl)cyclohexyl)imidazo[1,5-a]pyrazin-1-yl)phenylcarbamate, (S)-pentan-2-yl 4-(3-(1-(2-aminoacetyl)piperidin-4-yl)-8-methylimidazo[1,5-a]pyrazin-1-yl)-2-methoxyphenylcarbamate, N-(4-(3-(1-(2-aminoacetyl)piperidin-4-yl)-8-methylimidazo[1,5-a]pyrazin-1-yl)-2-methoxyphenyl)-4-methoxy-1-methyl-1H-indole-2-carboxamide, N-(4-(3-((trans)-4-(aminomethyl)cyclohexyl)-8-methylimidazo[1,5-a]pyrazin-1-yl)-2-methoxyphenyl)-4-methoxy-1-methyl-1H-indole-2-carboxamide, (S)-pentan-2-yl 2-methoxy-4-(8-methyl-3-((cis)-4-morpholinocyclohexyl)imidazo[1,5-a]pyrazin-1-yl)phenylcarbamate, (S)-pentan-2-yl 2-methoxy-4-(8-methyl-3-(4-morpholinopiperidin-1-yl)imidazo[1,5-a]pyrazin-1-yl)phenylcarbamate, 4-methoxy-N-(2-methoxy-4-(8-methyl-3-(4-morpholinopiperidin-1-yl)imidazo[1,5-a]pyrazin-1-yl)phenyl)-1-methyl-1H-indole-2-carboxamide, 4-methoxy-N-(2-methoxy-4-(8-methyl-3-((trans)-3-(4-methylpiperazin-1-yl)cyclobutyl)imidazo[1,5-a]pyrazin-1-yl)phenyl)-1-methyl-1H-indole-2-carboxamide, 4-methoxy-N-(2-methoxy-4-(3-((trans)-4-(2-methoxyethylamino)cyclohexyl)-8-methylimidazo[1,5-a]pyrazin-1-yl)phenyl)-1-methyl-1H-indole-2-carboxamide, 4-methoxy-N-(2-methoxy-4-(3-((trans)-4-(N-(2-methoxyethyl)acetamido)cyclohexyl)-8-methylimidazo[1,5-a]pyrazin-1-yl)phenyl)-1-methyl-1H-indole-2-carboxamide, 4-methoxy-N-(2-methoxy-4-(8-methyl-3-morpholinoimidazo[1,5-a]pyrazin-1-yl)phenyl)-1-methyl-1H-indole-2-carboxamide, 4-methoxy-N-(2-methoxy-4-(3-((trans)-4-((2-methoxyethyl)(methyl)amino)cyclohexyl)-8-methylimidazo[1,5-a]pyrazin-1-yl)phenyl)-1-methyl-1H-indole-2-carboxamide, N-(4-(3-(1-(2-(dimethylamino)acetyl)piperidin-4-yl)-8-methylimidazo[1,5-a]pyrazin-1-yl)-2-methoxyphenyl)-4-methoxy-1-methyl-1H-indole-2-carboxamide, (S)-pentan-2-yl 4-(3-((trans)-4-(3,3-difluoroazetidin-1-yl)cyclohexyl)-8-methylimidazo[1,5-a]pyrazin-1-yl)-2-methoxyphenylcarbamate, (S)-pentan-2-yl 2-methoxy-4-(8-methyl-3-(4-(tetrahydro-2H-pyran-4-yl)piperazin-1-yl)imidazo[1,5-a]pyrazin-1-yl)phenylcarbamate, and N-(4-(3-((trans)-4-(3,3-difluoroazetidin-1-yl)cyclohexyl)-8-methylimidazo[1,5-a]pyrazin-1-yl)-2-methoxyphenyl)-1-methyl-1H-indole-2-carboxamide, The invention also relates to those compounds wherein all specific definitions for A, X, Y, Z, m, n, r, R1 through R9 and all substituent groups in the various aspects of the inventions defined here above occur in any combination within the definition of the 8-methyl-1-phenyl-imidazo[1,5-a]pyrazine compound of formula I.

The 8-methyl-1-phenyl-imidazo[1,5-a]pyrazine compounds of the invention stimulate the Lck receptor. All compounds of the invention have an IC50 of 10 µM or lower.

In another aspect the invention relates to compounds of formula I which have an IC50 of less than 100 nM. In yet another aspect the invention relates to compounds of formula I which have an IC50 of less than 10 nM.

The term IC50 means the concentration of the test compound that that is required for 50% inhibition in vitro.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide (Gaudet et al. A homogeneous fluorescence polarization assay adaptable for a range of protein serine/threonine and tyrosine kinases. J. Biomol. Screen (2003) 8, 164-175).

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I may contain both a basic moiety, such as, but not limited to a pyridine or imidazole, and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine and chlorine, such as 2H, 3H, 13C, 14C, 15N, 18O, 17O, 35S, 18F, and 36Cl, respectively.

Certain isotopically-labelled compounds of Formula I (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Isotopically-labeled compounds of Formula I can generally be prepared by following procedures analogous to those disclosed in the Schemes and/or in the Examples hereinbelow, by substituting an appropriate isotopically-labeled reagent for a non-isotopically labelled reagent.

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also relates to a pharmaceutical composition comprising a 8-methyl-1-phenyl-imidazo[1,5-a] pyrazine derivative or pharmaceutically acceptable salts thereof having the general formula I in a mixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The compounds according to the invention can be used in therapy.

A further aspect of the invention resides in the use of 8-methyl-1-phenyl-imidazo[1,5-a]pyrazine compounds or a pharmaceutically acceptable salt thereof, having the general formula I for the manufacture of a medicament to be used for the treatment of Lck-mediated diseases or Lck-mediated conditions.

A further aspect of the invention resides in the use of 8-methyl-1-phenyl-imidazo[1,5-a]pyrazine compounds having the general formula I for the manufacture of a medicament to be used for the treatment of chronic T cell disorders as well as acute inflammatory disorders in which T cells play a prominent role.

In yet another aspect the invention resides in the use of 8-methyl-1-phenyl-imidazo[1,5-a]pyrazine compounds having the general formula I for the manufacture of a medicament to be used for the treatment of Lck-mediated diseases or conditions. These include, but are not limited to, the treatment of chronic T cell disorders and acute inflammatory disorders in which T cells play a prominent role. These diseases or conditions include allergies, leukemia, inflammatory bowel disease, rheumatoid arthritis, glomerulonephritis, lung fibrosis, psoriasis, hypersensitivity reactions of the skin, atherosclerosis, restenosis, allergic asthma, multiple sclerosis, type 1 diabetes, multiple sclerosis, rheumatoid arthritis, atopic dermatitis, delayed type hypersensitivity (DTH), acute rejection of transplanted organs as well as Graft versus Host Disease (GvHD).

In particular the compounds can be used to treat Psoriasis, rheumatoid arthritis (RA), multiple sclerosis (MS) and transplant rejection.

Suitable methods to prepare 8-methyl-1-phenyl-imidazo[1,5-a]pyrazine derivatives;

Compounds of Formula I can be prepared from compounds of Formula II, in which the X substituent is a chloro, bromo or iodo substituent, using palladium-mediated cross-coupling reactions such as the Suzuki, Stille or Negishi reactions. Compounds of Formula II can be prepared from compounds of Formula III using halogenation reagents like N-chlorosuccinimide, N-bromosuccinimide, N-iodosuccinimide or bromine (Scheme 1).

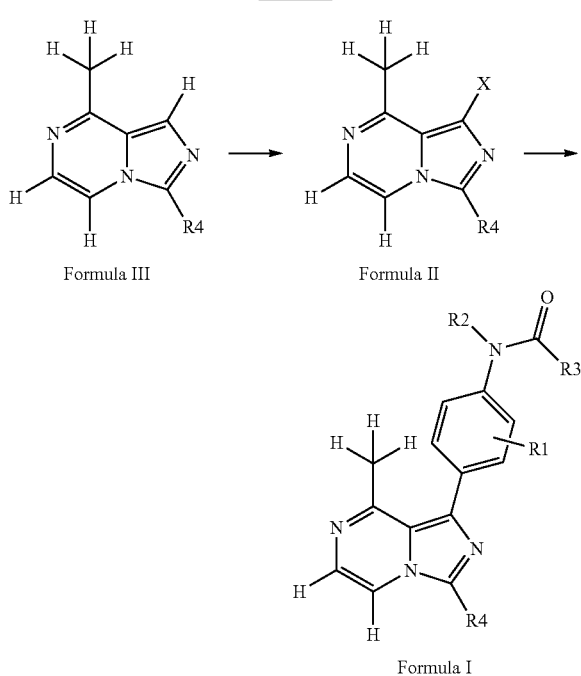

Compounds of Formula III can be prepared from compounds of formula IV using palladium mediated reaction to convert the 8-chloro substituent into the 8-methyl substituent. Suitable reagents are e.g bis(diphenylphosphino)ferrocene palladium (II) chloride complex with dichloromethane as palladium source and trimethylboroxine to provide the methyl group (Scheme 2). Compounds of Formula IV are described in literature (e.g. WO2007112005, WO2009008992).

Scheme 2

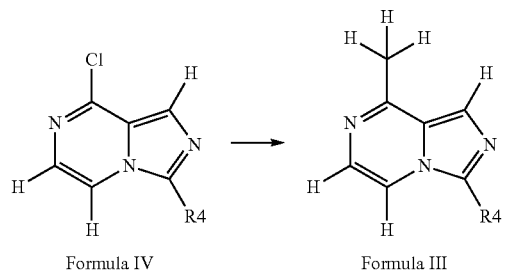

Formula IV          Formula III

Another method to prepare compounds of Formula III is from compounds of Formula V using cyclization conditions like heating with phosphorusoxychloride. Compounds of Formula V can be prepared from compounds of formula VI using a palladium mediated reaction to convert the chloro substituent into the methyl substituent as described before for the transformation of compounds of Formula IV into compounds of Formula III, as indicated in Scheme 3.

Scheme 3

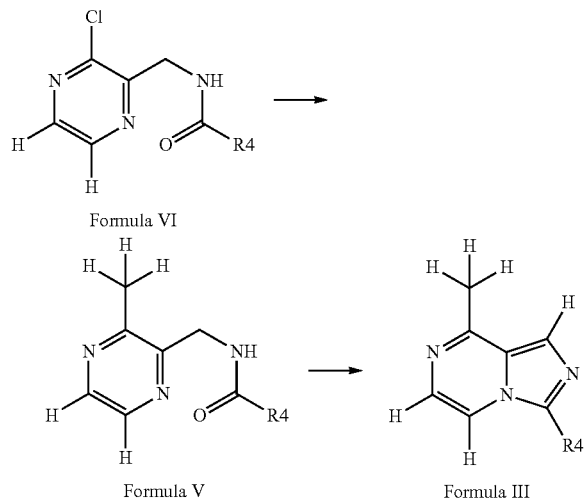

Formula VI

Formula V          Formula III

During the conversions involving compounds of Formula II-VI the R4 moiety can contain functionalities which are protected using a suitable protecting group, the R4 moiety can be modified, or R4 can undergo a combination of protection/deprotection and modification steps. Several protecting groups known in the art are described in "Protective Groups In Organic Synthesis" by Greene T. W. and Wuts P. G. M. (John Wiley & Sons, New York). An example of such synthetic strategy is the use of the benzyloxycarbonyl protecting group to protect an amine in R4 and after deprotection transform the resulting amine into an acetamide.

Scheme 4

Formula II

Formula VII

Formula I

Another method to prepare compounds of Formula I is from compounds of Formula VII using a amide formation reaction like treatment of compound VII with acid chlorides or carbamate formation reaction like treatment of compound VII with an chloroformate. Compounds of Formula VII can be prepared from compounds of Formula II using palladium-mediated cross-coupling reactions such as the Suzuki, Stille or Negishi reactions optionally combined with the use of protecting groups (Scheme 4).

An alternative way to prepare compounds of Formula VII is by reduction of the corresponding nitro compounds of Formula VIII (e.g. using zinc in acetic acid). Compounds of Formula VIII can be prepared from compounds of Formula IX by using palladium mediated reaction to convert the 8-chloro substituent into the 8-methyl substituent (Scheme 5). Suitable reagents are e.g bis(diphenylphosphino)ferrocene palladium (II) chloride complex with dichloromethane as palladium source and trimethylboroxine to provide the methyl group.

Scheme 5

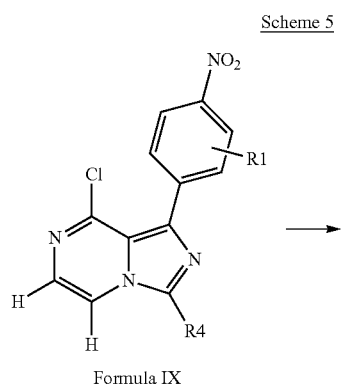

Formula IX

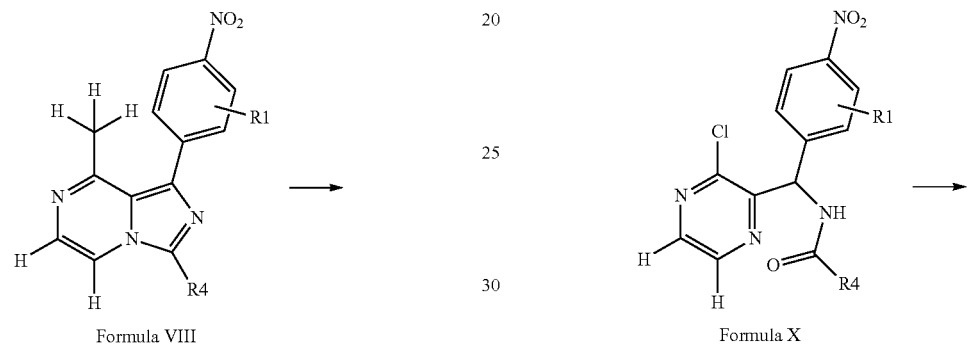

Formula VIII

Formula VII

Scheme 6

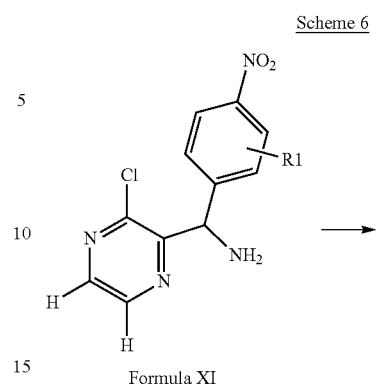

Formula XI

Formula X

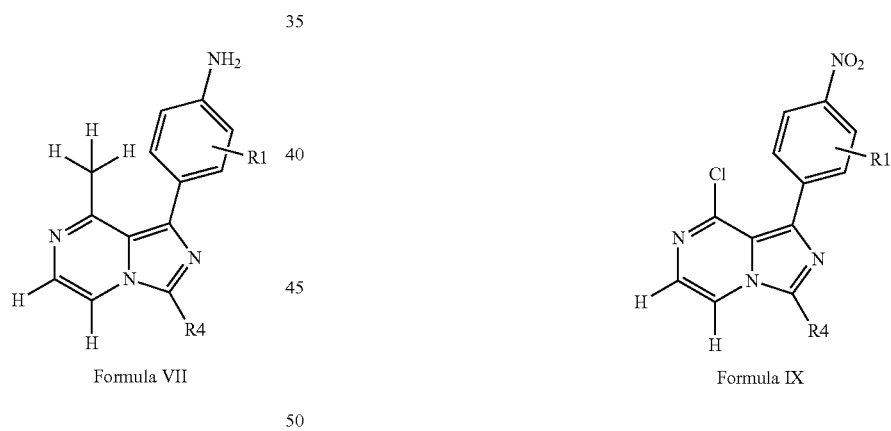

Formula IX

Compounds of Formula IX can be prepared from compounds of Formula X by a ring formation reaction using conditions like treatment with phosphorusoxychloride. The compounds of Formula X can be obtained from compounds of Formula XI using an amide formation reaction like treatment of compound XI with acid chlorides or with acid and peptide coupling reagent like 2-(1H-benzotriazol-1-yl)-1,1,3,3-tetramethyluronium tetrafluoroborate (Scheme 6).

Again, during the synthesis involving compounds of Formula VII-XI the moiety R4 can contain protective groups or undergo modifications.

Compounds of Formula XI can be prepared from compounds of Formula XII by using synthetic strategies well-known in the art for the transformation of an alcohol in an amine (Scheme 7). One strategy is transformation of the alcohol into chloride using thionyl chloride. This chloride is then transformed into an amine using ammonia. The chloride can also be transformed into an azide using sodium azide and this azide is then reduced e.g. by the Staudinger reaction using triphenylphosphine. Compounds of Formula XII can be prepared from aldehydes of Formula XIII and 2-chloropyrazine by deprotonation of the latter compound using a strong base such as lithium tetramethylpiperidine according to conditions described in literature (e.g. Bioorg. Med. Chem. 16, 1359, (2008)).

Scheme 7

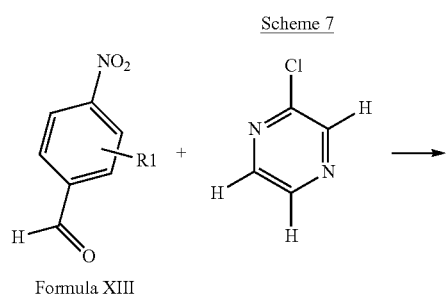

Formula XIII

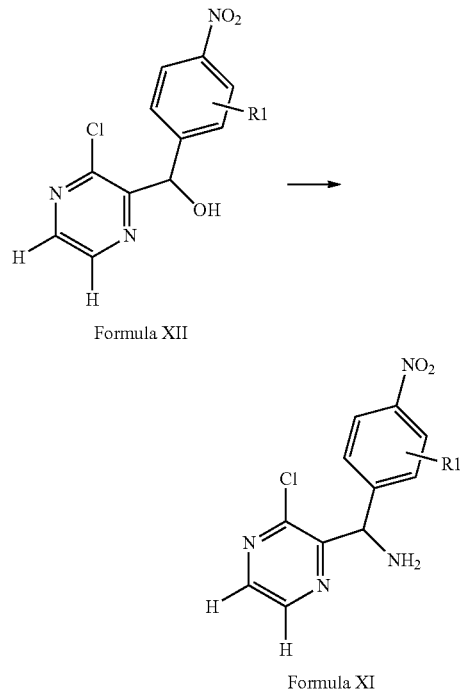

Formula XII

Formula XI

During all these conversions the R1 moiety may be unchanged, may contain a protective group or may undergo a modification. An example of the latter is transformation of a methoxy into a hydroxy group.

The invention is illustrated by the following examples.

EXAMPLES

General Comments

The structures of the examples were converted into a name using ChemDraw version 9.0.7. Cis and trans descriptors were used to describe the relationship between two ligands attached to separate atoms that are connected by a bouble bond or are contained in a ring (Pure and Appled Chemistry 68, 2193-2222 (1996)).

$^1$H NMR spectra were recorded on a Bruker spectrometer (400 MHz) with deuterochloroform as the solvent unless stated otherwise. Chemical shifts are reported as δ values (parts per million) relative to tetramethylsilane as an internal standard.

MS: Electro Spray spectra were recorded on the Applied Biosystems API-165 single quad MS in alternating positive and negative ion mode using Flow Injection. The mass range was 120-2000 Da and scanned with a step rate of 0.2 Da. and the capillary voltage was set to 5000 V. N2-gas was used for nebulasation.

LC-MS spectrometer (Waters) Detector: PDA (200-320 nm), Mass detector: ZQ

Eluens: A: acetonitrile with 0.05% trifluoroacetic acid, B: acetronitrile/water=1/9 (v/v) with 0.05% trifluoroacetic acid

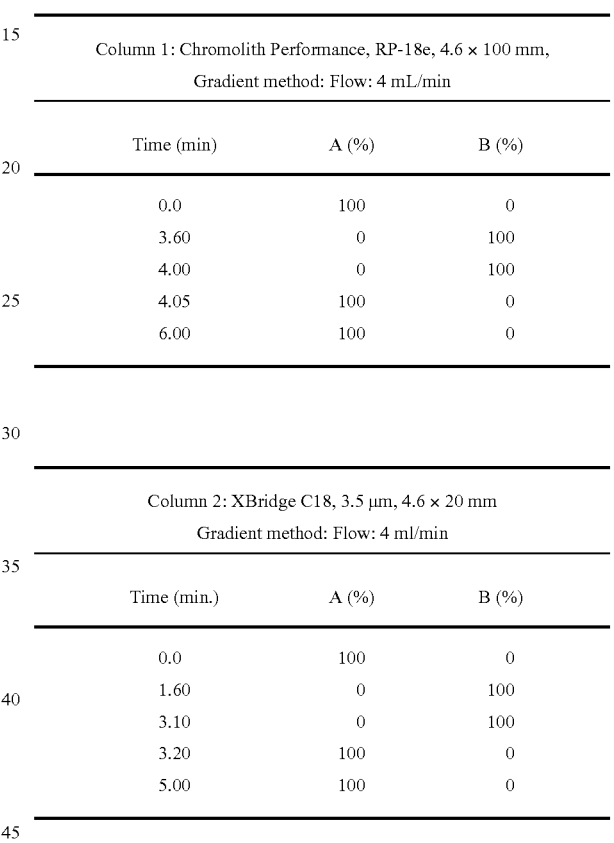

Column 1: Chromolith Performance, RP-18e, 4.6 × 100 mm, Gradient method: Flow: 4 mL/min

| Time (min) | A (%) | B (%) |
|---|---|---|
| 0.0 | 100 | 0 |
| 3.60 | 0 | 100 |
| 4.00 | 0 | 100 |
| 4.05 | 100 | 0 |
| 6.00 | 100 | 0 |

Column 2: XBridge C18, 3.5 μm, 4.6 × 20 mm Gradient method: Flow: 4 ml/min

| Time (min.) | A (%) | B (%) |
|---|---|---|
| 0.0 | 100 | 0 |
| 1.60 | 0 | 100 |
| 3.10 | 0 | 100 |
| 3.20 | 100 | 0 |
| 5.00 | 100 | 0 |

UPLC: Water acquity HPLC system; Column: BEH C18 1.7 μm, 2.1×100 mm, Detector: PDA (200-320 nm), Mass detector: SQD Eluens: A: acetonitrile with 0.035% trifluoroacetic acid, B: acetronitrile/water=1/9 (v/v) with 0.035% trifluoroacetic acid

| | Method 60_100 Flow: 0.75 mL/min | | Method 40_80 Flow: 0.65 mL/min | | Method 0_60 Flow: 0.60 mL/min | |
|---|---|---|---|---|---|---|
| Time (min) | A (%) | B (%) | A (%) | B (%) | A (%) | B (%) |
| 0.0 | 40 | 60 | 60 | 40 | 100 | 0 |
| 3.00 | 0 | 100 | 20 | 80 | 40 | 60 |
| 3.20 | 0 | 100 | 0 | 100 | 0 | 100 |
| 3.69 | 0 | 100 | 0 | 100 | 0 | 100 |
| 3.70 | 40 | 60 | 60 | 40 | 100 | 0 |

Example 1

N-[2-Methoxy-4-[8-methyl-3-(tetrahydro-2H-pyran-4-yl)imidazo[1,5-a]pyrazine]phenyl]-1-methyl-1H-indole-2-carboxamide

1a. Synthesis of N-[(3-chloro-2-pyrazinyl)methyl]-(tetrahydro-2H-pyrane)-4-carboxamide

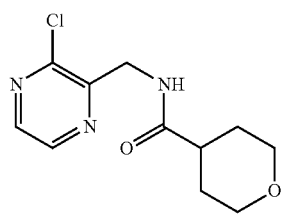

2-Aminomethyl-3-chloropyrazine hydrochloride (content 70%; 133 mmol, 17.36 g) was dissolved in dichloromethane (200 mL) and N,N-diisopropylethylamine (445 mmol, 77 mL) and 2-(1H-benzotriazol-1-yl)-1,1,3,3-tetramethyluronium tetrafluoroborate (133 mmol, 42.8 g) were added (temperature rise was observed). After stirring the reaction mixture for 15 minutes under a nitrogen atmosphere at room temperature tetrahydro-2H-pyran-4-carboxylic acid (89 mmol, 27.5 g) was added and the reaction mixture was stirred overnight at room temperature. Then water (600 mL) was added to the reaction mixture. The emulsions formed was filtered over dicalite and washed with dichloromethane and water. The layers were separated, the organic layer was washed with brine and the aqueous layer was extracted twice with dichloromethane. The organic layers were combined and concentrated to dryness. The residue was dissolved in ethyl acetate and toluene was added. The ethyl acetate was evaporated and the crystals were collected to yield 9.25 g of small grey needles of the title compound. Crystallization of the mother liquor afforded a second crop of 2.04 g of the title compound.

$^1$H NMR: δ 1.82-1.93 (m, 4H), 2.48-2.57 (m, 1H), 3.42-3.52 (m, 2H), 4.02-4.09 (m, 2H), 4.70 (d, J=4 Hz, 2H), 7.02 (brs, 1H), 8.35 (d, J=2 Hz, 1H), 8.47 (d, J=2 Hz, 1H).

1b. Synthesis of 8-chloro-3-(tetrahydro-2H-pyran-4-yl)imidazo[1,5-a]pyrazine

To N-[(3-chloro-2-pyrazinyl)methyl]-(tetrahydro-2H-pyrane)-4-carboxamide (43.8 mmol, 11.2 g) in acetonitrile (280 mL) at 55° C. under a nitrogen atmosphere were added N,N-dimethylformamide (25.7 mmol, 2 mL) and phosphorus oxychloride (219 mmol, 20.4 mL) (a small temperature rise to 60° C. was observed). After three hours the reaction mixture was concentrated to dryness and coevaporated twice with toluene. The residue was dissolved in acetonitrile and added dropwise to anhydrous 7N ammonia in methanol (140 mL). This mixture was concentrated again and dichloromethane and an aqueous sodium hydrogencarbonate solution (sat) were added. Layers were separated and the aqueous layer was extracted twice with dichloromethane. Organic layers were combined and concentrated to dryness giving 10.48 g of the title compound. From this crude product 2.2 gram was purified by column chromatography (silica gel, ethyl acetate) yielding 1.78 gram of 8-chloro-3-(tetrahydro-2H-pyran-4-yl)imidazo[1,5-a]pyrazine.

$^1$H NMR: δ 1.87-1.96 (m, 2H), 2.10-2.22 (m, 2H), 3.20-3.29 (m, 1H), 3.58-3.65 (m, 2H), 4.12-4.18 (m, 2H), 7.35 (d, J=5 Hz, 1H), 7.65 (d, J=5 Hz, 1H), 7.82 (s, 1H).

1c. Synthesis of 8-methyl-3-(tetrahydro-2H-pyran-4-yl)imidazo[1,5-a]pyrazine

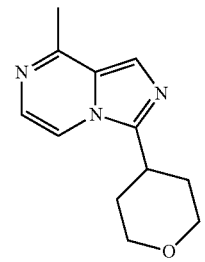 [SMILES: Cc1nccn2c(C3CCOCC3)ncc12]

Through a suspension of 8-chloro-3-(tetrahydro-2H-pyran-4-yl)imidazo[1,5-a]pyrazine (2.23 mmol, 531 mg) and potassium carbonate (3.35 mmol, 463 mg) in dioxane (1.5 mL) was bubbled nitrogen for 5 minutes and then trimethylboroxine (4.47 mmol, 1.249 mL, 50 wt % solution in tetrahydrofuran) and 1,1'-bis(diphenylphosphino)ferrocene palladium (II) chloride complex with dichloromethane (0.223 mmol, 181 mg) were added. After heating the reaction at 100° C. for one hour the reaction mixture was filtered and concentrated in vacuo. Dichloromethane and water were added, the organic layer separated, dried (sodium sulfate) and concentrated in vacuo to yield 374 mg 8-methyl-3-(tetrahydro-2H-pyran-4-yl)imidazo[1,5-a]pyrazine.

$^1$H NMR: δ 1.89-1.97 (m, 2H), 2.10-2.21 (m, 2H), 2.69 (s, 3H), 3.20-3.28 (m, 1H), 3.58-3.66 (m, 2H), 4.11-4.17 (m, 2H), 7.43 (d, J=5 Hz, 1H), 7.56 (d, J=5 Hz, 1H), 7.71 (s, 1H).

1d. Synthesis of 1-bromo-8-methyl-3-(tetrahydro-2H-pyran-4-yl)imidazo[1,5-a]pyrazine

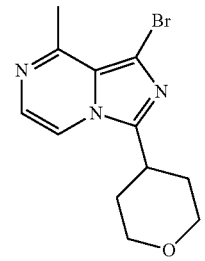 [SMILES: Cc1nccn2c(C3CCOCC3)nc(Br)c12]

To a solution of 8-methyl-3-(tetrahydro-2H-pyran-4-yl)imidazo[1,5-a]pyrazine (0.888 mmol, 193 mg) in dichloromethane (10 mL) was added N-bromosuccinimide (0.888 mmol, 158 mg) and the reaction mixture was heated at 50° C. (bath temperature) for 15 min. Dichloromethane and water were added, the organic layer separated, washed with an aqueous sodium hydrogencarbonate solution, dried (sodium sulfate) and concentrated in vacuo to afford 246 mg of 1-bromo-8-methyl-3-(tetrahydro-2H-pyran-4-yl)imidazo[1,5-a]pyrazine.

$^1$H NMR: δ 1.83-1.91 (m, 2H), 2.08-2.20 (m, 2H), 2.90 (s, 3H), 3.13-3.22 (m, 1H), 3.54-3.62 (m, 2H), 4.10-4.15 (m, 2H), 7.40 (d, J=5 Hz, 1H), 7.54 (d, J=5 Hz, 1H).

1e. Synthesis of N-(2-methoxy-4-(4,4,5,5-tetramethyl-1,3,2-dioxaborolan-2-yl)phenyl)-1-methyl-1H-indole-2-carboxamide

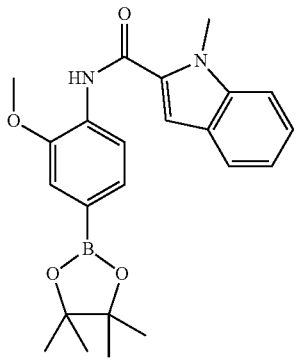 [SMILES: COc1cc(B2OC(C)(C)C(C)(C)O2)ccc1NC(=O)c1cc2ccccc2n1C]

1-Methylindole-2-carboxylic acid (35.4 mmol, 6.2 g) was suspended in dichloromethane (300 mL), N,N-dimethylformamide (0.389 mmol, 0.030 mL) was added and the mixture was cooled to 0° C. Then, oxalyl chloride (38.9 mmol, 3.70 mL) was added dropwise and the suspension was stirred for 6 hours. Then the reaction mixture was evaporated to dryness to afford 1-methyl-1H-indole-2-carbonyl chloride (6.9 g).

To a solution of 2-methoxy-4-(4,4,5,5-tetramethyl-1,3,2-dioxaborolan-2-yl)aniline (4.01 mmol, 1 g) and 4-dimethylaminopyridine (0.401 mmol, 0.049 g) in dichloromethane (5 ml) and pyridine (5 ml) was added 1-methyl-1H-indole-2-carbonyl chloride (5.22 mmol, 1.010 g) and this solution was stirred at room temperature for four days. The reaction mixture was concentrated and coevaporated with toluene. To the residue dichloromethane and water were added. The organic layer was separated, dried (sodium sulfate) and concentrated in vacuo. Purification using flash chromatography (silica gel, dichloromethane) yielded N-(2-methoxy-4-(4,4,5,5-tetramethyl-1,3,2-dioxaborolan-2-yl)phenyl)-1-methyl-1H-indole-2-carboxamide (1.5 g).

LC-MS column 1: Rt 5.05 min (M+H)$^+$=407.

1f. Synthesis of N-[2-methoxy-4-[8-methyl-3-(tetrahydro-2H-pyran-4-yl)imidazo[1,5-a]pyrazine]phenyl]-1-methyl-1H-indole-2-carboxamide

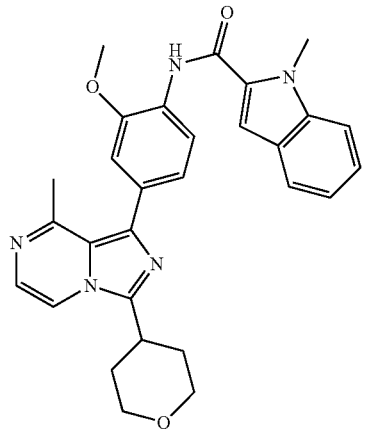 [SMILES: COc1cc(-c2nc(C3CCOCC3)n3ccnc(C)c23)ccc1NC(=O)c1cc2ccccc2n1C]

To a solution of 1-bromo-8-methyl-3-(tetrahydro-2H-pyran-4-yl)imidazo[1,5-a]pyrazine (0.101 mmol, 30 mg) and N-[2-methoxy-4-(4,4,5,5-tetramethyl-1,3,2-dioxaborolan-2-yl)phenyl]-1-methyl-1H-indole-2-carboxamide (0.101 mmol, 41.2 mg) in dioxane (1 mL) was added 2M potassium carbonate (aq) (0.406 mmol, 203 μl) and 1,1'-bis(diphenylphosphino)ferrocene palladium (II) chloride complex with dichloromethane (0.020 mmol, 16.38 mg). The reaction was heated in the micro wave at 140° C. for 12 minutes. Dichloromethane and water were added, the organic layer separated, dried (sodium sulfate) and concentrated. Purification using column chromatography (silica gel; gradient heptanes/ethyl acetate 3/10 to ethyl acetate) yielded 30 mg of the title compound.

$^1$H NMR: δ 1.92-1.99 (m, 2H), 2.17-2.31 (m, 2H), 2.50 (s, 3H), 3.23-3.32 (m, 1H), 3.59-3.66 (m, 2H), 4.01 (s, 3H), 4.13-4.19 (m, 2H), 4.15 (s, 3H), 7.08 (s, 1H), 7.17-7.21 (m, 3H), 7.34-7.44 (m, 3H), 7.58 (d, J=5 Hz, 1H), 7.71 (d, J=8 Hz, 1H), 8.57 (d, J=9 Hz, 1H), 8.69 (brs, 1H).

UPLC: Method 40_80: Rt=0.96 min, (M+H)$^+$=496

Example 2

N-(4-(3-((Trans)-4-(4-acetylpiperazin-1-yl)cyclohexyl)-8-methylimidazo[1,5-a]pyrazin-1-yl)-2-methoxyphenyl)-4-methoxy-1-methyl-1H-indole-2-carboxamide 2a. Synthesis of N-((3-chloropyrazin-2-yl)methyl)-4-oxocyclohexanecarboxamide

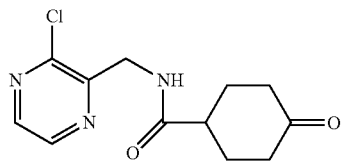 [SMILES: O=C1CCC(C(=O)NCc2nccnc2Cl)CC1]

To a stirred suspension of 2-aminomethyl-3-chloropyrazine hydrochloride (3.89 mmol, 0.70 g) in dichloromethane (25 mL) at room temperature was subsequently added triethylamine (7.78 mmol, 1.08 mL), O-(7-azabenzotriazol-1-yl)-1,1,3,3-tetramethyluroniumhexafluorophosphate (4.67 mmol, 1.77 g) and finally 4-oxocyclohexanecarboxylate (3.89 mmol, 553 mg). After stirring for 16 hours, the suspension filtered over decalite. The decalite was washed with dichloromethane. The filtrate was washed with water, dried (sodium sulfate) and concentrated in vacuo. The resulting crude product was purified by column chromatography on silica gel (ethyl acetate). The product was dissolved in dichloromethane, washed with water and concentrated in vacuo to afford 1.09 g of the title compound.

$^1$H NMR: δ 2.03-2.14 (m, 2H), 2.22-2.30 (m, 2H), 2.35-2.45 (m, 2H), 2.52-2.60 (m, 2H), 2.68-2.78 (m, 1H), 4.73 (d, J=4 Hz, 2H), 6.93 (brs, 1H), 8.34-8.37 (m, 1H), 8.46 (d, J=2 Hz, 1H).

2b. Synthesis of benzyl 4-[4-[(3-chloropyrazin-2-yl)methylcarbamoyl]cyclohexyl]piperazine-1-carboxylate

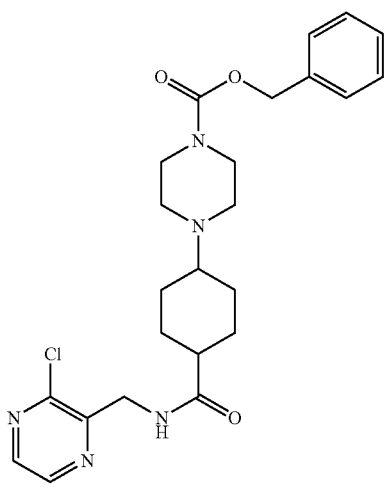 [SMILES: O=C(NCc1nccnc1Cl)C1CCC(N2CCN(C(=O)OCc3ccccc3)CC2)CC1]

N-((3-chloropyrazin-2-yl)methyl)-4-oxocyclohexanecarboxamide (3.7 mmol, 1 g) was dissolved in dichloromethane (10 mL) and acetic acid (0.1 mL) was added. To this solution benzyl 1-piperazinecarboxylate (11.2 mmol, 2.16 mL) and sodium cyanoborohydride (7.47 mmol, 0.47 g) were added subsequently. The mixture was stirred overnight at room temperature. Reaction was quenched with an aqueous sodium hydrogencarbonate solution and extracted twice with dichloromethane. The combined organic layers were dried over phase separation filter, concentrated under reduced pressure and purified using column chromatography (silica gel; dichloromethane/methanol) to yield 2.35 g of the title compound as a mixture of cis and trans isomers which was used in the next step without further purification.

LC-MS column 1: Rt 2.78 min (M+H)$^+$=472, Rt 2.85 min (M+H)$^+$=472

2c. Synthesis of benzyl trans-4-(4-(8-chloroimidazo[1,5-a]pyrazin-3-yl)cyclohexyl)piperazine-1-carboxylate

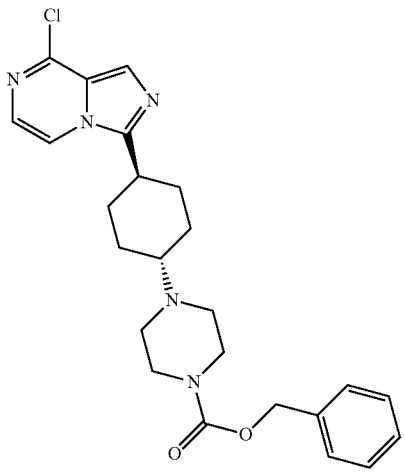 [SMILES: O=C(OCc1ccccc1)N1CCN([C@H]2CC[C@H](c3ncc4c(Cl)nccn43)CC2)CC1]

Benzyl 4-[4-[(3-chloropyrazin-2-yl)methylcarbamoyl]cyclohexyl]piperazine-1-carboxylate (4.03 mmol, 1.9 g) was used to give after reaction at 70° C. for one hour using the procedure described example 1 step 1b the crude product. Purification of this crude product using column chromatography (silica gel; gradient toluene/acetone (85/15 containing 0.1% triethylamine to 1/1, followed by dichloromethane/methanol 4/1) gave 0.14 g of the cis isomer and 0.30 g of the title compound.

$^1$H NMR: δ 1.38-1.54 (m, 2H), 1.79-1.91 (m, 2H), 2.04-2.17 (m, 4H), 2.43-2.64 (m, 5H), 2.83-2.95 (m, 1H), 3.50-3.58 (m, 4H), 5.14 (s, 2H), 7.14-7.39 (m, 6H), 7.60 (d, J=4 Hz, 1H), 7.79 (s, 1H).

2d. Synthesis of benzyl trans-4-(4-(8-methylimidazo[1,5-a]pyrazin-3-yl)cyclohexyl)piperazine-1-carboxylate

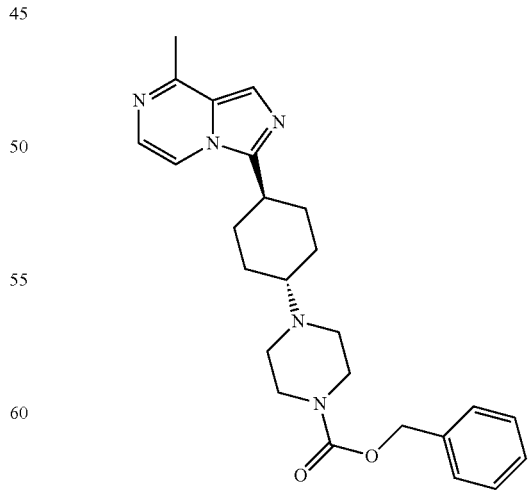

To benzyl trans-4-(4-(8-chloroimidazo[1,5-a]pyrazin-3-yl)cyclohexyl)piperazine-1-carboxylate (0.66 mmol, 300 mg) and potassium carbonate (0.991 mmol, 137 mg) in dioxane (2 ml). was added trimethylboroxine (1.982 mmol, 0.559 ml, 50 wt % solution in tetrahydrofuran) and nitrogen was bubbled through the suspension for a couple of minutes. Then 1,1'-bis(diphenylphosphino)ferrocene palladium (II) chloride, complex with dichloromethane (0.066 mmol, 53.4 mg) was added and the reaction was stirred at 100° C. After two hours the reaction was cooled, filtered through decalite and rinsed with ethyl acetate and the filtrate concentrated under reduced pressure. The residue was purified using column chromatography (silica gel; dichloromethane/methanol 9/1) to give 224 mg of benzyl trans-4-(4-(8-methylimidazo[1,5-a]pyrazin-3-yl)cyclohexyl)piperazine-1-carboxylate.

$^1$H NMR: δ 1.39-1.52 (m, 2H), 1.77-1.92 (m, 2H), 2.03-2.17 (m, 4H), 2.43-2.65 (m, 5H), 2.67 (s, 3H), 2.85-2.94 (m, 1H), 3.51-3.57 (m, 4H), 5.15 (s, 2H), 7.30-7.39 (m, 5H), 7.42 (d, J=4 Hz, 1H), 7.53 (d, J=4 Hz, 1H), 7.68 (s, 1H).

2e. Synthesis of 1-(4-((trans)-4-(8-methylimidazo[1,5-a]pyrazin-3-yl)cyclohexyl)piperazin-1-yl)ethanone

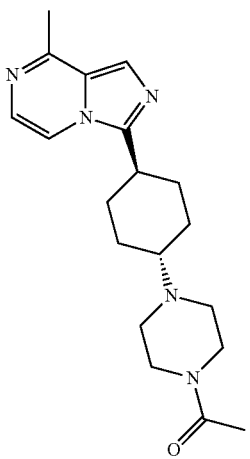 [SMILES: CC(=O)N1CCN([C@H]2CC[C@H](c3ncc4c(C)nccn43)CC2)CC1]

Benzyl trans-4-(4-(8-chloroimidazo[1,5-a]pyrazin-3-yl)cyclohexyl)piperazine-1-carboxylate (0.507 mmol, 0.22 g) was dissolved in 37% hydrochloric acid (23.70 mmol, 2 mL,) and after stirring for 16 hours at room temperature water (4 mL) was added. This mixture was washed with diethyl ether (5 mL), the aqueous fraction was concentrated under reduced pressure and coevaporated with ethanol and dichloromethane to give 190 mg of amine.

To this amine was added dichloromethane (2 mL) and the resulting suspension was stirred and cooled to 0° C. Triethylamine (5.66 mmol, 0.79 mL) was added followed by acetyl chloride (0.849 mmol, 0.061 ml). The reaction was monitored by LCMS (product rt:0.49 min). Upon complete conversion the reaction was quenched by adding a saturated aqueous sodium hydrogencarbonate solution and extracted twice with dichloromethane. The organic layers were combined, dried over a phase separation filter and concentrated under reduced pressure. Purification using chromatography on silica gel (gradient dichloromethane (containing 1% triethylamine)/methanol 100/0 to 85/15) gave 144 mg of the title compound.

$^1$H NMR: δ 1.40-1.57 (m, 2H), 1.79-1.92 (m, 2H), 2.05-2.18 (m, 4H), 2.11 (s, 3H), 2.48-2.72 (m, 5H), 2.77 (s, 3H), 2.86-2.96 (m, 1H), 3.47-3.71 (m, 4H), 7.42 (d, J=4 Hz, 1H), 7.54 (d, J=4 Hz, 1H), 7.68 (s, 1H).

2f. Synthesis of 1-(4-((trans)-4-(1-bromo-8-methylimidazo[1,5-a]pyrazin-3-yl)cyclohexyl)piperazin-1-yl)ethanone

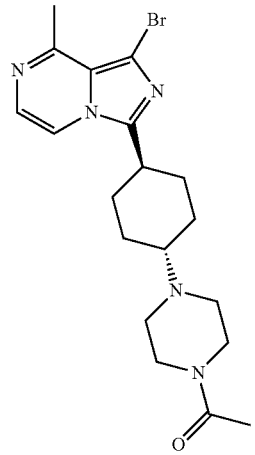 [SMILES: CC(=O)N1CCN([C@H]2CC[C@H](c3nc(Br)c4c(C)nccn43)CC2)CC1]

To a stirred solution of 1-(4-((trans)-4-(8-methylimidazo[1,5-a]pyrazin-3-yl)cyclohexyl)piperazin-1-yl)ethanone (0.422 mmol, 144 mg) in N,N-dimethylformamide (2 mL) was added N-bromosuccinimide (0.422 mmol, 75 mg). After two hours at 60° C. the reaction was quenched with a saturated aqueous sodium hydrogencarbonate solution and extracted twice with ethyl acetate. The organic extracts were washed twice with water and brine, dried (sodium sulfate) and concentrated under reduced pressure. The crude product was purified with column chromatography on silica gel (dichloromethane/methanol) to afford 176 mg of the title compound.

$^1$H NMR: δ 1.40-1.57 (m, 2H), 1.78-1.92 (m, 2H), 2.04-2.13 (m, 4H), 2.11 (s, 3H), 2.44-2.72 (m, 5H), 2.81-2.90 (m, 1H), 2.88 (s, 3H), 3.46-3.71 (m, 4H), 7.38 (d, J=4 Hz, 1H), 7.51 (d, J=4 Hz, 1H).

2g. Synthesis of 4-methoxy-N-(2-methoxy-4-(4,4,5,5-tetramethyl-1,3,2-dioxaborolan-2-yl)phenyl)-1-methyl-1H-indole-2-carboxamide

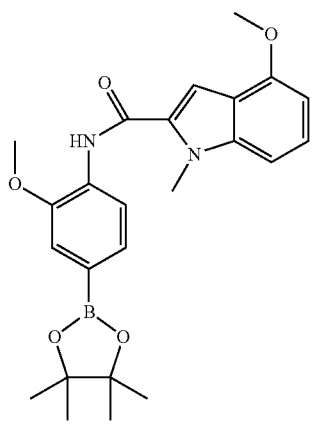 [SMILES: COc1cc(B2OC(C)(C)C(C)(C)O2)ccc1NC(=O)c1cc2c(OC)cccc2n1C]

To 4-methoxy-1-methyl-1H-indole-2-carboxylic acid (24.4 mmol, 5 g) and oxalyl chloride (24.4 mmol, 2.3 mL) in dichloromethane (60 mL) N,N-dimethylformamide (1.22 mmol, 95 µL) was added and the mixture was stirred at room temperature until it formed a clear solution (approximately 4 hours). The mixture was concentrated in vacuo. The residue, 4-methoxy-1-methyl-1H-indole-2-carbonyl chloride, was added to a solution of 4-amino-3-methoxyphenylboronic acid pinacol ester (24.2 mmol, 6.03 g) and 4-dimethylaminopyridine (2.419 mmol, 0.296 g) in pyridine (30 mL) and dichloromethane (30 mL). After stirring at room temperature overnight the reaction mixture was diluted with dichloromethane and 2N hydrochloric acid. The organic layer was separated and the aqueous layer extracted with dichloromethane. The combined organic layers were dried (sodium sulfate) and concentrated in vacuo to yield 10.55 g of the title compound.

$^1$H NMR: δ 1.35 (s, 12H) 3.99 (s, 6H) 4.10 (s, 3H), 6.55 (d, J=9 Hz, 1H), 7.02 (d, J=9 Hz, 1H), 7.02 (s, 1H), 7.24-7.51 (m, 3H), 8.51 (d, J=9 Hz, 1H), 8.73 (brs, 1H).

2h. Synthesis of N-(4-(3-((trans)-4-(4-acetylpiperazin-1-yl)cyclohexyl)-8-methylimidazo[1,5-a]pyrazin-1-yl)-2-methoxyphenyl)-4-methoxy-1-methyl-1H-indole-2-carboxamide

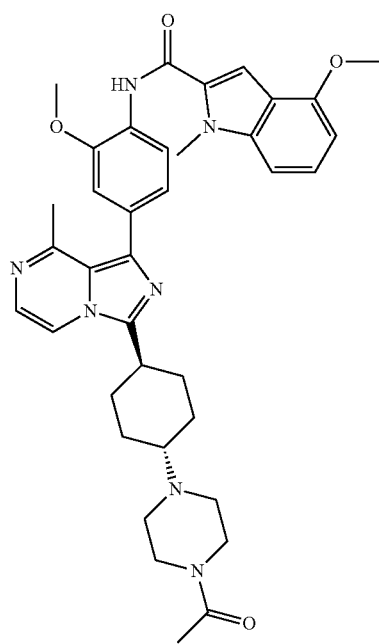 [SMILES: COc1cc(-c2nc([C@H]3CC[C@H](N4CCN(C(C)=O)CC4)CC3)n3ccnc(C)c23)ccc1NC(=O)c1cc2c(OC)cccc2n1C]

Using the procedure described in example 1 step 1f 1-(4-((trans)-4-(1-bromo-8-methylimidazo[1,5-a]pyrazin-3-yl)cyclohexyl)piperazin-1-yl)ethanone (0.059 mmol, 25 mg) and 4-methoxy-N-(2-methoxy-4-(4,4,5,5-tetramethyl-1,3,2-dioxaborolan-2-yl)phenyl)-1-methyl-1H-indole-2-carboxamide (0.059 mmol, 26 mg) gave after purification on prep-HPLC (column Luna C18(2); gradient acetonitrile/water with constant 0.003M trifluoroacetic acid) 11 mg of the title compound.

$^1$H NMR: δ 1.35-2.15 (m, 8H), 2.03 (s, 3H), 2.41 (s, 3H), 2.42-2.58 (m, 5H), 2.83-2.93 (m, 1H), 3.40-3.59 (m, 4H), 3.93 (s, 3H), 3.94 (s, 3H), 4.06 (s, 3H), 6.50 (d, J=9 Hz, 1H), 6.97 (d, J=9 Hz, 1H), 7.08 (s, 1H), 7.09-7.23 (m, 3H), 7.36 (d, J=5 Hz, 1H), 7.54 (d, J=5 Hz, 1H), 8.49 (d, J=9 Hz, 1H), 8.61 (brs, 1H).

UPLC: Method 0_60: Rt=2.25 min, (M+H)$^+$=650

Example 3

(S)-pentan-2-yl 4-(3-(azetidin-1-yl)-8-methylimidazo[1,5-a]pyrazin-1-yl)-2-methoxyphenylcarbamate 3a. Synthesis of N-((3-chloropyrazin-2-yl)methyl)azetidine-1-carboxamide

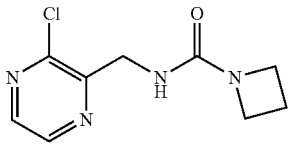 [SMILES: O=C(NCc1nccnc1Cl)N1CCC1]

A stirred solution of trichloromethyl chloroformate (105 mmol, 12.68 mL) in tetrahydrofuran (100 mL) was cooled to 0° C. and a solution of azetidine (88 mmol, 5 g) and N,N-diisopropylethylamine (193 mmol, 33.6 mL) in tetrahydrofuran (100 mL) was added slowly in 25 minutes. After stirring at 0° C. for one hour the solids were removed by filtration and the filtrate was concentrated at 50 mbar (50° C. bath temperature). The residue was added to a solution of 2-aminomethyl-3-chloropyrazine hydrochloride (66.7 mmol, 12 g) and triethylamine (200 mmol, 27.9 mL) in dichloromethane (200 mL) and the reaction mixture was stirred for three hours. The solids were removed by filtration and the filtrate was concentrated in vacuo. Purification using column chromatography (silica gel; gradient dichloromethane/methanol 100:0 to 95:5) yielded 9.5 g of N-((3-chloropyrazin-2-yl)methyl)azetidine-1-carboxamide.

$^1$H NMR: δ 2.30 (quintet, J=9 Hz, 2H), 4.06 (t, J=9 Hz, 4H), 4.66 (d, J=4 Hz, 2H), 5.3 (brs, 1H), 8.29 (d, J=2 Hz, 1H), 8.45 (d, J=2 Hz, 1H).

3b. Synthesis of 3-(azetidin-1-yl)-8-chloroimidazo[1,5-a]pyrazine

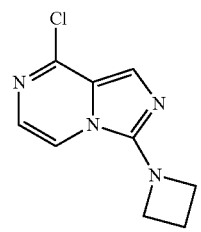 [SMILES: Clc1nccn2c(N3CCC3)ncc12]

To a stirred solution of N-((3-chloropyrazin-2-yl)methyl)azetidine-1-carboxamide (41.9 mmol, 9.5 g) in acetonitrile (130 mL) were added N,N-dimethylformamide (7.12 mmol, 0.55 mL), pyridine (419 mmol, 33.8 mL) and finally phosphorous oxychloride (210 mmol, 19.5 mL). After 7 minutes the reaction mixture was quenched by adding it to a cooled (0° C.) mixture of anhydrous 7N ammonia in methanol (150 mL) and acetonitrile (200 mL) and subsequently concentrated in vacuo. The residue was dissolved in dichloromethane, water (150 mL) and saturated aqueous sodium hydrogencarbonate (150 mL) were added and this mixture extracted six times with dichloromethane (100 mL). The combined organic extracts were dried (sodium sulfate) and concentrated in vacuo. Purification by column chromatography (silica gel; dichloromethane/methanol) gave 4.5 g of the title compound.

$^1$H NMR: δ 2.49 (quintet, J=9 Hz, 2H), 4.23 (t, J=9 Hz, 4H), 7.07 (d, J=5 Hz, 1H), 7.27 (d, J=5 Hz, 1H), 7.53 (s, 1H).

3c. Synthesis of (S)-pentan-2-yl 2-methoxy-4-(4,4,5,5-tetramethyl-1,3,2-dioxaborolan-2-yl)phenylcarbamate

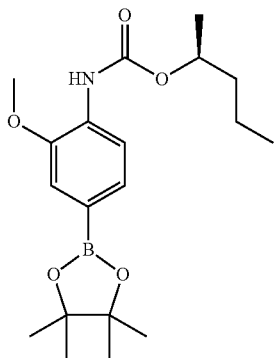 [SMILES: CCC[C@H](C)OC(=O)Nc1ccc(B2OC(C)(C)C(C)(C)O2)cc1OC]

To 4-amino-3-methoxyphenylboronic acid pinacol ester (24.08 mmol, 6 g) and charcoal (0.29 g) in ethyl acetate (50 ml), was added trichloromethyl chloroformate (48.2 mmol, 5.81 mL) and the mixture was stirred at 70° C. for two hours. After cooling to room temperature the solids were removed by filtration and the filtrate concentrated in vacuo to give 6.7 g of 2-(4-isocyanato-3-methoxyphenyl)-4,4,5,5-tetramethyl-1,3,2-dioxaborolane.

To a solution of (S)-(+)-2-pentanol in dichloromethane were added molsieves, 2-(4-isocyanato-3-methoxyphenyl)-4,4,5,5-tetramethyl-1,3,2-dioxaborolane (9.09 mmol, 2.5 g) and N,N-dimethylpyridin-4-amine (1.82 mmol, 0.22 g) and the reaction mixture was stirred at 40° C. overnight. The solids were removed by filtration, the filtrate concentrated in vacuo and the crude product was purified by column chromatography (silica gel; heptanes/ethyl acetate 1/1) to give 2.6 g of the title compound.

$^1$H NMR: δ 0.93 (t, J=8 Hz, 3H), 1.25-1.70 (m, 4H), 1.28 (d, J=7 Hz, 3H), 1.35 (s, 12H), 3.91 (s, 3H), 4.88-4.97 (m, 1H), 7.24-7.26 (m, 1H), 7.32 (brs, 1H), 7.42-7.46 (m, 1H), 8.10-8.15 (m, 1H).

3d. Synthesis of (S)-pentan-2-yl 4-(3-(azetidin-1-yl)-8-methylimidazo[1,5-a]pyrazin-1-yl)-2-methoxyphenylcarbamate

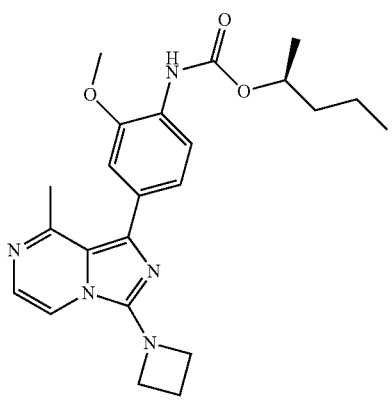 [SMILES: CCC[C@H](C)OC(=O)Nc1ccc(-c2nc(N3CCC3)n3ccnc(C)c23)cc1OC]

From 3-(azetidin-1-yl)-8-chloroimidazo[1,5-a]pyrazine (0.16 mmol, 33 mg) 11 mg of the title compound was pre- pared using the procedure described in example 2 step 2d and example 1 step 1d and example 2 step 2g (using (S)-pentan-2-yl 2-methoxy-4-(4,4,5,5-tetramethyl-1,3,2-dioxaborolan-2-yl)phenylcarbamate in this last step).

$^1$H NMR: δ 0.94 (t, J=8 Hz, 3H), 1.25-1.72 (m, 4H), 1.30 (d, J=7 Hz, 3H), 2.38 (s, 3H), 2.48 (quintet, J=9 Hz, 2H), 3.93 (s, 3H), 4.24 (t, J=9 Hz, 4H), 4.90-4.99 (m, 1H), 7.07-7.31 (m, 5H), 8.13-8.20 (m, 1H).

UPLC: Method 40_80: Rt=1.15 min, (M+H)$^+$=424

Example 4

(S)-pentan-2-yl 4-(3-((R)-1-(2-(dimethylamino)acetyl)pyrrolidin-3-yl)-8-methylimidazo[1,5-a]pyrazin-1-yl)-2-methoxyphenylcarbamate

4a. Synthesis of (R)-benzyl 3-(1-bromo-8-methylimidazo[1,5-a]pyrazin-3-yl)pyrrolidine-1-carboxylate

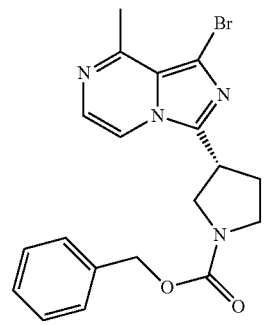 [SMILES: Cc1nccn2c([C@@H]3CCN(C(=O)OCc4ccccc4)C3)nc(Br)c12]

Using the procedure described for the preparation of N-[(3-chloro-2-pyrazinyl)methyl]-(tetrahydro-2H-pyrane)-4-carboxamide (example 1a) (R)-1-cbz-pyrrolidine-3-carboxylic acid (8.02 mmol, 2 g) gave after purification using column chromatography (silica gel, dichloromethane/methanol) (R)-benzyl 3-((3-chloropyrazin-2-yl)methylcarbamoyl)pyrrolidine-1-carboxylate (5.90 mmol, 2.21 g).

(R)-Benzyl 3-((3-chloropyrazin-2-yl)methylcarbamoyl)pyrrolidine-1-carboxylate (5.90 mmol, 2.21 g) was dissolved in ethyl acetate (20 ml) and N,N-dimethylformamide (1.538 ml). The stirred reaction mixture was cooled to 0° C. and phosphorous oxychloride (23.58 mmol, 2.198 mL) was added. After stirring at room temperature for 3 hours the reaction mixture was cooled to 0° C. and an excess of solid sodium hydrogencarbonate was added. The suspension was stirred at 0° C. for 10 minutes and 20 minutes at room temperature. Then it was cooled to 0° C. and water was added. The organic layer was separated and the aqueous layer extracted three times with ethyl acetate. The combined organic layers were washed with brine, dried (sodium sulfate) and concentrated in vacuo to yield (R)-benzyl 3-(8-chloroimidazo[1,5-a]pyrazin-3-yl)pyrrolidine-1-carboxylate (2.11 g).

Using the procedure described in example 2 step 2d (R)-benzyl 3-(8-chloroimidazo[1,5-a]pyrazin-3-yl)pyrrolidine-1-carboxylate (2.11 g) gave after purification using column chromatography (silica gel; dichloromethane/methanol) 1.94 g of (R)-benzyl 3-(8-methylimidazo[1,5-a]pyrazin-3-yl)pyrrolidine-1-carboxylate.

To (R)-benzyl 3-(8-methylimidazo[1,5-a]pyrazin-3-yl)pyrrolidine-1-carboxylate (1.332 mmol, 448 mg) in N,N- dimethylformamide (5 ml) was added N-bromosuccinimide (1.332 mmol, 237 mg). After stirring at room temperature for five minutes saturated aqueous sodium hydrogencarbonate solution was added, the organic layer was separated and the aqueous layer extracted three times with ethyl acetate. The combined organic layers were washed with water, brine, dried (sodium sulfate) and concentrated in vacuo. The residue was purified by column chromatography (silica gel; dichloromethane/methanol (gradient 0 to 10% methanol)) to give (R)-benzyl 3-(1-bromo-8-methylimidazo[1,5-a]pyrazin-3-yl)pyrrolidine-1-carboxylate (531 mg).

LC-MS column 1: Rt 3.11 min (M+H)$^+$=415 and 416 (Br-isotope pattern)

4b. Synthesis of (R)-1-(3-(1-bromo-8-methylimidazo [1,5-a]pyrazin-3-yl)pyrrolidin-1-yl)-2-(dimethylamino)ethanone

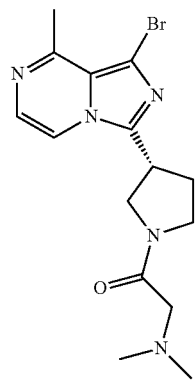 [SMILES: Cc1nccn2c([C@@H]3CCN(C(=O)CN(C)C)C3)nc(Br)c12]

(R)-Benzyl 3-(1-bromo-8-methylimidazo[1,5-a]pyrazin-3-yl)pyrrolidine-1-carboxylate (1.264 mmol, 525 mg) was dissolved in 37% hydrochloric acid (76 mmol, 6 mL) and stirred at room temperature. After four hours water (10 ml) was added and the mixture was washed twice with diethyl ether. The aqueous layer was concentrated under reduced pressure and coevaporated with toluene and ethanol to give 0.42 g of (R)-1-bromo-8-methyl-3-(pyrrolidin-3-yl)imidazo [1,5-a]pyrazine as hydrochloride. To 100 mg of this material in dichloromethane (5 ml) and N,N-diisopropylethylamine (1.778 mmol, 0.31 mL) were added N,N-dimethylglycine (0.534 mmol, 55.0 mg) and O-(7-azabenzotriazol-1-yl)1,1,3,3-tetramethyluronium hexafluorophosphate (HATU, 0.534 mmol, 203 mg) and stirred at room temperature for 16 hours. The reaction mixture was diluted with dichloromethane, washed with saturated aqueous sodium hydrogencarbonate solution, brine, dried (MgSO$_4$) and concentrated in vacuo. The residue was purified by column chromatography (silica gel; dichloromethane/methanol (gradient 0->35% methanol)) to give (R)-1-(3-(1-bromo-8-methylimidazo[1,5-a] pyrazin-3-yl)pyrrolidin-1-yl)-2-(dimethylamino)ethanone (77 mg).

LC-MS column 1: Rt 0.50 min (M+H)$^+$=366 and 368 (Br-isotope pattern)

4c. Synthesis of (S)-pentan-2-yl 4-(3-((R)-1-(2-(dimethylamino)acetyl)pyrrolidin-3-yl)-8-methylimidazo [1,5-a]pyrazin-1-yl)-2-methoxyphenylcarbamate

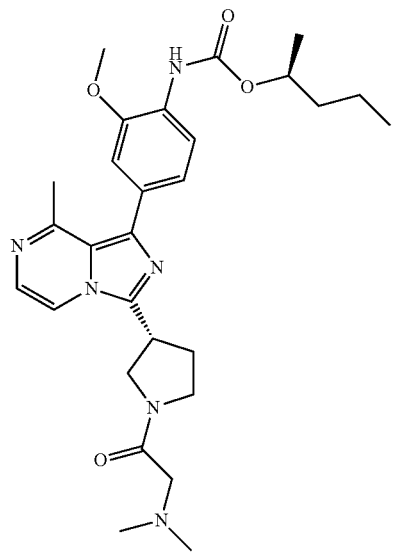 [SMILES: CCC[C@H](C)OC(=O)Nc1ccc(-c2nc([C@@H]3CCN(C(=O)CN(C)C)C3)n3ccnc(C)c23)cc1OC]

To a solution of (R)-1-(3-(1-bromo-8-methylimidazo[1,5-a]pyrazin-3-yl)pyrrolidin-1-yl)-2-(dimethylamino)ethanone (0.068 mmol, 25 mg) in dioxane (1.5 mL) was added 2 N potassium carbonate (aq) (0.273 mmol, 273 µl), N-[2-methoxy-4-(4,4,5,5-tetramethyl-1,3,2-dioxaborolan-2-yl)phenyl]-1-methyl-1H-indole-2-carboxamide (0.075 mmol, 27.3 mg) and 1,1'-bis(diphenylphosphino)ferrocene palladium (II) chloride complex with dichloromethane (0.014 mmol, 11.04 mg). The reaction was heated in the micro wave at 140° C. for 12 minutes. Acetonitrile and sodium sulfate were added, the mixture was filtered and the filtrate concentrated in vacuo. Purification on prep-HPLC (column Luna C18(2); gradient acetonitrile/water with constant 0.003M trifluoroacetic acid) yielded 9 mg of the title compound.

$^1$H NMR: δ 0.8-1.8 (m, 10H), 2.32 (s, 3H), 2.35 (s, 3H), 2.48 (s, 3H), 2.3-2.8 (m, 3H), 3.06-3.22 (m, 3H), 3.51-4.19 (m, 4H), 3.93 (s, 3H), 7.08 (s, 1H), 7.05-7.12 (m, 2H), 7.25-7.29 (m, 1H), 7.44-7.60 (m, 2H), 8.2 (brs, 1H).

UPLC: Method 0_60: Rt=2.09 min, (M+H)$^+$=523

Example 5

(Trans)-4-(1-(3-methoxy-4-(4-methoxy-1-methyl-1H-indole-2-carboxamido)phenyl)-8-methylimidazo [1,5-a]pyrazin-3-yl)cyclohexyl acetate 5a. Synthesis of (trans)-4-(8-methylimidazo[1,5-a] pyrazin-3-yl)cyclohexyl acetate

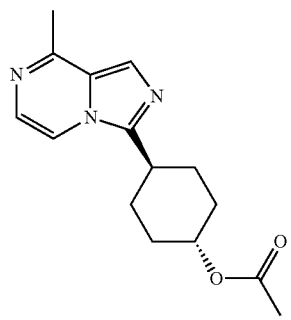 [SMILES: CC(=O)O[C@H]1CC[C@H](c2ncc3c(C)nccn32)CC1]

2-Aminomethyl-3-chloropyrazine hydrochloride (content 77%; 34.7 mmol, 6.47 g), trans-4-hydroxycyclohexanecarboxylic acid (34.7 mmol, 5 g), N,N-diisopropylethylamine (104 mmol, 18.12 ml, 13.45 g), 4-dimethylaminopyridine (3.47 mmol, 0.424 g) and 1-ethyl-3-(3-dimethylaminopropyl) carbodiimide hydrochloride (45.1 mmol, 8.64 g) in dichloromethane (100 ml) were stirred at room temperature. After 16 hours the reaction mixture was diluted with 2N hydrochloric acid and extracted with dichloromethane three times. The organic layer was dried (sodium sulfate) and concentrated in vacuo. The crude product was triturated with dichloromethane to give 2 g of solid (trans)-N-((3-chloropyrazin-2-yl)methyl)-4-hydroxycyclohexanecarboxamide. The mother liquor was dissolved in ethyl acetate and washed with aqueous sodium hydrogencarbonate solution, dried (sodium sulfate) and concentrated to give an additional crop of 0.7 g of (trans)-N-((3-chloropyrazin-2-yl)methyl)-4-hydroxycyclohexanecarboxamide.

The total harvest of (trans)-N-((3-chloropyrazin-2-yl)methyl)-4-hydroxycyclohexanecarboxamide (10 mmol, 2.7 g) and 4-dimethylaminopyridine (1.0 mmol, 0.12 g) were dissolved in pyridine (25 ml), acetic anhydride (10.51 mmol, 0.994 ml) was added and the mixture was stirred at room temperature. After 1 hour the reaction was quenched in 185 mL of 2N hydrochloric acid (pH becomes four) and extracted with ethyl acetate three times. The combined organic layers were dried (sodium sulfate) and concentrated to give 2.8 g of (trans)-4-((3-chloropyrazin-2-yl)methylcarbamoyl)cyclohexyl acetate.

(Trans)-4-((3-chloropyrazin-2-yl)methylcarbamoyl)cyclohexyl acetate (2.8 g) was transformed into (trans)-4-(8-chloroimidazo[1,5-a]pyrazin-3-yl)cyclohexyl acetate (2.2 g) using the procedure described in example 1 step 1b using a reaction temperature of 60° C. for 16 hours. Reaction of the latter compound (2.6 g) yielded (trans)-4-(8-methylimidazo[1,5-a]pyrazin-3-yl)cyclohexyl acetate (1.6 g) using the procedure described in example 2 step 2d.

$^1$H NMR: δ 1.50-1.62 (m, 2H), 1.87-1.98 (m, 2H), 2.06-2.24 (m, 4H), 2.07 (s, 3H), 2.77 (s, 3H), 2.92-3.00 (m, 1H), 4.81-4.89 (m, 1H), 7.42 (d, J=5 Hz, 1H), 7.54 (d, J=5 Hz, 1H), 7.69 (s, 1H).

5b. Synthesis of (trans)-4-(1-bromo-8-methylimidazo[1,5-a]pyrazin-3-yl)cyclohexyl acetate

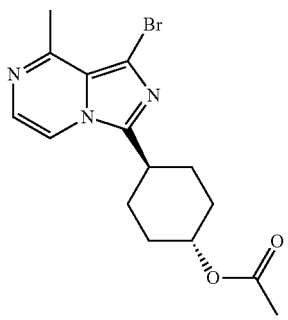 [SMILES: CC(=O)O[C@H]1CC[C@H](c2nc(Br)c3c(C)nccn32)CC1]

To (trans)-4-(8-methylimidazo[1,5-a]pyrazin-3-yl)cyclohexyl acetate (5.49 mmol, 1.5 g) in N,N-dimethylformamide (15 ml) was added N-bromosuccinimide (5.49 mmol, 0.977 g) and the mixture was stirred at room temperature. After one hour saturated aqueous sodium hydrogencarbonate solution was added and extracted with dichloromethane three times. The combined organic extracts were dried (sodium sulfate) and concentrated in vacuo. The crude product was purified using column chromatography (silica gel; dichloromethane/methanol (gradient 0 to 5% methanol)) to give the title compound (1.8 g).

$^1$H NMR: δ 1.47-1.59 (m, 2H), 1.86-1.97 (m, 2H), 2.03-2.11 (m, 2H), 2.07 (s, 3H), 2.16-2.23 (m, 2H), 2.86-2.97 (m, 1H), 2.89 (s, 3H), 4.78-4.88 (m, 1H), 7.39 (d, J=5 Hz, 1H), 7.51 (d, J=5 Hz, 1H).

5c. Synthesis of (trans)-4-(1-(3-methoxy-4-(4-methoxy-1-methyl-1H-indole-2-carboxamido)phenyl)-8-methylimidazo[1,5-a]pyrazin-3-yl)cyclohexyl acetate

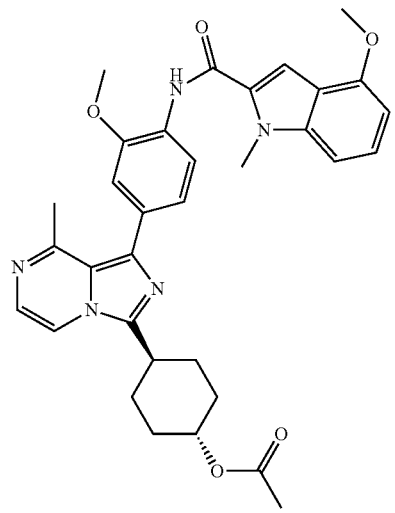 [SMILES: COc1cc(-c2nc([C@H]3CC[C@H](OC(C)=O)CC3)n3ccnc(C)c23)ccc1NC(=O)c1cc2c(OC)cccc2n1C]

Using the procedure described in example 1 step 1f (trans)-4-(1-bromo-8-methylimidazo[1,5-a]pyrazin-3-yl)cyclohexyl acetate (0.568 mmol, 200 mg) and 4-methoxy-N-(2-methoxy-4-(4,4,5,5-tetramethyl-1,3,2-dioxaborolan-2-yl)phenyl)-1-methyl-1H-indole-2-carboxamide (0.568 mmol, 248 mg) gave after purification using column chromatography (silica gel; gradient heptanes/ethyl acetate 1/1 to ethyl acetate) the title compound (245 mg).

$^1$H NMR: δ 1.51-1.63 (m, 2H), 1.96-2.27 (m, 6H), 2.08 (s, 3H), 2.50 (s, 3H), 2.96-3.04 (m, 1H), 4.00 (s, 6H), 4.12 (s, 3H), 4.82-4.89 (m, 1H), 6.58 (d, J=9 Hz, 1H), 7.03-7.31 (m, 5H), 7.43 (d, J=5 Hz, 1H), 7.55 (d, J=5 Hz, 1H), 8.57 (d, J=10 Hz, 1H), 8.69 (brs, 1H).

UPLC: Method 40_80: Rt=1.64 min, (M+H)$^+$=582

Example 6

N-(4-(3-((trans)-4-hydroxycyclohexyl)-8-methylimidazo[1,5-a]pyrazin-1-yl)-2-methoxyphenyl)-4-methoxy-1-methyl-1H-indole-2-carboxamide

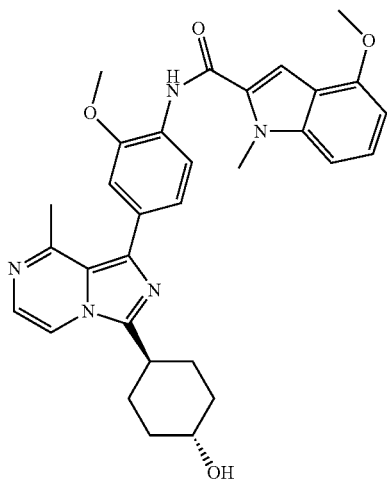 [SMILES: COc1cc(-c2nc([C@H]3CC[C@H](O)CC3)n3ccnc(C)c23)ccc1NC(=O)c1cc2c(OC)cccc2n1C]

To (trans)-4-(1-(3-methoxy-4-(4-methoxy-1-methyl-1H-indole-2-carboxamido)phenyl)-8-methylimidazo[1,5-a]pyrazin-3-yl)cyclohexyl acetate (0.034 mmol, 20 mg) in acetonitrile (0.5 ml) and water (0.5 ml) was added potassium hydroxide (0.172 mmol, 9.65 mg) and the mixture was stirred at 110° C. After one hour the reaction mixture was neutralized with 2N hydrochloric acid, extracted with dichloromethane three times, the combined organic layers were dried (sodium sulfate) and concentrated in vacuo. The crude product was purified using column chromatography (silica gel; gradient dichloromethane to dichloromethane/methanol 25/1) to yield the title compound (7 mg).

$^1$H NMR: δ 1.45-1.63 (m, 2H), 1.88-2.22 (m, 6H), 2.49 (s, 3H), 2.92-3.00 (m, 1H), 3.77-3.83 (m, 1H), 4.00 (s, 3H), 4.01 (s, 3H), 4.12 (s, 3H), 6.57 (d, J=9 Hz, 1H), 7.02-7.31 (m, 5H), 7.42 (d, J=5 Hz, 1H), 7.56 (d, J=5 Hz, 1H), 8.56 (d, J=10 Hz, 1H), 8.69 (brs, 1H).

UPLC: Method 40_80: Rt=1.11 min, (M+H)$^+$=540

Example 7

4-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide

7a. Synthesis of (trans)-N-((3-chloropyrazin-2-yl)methyl)-4-(4-methylpiperazin-1-yl)cyclohexanecarboxamide

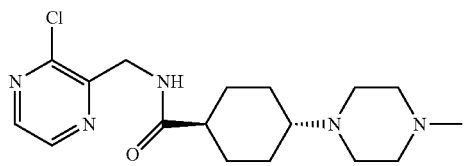 [SMILES: CN1CCN([C@H]2CC[C@H](C(=O)NCc3nccnc3Cl)CC2)CC1]

To a stirred solution of N-((3-chloropyrazin-2-yl)methyl)-4-oxocyclohexanecarboxamide (40.7 mmol, 10.9 g) in dichloromethane (145 ml) and acetic acid (1.450 ml) at room temperature was added 1-methylpiperazine (52.9 mmol, 5.87 ml, 5.30 g) and sodium cyanoborohydride (81 mmol, 5.12 g). After 16 hours at room temperature dichloromethane and an aqueous saturated sodium hydrogencarbonate solution (15 mL) were added and the organic layer was separated. This organic layer was washed with brine. The aqueous layers were washed with dichloromethane twice and the combined organic extracts dried (sodium sulfate). Concentration in vacuo gave the crude product (mixture of cis and trans), which was purified using column chromatography (silica gel; dichloromethane/methanol gradient (0 to 20% methanol) to afford the cis isomer (275 mg), the trans isomer (2.5 g) and a mixture of cis and trans isomers (5.5 g).

Trans isomer: $^1$H NMR: δ 1.23-2.75 (m, 18H), 2.22 (s, 3H), 4.69 (d, J=5 Hz, 3H), 6.78-6.83 (m, 1H), 8.33 (d, J=3 Hz, 1H), 8.46 (d, J=3 Hz, 1H).

Cis isomer: $^1$H NMR: δ 1.25-2.75 (m, 18H), 2.22 (s, 3H), 4.71 (d, J=5 Hz, 3H), 6.86-6.93 (m, 1H), 8.33 (d, J=3 Hz, 1H), 8.45 (d, J=3 Hz, 1H).

7b. Synthesis of 4-methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide

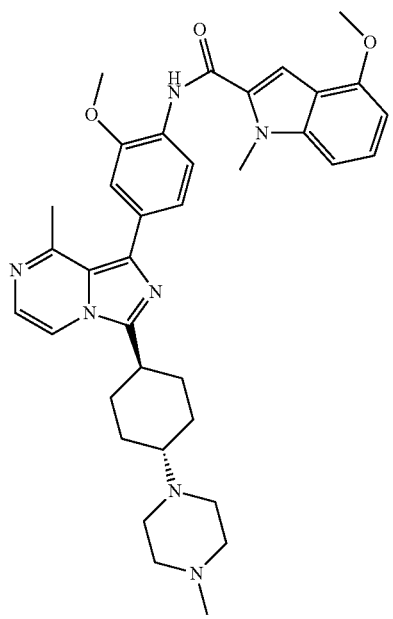 [SMILES: COc1cc(-c2nc([C@H]3CC[C@H](N4CCN(C)CC4)CC3)n3ccnc(C)c23)ccc1NC(=O)c1cc2c(OC)cccc2n1C]

Using the procedure described in example 1 step 1b (trans)-N-((3-chloropyrazin-2-yl)methyl)-4-(4-methylpiperazin-1- yl)cyclohexanecarboxamide (7.10 mmol, 2.5 g) was transformed into 8-chloro-3-((trans)-4-(4-methylpiperazin-1-yl)cyclohexyl)imidazo[1,5-a]pyrazine. The crude product was purified by crystallization from acetonitrile to afford 8-chloro-3-((trans)-4-(4-methylpiperazin-1-yl)cyclohexyl)imidazo[1,5-a]pyrazine (0.98 g). The mother liquor was purified using column chromatography (silica gel; dichloromethane gradient methanol 0% to 20%)) to afford an extra 0.30 g of 8-chloro-3-((trans)-4-(4-methylpiperazin-1-yl)cyclohexyl)imidazo[1,5-a]pyrazine.

Using the procedure described in example 2 step 2d 8-chloro-3-((trans)-4-(4-methylpiperazin-1-yl)cyclohexyl)imidazo[1,5-a]pyrazine (6.98 mmol, 2.33 g) gave 8-methyl-3-((trans)-4-(4-methylpiperazin-1-yl)cyclohexyl)imidazo[1,5-a]pyrazine (1.8 g).

To 8-methyl-3-((trans)-4-(4-methylpiperazin-1-yl)cyclohexyl)imidazo[1,5-a]pyrazine (2.086 mmol, 654 mg) in N,N-dimethylformamide (10 mL) was added N-bromosuccinimide (2.295 mmol, 408 mg) and the mixture was stirred at room temperature for one hour. The reaction mixture was evaporated to dryness. The residue was dissolved in dichloromethane/methanol 9/1 (100 mL) and this solution was washed with a mixture of water (2 ml), of saturated aqueous sodium hydrogencarbonate (2 mL) and a few drops of 2 N sodium hydroxide, the organic layer dried (sodium sulfate) and evaporated to dryness to yield crude 1-bromo-8-methyl-3-((trans)-4-(4-methylpiperazin-1-yl)cyclohexyl)imidazo[1,5-a]pyrazine (1.04 g)

To a stirred suspension of 1-bromo-8-methyl-3-((trans)-4-(4-methylpiperazin-1-yl)cyclohexyl)imidazo[1,5-a]pyrazine (1.04 g) and 4-methoxy-N-(2-methoxy-4-(4,4,5,5-tetramethyl-1,3,2-dioxaborolan-2-yl)phenyl)-1-methyl-1H-indole-2-carboxamide (2.227 mmol, 0.972 g) in dioxane (18 mL) and 2 M aqueous potassium carbonate (10.6 mmol, 5.3 mL) under a nitrogen atmosphere was added 1,1'-bis(diphenylphosphino)ferrocene palladium (II) chloride, complex with dichloromethane (0.212 mmol, 0.171 g) and the reaction mixture was heated by a preheated oil bath at 100° C. After two hours the reaction mixture was cooled to room temperature, water added and extracted with dichloromethane/methanol 9/1. The organic layer was separated and the water layer was extracted again with dichloromethane/methanol 9/1. The combined organic layers were washed with brine and dried (sodium sulfate) and evaporated to dryness to afford crude sample which was purified using column chromatography (silica gel; dichloromethane/methanol gradient (0 to 15% methanol)). Trituration with ethanol afforded 4-methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide (0.44 g).

$^1$H NMR: δ 1.42-2.77 (m, 17H), 2.32, (brs, 3H), 2.48 (s, 3H), 2.89-2.99 (m, 1H), 4.00 (s, 3H), 4.01 (s, 3H), 4.12 (s, 3H), 6.57 (d, J=9 Hz, 1H), 7.03-7.31 (m, 5H), 7.42 (d, J=5 Hz, 1H), 7.54 (d, J=5 Hz, 1H), 8.56 (d, J=10 Hz, 1H), 8.68 (brs, 1H).

UPLC: Method 0_60: Rt=2.07 min, (M+H)$^+$=622

Example 8

4-Methoxy-N-(2-methoxy-4-(8-methyl-3-((cis)-4-(4-methylpiperazin-1-yl)cyclohexyl)imidazo[1,5-a]pyrazin-1-yl)phenyl)-1-methyl-1H-indole-2-carboxamide

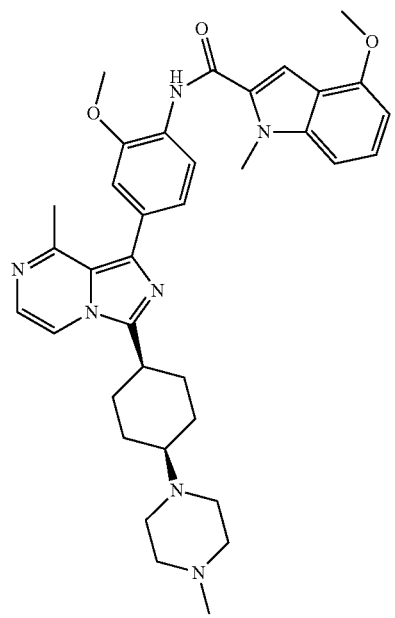 [SMILES: COc1cc(-c2nc([C@H]3CC[C@@H](N4CCN(C)CC4)CC3)n3ccnc(C)c23)ccc1NC(=O)c1cc2c(OC)cccc2n1C]

According to the procedures described in example 7 the title compound was prepared.

$^1$H NMR: δ 1.4-3.5 (m, 18H), 2.32, (brs, 3H), 2.50 (s, 3H), 2.89-2.99 (m, 1H), 4.00 (s, 3H), 4.01 (s, 3H), 4.13 (s, 3H), 6.57 (d, J=9 Hz, 1H), 7.03-7.33 (m, 5H), 7.41 (d, J=5 Hz, 1H), 7.66 (brd, J=5 Hz, 1H), 8.57 (d, J=10 Hz, 1H), 8.68 (brs, 1H).

UPLC: Method 0_60: Rt=2.06 min, (M+H)$^+$=622

Example 9

N-(4-(3-((trans)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide 9a. Synthesis of (trans)-N-((3-chloropyrazin-2-yl)methyl)-4-(3,3-difluoroazetidin-1-yl)cyclohexanecarboxamide

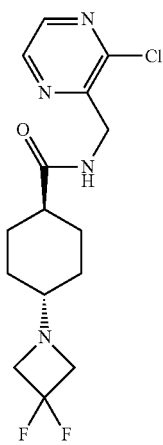 [SMILES: O=C(NCc1nccnc1Cl)[C@H]1CC[C@H](N2CC(F)(F)C2)CC1]

3,3-Difluoroazetidine hydrochloride (5.60 mmol, 0.726 g) was dissolved in dichloromethane/methanol (20 mL; 1/1) and 15 g Si-Carbonate (Silicycle, Loading 0.7 mmol/g) was added. After 20 minutes this slurry was put on a column with 7 g of Si-Carbonate (Silicycle, Loading 0.7 mmol/g) and eluated with dichloromethane/methanol (40 mL; 1/1). The solution was concentrated (900 mbar, bath 45 deg) to a volume of 30 mL. To this solution N-((3-chloropyrazin-2-yl)methyl)-4-oxocyclohexanecarboxamide (3.74 mmol, 1 g), acetic acid (0.1 mL) and sodium cyanoborohydride (7.47 mmol, 0.469 g) were added and the reaction mixture stirred at room temperature. After 3 days the reaction mixture was concentrated, dichloromethane added and washed with aqueous sodium hydrogencarbonate and water. Both aqueous layers were extracted four times with dichloromethane. The combined organic extracts were dried (sodium sulfate) and concentrated in vacuo. Purification by column chromatography (silica gel, gradient heptanes/ethyl acetate 2/1 to ethyl acetate) yielded (trans)-N-((3-chloropyrazin-2-yl)methyl)-4-(3,3-difluoroazetidin-1-yl)cyclohexanecarboxamide (0.47 g) and (cis)-N-((3-chloropyrazin-2-yl)methyl)-4-(3,3-difluoroazetidin-1-yl)cyclohexanecarboxamide (0.49 g).

Trans-isomer: $^1$H NMR: δ 1.09-1.21 (m, 2H), 1.51-1.63 (m, 2H), 1.83-2.26 (m, 6H), 3.57 (t, J=11 Hz, 4H), 4.69 (d, J=5 Hz, 3H), 6.8 (brs, 1H), 8.33 (d, J=3 Hz, 1H), 8.46 (d, J=3 Hz, 1H).

Cis-isomer: $^1$H NMR: δ 1.04-1.72 (m, 6H), 1.89-2.01 (m, 2H), 2.28-2.42 (m, 2H), 3.50 (t, J=12Hz, 4H), 4.69 (d, J=5 Hz, 3H), 6.87 (brs, 1H), 8.32 (d, J=3 Hz, 1H), 8.47 (d, J=3 Hz, 1H).

9b. Synthesis of N-(4-(3-((trans)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide

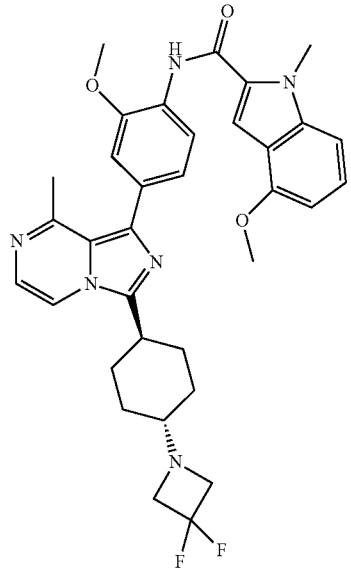 [SMILES: COc1cc(-c2nc([C@H]3CC[C@H](N4CC(F)(F)C4)CC3)n3ccnc(C)c23)ccc1NC(=O)c1cc2c(OC)cccc2n1C]

From (trans)-N-((3-chloropyrazin-2-yl)methyl)-4-(3,3-difluoroazetidin-1-yl)cyclohexane-carboxamide (0.46 g) 8-chloro-3-((trans)-4-(3,3-difluoroazetidin-1-yl)cyclohexyl)imidazo[1,5-a]pyrazine (0.405 g) was prepared according to the procedures in example 3 step 3b and purification by column chromatography (silica gel; ethyl acetate).

8-Chloro-3-((trans)-4-(3,3-difluoroazetidin-1-yl)cyclohexyl)imidazo[1,5-a]pyrazine (0.40 g) was transformed into 3-((trans)-4-(3,3-difluoroazetidin-1-yl)cyclohexyl)-8-methylimidazo[1,5-a]pyrazine (336 mg) using the procedures in example 2 step 2d and purification by column chromatography (silica gel; ethyl acetate/10% methanol).

According to the procedure described in example 2 step 2f 1-bromo-3-((trans)-4-(3,3-difluoroazetidin-1-yl)cyclohexyl)-8-methylimidazo[1,5-a]pyrazine (374 mg) was prepared from 3-((trans)-4-(3,3-difluoroazetidin-1-yl)cyclohexyl)-8-methylimidazo[1,5-a]pyrazine (333 mg).

Reaction and work-up according to the procedure described in example 1 step 1f using 1-bromo-3-((trans)-4-(3,3-difluoroazetidin-1-yl)cyclohexyl)-8-methylimidazo[1,5-a]pyrazine (58 mg) and purification by column chromatography (silica gel; dichloromethane/methanol 20/1) gave N-(4-(3-((trans)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide (44 mg).

$^1$H NMR: δ 1.23-1.37 (m, 2H), 1.85-2.28 (m, 7H), 2.49 (s, 3H), 2.90-3.00 (m, 1H), 3.60 (t, J=11 Hz, 4H), 4.00 (s, 3H), 4.01 (s, 3H), 4.12 (s, 3H), 6.57 (d, J=9 Hz, 1H), 7.02-7.32 (m, 5H), 7.43 (d, J=5 Hz, 1H), 7.55 (d, J=5 Hz, 1H), 8.57 (d, J=10 Hz, 1H), 8.68 (brs, 1H).

UPLC: Method 0_60: Rt=2.46 min, (M+H)$^+$=615

Example 10

N-(4-(3-((cis)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide

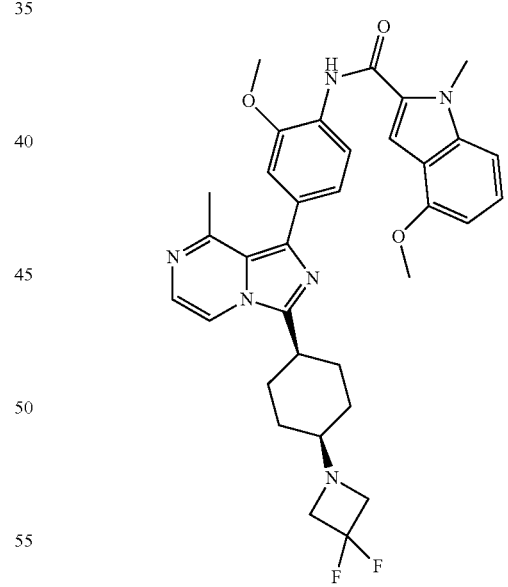

According to the procedures described in example 9 the title compound was prepared.

$^1$H NMR: δ 1.56-2.54 (m, 9H), 2.48 (s, 3H), 3.02-3.11 (m, 1H), 3.53 (t, J=12Hz, 4H), 4.00 (s, 3H), 4.01 (s, 3H), 4.12 (s, 3H), 6.57 (d, J=9 Hz, 1H), 7.02-7.31 (m, 5H), 7.41 (d, J=5 Hz, 1H), 7.58 (d, J=5 Hz, 1H), 8.57 (d, J=10 Hz, 1H), 8.69 (brs, 1H).

UPLC: Method 0_60: Rt=2.48 min, (M+H)$^+$=615

Example 11

(S)-Pentan-2-yl 2-methoxy-4-(3-((trans)-4-(2-methoxyethylamino)cyclohexyl)-8-methyl-imidazo[1,5-a]pyrazin-1-yl)phenylcarbamate

11a. Synthesis of benzyl(trans)-4-(8-chloroimidazo[1,5-a]pyrazin-3-yl)cyclohexyl(2-methoxyethyl)carbamate

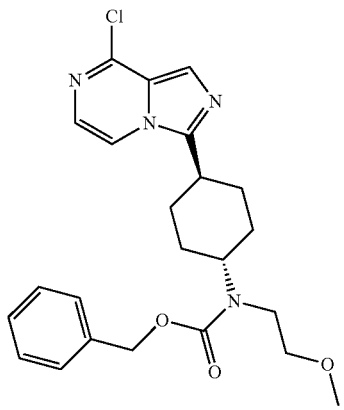 [SMILES: COCCN(C(=O)OCc1ccccc1)[C@H]1CC[C@H](c2ncc3c(Cl)nccn32)CC1]

Using the procedure described in example 7 step 7a N-((3-chloropyrazin-2-yl)methyl)-4-oxocyclo-hexanecarboxamide (1 g) and 2-methoxyethanamine (0.281 g) gave N-((3-chloropyrazin-2-yl)methyl)-4-(2-methoxyethylamino)cyclohexanecarboxamide (1.15 g, mixture of cis and trans).

To a solution of N-((3-chloropyrazin-2-yl)methyl)-4-(2-methoxyethylamino)cyclohexane-carboxamide (3.15 mmol, 1.03 g) in dioxane (10 ml) and water (10 ml) were added triethylamine (3.36 mmol, 0.47 ml) and N-(benzyloxycarbonyloxy)succinimide (3.31 mmol, 825 mg). After stirring for two hours at room temperature water and 2N hydrochloric acid (1.5 ml) were added and this mixture extracted twice with dichloromethane. The combined organic layers were washed with saturated aqueous sodium hydrogencarbonate solution, dried (sodium sulfate) and concentrated in vacuo to give benzyl 4-((3-chloropyrazin-2-yl)methylcarbamoyl)cyclohexyl(2-methoxyethyl)carbamate (1.45 g).

Using the procedure described in example 2 step 2f and purification by column chromatography (silica gel; dichloromethane/methanol 20/1) the latter compound (1.45 g) was transformed into benzyl-4-(8-chloroimidazo[1,5-a]pyrazin-3-yl)cyclohexyl(2-methoxyethyl)carbamate. Column chromatography (silica gel; heptanes/ethyl acetate 1/1) afforded 337 mg of a mixture of cis and trans-isomer and 422 mg of mainly trans-isomer.

Trans-isomer: $^1$H NMR: δ 1.61-2.17 (m, 8H), 2.83-2.97 (m, 1H), 3.26-3.58 (m, 7H), 3.87-3.98 (m, 1H), 5.17 (s, 2H), 7.30-7.40 (m, 6H), 7.59 (d, J=5 Hz, 1H), 7.78 (s, 1H).

Cis-isomer: $^1$H NMR: δ 1.62-2.25 (m, 8H), 3.25-3.58 (m, 8H), 4.08-4.20 (m, 1H), 5.17 (s, 2H), 7.30-7.39 (m, 6H), 7.56 (d, J=5 Hz, 1H), 7.80 (brs, 1H).

11b. Synthesis of (S)-pentan-2-yl 2-methoxy-4-(3-((trans)-4-(2-methoxyethylamino)cyclohexyl)-8-methyl-imidazo[1,5-a]pyrazin-1-yl)phenylcarbamate

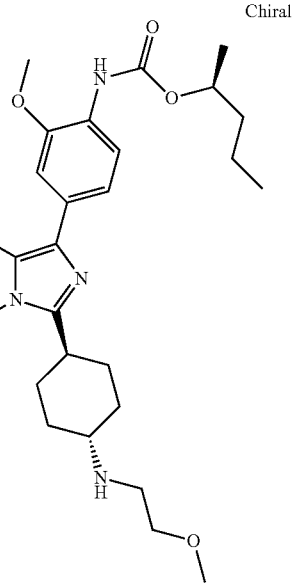

According to the procedure described in example 2 step 2f benzyl(trans)-4-(8-chloroimidazo[1,5-a]pyrazin-3-yl)cyclohexyl(2-methoxyethyl)carbamate (422 mg) yielded benzyl 2-methoxyethyl((trans)-4-(8-methylimidazo[1,5-a]pyrazin-3-yl)cyclohexyl)carbamate (264 mg) after purification by column chromatography (silica gel, gradient heptanes/ethyl acetate 1/0 to 0/1).

To a solution of 2-methoxyethyl((trans)-4-(8-methylimidazo[1,5-a]pyrazin-3-yl)cyclo-hexyl)carbamate (264 mg) in dichloromethane was added N-bromosuccinimide (0.687 mmol, 122 mg) and the reaction mixture was heated at room temperature for one hour. The reaction mixture was washed with saturated aqueous sodium hydrogencarbonate, dried (sodium sulfate) and concentrated to give 295 mg of benzyl (trans)-4-(1-bromo-8-methylimidazo[1,5-a]pyrazin-3-yl)cyclohexyl(2-methoxyethyl) carbamate.

The latter compound (295 mg) was dissolved in 37% hydrochloric acid (3.4 mL) and after stirring for one hour at room temperature water (4 mL) was added. This mixture was washed with diethyl ether (5 mL) twice, the aqueous layer cooled and made basic with 2N aqueous sodium hydroxide. This basic aqueous mixture was extracted with dichloromethane twice. The combined organic extracts were dried (sodium sulfate) and concentrated to give (trans)-4-(1-bromo-8-methylimidazo[1,5-a]pyrazin-3-yl)-N-(2-methoxyethyl)cyclohexanamine (188 mg).

Using the procedure described in example 1 step 1f and purification by column chromatography (silica gel; dichloromethane/methanol 20/1) the latter compound (23 mg) and (S)-pentan-2-yl 2-methoxy-4-(4,4,5,5-tetramethyl-1,3,2-dioxaborolan-2-yl)phenylcarbamate (23 mg) gave (S)-pentan-2-yl 2-methoxy-4-(3-((trans)-4-(2-methoxyethylamino)cyclohexyl)-8-methyl-imidazo[1,5-a]pyrazin-1-yl)phenylcarbamate (9 mg).

$^1$H NMR: δ 0.95 (t, J=8 Hz, 3H), 1.30 (d, J=7 Hz, 3H), 1.35-2.22 (m, 11H), 2.44 (s, 3H), 2.70-2.79 (m, 1H), 2.92-3.03 (m, 3H), 3.40 (s, 3H), 3.57-3.62 (m, 2H), 3.92 (s, 3H), 4.91-4.99 (m, 1H), 7.07-7.12 (m, 2H), 7.24-7.92 (m, 1H), 7.41 (d, J=5 Hz, 1H), 7.55 (d, J=5 Hz, 1H), 8.15-8.21 (m, 1H).

UPLC: Method 0_60: Rt=2.46 min, (M+H)$^+$=424

Example 12

N-(2-methoxy-4-(8-methyl-3-((trans)-4-morpholinocyclohexyl)imidazo[1,5-a]pyrazin-1-yl)phenyl)-1-methyl-1H-indole-2-carboxamide

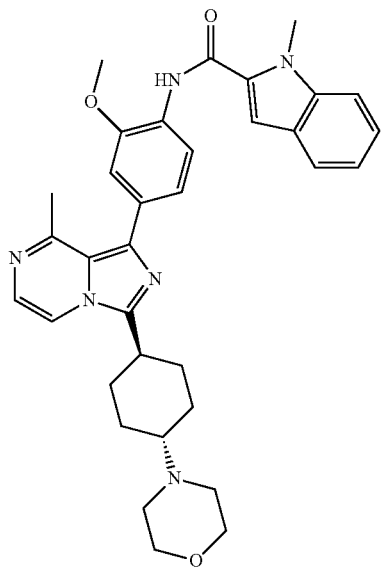 [SMILES: COc1cc(-c2nc([C@H]3CC[C@H](N4CCOCC4)CC3)n3ccnc(C)c23)ccc1NC(=O)c1cc2ccccc2n1C]

According to the procedure described in example 7 step 7a N-((3-chloropyrazin-2-yl)methyl)-4-oxocyclohexanecarboxamide (1 g) and morpholine (0.44 mL) gave after work-up N-((3-chloropyrazin-2-yl)methyl)-4-morpholinocyclohexanecarboxamide (1.28 g). This crude product was used in the next step without further purification.

To N-((3-chloropyrazin-2-yl)methyl)-4-morpholinocyclohexanecarboxamide (3.78 mmol, 1.28 g) in acetonitrile (20 mL) was added phosphorus oxychloride (18.9 mmol, 1.71 ml) and heated at 70° C. After four hours the reaction mixture was concentrated to dryness and coevaporated twice with toluene. The residue was dissolved in acetonitrile and added dropwise to anhydrous 7N ammonia in methanol (27 mL). Dichloromethane was added, filtered and concentrated again. This crude product (1.37 g) was purified over silica gel (toluene/acetone 15/85) and rinsing the column with dichloromethane/methanol 4/1 yielding 4-((cis)-4-(8-chloroimidazo[1,5-a]pyrazin-3-yl)cyclohexyl)morpholine (412 mg) and 4-((trans)-4-(8-chloroimidazo[1,5-a]pyrazin-3-yl)cyclohexyl)morpholine (387 mg) which contained some cis-isomer According to the procedure described in example 2 step 2d 4-((trans)-4-(8-chloroimidazo[1,5-a]pyrazin-3-yl)cyclohexyl)morpholine (387 mg) yielded 4-((trans)-4-(8-methylimidazo[1,5-a]pyrazin-3-yl)cyclohexyl)morpholine (238 mg) which still contained some cis-isomer after purification by column chromatography (silica gel; dichloromethane/methanol 95/5). Additional purification of 114 mg of the latter material yielded 94 mg of 4-((trans)-4-(8-methylimidazo[1,5-a]pyrazin-3-yl)cyclohexyl)morpholine.

Using the procedure described in example 2 step 2f and purification by column chromatography (silica gel; dichloromethane gradient methanol 0 to 15%) 4-((trans)-4-(8-methylimidazo[1,5-a]pyrazin-3-yl)cyclohexyl)morpholine (91 mg) gave 4-((trans)-4-(1-bromo-8-methylimidazo[1,5-a]pyrazin-3-yl)cyclohexyl)morpholine (87 mg).

Using the procedure described in example 1 step 1f and purification by column chromatography (silica gel; dichloromethane gradient methanol 0 to 15%) the latter compound (40 mg) and N-[2-methoxy-4-(4,4,5,5-tetramethyl-1,3,2-dioxaborolan-2-yl)phenyl]-1-methyl-1H-indole-2-carboxamide (47 mg) yielded N-(2-methoxy-4-(8-methyl-3-((trans)-4-morpholinocyclohexyl)imidazo[1,5-a]pyrazin-1-yl)phenyl)-1-methyl-1H-indole-2-carboxamide (37 mg).

$^1$H NMR: δ 1.40-1.53 (m, 2H), 1.88-2.00 (m, 2H), 2.11-2.21 (m, 4H), 2.37-2.46 (m, 1H), 2.48 (s, 3H), 2.60-2.65 (m, 4H), 2.90-2.99 (m, 1H), 3.73-3.78 (m, 4H), 4.00 (s, 3H), 4.14 (s, 3H), 7.08 (s, 1H), 7.16-7.46 (m, 6H), 7.55 (d, J=5 Hz, 1H), 7.71 (d, J=5 Hz, 1H), 8.77 (d, J=9 Hz, 1H), 8.68 (brs, 1H).

UPLC: Method 0_60: Rt=2.28 min, (M+H)$^+$=579

Example 13

4-Methoxy-N-(2-methoxy-4-(8-methyl-3-(3-methyloxetan-3-yl)imidazo[1,5-a]pyrazin-1-yl)phenyl)-1-methyl-1H-indole-2-carboxamide

13a. Synthesis of N-((3-chloropyrazin-2-yl)methyl)-3-methyloxetane-3-carboxamide

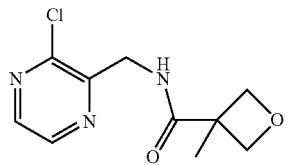 [SMILES: CC1(C(=O)NCc2nccnc2Cl)COC1]

To a stirred suspension of 2-aminomethyl-3-chloropyrazine hydrochloride (content 77%; 4.34 mmol, 0.81 g) in dichloromethane (150 ml) were added 3-methyl-3-oxetanecarboxylic acid (4.34 mmol, 0.504 g), triethylamine (9.56 mmol, 1.33 ml), 4-dimethylaminopyridine (0.434 mmol, 0.053 g) and 1-(3-dimethylaminopropyl)-3-ethylcarbodiimide hydrochloride (8.69 mmol, 1.67 g). After stirring for 16 hours at room temperature the suspension was filtered over decalite and the decalite was washed with dichloromethane. The combined filtrates were washed with 0.3 N hydrochloric acid (350 mL), 0.03 N hydrochloric acid (350 mL) and sodium hydrogencarbonate (aq). All aqueous layers were twice extracted with dichloromethane. The combined organic extracts were dried (sodium sulfate) and concentrated in vacuo to give crude material. Solid sodium chloride was added to all aqueous layers and these were extracted five times with dichloromethane. The combined organic extracts were dried (sodium sulfate) and concentrated in vacuo to give a second crop of crude material. The combined crude products were purified using chromatography (silica gel, ethyl acetate) to yield N-((3-chloropyrazin-2-yl)methyl)-3-methyloxetane-3-carboxamide (0.58 g).

$^1$H NMR: δ 1.68 (s, 3H), 4.52 (d, J=6 Hz, 2H), 4.76 (d, J=5 Hz, 2H), 4.98 (d, J=6 Hz, 2H), 7.13 (brs, 1H), 8.35 (d, J=2 Hz, 1H), 8.47 (d, J=2 Hz, 1H).

13b. Synthesis of 4-Methoxy-N-(2-methoxy-4-(8-methyl-3-(3-methyloxetan-3-yl)imidazo[1,5-a]pyrazin-1-yl)phenyl)-1-methyl-1H-indole-2-carboxamide

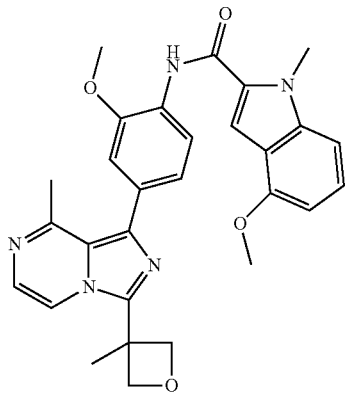 [SMILES: COc1cc(-c2nc(C3(C)COC3)n3ccnc(C)c23)ccc1NC(=O)c1cc2c(OC)cccc2n1C]

To a stirred solution of N-((3-chloropyrazin-2-yl)methyl)-3-methyloxetane-3-carboxamide (1.945 mmol, 0.47 g) in dichloromethane (10 ml) cooled in an ice-bath was added pyridine (27.2 mmol, 2.198 ml) and trifluoromethane sulfonic anhydride (11.67 mmol, 1.971 ml). The ice-bath was removed and the reaction was stirred at room temperature. After 2 hours the reaction mixture was cooled in ice-bath, diluted with ethyl acetate (5 mL) and quenched with aqueous sodium hydrogencarbonate. The organic layer separated and the aqueous layer washed four times with ethyl acetate. The combined organic extracts were dried (sodium sulfate) and concentrated in vacuo. Purification by column chromatography (silica gel, ethyl acetate) yielded 8-chloro-3-(3-methyloxetan-3-yl)imidazo[1,5-a]pyrazine (0.56 g).

According to the procedure described in example 2 step 2d 8-chloro-3-(3-methyloxetan-3-yl)imidazo[1,5-a]pyrazine (0.5 g) yielded 8-methyl-3-(3-methyloxetan-3-yl)imidazo[1,5-a]pyrazine (0.56 g) after purification by column chromatography (silica gel; ethyl acetate/methanol 9/1).

Using the procedure described in example 2 step 2f and purification by column chromatography (silica gel; dichloromethane/methanol=100/3) 8-methyl-3-(3-methyloxetan-3-yl)imidazo[1,5-a]pyrazine (0.2 g) gave 1-bromo-8-methyl-3-(3-methyloxetan-3-yl)imidazo[1,5-a]pyrazine (88 mg).

Using the procedure described in example 1 step 1f and purification by column chromatography (silica gel; dichloromethane/methanol=100/3) 1-bromo-8-methyl-3-(3-methyloxetan-3-yl)imidazo[1,5-a]pyrazine (40 mg) and 4-methoxy-N-(2-methoxy-4-(4,4,5,5-tetramethyl-1,3,2-dioxaborolan-2-yl)phenyl)-1-methyl-1H-indole-2-carboxamide (68 mg) yielded 4-methoxy-N-(2-methoxy-4-(8-methyl-3-(3-methyloxetan-3-yl)imidazo[1,5-a]pyrazin-1-yl)phenyl)-1-methyl-1H-indole-2-carboxamide (44 mg).

$^1$H NMR: δ 1.91 (s, 3H), 2.53 (s, 3H), 4.01 (s, 6H), 4.13 (s, 3H), 4.83 (d, J=5 Hz, 2H), 5.53 (d, J=5 Hz, 2H), 6.57 (d, J=9 Hz, 1H), 7.03-7.31 (m, 5H), 7.37 (d, J=5 Hz, 1H), 7.46 (d, J=5 Hz, 1H), 8.58 (d, J=9 Hz, 1H), 8.69 (brs, 1H).

UPLC: Method 40_80: Rt=1.07 min, (M+H)$^+$=512

Example 14

N-(4-(3-(hydroxymethyl)-8-methylimidazo[1,5-a]pyrazin-1-yl)-2-methoxyphenyl)-4-methoxy-1-methyl-1H-indole-2-carboxamide

14a. Synthesis of 1-bromo-8-methylimidazo[1,5-a]pyrazin-3-yl)methanol

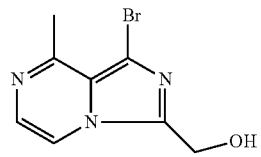

According to the procedure described in example 13 step 13a acetoxyacetic acid (0.667 g) and 2-aminomethyl-3-chloropyrazine hydrochloride (content 77%; 0.81 g) gave 2-((3-chloropyrazin-2-yl)methylamino)-2-oxoethyl acetate (0.99 g) after purification by column chromatography (silica gel; gradient of dichloromethane to dichloromethane/ethyl acetate 1/1).

2-((3-Chloropyrazin-2-yl)methylamino)-2-oxoethyl acetate (0.765 g) was transformed into (8-chloroimidazo[1,5-a]pyrazin-3-yl)methyl acetate (0.11 g) using the procedures described in example 3 step 3b using phosphorus oxychloride in acetonitrile and pyridine without N,N-dimethylformamide in the reaction and purification by column chromatography (silica gel; dichloromethane/ethyl acetate 1/1).

According to the procedure described in example 2 step 2d (8-chloroimidazo[1,5-a]pyrazin-3-yl)methyl acetate (0.19 g) yielded (8-methylimidazo[1,5-a]pyrazin-3-yl)methyl acetate (153 mg) after purification by column chromatography (silica gel; ethyl acetate/methanol 9/1).

Using the procedure described in example 2 step 2f and purification by column chromatography (silica gel; ethyl acetate) (8-methylimidazo[1,5-a]pyrazin-3-yl)methyl acetate (0.15 g) yielded (1-bromo-8-methylimidazo[1,5-a]pyrazin-3-yl)methyl acetate (0.19 g)

To (1-bromo-8-methylimidazo[1,5-a]pyrazin-3-yl)methyl acetate (0.669 mmol, 0.19 g) in ethanol (1 mL) was added 2M sodium hydroxide (1.337 mmol, 0.669 mL). After 15 minutes at room temperature 2 M hydrochloric acid (0.4 mL) was added. Then, saturated aqueous sodium hydrogencarbonate (3 mL) was added and extracted four times with ethyl acetate. The extracts were dried (sodium sulfate) and concentrated in vacuo to yield 1-bromo-8-methylimidazo[1,5-a]pyrazin-3-yl)methanol (145 mg).

$^1$H NMR: δ 2.30 (t, J=7 Hz, 1H), 2.92 (s, 3H), 5.02 (d, J=7 Hz, 2H), 7.48 (d, J=5 Hz, 1H), 7.85 (d, J=5 Hz, 1H).

14b. Synthesis of N-(4-(3-(hydroxymethyl)-8-methylimidazo[1,5-a]pyrazin-1-yl)-2-methoxyphenyl)-4-methoxy-1-methyl-1H-indole-2-carboxamide,

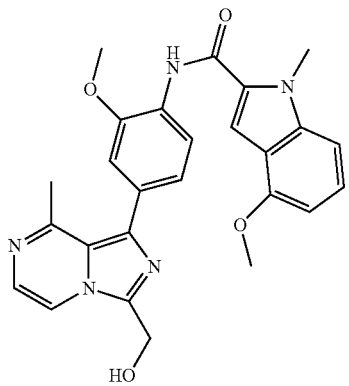 [SMILES: COc1cc(-c2nc(CO)n3ccnc(C)c23)ccc1NC(=O)c1cc2c(OC)cccc2n1C]

Using the procedure described in example 1 step 1f and purification by column chromatography (silica gel; dichloromethane with gradient methanol 0 to 10%) (1-bromo-8-methylimidazo[1,5-a]pyrazin-3-yl)methanol (25 mg) and 4-methoxy-N-(2-methoxy-4-(4,4,5,5-tetramethyl-1,3,2-dioxaborolan-2-yl)phenyl)-1-methyl-1H-indole-2-carboxamide (50 mg) yielded N-(4-(3-(hydroxymethyl)-8-methylimidazo[1,5-a]pyrazin-1-yl)-2-methoxyphenyl)-4-methoxy-1-methyl-1H-indole-2-carboxamide (31 mg)

$^1$H NMR: δ 2.53 (s, 3H), 3.99 (s, 3H), 4.01 (s, 3H), 4.12 (s, 3H), 5.08 (brs, 2H), 6.57 (d, J=9 Hz, 1H), 7.03-7.32 (m, 5H), 7.49 (d, J=5 Hz, 1H), 7.84 (d, J=5 Hz, 1H), 8.57 (d, J=9 Hz, 1H), 8.68 (brs, 1H).
UPLC: Method 40_80: Rt=1.04 min, (M+H)$^+$=472

Example 15

N-(4-(3-((1H-imidazol-1-yl)methyl)-8-methylimidazo[1,5-a]pyrazin-1-yl)-2-methoxyphenyl)-4-methoxy-1-methyl-1H-indole-2-carboxamide

15a. Synthesis of 3-((1H-imidazol-1-yl)methyl)-1-bromo-8-methylimidazo[1,5-a]pyrazine

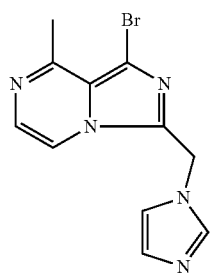 [SMILES: Cc1nccn2c(Cn3ccnc3)nc(Br)c12]

To 1-bromo-8-methylimidazo[1,5-a]pyrazin-3-yl)methanol (0.475 mmol, 115 mg) in dichloromethane (5 mL) (suspension) at 0° C. was added thionyl chloride (0.950 mmol, 0.069 mL). The reaction mixture was allowed to warm to room temperature and acetonitrile (4 mL) was added. After one hour imidazole (2.375 mmol, 162 mg) was added and again after one hour triethylamine (1.900 mmol, 0.265 mL) was added. After stirring the reaction for 3 days at room temperature the reaction mixture was concentrated in vacuo.

To the residue dichloromethane and saturated aqueous sodium hydrogencarbonate was added. The organic layer was separated and the aqueous layer washed twice with dichloromethane. The combined organic extracts were dried (sodium sulfate) and concentrated in vacuo. Purification using column chromatography (silicagel dichloromethane/Methanol 10/1) yielded 3-((1H-imidazol-1-yl)methyl)-1-bromo-8-methylimidazo[1,5-a]pyrazine (0.11 g)

$^1$H NMR: δ 2.94 (s, 3H), 5.52 (s, 2H), 6.94-7.70 (m, 5H).

15b. Synthesis of N-(4-(3-((1H-imidazol-1-yl)methyl)-8-methylimidazo[1,5-a]pyrazin-1-yl)-2-methoxyphenyl)-4-methoxy-1-methyl-1H-indole-2-carboxamide

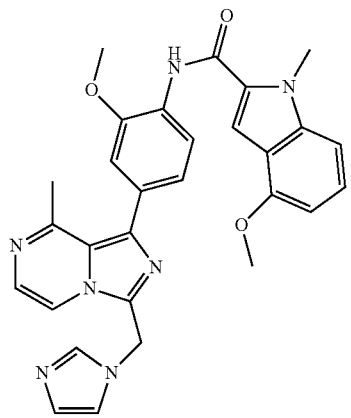 [SMILES: COc1cc(-c2nc(Cn3ccnc3)n3ccnc(C)c23)ccc1NC(=O)c1cc2c(OC)cccc2n1C]

Using the procedure described in example 1 step 1f and purification by column chromatography (silica gel; dichloromethane with gradient 10 to 17% methanol) 3-((1H-imidazol-1-yl)methyl)-1-bromo-8-methylimidazo[1,5-a]pyrazine (32 mg) and 4-methoxy-N-(2-methoxy-4-(4,4,5,5-tetramethyl-1,3,2-dioxaborolan-2-yl)phenyl)-1-methyl-1H-indole-2-carboxamide (60 mg) yielded N-(4-(3-((1H-imidazol-1-yl)methyl)-8-methylimidazo[1,5-a]pyrazin-1-yl)-2-methoxyphenyl)-4-methoxy-1-methyl-1H-indole-2-carboxamide (35 mg).

$^1$H NMR: δ 2.56 (s, 3H), 4.01 (s, 3H), 4.03 (s, 3H), 4.13 (s, 3H), 5.60 (s, 2H), 6.57 (d, J=9 Hz, 1H), 7.00-7.68 (m, 9H), 8.62 (d, J=9 Hz, 1H), 8.71 (brs, 1H).
UPLC: Method 0_60: Rt=2.26 min, (M+H)$^+$=522

Example 16

4-Methoxy-N-(2-methoxy-4-(8-methyl-3-(1-(tetrahydro-2H-pyran-4-yl)azetidin-3-yl)imidazo[1,5-a]pyrazin-1-yl)phenyl)-1-methyl-1H-indole-2-carboxamide

16a. Synthesis of benzyl 3-((3-chloropyrazin-2-yl)methylcarbamoyl)azetidine-1-carboxylate

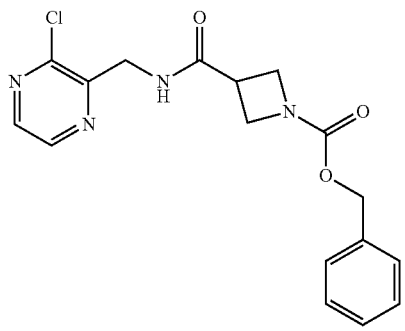 [SMILES: O=C(NCc1nccnc1Cl)C1CN(C(=O)OCc2ccccc2)C1]

To azetidine-3-carboxylic acid (49.5 mmol, 5 g) in dioxane (150 ml), water (150 ml) and triethylamine (54.4 mmol, 7.58 ml) was added N-(benzyloxycarbonyloxy)succinimide (51.9 mmol, 12.94 g) and stirred at room temperature for half an hour. The reaction mixture was quenched with water and 30 ml of 2N hydrochloric acid and extracted three times with dichloromethane. The organic layers were combined, filtered through a phase separation filter and concentrated in vacuo. The residue was dissolved in dichloromethane and extracted three times with aqueous saturated sodium hydrogencarbonate solution. The aqueous layers were combined, acidified with 2N hydrochloric acid and extracted three times with dichloromethane. The organic layers were combined, washed with brine, filtered through a phase separation filter and concentrated in vacuo to give 1-(benzyloxycarbonyl)azetidine-3-carboxylic acid (10.27 g).

To a solution of 1-(benzyloxycarbonyl)azetidine-3-carboxylic acid (21.25 mmol, 5 g) in dichloromethane (60 ml) under a nitrogen atmosphere were added N,N-dimethylformamide (1.063 mmol, 0.083 ml) and oxalyl chloride (2M solution in dichloromethane, 25.00 mmol, 12.5 ml). After stirring at room temperature for two hours the reaction mixture was concentrated in vacuo to give 5.53 gram of crude benzyl 3-(chlorocarbonyl)azetidine-1-carboxylate.

N,N-diisopropylethylamine (109 mmol, 18.01 ml) and a solution of benzyl 3-(chlorocarbonyl)azetidine-1-carboxylate (5.53 g) in dichloromethane (32.5 ml) were added to a stirred suspension of 2-aminomethyl-3-chloropyrazine hydrochloride (content 77%; 21.80 mmol, 5.10 g) in dichloromethane (55 ml) at room temperature to give a dark brown solution. After stirring at room temperature for two hours the reaction mixture was quenched with water and filtered over decalite. Layers were separated and to the aqueous layer saturated aqueous sodium hydrogencarbonate solution was added and the layer was extracted three times with dichloromethane. The organic layers were combined, washed with brine, dried (sodium sulfate), and concentrated in vacuo. The residue was purified by column chromatography (silica gel, dichloromethane/methanol gradient 10/0 to 9/1) to give benzyl 3-((3-chloropyrazin-2-yl)methylcarbamoyl)azetidine-1-carboxylate (6.46 g).

NMR: δ 3.37-3.45 (m, 1H), 4.16-4.30 (m, 4H), 4.71 (d, J=5 Hz, 2H), 5.10 (s, 2H), 6.92-6.97 (m, 1H), 7.28-7.47 (m, 5H), 8.33 (d, J=2 Hz, 1H), 8.44 (d, J=2 Hz, 1H).

16b. Synthesis of 4-methoxy-N-(2-methoxy-4-(8-methyl-3-(1-(tetrahydro-2H-pyran-4-yl)azetidin-3-yl)imidazo[1,5-a]pyrazin-1-yl)phenyl)-1-methyl-1H-indole-2-carboxamide; IDR 0998, IDR 0993, IDR0988, IDR0989, IDR 0983, IDR 0981

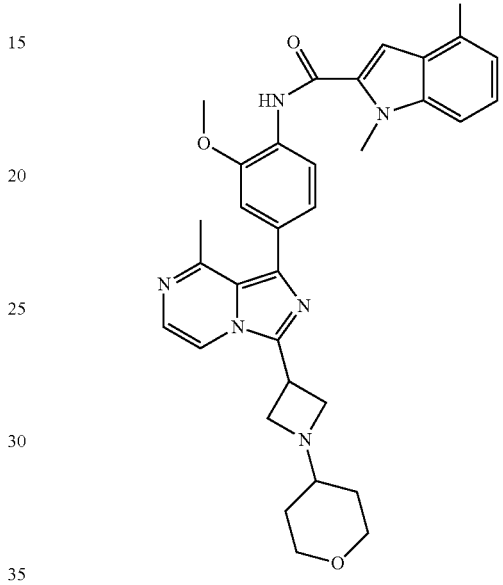

Benzyl 3-((3-chloropyrazin-2-yl)methylcarbamoyl)azetidine-1-carboxylate (5.88 g) was transformed into benzyl 3-(8-chloroimidazo[1,5-a]pyrazin-3-yl)azetidine-1-carboxylate (4.99 g) using the procedures described in example 3 step 3b by stirring the reaction at room temperature for one hour and by purification using column chromatography (silica gel; dichloromethane with gradient 0 to 10% methanol).

According to the procedure described in example 2 step 2d and purification by column chromatography (silica gel; dichloromethane/methanol gradient 95/5 to 8/2) 3-(8-chloroimidazo[1,5-a]pyrazin-3-yl)azetidine-1-carboxylate (4.99 g) afforded benzyl 3-(8-methylimidazo[1,5-a]pyrazin-3-yl)azetidine-1-carboxylate (3.98 g)

Using the procedure described in example 2 step 2f and purification by column chromatography (silica gel; dichloromethane/methanol gradient 10/0 to 9/1) benzyl 3-(8-methylimidazo[1,5-a]pyrazin-3-yl)azetidine-1-carboxylate (1 g) yielded benzyl 3-(1-bromo-8-methylimidazo[1,5-a]pyrazin-3-yl)azetidine-1-carboxylate (1.58 g).

Benzyl 3-(1-bromo-8-methylimidazo[1,5-a]pyrazin-3-yl)azetidine-1-carboxylate (1.58 g) was dissolved in 37% hydrochloric acid (14.84 ml) and stirred at room temperature. After one hour the reaction mixture was concentrated in vacuo and coevaporated with toluene. Then the residue was dissolved in dichloromethane/methanol, 15 gram of Silica-carbonate (0.77 mmol/gram) was added and the suspension was stirred for 15 minutes. The suspension was filtered, the solids rinsed with methanol and the filtrate was concentrated in vacuo to give crude 3-(azetidin-3-yl)-1-bromo-8-methylimidazo[1,5-a]pyrazine (1.1 g).

To tetrahydro-4-h-pyran-4-one (3.74 mmol, 0.346 ml) in dichloromethane (5 ml) and acetic acid (0.306 ml) was added 3-(azetidin-3-yl)-1-bromo-8-methylimidazo[1,5-a]pyrazine (1.872 mmol, 500 mg) in dichloromethane (10 ml) and after stirring for 20 minutes under a nitrogen atmosphere at room temperature sodium cyanoborohydride (3.74 mmol, 235 mg) was added in portions. After one hour the reaction mixture was quenched with water, a saturated aqueous sodium hydrogencarbonate solution was added (pH of reaction mixture ~7) followed by 2M sodium hydroxide until the pH reached 11 and extracted three times with dichloromethane. The organic layers were combined, filtered through a phase separation filter and concentrated in vacuo. Purification by column chromatography (silica gel; dichloromethane with gradient 0 to 10% methanol) gave 1-bromo-8-methyl-3-(1-(tetrahydro-2H-pyran-4-yl)azetidin-3-yl)imidazo[1,5-a]pyrazine (38 mg).

Using the procedure described in example 4 step 4c and purification by column chromatography (silica gel; dichloromethane with gradient 10 to 15% methanol) 1-bromo-8-methyl-3-(1-(tetrahydro-2H-pyran-4-yl)azetidin-3-yl)imidazo[1,5-a]pyrazine (37.8 mg) and 4-methoxy-N-(2-methoxy-4-(4,4,5,5-tetramethyl-1,3,2-dioxaborolan-2-yl)phenyl)-1-methyl-1H-indole-2-carboxamide (47.0 mg) yielded 83 mg of impure product. Additional purification on prep-HPLC (column Luna C18(2); gradient acetonitrile/water with constant 0.003M trifluoroacetic acid) yielded 6 mg of 4-methoxy-N-(2-methoxy-4-(8-methyl-3-(1-(tetrahydro-2H-pyran-4-yl)azetidin-3-yl)imidazo[1,5-a]pyrazin-1-yl)phenyl)-1-methyl-1h-indole-2-carboxamide.

$^1$H NMR: δ 1.35-1.77 (m, 4H), 2.42-2.52 (m, 1H), 2.50 (s, 3H), 3.36-3.44 (m, 2H), 3.57-3.63 (m, 2H), 3.87-4.14 (m, 5H), 4.01 (s, 6H), 4.13 (s, 3H), 6.57 (d, J=9 Hz, 1H), 7.03-7.32 (m, 5H), 7.46 (d, J=5 Hz, 1H), 7.65 (d, J=5 Hz, 1H), 8.58 (d, J=9 Hz, 1H), 8.69 (brs, 1H).

UPLC: Method 0_60: Rt=2.43 min, (M+H)$^+$=581

Example 17

4-Methoxy-N-(2-methoxy-4-(8-methyl-3-(piperidin-4-yl)imidazo[1,5-a]pyrazin-1-yl)phenyl)-1-methyl-1H-indole-2-carboxamide

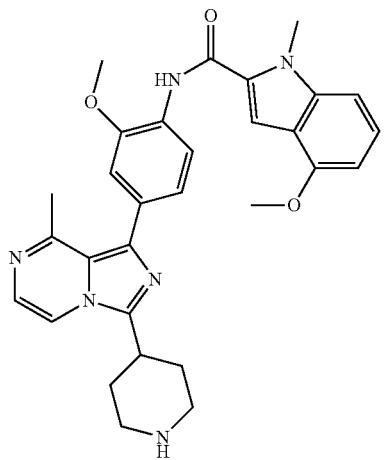 [SMILES: COc1cc(-c2nc(C3CCNCC3)n3ccnc(C)c23)ccc1NC(=O)c1cc2c(OC)cccc2n1C]

Using the procedures described in example 16 step 16a 1-[(benzyloxy)carbonyl]piperidine-4-carboxylic acid (2.5 g) was transformed into 2.75 g of crude benzyl 4-(chlorocarbonyl)piperidine-1-carboxylate and the latter compound was coupled with 2-aminomethyl-3-chloropyrazine hydrochloride (content 77%; 2.28 g) to give benzyl 4-((3-chloropyrazin-2-yl)methylcarbamoyl)piperidine-1-carboxylate (3.08 g) after purification by column chromatography (silica gel, dichloromethane/methanol gradient 100/0 to 90/10).

Benzyl 4-((3-chloropyrazin-2-yl)methylcarbamoyl)piperidine-1-carboxylate (3.08 g) was transformed into benzyl 4-(8-chloroimidazo[1,5-a]pyrazin-3-yl)piperidine-1-carboxylate (2.97 g) using the procedures described in example 1 step 1b by stirring the reaction at 70° C. for 1.5 hour and purification using column chromatography (silica gel; dichloromethane with gradient 0 to 10% methanol).

Benzyl 4-(8-chloroimidazo[1,5-a]pyrazin-3-yl)piperidine-1-carboxylate (2 g) was transformed into benzyl 4-(8-methylimidazo[1,5-a]pyrazin-3-yl)piperidine-1-carboxylate (1.50 g) according to the reaction procedure described in example 2 step 2d, work-up using extraction ethyl acetate/saturated aqueous sodium hydrogen carbonate and purification by column chromatography (silica gel: dichloromethane/methanol gradient 10/0 to 9/1)

Using the procedure described in example 2 step 2f performing the reaction at room temperature and no purification by column chromatography benzyl 4-(8-methylimidazo[1,5-a]pyrazin-3-yl)piperidine-1-carboxylate (165 mg) gave crude benzyl 4-(1-bromo-8-methylimidazo[1,5-a]pyrazin-3-yl)piperidine-1-carboxylate (239 mg) which was used as such in the next step.

Benzyl 4-(1-bromo-8-methylimidazo[1,5-a]pyrazin-3-yl)piperidine-1-carboxylate (0.471 mmol, 202 mg) was dissolved in 37% hydrochloric acid (32.9 mmol, 2.745 ml). The reaction mixture was stirred at room temperature for one hour. Water was added and the aqueous mixture washed twice with diethyl ether. The aqueous layer was basified with aqueous sodium hydroxide and extracted twice with dichloromethane. The combined organic extracts were dried (sodium sulfate) and concentrated in vacuo to give 1-bromo-8-methyl-3-(piperidin-4-yl)imidazo[1,5-a]pyrazine (100 mg).

Using the procedure described in example 4 step 4c and purification by column chromatography (silica gel; dichloromethane with gradient 0 to 20% methanol) 1-bromo-8-methyl-3-(piperidin-4-yl)imidazo[1,5-a]pyrazine (30 mg) and 4-methoxy-N-(2-methoxy-4-(4,4,5,5-tetramethyl-1,3,2-dioxaborolan-2-yl)phenyl)-1-methyl-1H-indole-2-carboxamide (44 mg) yielded 18 mg of impure product. Additional purification on prep-HPLC (column Luna C18(2); gradient acetonitrile/water with constant 0.003M trifluoroacetic acid) yielded 3.3 mg of 4-methoxy-N-(2-methoxy-4-(8-methyl-3-(piperidin-4-yl)imidazo[1,5-a]pyrazin-1-yl)phenyl)-1-methyl-1H-indole-2-carboxamide.

UPLC: Method 0_60: Rt=2.15 min, (M+H)$^+$=525

Example 18

N-(4-(3-(1-(2-(dimethylamino)-2-oxoethyl)piperidin-4-yl)-8-methylimidazo[1,5-a]pyrazin-1-yl)-2-methoxyphenyl)-1-methyl-1H-indole-2-carboxamide

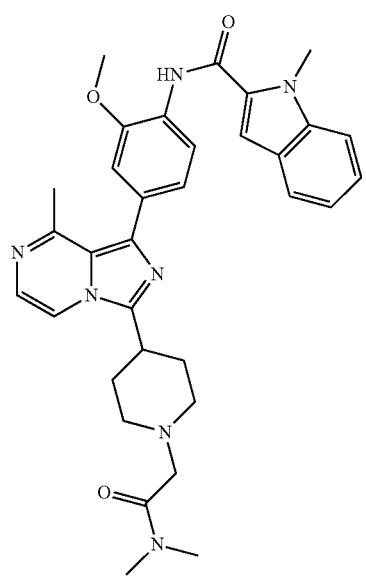 [SMILES: COc1cc(-c2nc(C3CCN(CC(=O)N(C)C)CC3)n3ccnc(C)c23)ccc1NC(=O)c1cc2ccccc2n1C]

To 1-bromo-8-methyl-3-(piperidin-4-yl)imidazo[1,5-a]pyrazine (0.447 mmol, 132 mg) in toluene (1 ml) and N,N-dimethylformamide (1 ml) were added triethylamine (0.894 mmol, 0.125 ml) and 2-chloro-N,N-dimethylacetamide (0.447 mmol, 0.046 ml). After stirring at room temperature for two hours water and dichloromethane were added, mixture was put on a phase separation filter and concentrated in vacuo. Purification by column chromatography (silica gel; dichloromethane with gradient 0 to 20% methanol) gave 2-(4-(1-bromo-8-methylimidazo[1,5-a]pyrazin-3-yl)piperidin-1-yl)-N,N-dimethylacetamide (100 mg).

Using the procedure described in example 4 step 4c and purification by prep-HPLC (column Luna C18(2); gradient acetonitrile/water with constant 0.003M trifluoroacetic acid) 2-(4-(1-bromo-8-methylimidazo[1,5-a]pyrazin-3-yl)piperidin-1-yl)-N,N-dimethylacetamide (33 mg) and N-(2-methoxy-4-(4,4,5,5-tetramethyl-1,3,2-dioxaborolan-2-yl)phenyl)-1-methyl-1H-indole-2-carboxamide (35.3 mg) yielded N-(4-(3-(1-(2-(dimethylamino)-2-oxoethyl)piperidin-4-yl)-8-methylimidazo[1,5-a]pyrazin-1-yl)-2-methoxyphenyl)-1-methyl-1H-indole-2-carboxamide (6 mg)

UPLC: Method 0_60: Rt=2.34 min, (M+H)$^+$=580

Example 19

N-(4-(3-(1-(2-(dimethylamino)acetyl)piperidin-4-yl)-8-methylimidazo[1,5-a]pyrazin-1-yl)-2-methoxyphenyl)-1-methyl-1H-indole-2-carboxamide

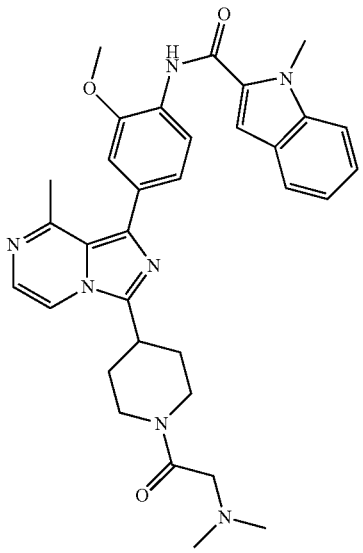 [SMILES: COc1cc(-c2nc(C3CCN(C(=O)CN(C)C)CC3)n3ccnc(C)c23)ccc1NC(=O)c1cc2ccccc2n1C]

To N,N-dimethylglycine (0.445 mmol, 45.9 mg) in dichloromethane (1 ml) and N,N-dimethylformamide (0.5 ml). were added N,N-diisopropylethylamine (1.762 mmol, 0.291 ml) and O-(benzotriazol-1-yl)-N,N,N',N'-tetramethyluronium tetrafluoroborate (0.617 mmol, 198 mg) and stirred at room temperature for 10 minutes. Then 1-bromo-8-methyl-3-(piperidin-4-yl)imidazo[1,5-a]pyrazine (0.440 mmol, 130 mg) dissolved in dichloromethane (2 ml) and N,N-dimethylformamide (0.5 ml) was added. After stirring at room temperature for two hours water and dichloromethane were added, mixture was put on a phase separation filter and concentrated in vacuo. Purification by column chromatography (silica gel; dichloromethane with gradient 0 to 20% methanol) gave 1-(4-(1-bromo-8-methylimidazo[1,5-a]pyrazin-3-yl)piperidin-1-yl)-2-(dimethylamino)ethanone (141 mg).

Using the procedure described in example 4 step 4c and purification by column chromatography (silica gel; dichloromethane with gradient 0 to 20% methanol) 1-(4-(1-bromo-8-methylimidazo[1,5-a]pyrazin-3-yl)piperidin-1-yl)-2-(dimethylamino)ethanone (46 mg) and 4-methoxy-N-(2-methoxy-4-(4,4,5,5-tetramethyl-1,3,2-dioxaborolan-2-yl)phenyl)-1-methyl-1H-indole-2-carboxamide (49 mg) yielded impure product. Additional purification on prep-HPLC (column Luna C18(2); gradient acetonitrile/water with constant 0.003M trifluoroacetic acid) yielded 15 mg of N-(4-(3-(1-(2-(dimethylamino)acetyl)piperidin-4-yl)-8-methylimidazo[1,5-a]pyrazin-1-yl)-2-methoxyphenyl)-1-methyl-1H-indole-2-carboxamide.

UPLC: Method 0_60: Rt=2.31 min, (M+H)$^+$=580

Example 20

N-(4-(3-(1-(2-Aminoacetyl)piperidin-4-yl)-8-methylimidazo[1,5-a]pyrazin-1-yl)-2-methoxyphenyl)-1-methyl-1H-indole-2-carboxamide

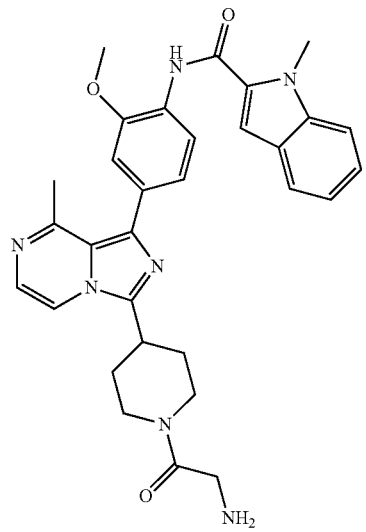 [SMILES: COc1cc(-c2nc(C3CCN(C(=O)CN)CC3)n3ccnc(C)c23)ccc1NC(=O)c1cc2ccccc2n1C]

Using the procedure reaction of Boc-aminoxyacetic acid (78 mg) and 1-bromo-8-methyl-3-(piperidin-4-yl)imidazo[1,5-a]pyrazine (130 mg) gave tert-butyl 2-(4-(1-bromo-8-methylimidazo[1,5-a]pyrazin-3-yl)piperidin-1-yl)-2-oxoethylcarbamate (319 mg) as crude product which was used without further purification. Again using the procedures described in example 19 the latter compound (50 mg) gave tert-butyl 2-(4-(1-(3-methoxy-4-(4-methoxy-1-methyl-1H-indole-2-carboxamido)phenyl)-8-methylimidazo[1,5-a]pyrazin-3-yl)piperidin-1-yl)-2-oxoethylcarbamate (31 mg). The latter compound (31 mg) was dissolved in dichloromethane (2 ml) and trifluoroacetic acid (1.2 ml) was added. After stirring at room temperature for 18 hours water, aqueous sodium hydrogencarbonate and potassium hydroxide (until pH>9) were added. Extraction with dichloromethane/methanol (9/1) twice, filtering over a phase separation filter and concentrating in vacuo gave N-(4-(3-(1-(2-aminoacetyl)piperidin-4-yl)-8-methylimidazo[1,5-a]pyrazin-1-yl)-2-methoxyphenyl)-1-methyl-1H-indole-2-carboxamide (14 mg).

UPLC: Method 0_60: Rt=2.22 min, (M+H)$^+$=552

Example 21

N-(4-(3-(1-carbamoylpiperidin-4-yl)-8-methylimidazo[1,5-a]pyrazin-1-yl)-2-methoxyphenyl)-4-methoxy-1-methyl-1H-indole-2-carboxamide

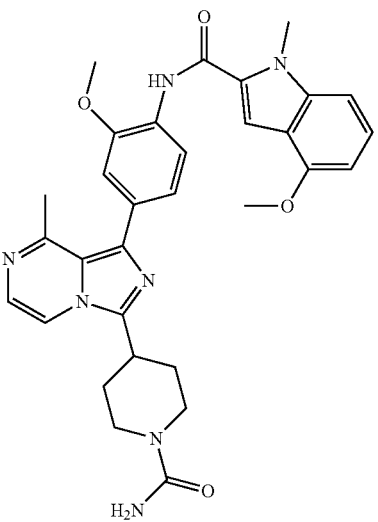 [SMILES: COc1cc(-c2nc(C3CCN(C(N)=O)CC3)n3ccnc(C)c23)ccc1NC(=O)c1cc2c(OC)cccc2n1C]

1-Bromo-8-methyl-3-(piperidin-4-yl)imidazo[1,5-a]pyrazine (0.169 mmol, 50 mg) was dissolved in dichloromethane (1 ml) and triethylamine (0.545 mmol, 76 μl) and trimethylsilyl isocyanate (0.186 mmol, 25.3 μl) were added at 0° C. After stirring at room temperature for one hour water and 2N hydrochloric acid was added and stirred for 15 minutes. The reaction mixture was basified with 2 N aqueous sodium hydroxide until pH=10 and extracted three times with dichloromethane. The combined organic extracts were dried (sodium sulfate) and concentrate in vacuo to afford 4-(1-bromo-8-methylimidazo[1,5-a]pyrazin-3-yl)piperidine-1-carboxamide (40 mg).

Using the procedure described in example 4 step 4c and purification by column chromatography (silica gel; dichloromethane with gradient 0 to 20% methanol) 4-(1-bromo-8-methylimidazo[1,5-a]pyrazin-3-yl)piperidine-1-carboxamide (20 mg) and 4-methoxy-N-(2-methoxy-4-(4,4,5,5-tetramethyl-1,3,2-dioxaborolan-2-yl)phenyl)-1-methyl-1H-indole-2-carboxamide (26 mg) gave N-(4-(3-(1-carbamoylpiperidin-4-yl)-8-methylimidazo[1,5-a]pyrazin-1-yl)-2-methoxyphenyl)-4-methoxy-1-methyl-1H-indole-2-carboxamide (10.5 mg).

UPLC: Method 0_60: Rt=2.45 min, (M+H)$^+$=568.

Example 22

Methyl 4-(1-(3-methoxy-4-(4-methoxy-1-methyl-1H-indole-2-carboxamido)phenyl)-8-methylimidazo[1,5-a]pyrazin-3-yl)piperidine-1-carboxylate

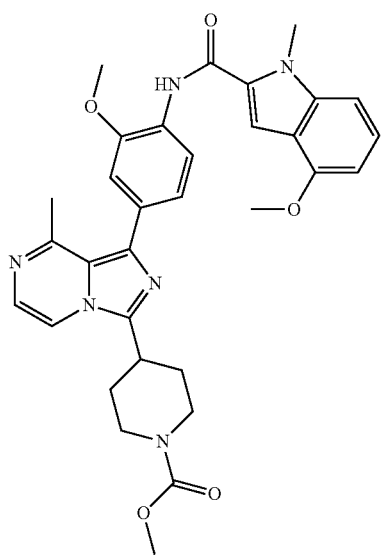 [SMILES: COC(=O)N1CCC(c2nc(-c3ccc(NC(=O)c4cc5c(OC)cccc5n4C)c(OC)c3)c3c(C)nccn23)CC1]

1-Bromo-8-methyl-3-(piperidin-4-yl)imidazo[1,5-a]pyrazine (0.169 mmol, 50 mg) was dissolved in dichloromethane (1 ml) and triethylamine (0.337 mmol, 47 µl) and methyl chloroformate (0.186 mmol, 14.40 µl) were added at 0° C. After stirring at room temperature for one hour water and dichloromethane were added. The organic layer was separated, dried (sodium sulfate) and concentrated in vacuo to give methyl 4-(1-bromo-8-methylimidazo[1,5-a]pyrazin-3-yl)piperidine-1-carboxylate (51 mg).

Using the procedure described in example 4 step 4c and purification by column chromatography (silica gel; dichloromethane with gradient 0 to 20% methanol) methyl 4-(1-bromo-8-methylimidazo[1,5-a]pyrazin-3-yl)piperidine-1-carboxylate (25 mg) and 4-methoxy-N-(2-methoxy-4-(4,4,5,5-tetramethyl-1,3,2-dioxaborolan-2-yl)phenyl)-1-methyl-1H-indole-2-carboxamide (31 mg) yielded impure product. Additional purification on prep-HPLC (column Luna C18(2); gradient acetonitrile/water with constant 0.003M trifluoroacetic acid) yielded methyl 4-(1-(3-methoxy-4-(4-methoxy-1-methyl-1H-indole-2-carboxamido)phenyl)-8-methylimidazo[1,5-a]pyrazin-3-yl)piperidine-1-carboxylate (5 mg).

UPLC: Method 40_80: Rt=1.00 min, (M+H)$^+$=583.

Example 23

N-(2-methoxy-4-(8-methyl-3-(4-methylpiperazin-1-yl)imidazo[1,5-a]pyrazin-1-yl)phenyl)-1-methyl-1H-indole-2-carboxamide

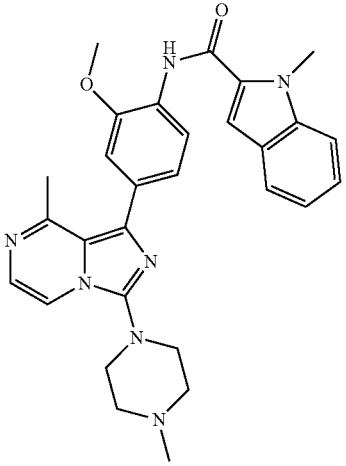 [SMILES: COc1cc(-c2nc(N3CCN(C)CC3)n3ccnc(C)c23)ccc1NC(=O)c1cc2ccccc2n1C]

To 2-aminomethyl-3-chloropyrazine hydrochloride (content 80%; 4.44 mmol, 1 g) and N,N-diisopropylethylamine (17.77 mmol, 3.10 ml) in dichloromethane (20 ml) under N$_2$ at 0° C. was added N-methylpiperazin-4-carbamoyl chloride hydrochloride (4.89 mmol, 0.973 g). After stirring at room temperature for 18 hours water was added and the mixture extracted three times with ethyl acetate. The combined organic layers were washed with brine, dried (sodium sulfate) and concentrated in vacuo. Purification by column chromatography (silica gel; dichloromethane with gradient 0 to 10% methanol) gave N-((3-chloropyrazin-2-yl)methyl)-4-methylpiperazine-1-carboxamide (513 mg).

To N-((3-chloropyrazin-2-yl)methyl)-4-methylpiperazine-1-carboxamide (485 mg) in acetonitrile (3 mL) under a N$_2$ flow was added phosphorus oxychloride (878 µl) and heated at 60° C. (bath temperature) for five hours and at 80° C. for one hour. Then the reaction mixture was concentrated in vacuo. Toluene was added and the mixture was concentrated in vacuo. Residue was taken up with acetonitrile, 7N ammonia in methanol was added with cooling and the suspension was stirred for 16 hours, then filtered and the filtrate concentrated in vacuo. Dichloromethane was added to the residue, again filtered and the filtrate concentrated in vacuo to give 8-chloro-3-(4-methylpiperazin-1-yl)imidazo[1,5-a]pyrazine (400 mg).

8-Chloro-3-(4-methylpiperazin-1-yl)imidazo[1,5-a]pyrazine (51 mg) was transformed into 8-methyl-3-(4-methylpiperazin-1-yl)imidazo[1,5-a]pyrazine (31 mg) according to the reaction procedure described in example 2 step 2d and purification by column chromatography (silica gel; ethyl acetate).

Using the procedure described in example 1 step 1d performing the reaction at 50° C. for one hour and purification by column chromatography (silica gel; ethyl acetate) 8-methyl-3-(4-methylpiperazin-1-yl)imidazo[1,5-a]pyrazine (31 mg) gave 1-bromo-8-methyl-3-(4-methylpiperazin-1-yl)imidazo[1,5-a]pyrazine (16 mg).

Using the procedure described in example 4 step 4c and purification by column chromatography (silica gel; dichloromethane with gradient 0 to 5% methanol 1-bromo-8-methyl-3-(4-methylpiperazin-1-yl)imidazo[1,5-a]pyrazine (16 mg) and N-(2-methoxy-4-(4,4,5,5-tetramethyl-1,3,2-dioxaborolan-2-yl)phenyl)-1-methyl-1H-indole-2-carboxamide (23 mg) yielded impure product. Additional purification on prep-HPLC (column Luna C18(2); gradient acetonitrile/water with constant 0.003M trifluoroacetic acid) yielded N-(2-methoxy-4-(8-methyl-3-(4-methylpiperazin-1-yl)imidazo[1,5-a]pyrazin-1-yl)phenyl)-1-methyl-1H-indole-2-carboxamide (12 mg).

UPLC: Method 0_60: Rt=2.29 min, (M+H)+=510.

Example 24

N-(2-methoxy-4-(8-methyl-3-(morholin-4-yl)imidazo[1,5-a]pyrazin-1-yl)phenyl)-1-methyl-1H-indole-2-carboxamide

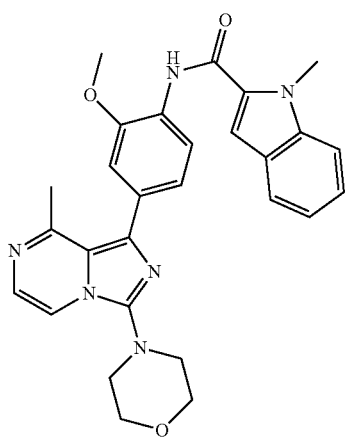 [SMILES: COc1cc(-c2nc(N3CCOCC3)n3ccnc(C)c23)ccc1NC(=O)c1cc2ccccc2n1C]

According to the procedures described for example 23 using morpholine-4-carbonyl chloride instead of N-methylpiperazin-4-carbamoyl chloride the title compound was prepared.

UPLC: Method 40_80: Rt=1.08 min, (M+H)+=497.

Example 25

Isopropyl 2-methoxy-4-(8-methyl-3-(4-morpholinopiperidin-1-yl)imidazo[1,5-a]pyrazin-1-yl)phenylcarbamate 25a. Synthesis of isopropyl 2-methoxy-4-(4,4,5,5-tetramethyl-1,3,2-dioxaborolan-2-yl)phenylcarbamate

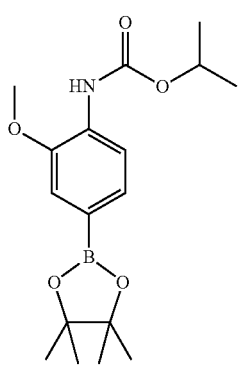 [SMILES: COc1cc(B2OC(C)(C)C(C)(C)O2)ccc1NC(=O)OC(C)C]

To a solution of triphosgene (1.485 mmol, 0.441 g) in tetrahydrofuran (20 ml) was added drop wise a solution of 4-amino-3-methoxyphenylboronic acid, pinacol ester (4.01 mmol, 1 g) and N,N-diisopropylethylamine (5.02 mmol, 0.829 ml) in tetrahydrofuran (30 ml) at room temperature. The temperature was kept between 20 and 30° C. After 30 minutes a solution of 2-propanol (8.03 mmol, 0.614 ml) and N,N-diisopropylethylamine (5.02 mmol, 0.829 ml) in tetrahydrofuran (20 ml) was added drop wise to the reaction mixture keeping the temperature between the 20-30° C. The reaction mixture was heated till reflux. After two hours an additional 10 ml of 2-propanol was added and the reaction mixture stirred at reflux temperature for 3 days. The reaction mixture was poured in water (150 ml) and extracted with ethyl acetate (150 ml). The organic layer was washed with 10% sodium chloride solution (10 ml), dried (magnesium sulfate) and evaporated till dryness to yield isopropyl 2-methoxy-4-(4,4,5,5-tetramethyl-1,3,2-dioxaborolan-2-yl)phenylcarbamate (1.18 g) as a dark brown oil $^1$H NMR: δ 1.30 (d, J=7 Hz, 6H), 1.34 (s, 12H), 3.91 (s, 3H), 5.03 (hepted, 1H), 7.24-7.26 (m, 1H), 7.31 (brs, 1H), 7.42-7.46 (m, 1H), 8.09-8.15 (m, 1H).

25b Synthesis of isopropyl 2-methoxy-4-(8-methyl-3-(4-morpholinopiperidin-1-yl)imidazo[1,5-a]pyrazin-1-yl)phenylcarbamate

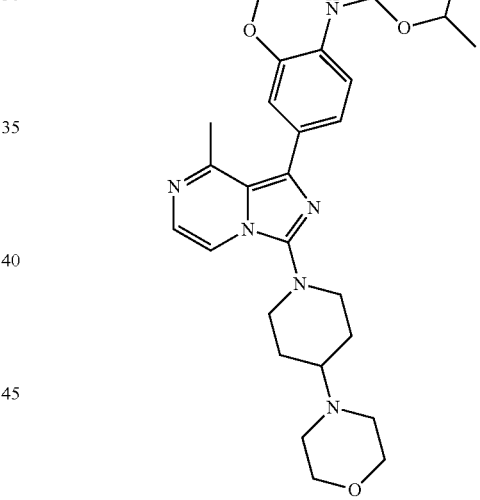

To trichloromethyl chloroformate (4.19 mmol, 0.505 ml) in ethyl acetate (5 ml) at 0° C. was added dropwise 1,4-dioxa-8-azaspiro[4.5]decane (6.98 mmol, 0.895 ml) in ethyl acetate (5 ml) and N,N-diisopropylethylamine (6.98 mmol, 1.217 ml). After one hour the mixture was concentrated, the residue was dissolved in dichloromethane (25 ml) and 2-aminomethyl-3-chloropyrazine hydrochloride (content 60%; 10.00 mmol, 3 g) and triethylamine (27.9 mmol, 3.89 ml) were added. After stirring for 16 hours at room temperature the reaction mixture was diluted with water, filtered over decalite, washed with water, filtered over a phase separation filter and concentrated in vacuo. The crude product was dissolved in dichloromethane containing 1% triethylamine and purification by column chromatography (silica gel; dichloromethane containing 1% triethylamine) gave N-((3-chloropyrazin-2-yl)methyl)-1,4-dioxa-8-azaspiro[4.5]decane-8-carboxamide (1.5 g).

N-((3-chloropyrazin-2-yl)methyl)-1,4-dioxa-8-azaspiro[4.5]decane-8-carboxamide (1.2 g) was transformed into 8-(8-chloroimidazo[1,5-a]pyrazin-3-yl)-1,4-dioxa-8-azaspiro[4.5]decane (0.44 g) using the procedure described in example 3 step 3b and purification by column chromatography (silica gel; dichloromethane with gradient 0 to 10% methanol and continuous 1% triethylamine).

8-(8-Chloroimidazo[1,5-a]pyrazin-3-yl)-1,4-dioxa-8-azaspiro[4.5]decane (840 mg) was transformed into 8-(8-methylimidazo[1,5-a]pyrazin-3-yl)-1,4-dioxa-8-azaspiro[4.5]decane (650 mg) according to the reaction procedure described in example 2 step 2d and purification by column chromatography (silica gel; dichloromethane/methanol 99/1 and continuous 1% triethylamine).

Using the procedure described in example 2 step 2f performing the reaction at room temperature and purification by column chromatography (silica gel; dichloromethane/methanol 99/1 and continuous 1% triethylamine) 8-(8-methylimidazo[1,5-a]pyrazin-3-yl)-1,4-dioxa-8-azaspiro[4.5]decane (650 mg) gave 8-(1-bromo-8-methylimidazo[1,5-a]pyrazin-3-yl)-1,4-dioxa-8-azaspiro[4.5]decane (280 mg).

To 8-(1-bromo-8-methylimidazo[1,5-a]pyrazin-3-yl)-1,4-dioxa-8-azaspiro[4.5]decane (1.246 mmol, 440 mg) in acetone (5 ml) was added 36% hydrochloric acid (12.46 mmol, 1.3 ml). After 16 hours at 60° C. the reaction mixture was concentrated, the residue dissolved in dichloromethane, neutralized with saturated aqueous sodium hydrogencarbonate solution, filtered over a phase separation filter and concentrated. The crude product was dissolved in dichloromethane and purified by column chromatography on silica gel (heptane/ethyl acetate gradient 1:1 to 0:1) to give 0.2 g of a mixture of starting material and product. This mixture was dissolved in tetrahydrofuran (1 ml), aqueous 10% $H_2SO_4$ solution (2 ml) was added and the mixture was stirred at room temperature. The mixture was neutralized with solid sodium hydrogencarbonate, extracted with dichloromethane, dried (sodium sulfate) and concentrated in vacuo. The crude product was dissolved in dichloromethane and purified by column chromatography on silica gel (dichloromethane) to give 1-(1-bromo-8-methylimidazo[1,5-a]pyrazin-3-yl)piperidin-4-one (60 mg).

According to the procedure described in example 2 step 2b and purification by column chromatography (silica gel; dichloromethane) 1-(1-bromo-8-methylimidazo[1,5-a]pyrazin-3-yl)piperidin-4-one (60 mg) gave 4-(1-(1-bromo-8-methylimidazo[1,5-a]pyrazin-3-yl)piperidin-4-yl)morpholine (70 mg).

Using the procedure described in example 4 step 4c and purification on prep-HPLC (column Luna C18(2); gradient acetonitrile/water with constant 0.003M trifluoroacetic acid) 4-(1-(1-bromo-8-methylimidazo[1,5-a]pyrazin-3-yl)piperidin-4-yl)morpholine (30 mg) and isopropyl 2-methoxy-4-(4,4,5,5-tetramethyl-1,3,2-dioxaborolan-2-yl)phenylcarbamate (26.4 mg) yielded isopropyl 2-methoxy-4-(8-methyl-3-(4-morpholinopiperidin-1-yl)imidazo[1,5-a]pyrazin-1-yl)phenylcarbamate (7 mg).

UPLC: Method 0_60: Rt=2.03 min, (M+H)$^+$=509.

Example 26

Using the procedures described in the previous experiments, in particular in example 2, 7, 9 and 12, the following compounds were prepared from N-((3-chloropyrazin-2-yl)methyl)-4-oxocyclohexanecarboxamide.

26a. (S)-pentan-2-yl 2-methoxy-4-(3-((trans)-4-((2-methoxyethyl)(methyl)amino)cyclohexyl)-8-methylimidazo[1,5-a]pyrazin-1-yl)phenylcarbamate

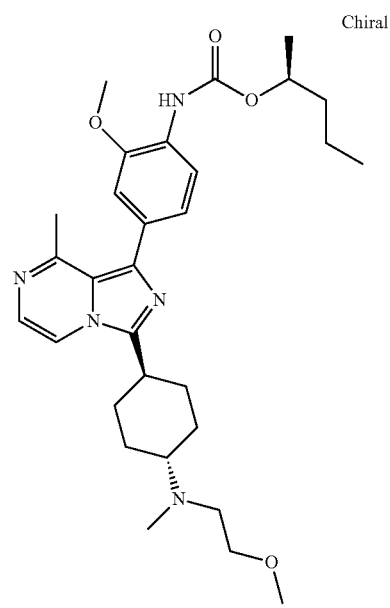 [SMILES: CCC[C@H](C)OC(=O)Nc1ccc(-c2nc([C@H]3CC[C@H](N(C)CCOC)CC3)n3ccnc(C)c23)cc1OC]

UPLC: Method 0_60: Rt=2.28 min, (M+H)$^+$=538.

26b. N-(4-(3-((trans)-4-(dimethylamino)cyclohexyl)-8-methylimidazo[1,5-a]pyrazin-1-yl)-2-methoxyphenyl)-4-methoxy-1-methyl-1H-indole-2-carboxamide

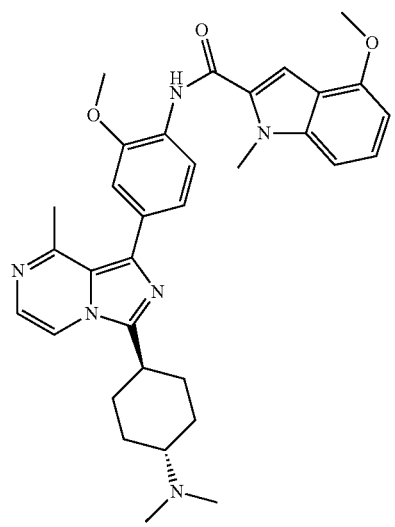 [SMILES: COc1cc(-c2nc([C@H]3CC[C@H](N(C)C)CC3)n3ccnc(C)c23)ccc1NC(=O)c1cc2c(OC)cccc2n1C]

UPLC: Method 0_60: Rt=2.25 min, (M+H)$^+$=567.

26c. 4-methoxy-N-(2-methoxy-4-(3-((cis)-4-((2-methoxyethyl)(methyl)amino)cyclo-hexyl)-8-methylimidazo[1,5-a]pyrazin-1-yl)phenyl)-1-methyl-1H-indole-2-carboxamide

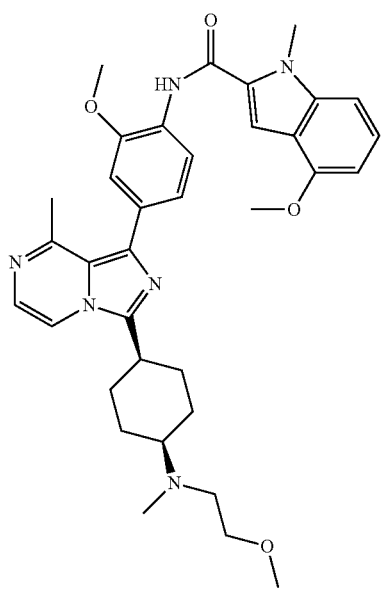 [SMILES: COCCN(C)[C@H]1CC[C@@H](c2nc(-c3ccc(NC(=O)c4cc5c(OC)cccc5n4C)c(OC)c3)c3c(C)nccn32)CC1]

UPLC: Method 0__60: Rt=2.43 min, (M+H)$^+$=611.

26d. 4-methoxy-N-(2-methoxy-4-(8-methyl-3-((cis)-4-morpholinocyclohexyl)imidazo[1,5-a]pyrazin-1-yl)phenyl)-1-methyl-1H-indole-2-carboxamide

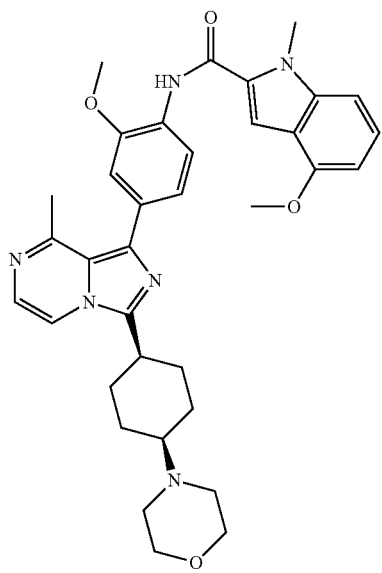 [SMILES: COc1cc(-c2nc([C@H]3CC[C@@H](N4CCOCC4)CC3)n3ccnc(C)c23)ccc1NC(=O)c1cc2c(OC)cccc2n1C]

UPLC: Method 0__60: Rt=2.42 min, LC-MS column 1: Rt 2.45 min (M+H)$^+$=609

26e. N-(4-(3-((cis)-4-(dimethylamino)cyclohexyl)-8-methylimidazo[1,5-a]pyrazin-1-yl)-2-methoxyphenyl)-4-methoxy-1-methyl-1H-indole-2-carboxamide

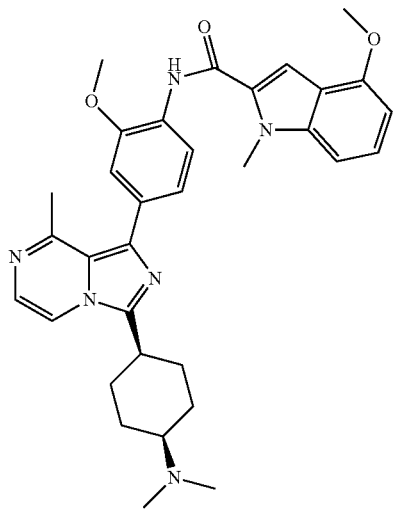 [SMILES: COc1cc(-c2nc([C@H]3CC[C@@H](N(C)C)CC3)n3ccnc(C)c23)ccc1NC(=O)c1cc2c(OC)cccc2n1C]

UPLC: Method 0__60: Rt=2.32 min, (M+H)$^+$=567.

26f. (S)-pentan-2-yl 4-(3-((cis)-4-(4-acetylpiperazin-1-yl)cyclohexyl)-8-methylimidazo[1,5-a]pyrazin-1-yl)-2-methoxyphenylcarbamate

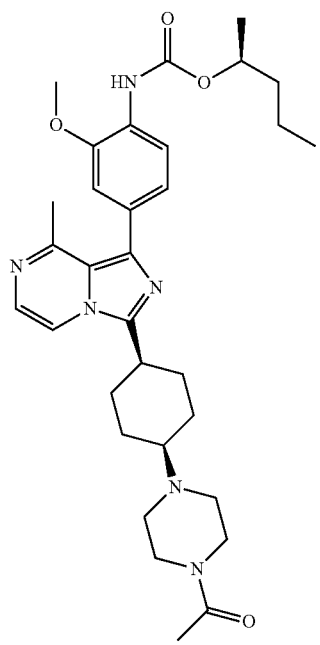 [SMILES: CCC[C@H](C)OC(=O)Nc1ccc(-c2nc([C@H]3CC[C@@H](N4CCN(C(C)=O)CC4)CC3)n3ccnc(C)c23)cc1OC]

UPLC: Method 0__60: Rt=2.17 min, (M+H)$^+$=577.

26g. (S)-pentan-2-yl 4-(3-((cis)-4-(3,3-difluoroazetidin-1-yl)cyclohexyl)-8-methylimidazo[1,5-a]pyrazin-1-yl)-2-methoxyphenylcarbamate

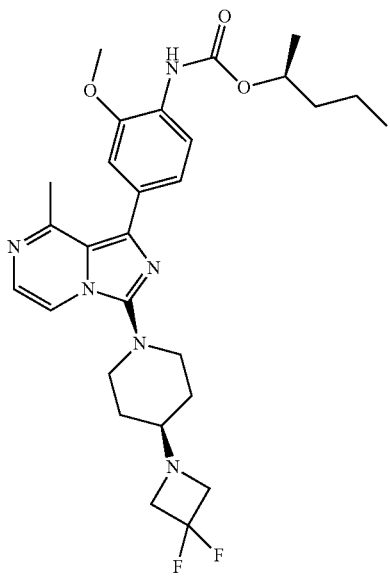

UPLC: Method 0_60: Rt=2.43 min, (M+H)$^+$=542.

Example 27

(S)-Pentan-2-yl 2-methoxy-4-(8-methyl-3-((1r,3r)-3-(4-methylpiperazin-1-yl)cyclobutyl)imidazo[1,5-a]pyrazin-1-yl)phenylcarbamate

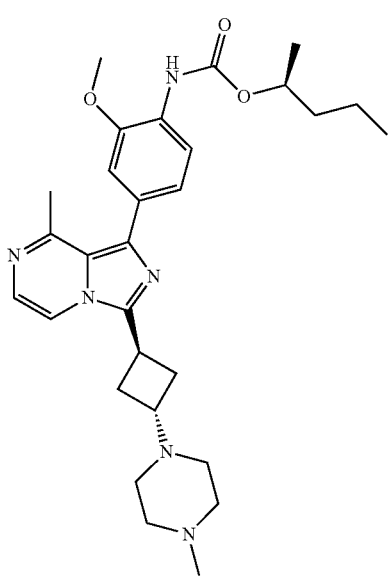 [SMILES: CCC[C@H](C)OC(=O)Nc1ccc(-c2nc([C@H]3C[C@H](N4CCN(C)CC4)C3)n3ccnc(C)c23)cc1OC]

The procedures described in example 2 step 2a, using 3-oxo-cyclobutanecarboxylic acid instead of 4-oxocyclohexanecarboxylate, were applied to prepare N-((3-chloropyrazin-2-yl)methyl)-3-oxocyclobutane-carboxamide. Using the procedures described in example 7 the latter compound was used to prepare (S)-pentan-2-yl 2-methoxy-4-(8-methyl-3-((1r,3r)-3-(4-methylpiperazin-1-yl)cyclobutyl)imidazo[1,5-a]pyrazin-1-yl)phenylcarbamate.

UPLC: Method 0_60: Rt=2.04 min, LC-MS column 2: Rt 2.31 min (M+H)$^+$=521.

Example 28

(S)-Pentan-2-yl 2-methoxy-4-(8-methyl-3-(3-(4-methylpiperazin-1-yl)cyclopentyl)imidazo[1,5-a]pyrazin-1-yl)phenylcarbamate

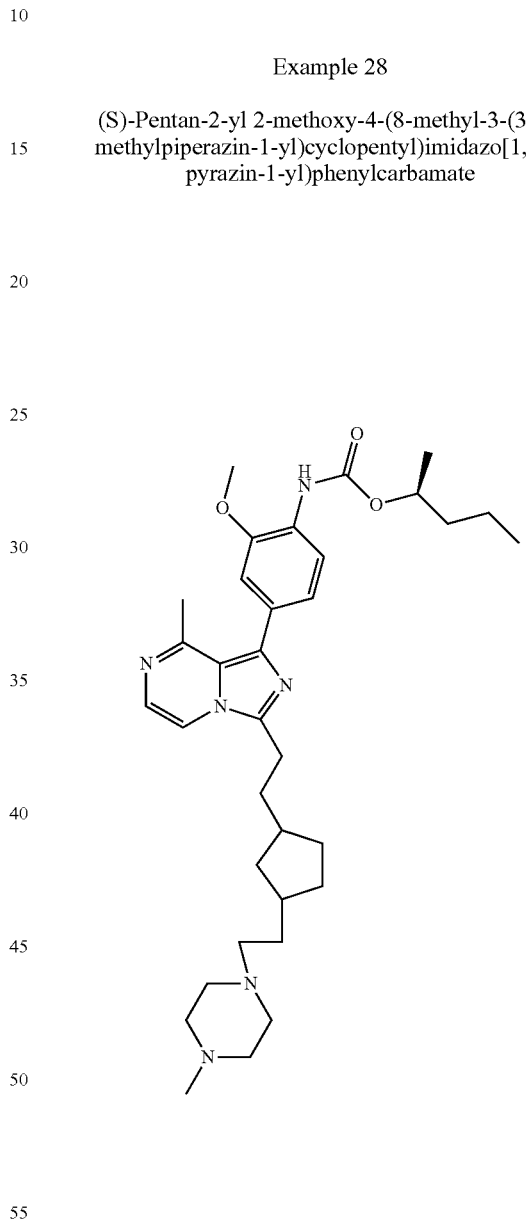

According to example 2 step 2a but using 3-oxo-1-cyclopentanecarboxylic acid instead of 4-oxocyclohexanecarboxylate N-((3-chloropyrazin-2-yl)methyl)-3-oxocyclobutane-carboxamide was prepared. Using the procedures described in example 7 the latter compound was used to prepare (S)-pentan-2-yl 2-methoxy-4-(8-methyl-3-(3-(4-methylpiperazin-1-yl)cyclopentyl) imidazo[1,5-a]pyrazin-1-yl) phenylcarbamate which was isolated as a racemic mixture of cis and trans isomers.

UPLC: Method 0_60: Rt=2.68 min and 2.72 min, (M+H)$^+$=535.

Example 29

(S)-Pentan-2-yl 2-methoxy-4-(3-((trans)-4-(N-(2-methoxyethyl)acetamido)cyclohexyl)-8-methylimidazo[1,5-a]pyrazin-1-yl)phenylcarbamate

Example 30

4-Methoxy-N-(2-methoxy-4-(8-methyl-3-(1-(tetrahydro-2H-pyran-4-yl)piperidin-4-yl)imidazo[1,5-a]pyrazin-1-yl)phenyl)-1-methyl-1H-indole-2-carboxamide

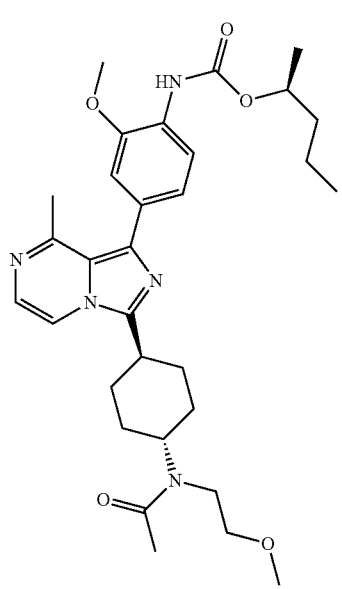 [SMILES: CCC[C@H](C)OC(=O)Nc1ccc(-c2nc([C@H]3CC[C@H](N(CCOC)C(C)=O)CC3)n3ccnc(C)c23)cc1OC]

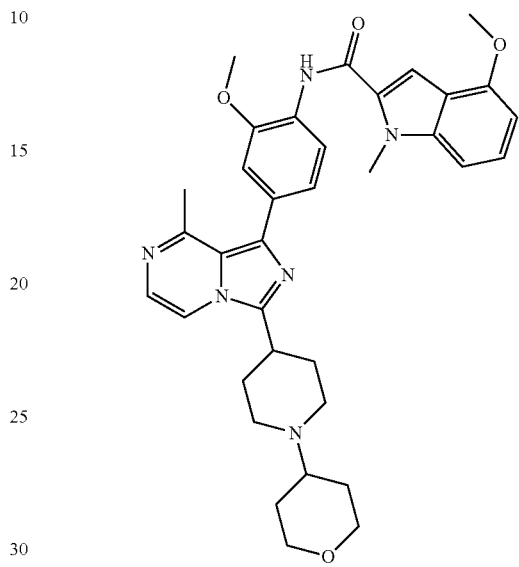

To (trans)-4-(1-bromo-8-methylimidazo[1,5-a]pyrazin-3-yl)-N-(2-methoxyethyl)cyclohexanamine (0.182 mmol, 67 mg) in dichloromethane (2 ml) and triethylamine (0.912 mmol, 0.127 ml) at 0° C. was added acetyl chloride (0.274 mmol, 0.020 ml). After stirring for 1 hour dichloromethane and water were added. The organic layer was separated, dried over a phase separation filter and concentrated in vacuo to give N-((trans)-4-(1-bromo-8-methylimidazo[1,5-a]pyrazin-3-yl)cyclohexyl)-N-(2-methoxyethyl)acetamide (72 mg).

Using the procedure described in example 4 step 4c and purification on prep-HPLC (column Luna C18(2); gradient acetonitrile/water with constant 0.003M trifluoroacetic acid) N-((trans)-4-(1-bromo-8-methylimidazo[1,5-a]pyrazin-3-yl)cyclohexyl)-N-(2-methoxyethyl)acetamide (22 mg) and (S)-pentan-2-yl 2-methoxy-4-(4,4,5,5-tetramethyl-1,3,2-dioxaborolan-2-yl)phenylcarbamate (19.5 mg) yielded (S)-pentan-2-yl 2-methoxy-4-(3-((trans)-4-(N-(2-methoxyethyl)acetamido)cyclohexyl)-8-methylimidazo[1,5-a]pyrazin-1-yl)phenylcarbamate (10 mg).

UPLC: Method 40_80: Rt=0.91 min, LC-MS column 2: Rt 2.61 min (M+H)$^+$=566.

Benzyl 4-(8-methylimidazo[1,5-a]pyrazin-3-yl)piperidine-1-carboxylate (3.71 mmol, 1.30 g) was dissolved in 37% hydrochloric acid (240 mmol, 20 ml). The reaction mixture was stirred at room temperature for two hours, then poured in water and washed twice with diethyl ether. The aqueous layer was concentrated in vacuo and co-evaporated with toluene and ethanol. The residue was dissolved in methanol and eluted twice over a column of Si-Carbonate (Silicycle, Loading 0.7 mmol/g) to give 8-methyl-3-(piperidin-4-yl)imidazo[1,5-a]pyrazine (0.93 g).

8-Methyl-3-(piperidin-4-yl)imidazo[1,5-a]pyrazine (172 mg) was transformed into 8-methyl-3-(1-(tetrahydro-2H-pyran-4-yl)piperidin-4-yl)imidazo[1,5-a]pyrazine (103 mg) according to the procedure described in example 2 step 2b using additional aqueous potassium hydroxide to adjust the water layer in the extraction to pH 10 and purification by column chromatography (silica gel; gradient dichloromethane to dichloromethane/methanol 9/1 with continuous 1% triethylamine present).

8-Methyl-3-(1-(tetrahydro-2H-pyran-4-yl)piperidin-4-yl)imidazo[1,5-a]pyrazine (0.303 mmol, 91 mg) was dissolved in dichloromethane (2 ml) and acetic acid (30.3 mmol, 1.734 ml). With stirring, bromine (0.303 mmol, 0.016 ml) in dichloromethane (0.2 mL) was added. After stirring at room temperature for one hour water was added and the mixture concentrated in vacuo. To the residue was added saturated aqueous sodium hydrogencarbonate and the mixture extracted twice with dichloromethane/methanol. The combined organic layers were concentrated in vacuo to yield 1-bromo-8-methyl-3-(1-(tetrahydro-2H-pyran-4-yl)piperidin-4-yl)imidazo[1,5-a]pyrazine (88 mg).

Using the procedure described in example 4 step 4c and purification on prep-HPLC (column Luna C18(2); gradient acetonitrile/water with constant 0.003M trifluoroacetic acid) 1-bromo-8-methyl-3-(1-(tetrahydro-2H-pyran-4-yl)piperidin-4-yl)imidazo[1,5-a]pyrazine (29 mg) and 4-methoxy-N-(2-methoxy-4-(4,4,5,5-tetramethyl-1,3,2-dioxaborolan-2-yl)phenyl)-1-methyl-1H-indole-2-carboxamide (33.4 mg) yielded 4-methoxy-N-(2-methoxy-4-(8-methyl-3-(1-(tetrahydro-2H-pyran-4-yl)piperidin-4-yl)imidazo[1,5-a]pyrazin-1-yl)phenyl)-1-methyl-1H-indole-2-carboxamide (5.7 mg).

UPLC: Method 0_60: Rt=2.28 min, (M+H)+=609.

Example 31

(S)-Pentan-2-yl 4-(3-(4-acetylpiperazin-1-yl)-8-methylimidazo[1,5-a]pyrazin-1-yl)-2-methoxyphenylcarbamate

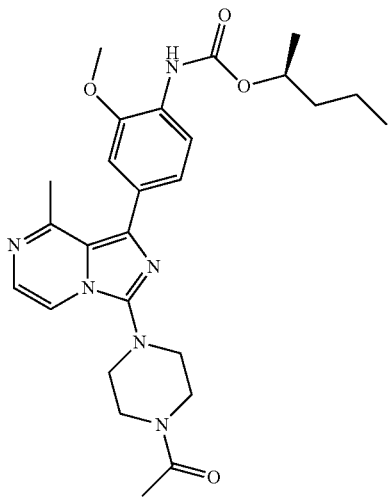 [SMILES: CCC[C@H](C)OC(=O)Nc1ccc(-c2nc(N3CCN(C(C)=O)CC3)n3ccnc(C)c23)cc1OC]

Trichloromethyl chloroformate (5.45 mmol, 0.657 ml) in tetrahydrofuran (20 ml) was cooled to 0° C. and a solution of benzyl 1-piperazinecarboxylate (4.54 mmol, 0.876 ml) and N,N-diisopropylethylamine (9.99 mmol, 1.651 ml) in tetrahydrofuran (20 ml) was added dropwise. After stirring for one hour at 0° C. the solids were removed by filtration over decalite and the filtrate was concentrated in vacuo to give crude benzyl 4-(chlorocarbonyl)piperazine-1-carboxylate. The latter compound was added to 2-aminomethyl-3-chloropyrazine hydrochloride (content 69%; 3.49 mmol, 0.91 g) in dichloromethane (15 ml) and triethylamine (10.46 mmol, 1.458 ml) and the reaction mixture was stirred over night at room temperature. Then the reaction mixture was filtered over decalite (washed with dichloromethane). The filtrate was concentrated and the crude product was purified using column chromatography (silica gel; dichloromethane with gradient 0 to 10% methanol) to give benzyl 4-((3-chloropyrazin-2-yl)methylcarbamoyl)piperazine-1-carboxylate (1.15 g).

Benzyl 4-((3-chloropyrazin-2-yl)methylcarbamoyl)piperazine-1-carboxylate (1.15 g) was transformed into benzyl 4-(8-chloroimidazo[1,5-a]pyrazin-3-yl)piperazine-1-carboxylate (522 mg) using the procedures described in example 1 step 1b performing the reaction at 70° C. for 2 hours and purification using column chromatography (silica gel; dichloromethane with gradient 0 to 10% methanol).

Benzyl 4-(8-chloroimidazo[1,5-a]pyrazin-3-yl)piperazine-1-carboxylate (522 mg) was transformed into benzyl 4-(8-methylimidazo[1,5-a]pyrazin-3-yl)piperazine-1-carboxylate (486 mg) using the procedure described in example 2 step 2d and purification using column chromatography (silica gel; dichloromethane with gradient 0 to 10% methanol).

Benzyl 4-(8-methylimidazo[1,5-a]pyrazin-3-yl)piperazine-1-carboxylate (486 mg) in 37% hydrochloric acid (97 mmol, 8 ml) was stirred at room temperature for two hours. Then water (16 ml) was added and the mixture washed twice with diethyl ether. The aqueous layer was concentrated in vacuo and co-evaporated with toluene and ethanol to give 8-methyl-3-(piperazin-1-yl)imidazo[1,5-a]pyrazine hydrochloride (322 mg).

To 8-methyl-3-(piperazin-1-yl)imidazo[1,5-a]pyrazine hydrochloride (0.359 mmol, 91 mg) and triethylamine (1.793 mmol, 0.250 ml) in dichloromethane (5 ml) was added acetic anhydride (0.538 mmol, 0.051 ml). After stirring at room temperature for 20 hours saturated aqueous sodium hydrogencarbonate solution was added and the mixture extracted three times with ethyl acetate. The combined organic layers were washed with brine, dried (sodium sulfate), and concentrated in vacuo to give 24 mg of crude product. To the aqueous layer solid sodium chloride was added and the mixture extracted three times with dichloromethane/methanol (4/1). The combined organic layers were washed with brine, dried (sodium sulfate), and concentrated in vacuo to give an additional 47 mg of crude product. The combined crude samples were purified using column chromatography (silica gel; dichloromethane with gradient 0 to 10% methanol) to give 1-(4-(8-methylimidazo[1,5-a]pyrazin-3-yl)piperazin-1-yl)ethanone (56 mg).

To 1-(4-(8-methylimidazo[1,5-a]pyrazin-3-yl)piperazin-1-yl)ethanone (0.208 mmol, 54 mg) in dichloromethane (1 ml) at room temperature was added N-bromosuccinimide (0.208 mmol, 37.1 mg). After stirring at room temperature for 5 minutes water was added and the mixture extracted three times with dichloromethane. The combined organic extracts were dried over a phase separation filter and concentrated in vacuo to give 1-(4-(1-bromo-8-methylimidazo[1,5-a]pyrazin-3-yl)piperazin-1-yl)ethanone (62 mg).

Using the procedure described in example 4 step 4c and purification using column chromatography (silica gel; dichloromethane with gradient 0 to 20% methanol) 1-(4-(1-bromo-8-methylimidazo[1,5-a]pyrazin-3-yl)piperazin-1-yl)ethanone (30 mg) and (S)-pentan-2-yl 2-methoxy-4-(4,4,5,5-tetramethyl-1,3,2-dioxaborolan-2-yl)phenylcarbamate (35.4 mg) yielded ((S)-pentan-2-yl 4-(3-(4-acetylpiperazin-1-yl)-8-methylimidazo[1,5-a]pyrazin-1-yl)-2-methoxyphenylcarbamate (23 mg).

UPLC: Method 40_80: Rt=0.94 min, (M+H)+=495.

Example 32

N-(4-(3-(4-(1-Acetylpiperidin-4-yl)piperazin-1-yl)-8-methylimidazo[1,5-a]pyrazin-1-yl)-2-methoxyphenyl)-4-methoxy-1-methyl-1H-indole-2-carboxamide

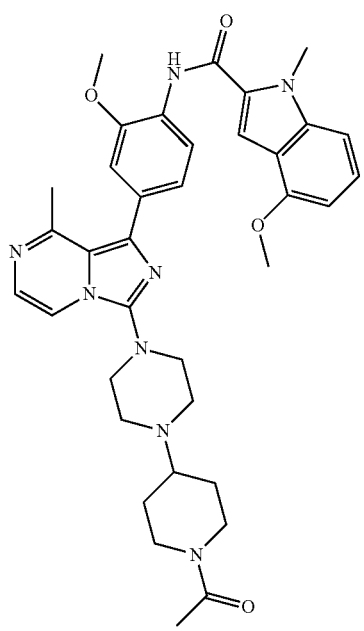 [SMILES: COc1cc(-c2nc(N3CCN(C4CCN(C(C)=O)CC4)CC3)n3ccnc(C)c23)ccc1NC(=O)c1cc2c(OC)cccc2n1C]

To 8-methyl-3-(piperazin-1-yl)imidazo[1,5-a]pyrazine hydrochloride (299 mg) in methanol was added a small amount of Si-Carbonate (Silicycle, Loading 0.7 mmol/g) and the solvent was removed under vacuum. The residue was put on a column with Si-carbonate (3 g), eluted with dichloromethane/methanol (4:1) to give 8-methyl-3-(piperazin-1-yl)imidazo[1,5-a]pyrazine (196 mg). The latter compound (50 mg) was transformed into 1-(4-(4-(8-methylimidazo[1,5-a]pyrazin-3-yl)piperazin-1-yl)piperidin-1-yl)ethanone (99 mg) according to the procedure described in example 2 step 2b and purification by column chromatography (silica gel; gradient dichloromethane to dichloromethane/methanol 85/15).

To 1-(4-(4-(8-methylimidazo[1,5-a]pyrazin-3-yl)piperazin-1-yl)piperidin-1-yl)ethanone (0.102 mmol, 35 mg) in dichloromethane (1 ml) at room temperature was added N-bromosuccinimide (0.102 mmol, 18.19 mg). After stirring at room temperature for 5 minutes water was added and the mixture extracted three times with dichloromethane. The combined organic extracts were dried over a phase separation filter and concentrated in vacuo to give 1-(4-(4-(1-bromo-8-methylimidazo[1,5-a]pyrazin-3-yl)piperazin-1-yl)piperidin-1-yl)ethanone (32 mg).

Using the procedure described in example 4 step 4c and purification by column chromatography (silica gel; dichloromethane with gradient 0 to 20% methanol) 1-(4-(4-(1-bromo-8-methylimidazo[1,5-a]pyrazin-3-yl)piperazin-1-yl)piperidin-1-yl)ethanone (30 mg) and 4-methoxy-N-(2-methoxy-4-(4,4,5,5-tetramethyl-1,3,2-dioxaborolan-2-yl)phenyl)-1-methyl-1H-indole-2-carboxamide (34.2 mg) yielded impure product. Additional purification on prep-HPLC (column Luna C18(2); gradient acetonitrile/water with constant 0.003M trifluoroacetic acid) yielded N-(4-(3-(4-(1-acetylpiperidin-4-yl)piperazin-1-yl)-8-methylimidazo[1,5-a]pyrazin-1-yl)-2-methoxyphenyl)-4-methoxy-1-methyl-1H-indole-2-carboxamide (11 mg).

UPLC: Method 0_60: Rt=2.22 min, (M+H)$^+$=651.

Example 33

Using procedures analogue to the one described in example 4 step 4c the following compounds were prepared from the 1-bromo-8-methylimidazo[1,5-a]pyrazine derivatives 33a. (S)-pentan-2-yl 2-methoxy-4-(8-methyl-3-((trans)-4-(4-methylpiperazin-1-yl)cyclohexyl)imidazo[1,5-a]pyrazin-1-yl)phenylcarbamate

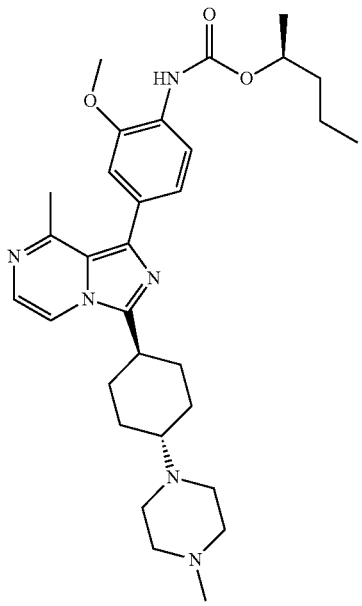 [SMILES: CCC[C@H](C)OC(=O)Nc1ccc(-c2nc([C@H]3CC[C@H](N4CCN(C)CC4)CC3)n3ccnc(C)c23)cc1OC]

UPLC: Method 0_60: Rt=2.06 min, (M+H)$^+$=549.

93

33b. N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide 2,2,2-trifluoroacetate

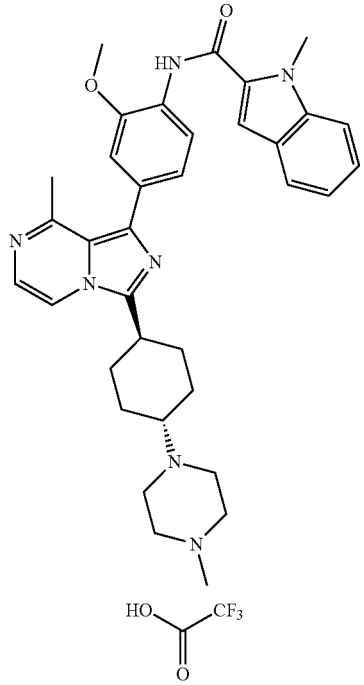

UPLC: Method 0_60: Rt=2.27 min, (M+H)⁺=592.

33c. N-(4-(3-((trans)-4-(4-acetylpiperazin-1-yl)cyclohexyl)-8-methylimidazo[1,5-a]pyrazin-1-yl)-2-methoxyphenyl)-1-methyl-1H-indole-2-carboxamide

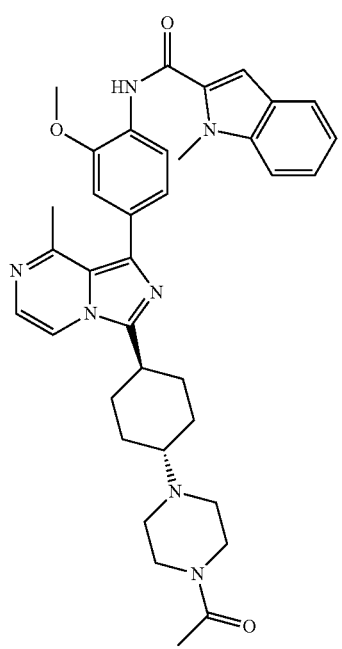 [SMILES: COc1cc(-c2nc([C@H]3CC[C@H](N4CCN(C(C)=O)CC4)CC3)n3ccnc(C)c23)ccc1NC(=O)c1cc2ccccc2n1C]

UPLC: Method 0_60: Rt=2.23 min, (M+H)⁺=620.

94

33d. (S)-pentan-2-yl 4-(3-((trans)-4-(4-acetylpiperazin-1-yl)cyclohexyl)-8-methylimidazo[1,5-a]pyrazin-1-yl)-2-methoxyphenylcarbamate

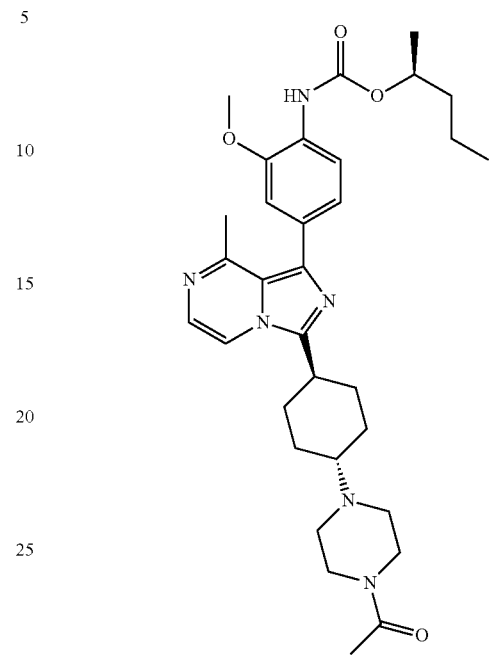

UPLC: Method 0_60: Rt=2.19 min, (M+H)⁺=577.

33e. (R)—N-(4-(3-(1-(2-(dimethylamino)acetyl)pyrrolidin-3-yl)-8-methylimidazo[1,5-a]pyrazin-1-yl)-2-methoxyphenyl)-4-methoxy-1-methyl-1H-indole-2-carboxamide

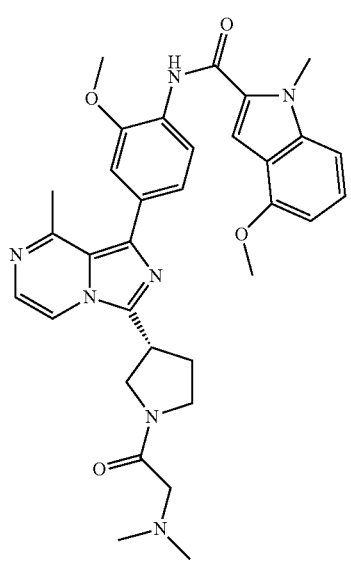 [SMILES: COc1cc(-c2nc([C@@H]3CCN(C(=O)CN(C)C)C3)n3ccnc(C)c23)ccc1NC(=O)c1cc2c(OC)cccc2n1C]

UPLC: Method 0_60: Rt=2.17 min, (M+H)⁺=596.

33f. (S)-pentan-2-yl 2-methoxy-4-(8-methyl-3-((cis)-4-(4-methylpiperazin-1-yl)cyclohexyl)imidazo[1,5-a]pyrazin-1-yl)phenylcarbamate

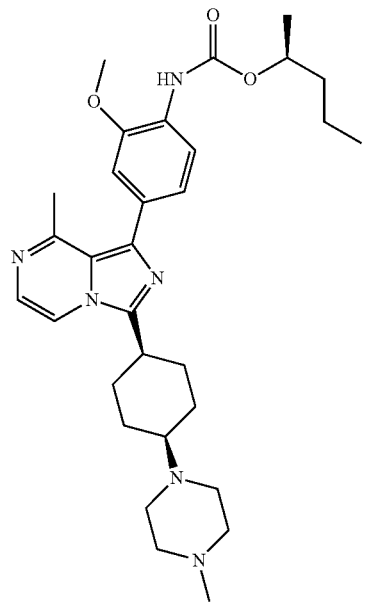 [SMILES: CCC[C@H](C)OC(=O)Nc1ccc(-c2nc([C@H]3CC[C@@H](N4CCN(C)CC4)CC3)n3ccnc(C)c23)cc1OC]

UPLC: Method 0_60: Rt=1.96 min, (M+H)+=549.

33g. N-(4-(3-(4-acetylpiperazin-1-yl)-8-methylimidazo[1,5-a]pyrazin-1-yl)-2-methoxyphenyl)-4-methoxy-1-methyl-1H-indole-2-carboxamide

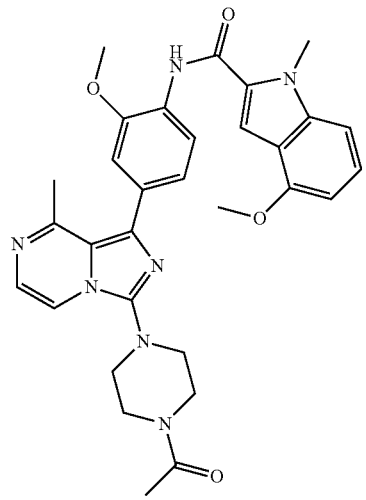 [SMILES: COc1cc(-c2nc(N3CCN(C(C)=O)CC3)n3ccnc(C)c23)ccc1NC(=O)c1cc2c(OC)cccc2n1C]

UPLC: Method 40_80: Rt=0.92 min, (M+H)+=568.

Example 34

4-Methoxy-N-(2-methoxy-4-(8-methyl-3-(4-(tetrahydro-2H-pyran-4-yl)piperazin-1-yl)imidazo[1,5-a]pyrazin-1-yl)phenyl)-1-methyl-1H-indole-2-carboxamide

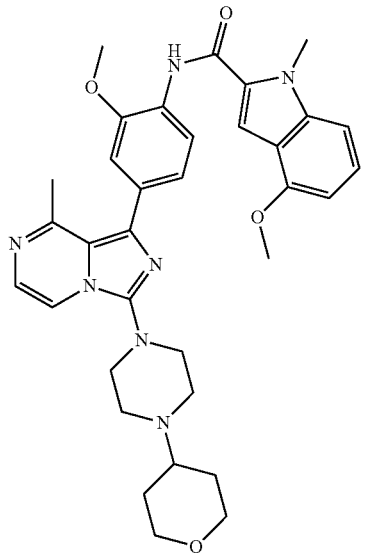 [SMILES: COc1cc(-c2nc(N3CCN(C4CCOCC4)CC3)n3ccnc(C)c23)ccc1NC(=O)c1cc2c(OC)cccc2n1C]

4-Methoxy-N-(2-methoxy-4-(8-methyl-3-(4-(tetrahydro-2H-pyran-4-yl)piperazin-1-yl)imidazo[1,5-a]pyrazin-1-yl)phenyl)-1-methyl-1H-indole-2-carboxamide was prepared from 8-methyl-3-(piperazin-1-yl)imidazo[1,5-a]pyrazine and tetrahydro-4-h-pyran-4-one using the procedures described in example 32.

UPLC: Method 0_60: Rt=2.19 min, (M+H)+=610.

Example 35

(R)-4-methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide

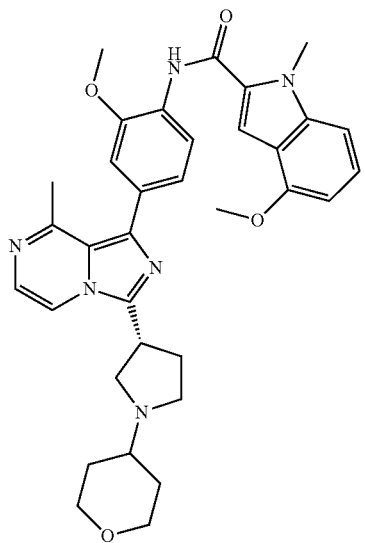 [SMILES: COc1cc(-c2nc([C@@H]3CCN(C4CCOCC4)C3)n3ccnc(C)c23)ccc1NC(=O)c1cc2c(OC)cccc2n1C]

Using the procedures described in example 32 (R)-1-bromo-8-methyl-3-(pyrrolidin-3-yl)imidazo[1,5-a]pyrazine hydrochloride was transformed into (R)-4-methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide.

UPLC: Method 0_60: Rt=2.59 min, (M+H)⁺=595.

Example 36

(S)-4-Methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide

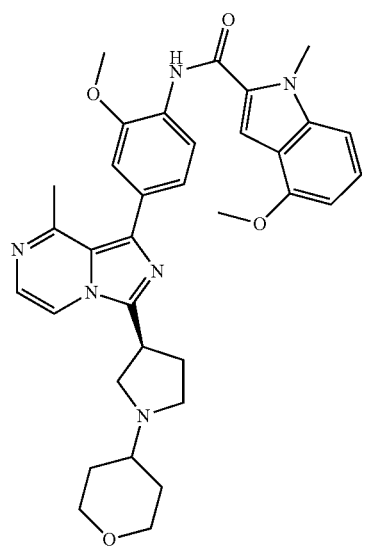 [SMILES: COc1cc(-c2nc([C@H]3CCN(C4CCOCC4)C3)n3ccnc(C)c23)ccc1NC(=O)c1cc2c(OC)cccc2n1C]

The title compound was prepared using the same methods as were applied for the R-isomer UPLC: Method 0_60: Rt=2.51 min, (M+H)⁺=595.

Example 37

4-Methoxy-N-(2-methoxy-4-(8-methyl-3-(3-(trifluoromethyl)-5,6-dihydro-[1,2,4]triazolo[4,3-a]pyrazin-7(8H)-yl)imidazo[1,5-a]pyrazin-1-yl)phenyl)-1-methyl-1H-indole-2-carboxamide

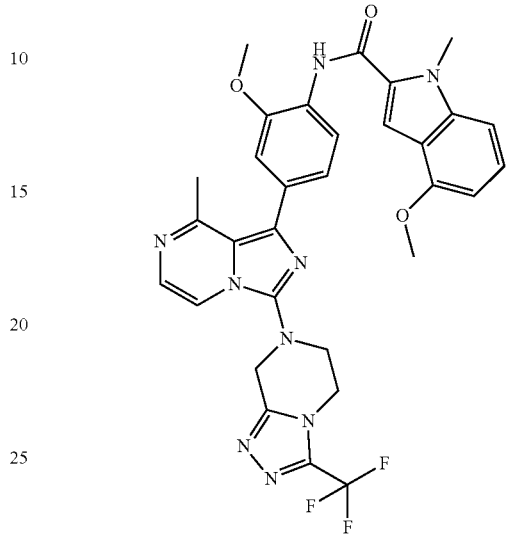

A suspension of 3-(trifluoromethyl)-1,2,4-triazolo[4,3-a]piperazine hydrochloride (10.94 mmol, 2.5 g) in a mixture of tetrahydrofuran (50 ml) and N,N-diisopropylethylamine (32.8 mmol, 5.42 ml) was added to trichloromethyl chloroformate (13.12 mmol, 1.583 ml) in tetrahydrofuran (50 ml) at 0° C. After one hour at 0° C. the reaction mixture was filtered over decalite and the filter washed with tetrahydrofuran. Then the filtrate was concentrated in vacuo. The residue (4.52 g, crude) was added to 2-aminomethyl-3-chloropyrazine hydrochloride (content 77%; 8.43 mmol, 1.97 g) in a mixture of dichloromethane (50 ml) and triethylamine (25.3 mmol, 3.52 ml) and the reaction mixture was stirred over night at room temperature. Then the reaction mixture was filtered over decalite and the filter washed with dichloromethane. The filtrate was washed with water. The aqueous layer was extracted three times with dichloromethane. The combined organic extracts were washed with brine, dried (sodium sulfate) and concentrated in vacuo. The crude product was purification by column chromatography (silica gel; dichloromethane with gradient 0 to 10% methanol) to give N-((3-chloropyrazin-2-yl)methyl)-3-(trifluoromethyl)-5,6-dihydro-[1,2,4]triazolo[4,3-a]pyrazine-7(8H)-carboxamide (2.707 g).

To N-((3-chloropyrazin-2-yl)methyl)-3-(trifluoromethyl)-5,6-dihydro-[1,2,4]triazolo[4,3-a]pyrazine-7(8H)-carboxamide (1.382 mmol, 500 mg) in ethyl acetate (5 ml) at 0° C. was added phosphorus oxychloride (5.53 mmol, 0.515 ml). The reaction mixture was stirred at room temperature for two days and at 60° C. for one day. The reaction mixture was cooled to 0° C., an excess solid sodium hydrogencarbonate was added and the suspension was stirred at 0° C. for 10 minutes and at room temperature for 20 minutes. Then the suspension was again cooled to 0° C., water was added and extracted three times with ethyl acetate. The combined organic layers were washed with brine, dried (sodium sulfate) and concentrated in vacuo. The residue was purified by column chromatography (silica gel; dichloromethane applying a gradient 0 to 10% methanol) to give 7-(8-chloroimidazo[1,5- a]pyrazin-3-yl)-3-(trifluoromethyl)-5,6,7,8-tetrahydro-[1,2,4]triazolo[4,3-a]pyrazine (119 mg).

7-(8-Chloroimidazo[1,5-a]pyrazin-3-yl)-3-(trifluoromethyl)-5,6,7,8-tetrahydro-[1,2,4]triazolo[4,3-a]pyrazine (269 mg) was transformed into 7-(8-methylimidazo[1,5-a]pyrazin-3-yl)-3-(trifluoromethyl)-5,6,7,8-tetrahydro-[1,2,4]triazolo[4,3-a]pyrazine (178 mg) using the procedure described in example 2 step 2d and purification using column chromatography (silica gel; dichloromethane with gradient 0 to 10% methanol).

Using the procedure described in example 2 step 2f and purification using column chromatography (silica gel; dichloromethane with gradient 0 to 10% methanol) 7-(8-methylimidazo[1,5-a]pyrazin-3-yl)-3-(trifluoromethyl)-5,6,7,8-tetrahydro-[1,2,4]triazolo[4,3-a]pyrazine (178 mg) was transformed into 7-(1-bromo-8-methylimidazo[1,5-a]pyrazin-3-yl)-3-(trifluoromethyl)-5,6,7,8-tetrahydro-[1,2,4]triazolo[4,3-a]pyrazine (151 mg).

Using the procedure described in example 4 step 4c and purification by column chromatography (silica gel; dichloromethane with gradient 0 to 20% methanol) 7-(1-bromo-8-methylimidazo[1,5-a]pyrazin-3-yl)-3-(trifluoromethyl)-5,6,7,8-tetrahydro-[1,2,4]triazolo[4,3-a]pyrazine (30 mg) and 4-methoxy-N-(2-methoxy-4-(4,4,5,5-tetramethyl-1,3,2-dioxaborolan-2-yl)phenyl)-1-methyl-1H-indole-2-carboxamide (35.8 mg) yielded 4-methoxy-N-(2-methoxy-4-(8-methyl-3-(3-(trifluoromethyl)-5,6-dihydro-[1,2,4]triazolo[4,3-a]pyrazin-7(8H)-yl)imidazo[1,5-a]pyrazin-1-yl)phenyl)-1-methyl-1H-indole-2-carboxamide (43 mg).

UPLC: Method 40_80: Rt=1.33 min, (M+H)$^+$=632.

Example 38

4-Methoxy-N-(2-methoxy-4-(8-methyl-3-(1-methyl-2-oxopiperidin-4-yl)imidazo[1,5-a]pyrazin-1-yl)phenyl)-1-methyl-1H-indole-2-carboxamide

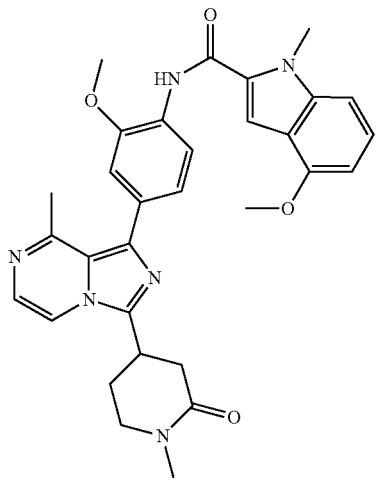 [SMILES: COc1cc(-c2nc(C3CCN(C)C(=O)C3)n3ccnc(C)c23)ccc1NC(=O)c1cc2c(OC)cccc2n1C]

2-Aminomethyl-3-chloropyrazine hydrochloride (content 77%; 5.36 mmol, 1.0 g) and 1-methyl-2-oxopiperidine-4-carboxylic acid (5.36 mmol, 0.843 g) were applied according to the procedure in example 13 step 13a and purified using column chromatography (silica gel; dichloromethane with 10% methanol) to give N-((3-chloropyrazin-2-yl)methyl)-1-methyl-2-oxopiperidine-4-carboxamide (940 mg).

Using the procedure described in example 3 step 3b and purification using column chromatography (silica gel; dichloromethane with 10% methanol) N-((3-chloropyrazin-2-yl)methyl)-1-methyl-2-oxopiperidine-4-carboxamide (407 mg) was transformed into 4-(8-chloroimidazo[1,5-a]pyrazin-3-yl)-1-methylpiperidin-2-one (140 mg).

4-(8-chloroimidazo[1,5-a]pyrazin-3-yl)-1-methylpiperidin-2-one (140 mg) was transformed into 1-methyl-4-(8-methylimidazo[1,5-a]pyrazin-3-yl)piperidin-2-one (50 mg) using the procedure described in example 2 step 2d and purification using column chromatography (silica gel; a gradient of heptanes/ethyl acetate 1/0 to 0/1 and then rinsing the column with dichloromethane containing 10% methanol).

To a solution of 1-methyl-4-(8-methylimidazo[1,5-a]pyrazin-3-yl)piperidin-2-one (0.205 mmol, 50 mg) in N,N-dimethylformamide (0.6 ml) was added N-bromosuccinimide (0.225 mmol, 40.1 mg) and the reaction mixture was stirred at room temperature for 15 minutes. Extraction dichloromethane/aqueous sodium hydrogen carbonate, drying (sodium sulfate) and concentrating in vacuo yielded the crude product. Purification by column chromatography (silica gel; dichloromethane with 10% methanol) yielded 4-(1-bromo-8-methylimidazo[1,5-a]pyrazin-3-yl)-1-methylpiperidin-2-one (46 mg).

Using the procedure described in example 4 step 4c and purification on prep-HPLC (column Luna C18(2); gradient acetonitrile/water with constant 0.003M trifluoroacetic acid) 4-(1-bromo-8-methylimidazo[1,5-a]pyrazin-3-yl)-1-methylpiperidin-2-one (46 mg) and 4-methoxy-N-(2-methoxy-4-(4,4,5,5-tetramethyl-1,3,2-dioxaborolan-2-yl)phenyl)-1-methyl-1H-indole-2-carboxamide (62.1 mg) yielded 4-methoxy-N-(2-methoxy-4-(8-methyl-3-(1-methyl-2-oxopiperidin-4-yl)imidazo[1,5-a]pyrazin-1-yl)phenyl)-1-methyl-1H-indole-2-carboxamide (15 mg).

UPLC: Method 40_80: Rt=0.94 min, (M+H)$^+$=553.

Example 39

N-(4-(3-((trans)-4-aminocyclohexyl)-8-methylimidazo[1,5-a]pyrazin-1-yl)-2-methoxyphenyl)-4-methoxy-1-methyl-1H-indole-2-carboxamide

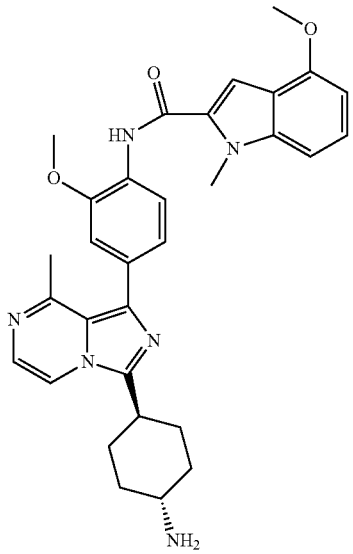 [SMILES: COc1cc(-c2nc([C@H]3CC[C@H](N)CC3)n3ccnc(C)c23)ccc1NC(=O)c1cc2c(OC)cccc2n1C]

Using the procedures described in example 17 (trans)-4-(benzyloxycarbonylamino)-cyclohexanecarboxylic acid was used to prepare N-(4-(3-((trans)-4-aminocyclohexyl)-8-methylimidazo[1,5-a]pyrazin-1-yl)-2-methoxyphenyl)-4-methoxy-1-methyl-1H-indole-2-carboxamide UPLC: Method 0_60: Rt=2.25 min, (M+H)$^+$=539.

Example 40

N-(4-(3-((trans)-4-(2,2-Difluoroethylamino)cyclohexyl)-8-methylimidazo[1,5-a]pyrazin-1-yl)-2-methoxyphenyl)-4-methoxy-1-methyl-1H-indole-2-carboxamide

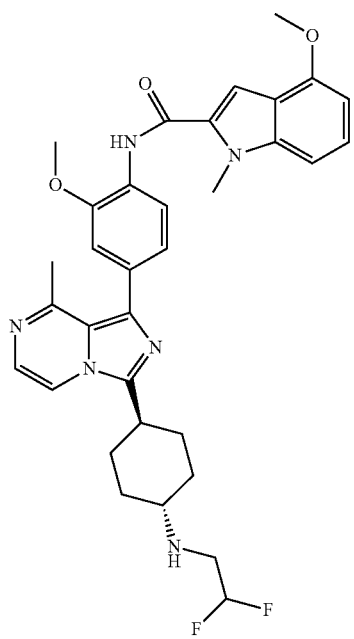 [SMILES: COc1cc(-c2nc([C@H]3CC[C@H](NCC(F)F)CC3)n3ccnc(C)c23)ccc1NC(=O)c1cc2c(OC)cccc2n1C]

Using the procedures described in example 17 (trans)-4-(benzyloxycarbonylamino)cyclohexanecarboxylic acid was used to prepare (trans)-4-(1-bromo-8-methylimidazo[1,5-a]pyrazin-3-yl)cyclohexanamine. The latter compound (0.217 mmol, 67.1 mg) was dissolved in N,N-dimethylformamide, potassium carbonate (0.651 mmol, 90 mg) was added followed by 2-bromo-1,1-difluoroethane (0.217 mmol, 17.47 µl, 31.5 mg) and the reaction mixture was stirred in the micro wave at 60° C. After one hour another amount of 2-bromo-1,1-difluoroethane (0.217 mmol, 17.47 µl, 31.5 mg) was added and the reaction mixture was stirred in the micro wave at 60° C. for another hour. The reaction mixture was filtered, the filter was rinsed with acetonitrile and the filtrate was concentrated. The residue was purified by column chromatography (silica gel, gradient dichloromethane/methanol 10/0 to 9/1) to give (trans)-4-(1-bromo-8-methylimidazo[1,5-a]pyrazin-3-yl)-N-(2,2-difluoroethyl)cyclohexanamine (39.8 mg).

Using the procedure described in example 4 step 4c and purification by column chromatography (silica gel; dichloromethane/methanol 4/1) (trans)-4-(1-bromo-8-methylimidazo[1,5-a]pyrazin-3-yl)-N-(2,2-difluoroethyl)cyclohexanamine (20 mg) and 4-methoxy-N-(2-methoxy-4-(4,4,5,5-tetramethyl-1,3,2-dioxaborolan-2-yl)phenyl)-1-methyl-1H-indole-2-carboxamide (23.4 mg) yielded impure product. Additional purification on prep-HPLC (column Luna C18(2); gradient acetonitrile/water with constant 0.003M trifluoroacetic acid) yielded N-(4-(3-((trans)-4-(2,2-difluoroethylamino)cyclohexyl)-8-methylimidazo[1,5-a]pyrazin-1-yl)-2-methoxyphenyl)-4-methoxy-1-methyl-1H-indole-2-carboxamide (9 mg).

UPLC: Method 0_60: Rt=2.34 min, (M+H)$^+$=603.

Example 41

Isopropyl 4-(3-((trans)-4-(3,3-difluoroazetidin-1-yl)cyclohexyl)-8-methylimidazo[1,5-a]pyrazin-1-yl)-2-methoxyphenyl(methyl)carbamate 41a. Synthesis of isopropyl 2-methoxy-4-(4,4,5,5-tetramethyl-1,3,2-dioxaborolan-2-yl)phenyl(methyl)carbamate

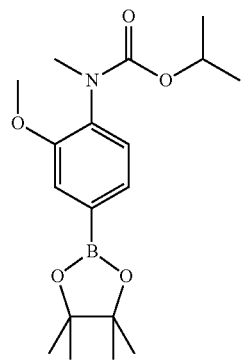 [SMILES: COc1cc(B2OC(C)(C)C(C)(C)O2)ccc1N(C)C(=O)OC(C)C]

To isopropyl 2-methoxy-4-(4,4,5,5-tetramethyl-1,3,2-dioxaborolan-2-yl)phenylcarbamate (0.298 mmol, 0.10 g) in tetrahydrofuran (1 ml) at room temperature were subsequently added sodium hydride (60% dispersion in mineral oil, 0.350 mmol, 0.014 g) and iodomethane (0.803 mmol, 0.05 ml). After 1 hour aqueous ammonium chloride solution was added and extracted with dichloromethane (three times). The combined organic extracts were dried (sodium sulfate) and concentrated in vacuo to yield isopropyl 2-methoxy-4-(4,4,5,5-tetramethyl-1,3,2-dioxaborolan-2-yl)phenyl(methyl)carbamate (0.14 g) which was used without further purification.

LC-MS column 1: Rt 4.43 min (M+H)$^+$=350.

41b. Synthesis of isopropyl 4-(3-((trans)-4-(3,3-difluoroazetidin-1-yl)cyclohexyl)-8-methylimidazo[1,5-a]pyrazin-1-yl)-2-methoxyphenyl(methyl)carbamate

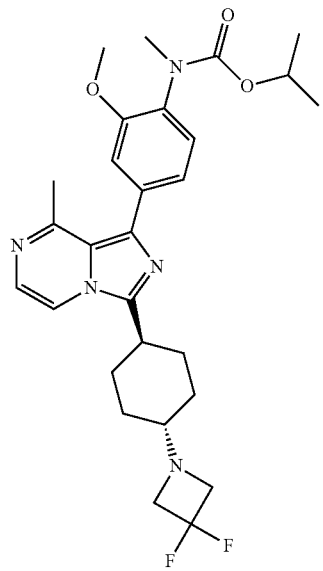 [SMILES: COc1cc(-c2nc([C@H]3CC[C@H](N4CC(F)(F)C4)CC3)n3ccnc(C)c23)ccc1N(C)C(=O)OC(C)C]

Using the procedure described in example 4 step 4c and purification by column chromatography (silica gel; ethyl acetate with gradient 0% to 5% of methanol) 1-bromo-3-((trans)-4-(3,3-difluoroazetidin-1-yl)cyclohexyl)-8-methylimidazo[1,5-a]pyrazine (20 mg) and isopropyl 2-methoxy-4-(4,4,5,5-tetramethyl-1,3,2-dioxaborolan-2-yl)phenyl (methyl)carbamate (23.4 mg) yielded isopropyl 4-(3-((trans)-4-(3,3-difluoroazetidin-1-yl)cyclohexyl)-8-methylimidazo[1,5-a]pyrazin-1-yl)-2-methoxyphenyl(methyl)carbamate (20 mg).

UPLC: Method 0_60: Rt=1.88 min, (M+H)⁺=528.

Example 42

5-methoxy-N-(2-methoxy-4-(8-methyl-3-(tetrahydro-2H-pyran-4-yl)imidazo[1,5-a]pyrazin-1-yl)phenyl)-1H-pyrrolo[3,2-b]pyridine-2-carboxamide

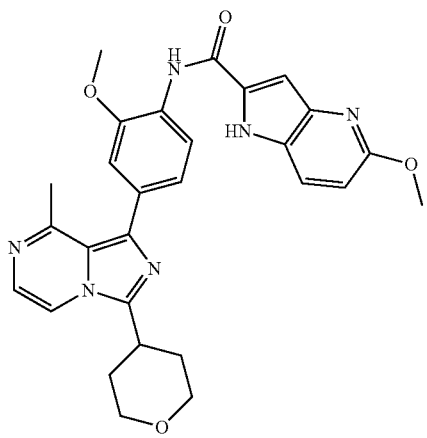 [SMILES: COc1ccc2[nH]c(C(=O)Nc3ccc(-c4nc(C5CCOCC5)n5ccnc(C)c45)cc3OC)cc2n1]

5-Methoxy-1 h-pyrrolo[3,2-b]pyridine-2-carboxylic acid (0.602 mmol, 116 mg) and O-(7-azabenzotriazol-1-yl)-1,1,3,3-tetramethyluronium hexafluorophosphate (0.662 mmol, 252 mg) were added to a solution of 4-amino-3-methoxyphenylboronic acid pinacol ester (0.602 mmol, 150 mg) in dichloromethane (2.5 ml) and pyridine (0.5 ml) at 0° C. After stirring the reaction mixture overnight at room temperature it was concentrated in vacuo. Dichloromethane and water were added to the residue, the organic layer separated and washed with water. Both aqueous layers were extracted with dichloromethane. The combined organic layers were dried (sodium sulfate) and concentrated in vacuo. The residue was purified by column chromatography (silica gel, dichloromethane) to give 5-methoxy-N-(2-methoxy-4-(4,4,5,5-tetramethyl-1,3,2-dioxaborolan-2-yl)phenyl)-1H-pyrrolo[3,2-b]pyridine-2-carboxamide (278 mg).

Using the procedure described in example 4 step 4c and purification by column chromatography (silica gel; heptanes using a gradient 30% to 100% of ethyl acetate) 1-bromo-8-methyl-3-(tetrahydro-2H-pyran-4-yl)imidazo[1,5-a]pyrazine (21 mg) and 5-methoxy-N-(2-methoxy-4-(4,4,5,5-tetramethyl-1,3,2-dioxaborolan-2-yl)phenyl)-1H-pyrrolo[3,2-b]pyridine-2-carboxamide (23.4 mg) yielded 5-methoxy-N-(2-methoxy-4-(8-methyl-3-(tetrahydro-2H-pyran-4-yl)imidazo[1,5-a]pyrazin-1-yl)phenyl)-1H-pyrrolo[3,2-b]pyridine-2-carboxamide (14 mg).

UPLC: Method 0_60: Rt=1.88 min, (M+H)⁺=513.

Example 43

N-(2-methoxy-4-(8-methyl-3-(1-methylpiperidin-4-yl)imidazo[1,5-a]pyrazin-1-yl)phenyl)-1-methyl-1H-indole-2-carboxamide

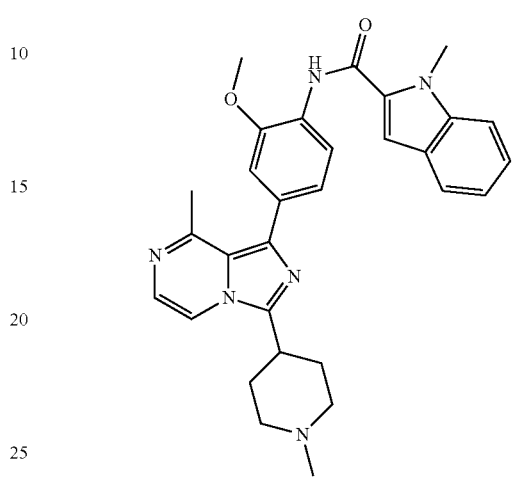

To a suspension of 1-methyl-piperidine-4-carboxylic acid hydrochloride (11.36 mmol, 2.04 g) and N,N-dimethylformamide (0.129 mmol, 0.01 ml, 9.40 mg) in dichloromethane (10 ml) at 0° C. was added oxalyl chloride (14.76 mmol, 1.40 ml) drop wise. The cooling bath was removed and the reaction mixture stirred at room temperature for 20 hours. Then the reaction mixture was concentrated in vacuo to give 1-methylpiperidine-4-carbonyl chloride hydrochloride (2.5 g).

To a solution of 2-aminomethyl-3-chloropyrazine hydrochloride (content 70%; 7.85 mmol, 1.7 g) in N,N-diisopropylethylamine (39.3 mmol, 6.84 ml) and dichloromethane (30 ml) at 0° C. was added carefully 1-methylpiperidine-4-carbonyl chloride hydrochloride (9.42 mmol, 2.2 g). Then the cooling bath was removed. After two hours saturated aqueous sodium hydrogencarbonate solution (40 mL) was added and extracted five times with dichloromethane (30 mL). The organic extracts were combined, dried and concentrated and co-evaporated twice with toluene to give N-((3-chloropyrazin-2-yl)methyl)-1-methylpiperidine-4-carboxamide (1.75 g)

To a solution of N-((3-chloropyrazin-2-yl)methyl)-1-methylpiperidine-4-carboxamide (6.51 mmol, 1.75 g) in acetonitrile (10 ml) was added phosphorus oxychloride (65.1 mmol, 6.36 ml) and this solution was heated at 80° C. for four hours. The reaction mixture was concentrated in vacuo and coevaporated with toluene. The residue was cooled in an ice bath and quenched with 7N ammonia in methanol (50 ml) and dichloromethane (50 ml). The solids were removed by filtration and the filtrate was concentrated. To the residue dichloromethane (50 ml) and of 7N ammonia in methanol (1 ml) was added. After 10 minutes at room temperature the solids were removed by filtration and the filtrate was concentrated. To the residue dichloromethane (50 ml) was added. After 10 minutes at room temperature the solids were removed by filtration and the filtrate was concentrated to give 8-chloro-3-(1-methylpiperidin-4-yl)imidazo[1,5-a]pyrazine (1.5 g).

8-Chloro-3-(1-methylpiperidin-4-yl)imidazo[1,5-a]pyrazine (0.6 g) was converted into 8-methyl-3-(1-methylpiperidin-4-yl)imidazo[1,5-a]pyrazine (0.2 g) using the procedures described in example 1 step 1c and purification by column chromatography (silica gel, gradient dichloromethane/methanol 10/0 to 9/1).

8-Methyl-3-(1-methylpiperidin-4-yl)imidazo[1,5-a]pyrazine (0.19 g) gave crude 1-bromo-8-methyl-3-(1-methylpiperidin-4-yl)imidazo[1,5-a]pyrazine (0.40 mg) applying the procedure described in example 2 step 2f without purification by column chromatography. This crude material (0.032 mmol, 10 mg) and N-(2-methoxy-4-(4,4,5,5-tetramethyl-1,3,2-dioxaborolan-2-yl)phenyl)-1-methyl-1H-indole-2-carboxamide (0.039 mmol, 15.77 mg) were dissolved in ethanol (0.8 ml), toluene (0.2 ml). Potassium carbonate (0.194 mmol, 0.097 ml) and tetrakis(triphenylphosphine) palladium(0) (1.617 μmol, 1.869 mg) were added and the reaction mixture was stirred for 10 minutes at 140° C. (micro wave). Dichloromethane and water were added, the organic layer separated, dried (sodium sulfate) and concentrated. Purification using prep-HPLC (column Luna C18(2); gradient acetonitrile/water with constant 0.003M trifluoroacetic acid) yielded N-(2-methoxy-4-(8-methyl-3-(1-methylpiperidin-4-yl)imidazo[1,5-a]pyrazin-1-yl)phenyl)-1-methyl-1H-indole-2-carboxamide (8.3 mg).

UPLC: Method 0_60: Rt=2.22 min, $(M+H)^+=509$.

Example 44

(S)-4-hydroxybutan-2-yl 2-methoxy-4-(8-methyl-3-(tetrahydro-2H-pyran-4-yl)imidazo[1,5-a]pyrazin-1-yl)phenylcarbamate

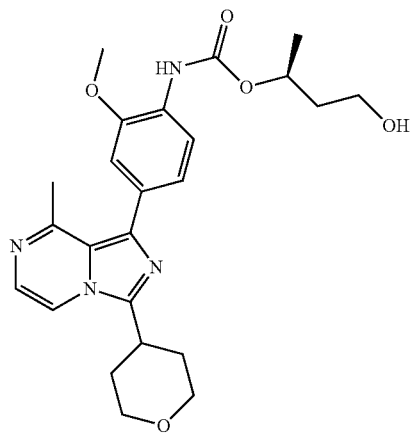 [SMILES: COc1cc(-c2nc(C3CCOCC3)n3ccnc(C)c23)ccc1NC(=O)O[C@@H](C)CCO]

(S)-(+)-Butane-1,3-diol (3.00 mmol, 0.270 g) was added to a stirred solution of imidazole (5.99 mmol, 0.41 g) and tert-butyldimethylsilyl chloride (3.00 mmol, 0.45 g) at room temperature. After six hours at room temperature water (50 mL) was added and extracted twice with dichloromethane (20 mL). The combined organic extracts were washed with brine, dried (sodium sulfate) and concentrated in vacuo to yield (S)-4-(tert-butyldimethylsilyloxy)butan-2-ol (0.654 g).

To (S)-4-(tert-butyldimethylsilyloxy)butan-2-ol (1.649 mmol, 337 mg) in dichloromethane (4 ml) were added mol sieves (4A), 2-(4-isocyanato-3-methoxyphenyl)-4,4,5,5-tetramethyl-1,3,2-dioxaborolane (1.374 mmol, 378 mg) and 4-dimethylaminopyridine (0.275 mmol, 33.6 mg) were added and the mixture was stirred at 40° C. (oil bath temperature) for 18 hours. The mol sieves were removed by filtration and the filtrate washed with water, dried (sodium sulfate) and concentrated in vacuo to give a crude product which was purified by column chromatography (silica gel, heptanes with gradient 10% to 50% of ethyl acetate) to afford (S)-4-(tert-butyldimethylsilyloxy)butan-2-yl 2-methoxy-4-(4,4,5,5-tetramethyl-1,3,2-dioxaborolan-2-yl)phenylcarbamate (443 mg). Tetrabutylammonium fluoride (1M in tetrahydrofuran, 1.22 mmol, 1.22 ml) was added to (S)-4-(tert-butyldimethylsilyloxy)butan-2-yl 2-methoxy-4-(4,4,5,5-tetramethyl-1,3,2-dioxaborolan-2-yl)phenylcarbamate (240 mg) in tetrahydrofuran (1 ml) at room temperature. After 20 hours water was added to the reaction mixture, extracted with dichloromethane, the organic extract dried (sodium sulfate) and concentration in vacuo to yield (S)-4-hydroxybutan-2-yl 2-methoxy-4-(4,4,5,5-tetramethyl-1,3,2-dioxaborolan-2-yl)phenylcarbamate (268 mg) which was used in the next step without further purification.

Using the procedure described in example 4 step 4c and purification by column chromatography (silica gel; dichloromethane with gradient 0 to 10% of methanol) 1-bromo-8-methyl-3-(tetrahydro-2H-pyran-4-yl)imidazo[1,5-a]pyrazine (35 mg) and (S)-4-hydroxybutan-2-yl 2-methoxy-4-(4,4,5,5-tetramethyl-1,3,2-dioxaborolan-2-yl)phenylcarbamate (61.7 mg) yielded (S)-4-hydroxybutan-2-yl 2-methoxy-4-(8-methyl-3-(tetrahydro-2H-pyran-4-yl)imidazo[1,5-a]pyrazin-1-yl)phenylcarbamate (15.5 mg).

UPLC: Method 0_60: Rt=1.65 min, $(M+H)^+=455$.

Example 45

4-fluoro-N-(2-methoxy-4-(8-methyl-3-(1-methylpiperidin-4-yl)imidazo[1,5-a]pyrazin-1-yl)phenyl)-1-methyl-1H-indole-2-carboxamide

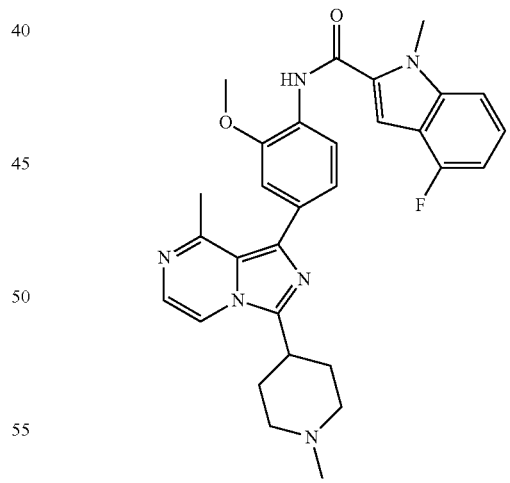

To methyl 4-fluoro-1h-indole-2-carboxylate (1.211 mmol, 234 mg) in N,N-dimethylformamide (10 ml) at 0° C. was added sodium hydride (1.817 mmol, 72.7 mg). The reaction mixture was stirred for one hour at room temperature before iodomethane (1.817 mmol, 0.113 ml, 258 mg) was added. After stirring for three hours water was added and the product was extracted with dichloromethane and concentrated in vacuo to give methyl 4-fluoro-1-methyl-1H-indole-2-carboxylate (264 mg). The latter compound was dissolved in ethanol (5 ml). Then 2 N aqueous sodium hydroxide (5.84 mmol, 2.92 ml) and potassium hydroxide (1.168 mmol, 65.5 mg) were added and the reaction mixture was stirred at 80° C. over night. 2N Hydrochloric acid was added to the reaction mixture and extracted three times with ethyl acetate. The combined organic layers were washed with brine, dried (sodium sulfate) and concentrated to give 4-fluoro-1-methyl-1H-indole-2-carboxylic acid (189 mg).

4-Fluoro-1-methyl-1H-indole-2-carboxylic acid (189 mg) and 4-amino-3-methoxyphenylboronic acid, pinacol ester (244 mg) were converted into 4-fluoro-N-(2-methoxy-4-(4,4,5,5-tetramethyl-1,3,2-dioxaborolan-2-yl)phenyl)-1-methyl-1H-indole-2-carboxamide (280 mg) using the procedure described in example 1 step 1e and purification by column chromatography (silca gel, heptanes with gradient 0 to 20% ethanol).

Using the procedure described in example 4 step 4c and purification using prep-HPLC (column Luna C18(2); gradient acetonitrile/water with constant 0.003M trifluoroacetic acid) crude 1-bromo-8-methyl-3-(1-methylpiperidin-4-yl)imidazo[1,5-a]pyrazine (see example 43, 43.7 mg) and 4-fluoro-N-(2-methoxy-4-(4,4,5,5-tetramethyl-1,3,2-dioxaborolan-2-yl)phenyl)-1-methyl-1H-indole-2-carboxamide (60 mg) yielded 4-fluoro-N-(2-methoxy-4-(8-methyl-3-(1-methylpiperidin-4-yl)imidazo[1,5-a]pyrazin-1-yl)phenyl)-1-methyl-1H-indole-2-carboxamide (4.8 mg).

UPLC: Method 0__60: Rt=2.39 min, (M+H)+=527.

Example 46

N-(5-fluoro-2-methoxy-4-(8-methyl-3-(tetrahydro-2H-pyran-4-yl)imidazo[1,5-a]pyrazin-1-yl)phenyl)-4-methoxy-1-methyl-1H-indole-2-carboxamide

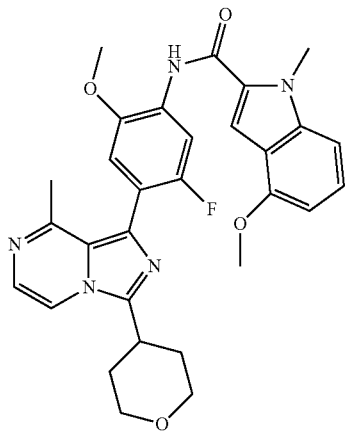 [SMILES: COc1cc(-c2nc(C3CCOCC3)n3ccnc(C)c23)c(F)cc1NC(=O)c1cc2c(OC)cccc2n1C]

4-Methoxy-1-methyl-1H-indole-2-carboxylic acid (0.225 mmol, 46.1 mg) and O-(7-azabenzotriazol-1-yl)-1,1,3,3-tetramethyluronium hexafluorophosphate (0.247 mmol, 94 mg) were added to a solution of 5-fluoro-2-methoxy-4-(4,4,5,5-tetramethyl-1,3,2-dioxaborolan-2-yl)aniline (0.225 mmol, 60 mg) in dichloromethane (2.5 mL) and pyridine (0.5 mL) at 0° C. After stirring the reaction mixture overnight at room temperature it was concentrated in vacuo. Water was added to the residue and extracted with dichloromethane. The organic extracts were washed with water. The combined organic layers were dried (sodium sulfate) and concentrated in vacuo. The residue was purified by column chromatography (silica gel, heptanes/ethyl acetate) to give impure N-(5-fluoro-2-methoxy-4-(4,4,5,5-tetramethyl-1,3,2-dioxaborolan-2-yl)phenyl)-4-methoxy-1-methyl-1H-indole-2-carboxamide (45 mg). The latter compound and 1-bromo-8-methyl-3-(tetrahydro-2H-pyran-4-yl)imidazo[1,5-a]pyrazine (35 mg) were reacted using the procedures described in example 4 step 4c and purification using column chromatography (silica gel, heptanes/ethyl acetate) gave N-(5-fluoro-2-methoxy-4-(8-methyl-3-(tetrahydro-2H-pyran-4-yl)imidazo[1,5-a]pyrazin-1-yl)phenyl)-4-methoxy-1-methyl-1H-indole-2-carboxamide (9.7 mg)

UPLC: Method 40__80: Rt=1.36 min, (M+H)+=544.

Example 47

5-Hydroxypentan-2-yl 5-fluoro-2-methoxy-4-(8-methyl-3-(tetrahydro-2h-pyran-4-yl)imidazo[1,5-a]pyrazin-1-yl)phenylcarbamate, FEIJ 0247, FEIJ 0251A001

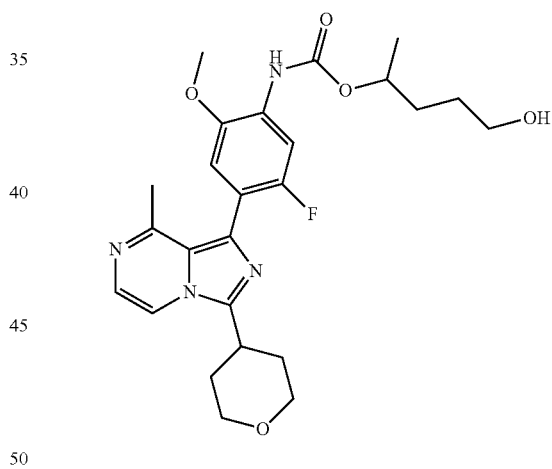

Reaction of 5-(tert-butyldimethylsilyloxy)pentan-2-yl 5-fluoro-2-methoxy-4-(4,4,5,5-tetramethyl-1,3,2-dioxaborolan-2-yl)phenylcarbamate (prepared according to the procedures described in example 44, 82 mg) and 1-bromo-8-methyl-3-(tetrahydro-2H-pyran-4-yl)imidazo[1,5-a]pyrazine (47.5 mg) according to the procedure described in example 4 step 4c and purification using prep-HPLC (column Luna C18(2); gradient acetonitrile/water with constant 0.003M trifluoroacetic acid) gave 5-hydroxypentan-2-yl 5-fluoro-2-methoxy-4-(8-methyl-3-(tetrahydro-2h-pyran-4-yl)imidazo[1,5-a]pyrazin-1-yl)phenylcarbamate (14 mg).

UPLC: Method 0__60: Rt=2.47 min, (M+H)+=487.

Example 48

(S)-sec-Butyl 2-methoxy-4-(8-methyl-3-((trans)-4-(4-methylpiperazin-1-yl)cyclohexyl)imidazo[1,5-a]pyrazin-1-yl)phenylcarbamate

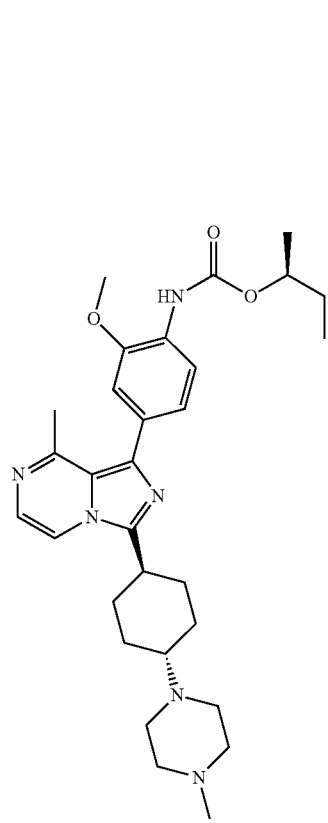 [SMILES: CC[C@H](C)OC(=O)Nc1ccc(-c2nc([C@H]3CC[C@H](N4CCN(C)CC4)CC3)n3ccnc(C)c23)cc1OC]

Reaction of 2-(4-isocyanato-3-methoxyphenyl)-4,4,5,5-tetramethyl-1,3,2-dioxaborolane (0.5 g) and (S)-butan-2-ol (0.135 g) according to the procedure described in example 3 step 3c gave (S)-sec-butyl 2-methoxy-4-(4,4,5,5-tetramethyl-1,3,2-dioxaborolan-2-yl)phenylcarbamate (0.70 g).

Using the procedure described in example 4 step 4c and purification by column chromatography (silica gel; dichloromethane with gradient 0 to 20% of methanol) 1-bromo-8-methyl-3-((trans)-4-(4-methylpiperazin-1-yl)cyclohexyl) imidazo[1,5-a]pyrazine (25 mg) and (S)-sec-butyl 2-methoxy-4-(4,4,5,5-tetramethyl-1,3,2-dioxaborolan-2-yl) phenylcarbamate (22 mg) yielded (S)-sec-butyl 2-methoxy-4-(8-methyl-3-((trans)-4-(4-methylpiperazin-1-yl)cyclohexyl)imidazo[1,5-a]pyrazin-1-yl)phenylcarbamate (15.5 mg).

UPLC: Method 0__60: Rt=1.87 min, (M+H)$^+$=535.

Example 49

N-(4-(3-(1'-acetyl-1,4'-bipiperidin-4-yl)-8-methylimidazo[1,5-a]pyrazin-1-yl)-2-methoxyphenyl)-4-methoxy-1-methyl-1H-indole-2-carboxamide

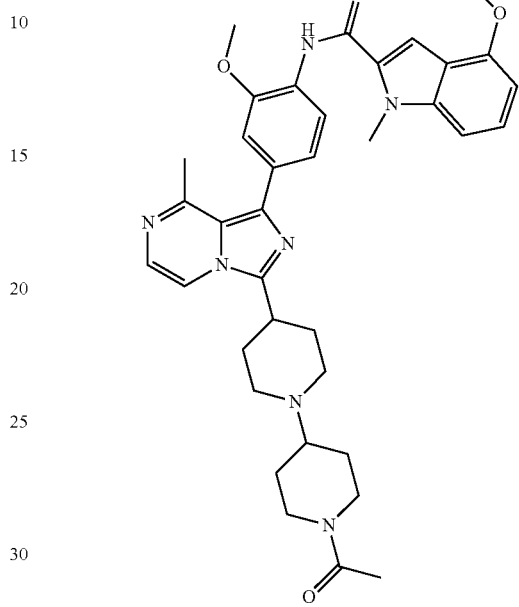

To 1-acetyl-4-piperidone (0.877 mmol, 0.109 ml) in dichloromethane (3 ml) and acetic acid (0.143 ml) under nitrogen atmosphere was added 8-methyl-3-(piperidin-4-yl) imidazo[1,5-a]pyrazine (0.797 mmol, 172 mg) in dichloromethane (4 ml) and methanol (1 ml). After 20 minutes, sodium cyanoborohydride (0.877 mmol, 55.1 mg) was added. After stirring at room temperature for one hour 1-acetyl-4-piperidone (0.877 mmol, 0.109 ml) and acetic acid (0.05 ml) were added. After 1.5 hours water was added to the reaction mixture and saturated aqueous sodium hydrogencarbonate solution were added to the water layer and made basic (pH 10) with potassium hydroxide. This aqueous basic mixture was extracted with dichloromethane/methanol (9/1) and the organic extracts concentrated in vacuo. The residue was purified by column chromatography (silica gel; dichloromethane containing 1% triethylamine with gradient 0 to 10% of methanol) to give 1-(4-(8-methylimidazo[1,5-a]pyrazin-3-yl)-1,4'-bipiperidin-1'-yl)ethanone (174 mg).

To 1-(4-(8-methylimidazo[1,5-a]pyrazin-3-yl)-1,4'-bipiperidin-1'-yl)ethanone (0.249 mmol, 85 mg) in dichloromethane (2 ml) and acetic acid (1.425 ml) was added bromine (0.249 mmol, 0.013 ml). After stirring at room temperature for one hour the reaction mixture was concentrated in vacuo. To the residue was added saturated aqueous sodium hydrogencarbonate solution. The pH was adjusted to ten using sodium hydroxide and this aqueous basic mixture was extracted twice with dichloromethane/methanol (9/1) and the organic extracts concentrated in vacuo to give 1-(4-(1-bromo-8-methylimidazo[1,5-a]pyrazin-3-yl)-1,4'-bipiperidin-1'-yl)ethanone (68 mg).

Reaction of 1-(4-(1-bromo-8-methylimidazo[1,5-a] pyrazin-3-yl)-1,4'-bipiperidin-1-yl)ethanone (22 mg) and 4-methoxy-N-(2-methoxy-4-(4,4,5,5-tetramethyl-1,3,2-dioxaborolan-2-yl)phenyl)-1-methyl-1H-indole-2-carboxamide (23 mg) according to the procedure described in example 4 step 4c and purification using prep-HPLC (column Luna C18(2); gradient acetonitrile/water with constant 0.003M trifluoroacetic acid) gave N-(4-(3-(1'-acetyl-1,4'-bipiperidin-4-yl)-8-methylimidazo[1,5-a]pyrazin-1-yl)-2-methoxyphenyl)-4-methoxy-1-methyl-1H-indole-2-carboxamide (5.1 mg).

UPLC: Method 0_60: Rt=2.22 min, (M+H)$^+$=650.

Example 50

(S)-pentan-2-yl 2-methoxy-4-(3-((S)-1-(2-methoxyacetyl)pyrrolidin-3-yl)-8-methylimidazo[1,5-a]pyrazin-1-yl)phenylcarbamate

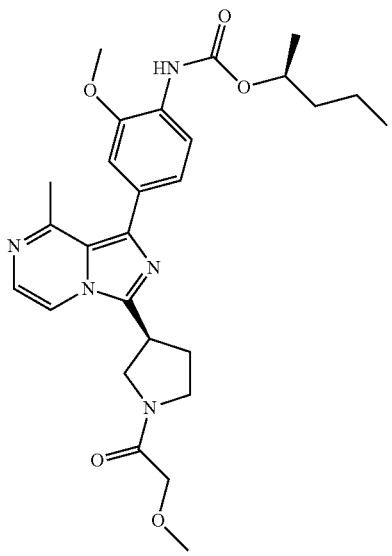 [SMILES: CCC[C@H](C)OC(=O)Nc1ccc(-c2nc([C@H]3CCN(C(=O)COC)C3)n3ccnc(C)c23)cc1OC]

(S)-1-Bromo-8-methyl-3-(pyrrolidin-3-yl)imidazo[1,5-a]pyrazine hydrochloride was prepared in a similar way as (R)-1-bromo-8-methyl-3-(pyrrolidin-3-yl)imidazo[1,5-a]pyrazine hydrochloride. To (S)-1-bromo-8-methyl-3-(pyrrolidin-3-yl)imidazo[1,5-a]pyrazine hydrochloride (0.31 mmol, 100 mg) in dichloromethane (5 ml) and N,N-diisopropylethylamine (1.778 mmol, 0.311 ml) at 0° C. was added a solution of methoxyacetyl chloride (0.534 mmol, 0.049 ml) in dichloromethane (0.5 ml). After stirring for one hour at room temperature the reaction mixture was diluted with dichloromethane, washed with saturated aqueous sodium hydrogencarbonate solution, water, brine, dried (MgSO$_4$) and concentrated in vacuo. The residue was purified by column chromatography (silica gel; dichloromethane with gradient 0 to 10% methanol) to give (S)-1-(3-(1-bromo-8-methylimidazo[1,5-a]pyrazin-3-yl)pyrrolidin-1-yl)-2-methoxyethanone (80 mg).

Using the procedure described in example 4 step 4c and purification by column chromatography (silica gel; dichloromethane with gradient 0 to 10% methanol) (S)-1-(3-(1-bromo-8-methylimidazo[1,5-a]pyrazin-3-yl)pyrrolidin-1-yl)-2-methoxyethanone (40 mg) and (S)-pentan-2-yl 2-methoxy-4-(4,4,5,5-tetramethyl-1,3,2-dioxaborolan-2-yl)phenylcarbamate (45.3 mg) yielded impure product. Additional purification on prep-HPLC (column Luna C18(2); gradient acetonitrile/water with constant 0.003M trifluoroacetic acid) yielded (S)-pentan-2-yl 2-methoxy-4-(3-((S)-1-(2-methoxyacetyl)pyrrolidin-3-yl)-8-methylimidazo[1,5-a]pyrazin-1-yl)phenylcarbamate (29 mg).

UPLC: Method 0_60: Rt=2.53 min, (M+H)$^+$=510.

Example 51

(trans)-4-(1-(3-Methoxy-4-(4-methoxy-1-methyl-1H-indole-2-carboxamido)phenyl)-8-methylimidazo[1,5-a]pyrazin-3-yl)cyclohexyl cyclopentylcarbamate

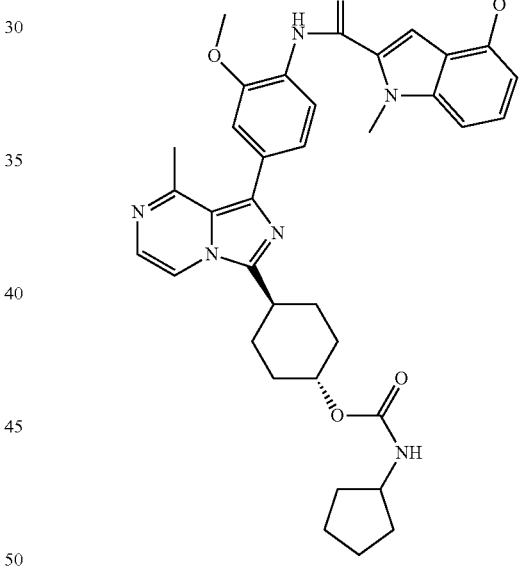

To N-(4-(3-((trans)-4-hydroxycyclohexyl)-8-methylimidazo[1,5-a]pyrazin-1-yl)-2-methoxyphenyl)-4-methoxy-1-methyl-1H-indole-2-carboxamide (0.037 mmol, 20 mg) and N,N-dimethylpyridin-4-amine (7.41 µmol, 0.906 mg) in dichloromethane (2 ml) was added cyclopentyl isocyanate (0.185 mmol, 20.60 mg) and the mixture was stirred at room temperature overnight. Then pyridine (2 ml) was added and the mixture was stirred overnight at 90° C. The reaction mixture was diluted with ethyl acetate and the obtained suspension was filtered. The filtrate was purified by column chromatography (silica gel; dichloromethane with gradient 0 to 5% methanol) to give (trans)-4-(1-(3-methoxy-4-(4-methoxy-1-methyl-1H-indole-2-carboxamido)phenyl)-8-methylimidazo[1,5-a]pyrazin-3-yl)cyclohexyl cyclopentylcarbamate (6 mg).

UPLC: Method 40_80: Rt=1.53 min, (M+H)$^+$=651.

Example 52

(R)—N-(4-(3-(1-(2-(dimethylamino)-2-oxoethyl)pyrrolidin-3-yl)-8-methylimidazo[1,5-a]pyrazin-1-yl)-2-methoxyphenyl)-4-methoxy-1-methyl-1H-indole-2-carboxamide THA 1803, THA 1816, THA 1819

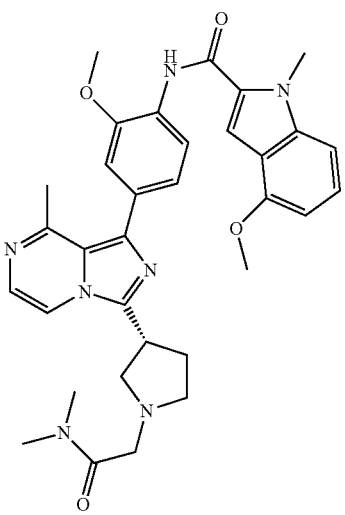 [SMILES: COc1cc(-c2nc([C@@H]3CCN(CC(=O)N(C)C)C3)n3ccnc(C)c23)ccc1NC(=O)c1cc2c(OC)cccc2n1C]

To (R)-1-bromo-8-methyl-3-(pyrrolidin-3-yl)imidazo[1,5-a]pyrazine hydrochloride (0.23 mmol, 75 mg) in N,N-dimethylformamide (4 ml) and N,N-diisopropylethylamine (1.334 mmol, 0.233 ml) was added dropwise a solution of 2-chloro-N,N-dimethylacetamide (0.280 mmol, 0.029 ml) in N,N-dimethylformamide (0.5 ml).

After stirring the reaction mixture at room temperature for 18 hours it was poured into water and extracted twice with dichloromethane. The combined organic layers were washed with water, brine, dried (magnesium sulfate), filtered and concentrated in vacuo. The residue was purified by column chromatography (silica gel; dichloromethane with gradient 0 to 20% methanol) to give (R)-2-(3-(1-bromo-8-methylimidazo[1,5-a]pyrazin-3-yl)pyrrolidin-1-yl)-N,N-dimethylacetamide (60 mg).

Reaction of (R)-2-(3-(1-bromo-8-methylimidazo[1,5-a]pyrazin-3-yl)pyrrolidin-1-yl)-N,N-dimethylacetamide (22 mg) and 4-methoxy-N-(2-methoxy-4-(4,4,5,5-tetramethyl-1,3,2-dioxaborolan-2-yl)phenyl)-1-methyl-1H-indole-2-carboxamide (23 mg) according to the procedure described in example 4 step 4c and purification using prep-HPLC (column Luna C18(2); gradient acetonitrile/water with constant 0.003M trifluoroacetic acid) gave (R)—N-(4-(3-(1-(2-(dimethylamino)-2-oxoethyl)pyrrolidin-3-yl)-8-methylimidazo[1,5-a]pyrazin-1-yl)-2-methoxyphenyl)-4-methoxy-1-methyl-1H-indole-2-carboxamide (28.6 mg).

UPLC: Method 0_60: Rt=2.22 min, (M+H)$^+$=650.

Example 53

(R)—N-(4-(3-(1-(2-hydroxyacetyl)pyrrolidin-3-yl)-8-methylimidazo[1,5-a]pyrazin-1-yl)-2-methoxyphenyl)-4-methoxy-1-methyl-1H-indole-2-carboxamide

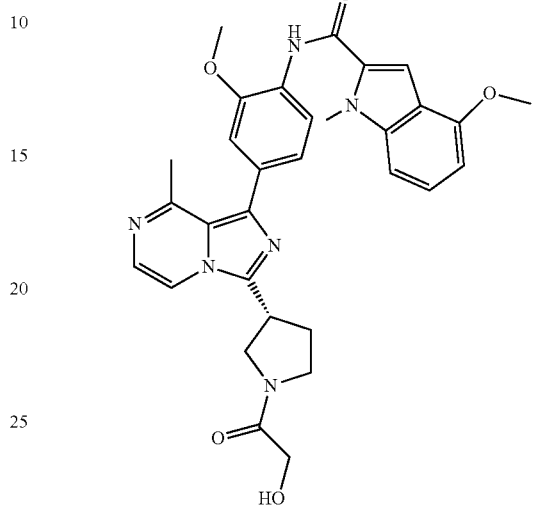

To (R)-1-bromo-8-methyl-3-(pyrrolidin-3-yl)imidazo[1,5-a]pyrazine hydrochloride (0.15 mmol, 50 mg) in dichloromethane (4 ml) and N,N-diisopropylethylamine (0.889 mmol, 0.155 ml) at 0° C. was added dropwise a solution of acetoxyacetyl chloride (0.187 mmol, 0.020 ml) in dichloromethane (0.5 ml). After stirring at room temperature for one hour the reaction mixture was diluted with dichloromethane, washed with saturated aqueous sodium hydrogencarbonate solution, water, brine, dried (MgSO$_4$) and concentrated in vacuo. The residue was purified by column chromatography (silica gel; dichloromethane with gradient 0 to 10% methanol) to give (R)-2-(3-(1-bromo-8-methylimidazo[1,5-a]pyrazin-3-yl)pyrrolidin-1-yl)-2-oxoethyl acetate (45 mg).

To (R)-2-(3-(1-bromo-8-methylimidazo[1,5-a]pyrazin-3-yl)pyrrolidin-1-yl)-2-oxoethyl acetate (0.105 mmol, 40 mg) in methanol (4 ml) was added potassium carbonate (0.126 mmol, 17.40 mg). After stirring the reaction mixture at room temperature for one hour, the solids were removed by filtration and the filtrate concentrated in vacuo to give (R)-1-(3-(1-bromo-8-methylimidazo[1,5-a]pyrazin-3-yl)pyrrolidin-1-yl)-2-hydroxyethanone (35.6 mg). Reaction of the latter compound (35.6 mg) and 4-methoxy-N-(2-methoxy-4-(4,4,5,5-tetramethyl-1,3,2-dioxaborolan-2-yl)phenyl)-1-methyl-1H-indole-2-carboxamide (50 mg) according to the procedure described in example 4 step 4c and purification using prep-HPLC (column Luna C18(2); gradient acetonitrile/water with constant 0.003M trifluoroacetic acid) gave ((R)—N-(4-(3-(1-(2-hydroxyacetyl)pyrrolidin-3-yl)-8-methylimidazo[1,5-a]pyrazin-1-yl)-2-methoxyphenyl)-4-methoxy-1-methyl-1H-indole-2-carboxamide (25.8 mg).

UPLC: Method 0_60: Rt=2.38 min, (M+H)$^+$=569.

Example 54

4-Methoxy-N-(2-methoxy-4-(8-methyl-3-((trans)-4-(piperazin-1-yl)cyclohexyl)imidazo[1,5-a]pyrazin-1-yl)phenyl)-1-methyl-1H-indole-2-carboxamide

Example 55

4-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrole-2-carboxamide

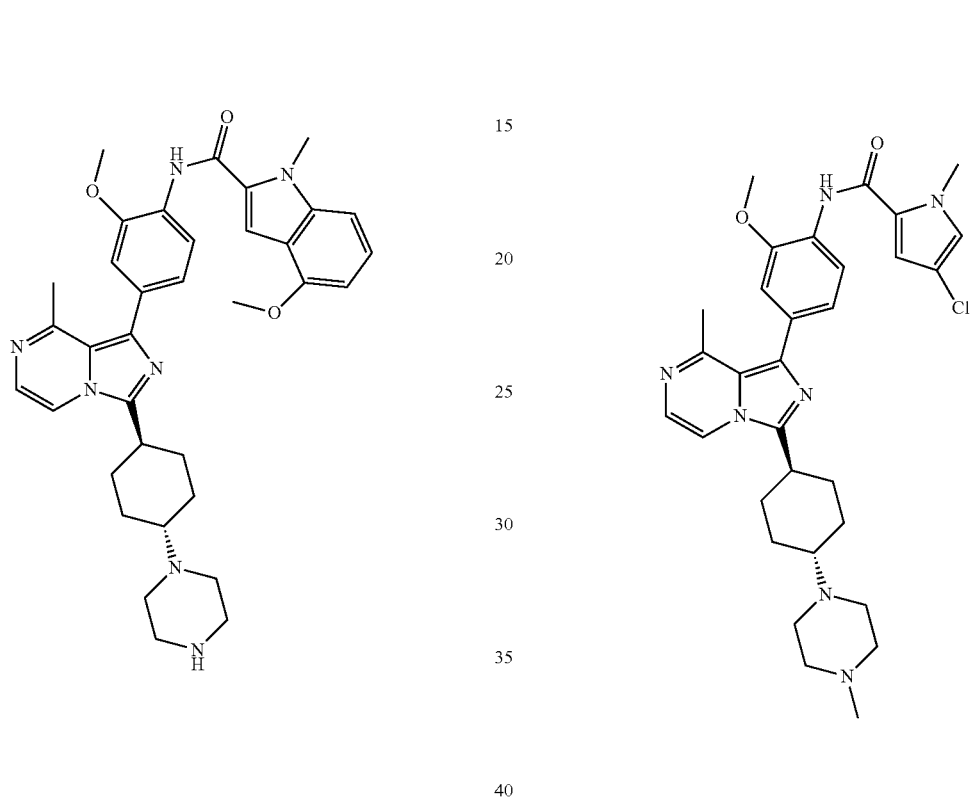

To 1-(4-((trans)-4-(1-bromo-8-methylimidazo[1,5-a]pyrazin-3-yl)cyclohexyl)piperazin-1-yl)ethanone (0.108 mmol, 45.4 mg) in ethanol was added 2 M hydrochloric acid (4.32 mmol, 2.16 ml) and stirred at reflux for four hours. The reaction mixture was cooled, concentrated in vacuo, coevaporated with toluene twice and washed with dichloromethane twice to give 1-bromo-8-methyl-3-((trans)-4-(piperazin-1-yl)cyclohexyl)imidazo[1,5-a]pyrazine hydrochloride (56 mg) product which was used without further purification.

Reaction of 1-bromo-8-methyl-3-((trans)-4-(piperazin-1-yl)cyclohexyl)imidazo[1,5-a]pyrazine hydrochloride (40 mg) and 4-methoxy-N-(2-methoxy-4-(4,4,5,5-tetramethyl-1,3,2-dioxaborolan-2-yl)phenyl)-1-methyl-1H-indole-2-carboxamide (42 mg) according to the procedure described in example 4 step 4c and purification by column chromatography (silica gel; dichloromethane with gradient 0 to 20% of methanol) gave 4-methoxy-N-(2-methoxy-4-(8-methyl-3-((trans)-4-(piperazin-1-yl)cyclohexyl)imidazo[1,5-a]pyrazin-1-yl)phenyl)-1-methyl-1H-indole-2-carboxamide (8 mg).

UPLC: Method 0_60: Rt=2.11 min, LC-MS column 2: Rt 2.29 min (M+H)$^+$=608.

According to the procedures described in example 1 step 1e and purification by column chromatography (silica gel; gradient of heptanes to heptanes/ethyl acetate 4/1) 4-chloro-1-methyl-1H-pyrrole-2-carboxylic acid (200 mg) was transformed into its acid chloride and reaction thereof with 2-methoxy-4-(4,4,5,5-tetramethyl-1,3,2-dioxaborolan-2-yl)aniline gave 4-chloro-N-(2-methoxy-4-(4,4,5,5-tetramethyl-1,3,2-dioxaborolan-2-yl)phenyl)-1-methyl-1H-pyrrole-2-carboxamide (240 mg).

Reaction of 4-chloro-N-(2-methoxy-4-(4,4,5,5-tetramethyl-1,3,2-dioxaborolan-2-yl)phenyl)-1-methyl-1H-pyrrole-2-carboxamide (30 mg) and 1-bromo-8-methyl-3-((trans)-4-(4-methylpiperazin-1-yl)cyclohexyl)imidazo[1,5-a]pyrazine (30 mg) according to the procedure described in example 4 step 4c and purification by column chromatography (silica gel; dichloromethane with gradient 0 to 20% of methanol) gave 4-chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrole-2-carboxamide (21 mg).

UPLC: Method 0_60: Rt=1.87 min, LC-MS column 2: Rt 2.20 min (M+H)$^+$=576.

Example 56

N-(2-methoxy-4-(8-methyl-3-((trans)-4-(4-methylpiperazin-1-yl)cyclohexyl)imidazo[1,5-a]pyrazin-1-yl)phenyl)-6-methyl-6H-thieno[2,3-b]pyrrole-5-carboxamide

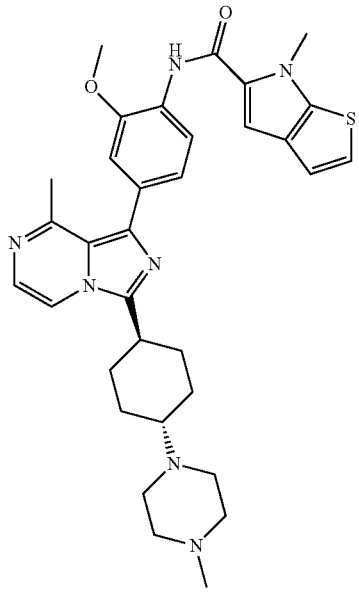 [SMILES: COc1cc(-c2nc([C@H]3CC[C@H](N4CCN(C)CC4)CC3)n3ccnc(C)c23)ccc1NC(=O)c1cc2ccsc2n1C]

To 4-amino-3-methoxyphenylboronic acid pinacol ester (1340 mg, 5.38 mmol) in tetrahydrofuran (20 ml) under a nitrogen atmosphere was added slowly a 2M solution of ethylmagnesium chloride in tetrahydrofuran (2.69 ml, 5.38 mmol) and the resulting solution was heated at reflux for one hour. Methyl 6-methyl-6H-thieno[2,3-b]pyrrole-5-carboxylate (500 mg, 2.56 mmol) was added and the reaction mixture was heated at reflux for 18 hours. The reaction mixture was cooled to room temperature and poured in brine. The mixture was extracted three times with ethyl acetate and the combined organic layers were washed subsequently with water and brine. The organic layer was dried (Na$_2$SO$_4$) and concentrated in vacuo. The residue was purified by column chromatography (silica gel; heptane with gradient of 0 to 50% of ethyl acetate). The product was dissolved in hot dichloromethane and the remaining solids were removed by filtration. The filtrate was concentrated, the residue dissolved in hot dichloromethane and diethylether was added. The formed solids were collected by filtration, washed with diethylether and dried to yield N-(2-methoxy-4-(4,4,5,5-tetramethyl-1,3,2-dioxaborolan-2-yl)phenyl)-6-methyl-6H-thieno[2,3-b]pyrrole-5-carboxamide (343 mg).

Reaction of N-(2-methoxy-4-(4,4,5,5-tetramethyl-1,3,2-dioxaborolan-2-yl)phenyl)-6-methyl-6H-thieno[2,3-b]pyrrole-5-carboxamide (32 mg) and 1-bromo-8-methyl-3-((trans)-4-(4-methylpiperazin-1-yl)cyclohexyl)imidazo[1,5-a]pyrazine (30 mg) according to the procedure described in example 4 step 4c and purification by column chromatography (silica gel; dichloromethane with gradient 0 to 20% of methanol) gave N-(2-methoxy-4-(8-methyl-3-((trans)-4-(4-methylpiperazin-1-yl)cyclohexyl)imidazo[1,5-a]pyrazin-1-yl)phenyl)-6-methyl-6H-thieno[2,3-b]pyrrole-5-carboxamide (13 mg)

UPLC: Method 0_60: Rt=2.07 min, (M+H)$^+$=598.

Example 57

N-(2-Methoxy-4-(8-methyl-3-((trans)-4-(4-methylpiperazin-1-yl)cyclohexyl)imidazo[1,5-a]pyrazin-1-yl)phenyl)-6H-thieno[2,3-b]pyrrole-5-carboxamide

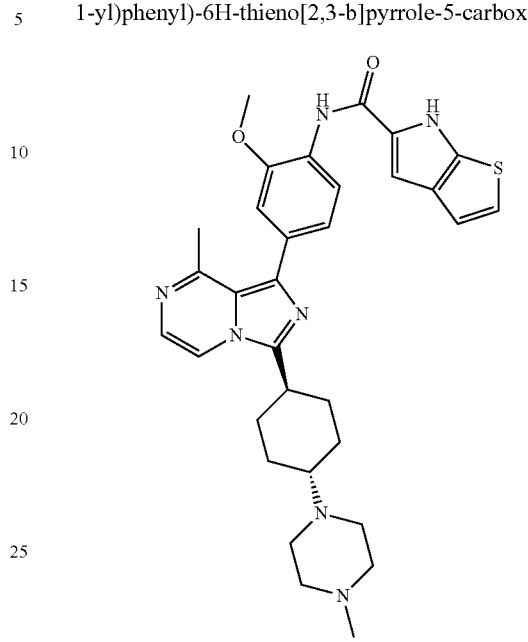

According to the procedure described in example 56 methyl 6H-thieno[2,3-b]pyrrole-5-carboxylate was used instead of methyl 6-methyl-6H-thieno[2,3-b]pyrrole-5-carboxylate to prepare N-(2-methoxy-4-(8-methyl-3-((trans)-4-(4-methylpiperazin-1-yl)cyclohexyl)imidazo[1,5-a]pyrazin-1-yl)phenyl)-6H-thieno[2,3-b]pyrrole-5-carboxamide UPLC: Method 0_60: Rt=1.80 min, (M+H)$^+$=584.

Example 58

4-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indole-2-carboxamide

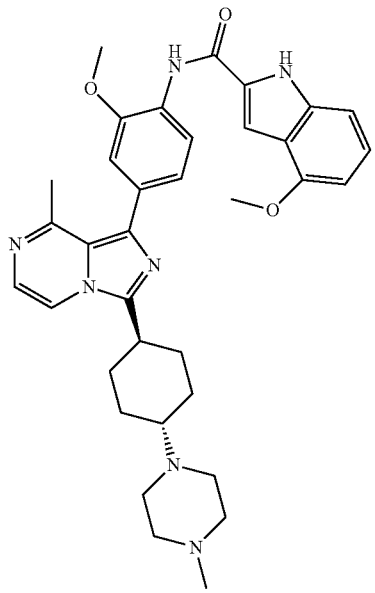 [SMILES: COc1cc(-c2nc([C@H]3CC[C@H](N4CCN(C)CC4)CC3)n3ccnc(C)c23)ccc1NC(=O)c1cc2c(OC)cccc2[nH]1]

To 4-methoxy-1H-indole-2-carboxylic acid (0.844 g, 4.42 mmol) and 2-methoxy-4-(4,4,5,5-tetramethyl-1,3,2-dioxaborolan-2-yl)aniline (1 g, 4.01 mmol) in dichloromethane (20 ml) at 0° C. under a nitrogen atmosphere were added 1-ethyl-3-(3-dimethylaminopropyl)carbodiimide) hydrochloride (0.846 g, 4.42 mmol) and 1-hydroxy-7-azabenzotriazole (0.546 g, 4.01 mmol). The resulting brown solution was stirred at room temperature overnight. The reaction mixture was poured in water, the solids were collected by filtration and washed with some water. The solid was dried in a vacuum oven at 40° C. The solids were suspended in acetonitril (50 ml) and methanol (10 ml) and heated at 60° C. for 1 hour. The solids were collected by filtration and washed with hot acetonitril. Then the solids were stirred over night in dichloromethane. The mixture was filtered over a filter. The filtrate was concentrated in vacuo and gave 4-methoxy-N-(2-methoxy-4-(4,4,5,5-tetramethyl-1,3,2-dioxaborolan-2-yl)phenyl)-1H-indole-2-carboxamide (1.1 g).

Reaction of 4-methoxy-N-(2-methoxy-4-(4,4,5,5-tetramethyl-1,3,2-dioxaborolan-2-yl)phenyl)-1H-indole-2-carboxamide (32 mg) and 1-bromo-8-methyl-3-((trans)-4-(4-methylpiperazin-1-yl)cyclohexyl)imidazo[1,5-a]pyrazine (30 mg) according to the procedure described in example 4 step 4c and purification by column chromatography (silica gel; dichloromethane with gradient 0 to 20% of methanol) gave 4-methoxy-N-(2-methoxy-4-(8-methyl-3-((trans)-4-(4-methylpiperazin-1-yl)cyclohexyl)imidazo[1,5-a]pyrazin-1-yl)phenyl)-1H-indole-2-carboxamide (11 mg)

UPLC: Method 0_60: Rt=1.95 min, (M+H)$^+$=608.

Example 59

4-Hydroxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide 59a Synthesis of 2-(2-methoxy-4-(4,4,5,5-tetramethyl-1,3,2-dioxaborolan-2-yl)phenylcarbamoyl)-1-methyl-1H-indol-4-yl acetate

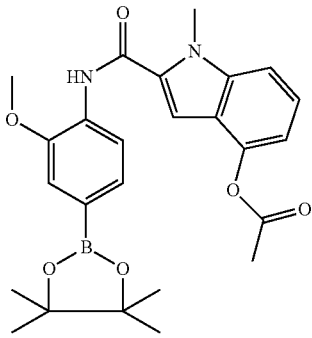 [SMILES: COc1cc(B2OC(C)(C)C(C)(C)O2)ccc1NC(=O)c1cc2c(OC(C)=O)cccc2n1C]

To 4-methoxy-1-methyl-1H-indole-2-carboxylic acid (2.92 mmol, 600 mg) in dichloromethane (30 ml) under a nitrogen atmosphere was added boron tribromide (6.96 mmol, 671 µl, 1745 mg) keeping the temperature at 0 to 5° C. After stirring the reaction mixture at room temperature for three hours it was treated with 2N aqueous sodium hydroxide (to give a pH of 9) and stirred for additional 10 minutes. The aqueous phase was separated and neutralized with 2 N hydrochloric acid at 0° C. (pH between 6 and 7). The precipitate thus obtained was collected by filtration and coevaporated with toluene twice to yield 4-hydroxy-1-methyl-1H-indole-2-carboxylic acid (223 mg).

To 4-hydroxy-1-methyl-1H-indole-2-carboxylic acid (0.262 mmol, 50 mg) in dichloromethane (1 ml) and triethylamine (2.62 mmol, 365 µl) at 0° C. was added acetyl chloride (0.266 mmol, 19 µl) and the reaction mixture stirred at room temperature for one hour. The reaction was quenched with saturated aqueous sodium hydrogencarbonate and extracted twice with dichloromethane. The organic layers were combined, dried ($Na_2SO_4$) and concentrated under reduced pressure to yield 4-acetoxy-1-methyl-1H-indole-2-carboxylic acid (67 mg).

To 2-methoxy-4-(4,4,5,5-tetramethyl-1,3,2-dioxaborolan-2-yl)aniline (0.201 mmol, 50 mg) and N,N-diisopropylethylamine (0.401 mmol, 0.066 ml) in dichloromethane under a nitrogen atmosphere at 0° C. were added 4-acetoxy-1-methyl-1H-indole-2-carboxylic acid (0.201 mmol, 46.8 mg) and O-(7-azobenzotriazol-1-yl)-1,1,3,3-tetramethyluronium hexafluorophosphate (0.221 mmol, 84 mg). The reaction mixture was stirred at room temperature for 5 days. The reaction mixture was concentrated in vacuo and purified by column chromatography (silica gel; dichloromethane) to give 2-(2-methoxy-4-(4,4,5,5-tetramethyl-1,3,2-dioxaborolan-2-yl)phenylcarbamoyl)-1-methyl-1H-indol-4-ylacetate (53 mg).

$^1$H NMR: δ 1.35 (s, 12H) 2.45 (s, 3H) 3.99 (s, 3H) 4.10 (s, 3H), 6.90 (s, 1H), 6.92 (m, 1H), 7.25-7.38 (m, 3H), 7.50 (d, J=9 Hz, 1H), 8.48 (d, J=9 Hz, 1H), 8.68 (brs, 1H)

59b Synthesis of 4-hydroxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide

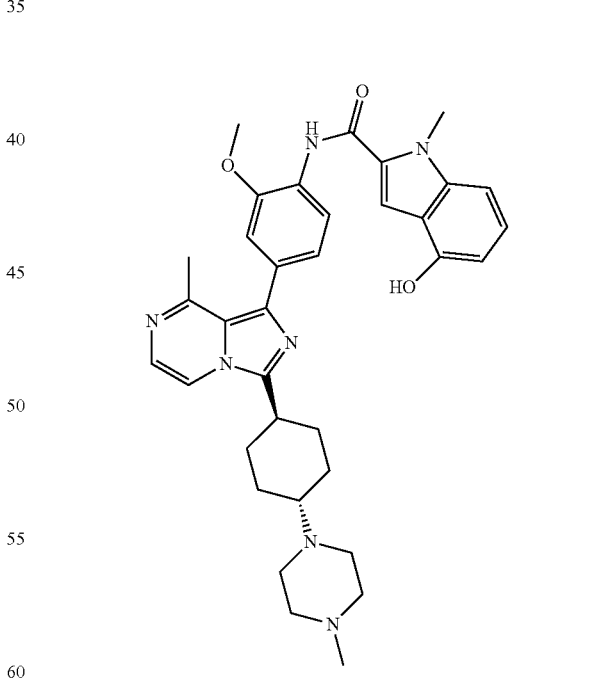

Reaction of 2-(2-methoxy-4-(4,4,5,5-tetramethyl-1,3,2-dioxaborolan-2-yl)phenylcarbamoyl)-1-methyl-1H-indol-4-yl acetate (36 mg) and 1-bromo-8-methyl-3-((trans)-4-(4-methylpiperazin-1-yl)cyclohexyl)imidazo[1,5-a]pyrazine (30 mg) according to the procedure described in example 4 step 4c and purification by column chromatography (silica gel; dichloromethane with gradient 0 to 20% methanol (+ few drops ammonia)) gave 2-(2-methoxy-4-(8-methyl-3-((trans)-4-(4-methylpiperazin-1-yl)cyclohexyl)imidazo[1,5-a]pyrazin-1-yl)phenylcarbamoyl)-1-methyl-1H-indol-4-yl acetate. This product was stirred with 7N ammonia in methanol for 1 h by room temperature, concentrated in vacuo, solved in acetonitril and filtered. The filtrate was concentrated in vacuo to give 4-hydroxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide (15 mg)

UPLC: Method 0_60: Rt=2.07 min, (M+H)$^+$=608.

Example 60

(S)-Pentan-2-yl 4-(3-((trans)-4-(aminomethyl)cyclohexyl)-8-methylimidazo[1,5-a]pyrazin-1-yl)-2-methoxyphenylcarbamate

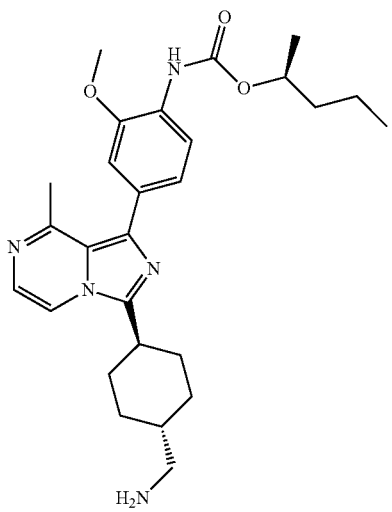 [SMILES: CCC[C@H](C)OC(=O)Nc1ccc(-c2nc([C@H]3CC[C@H](CN)CC3)n3ccnc(C)c23)cc1OC]

To (trans)-4-(aminomethyl)cyclohexanecarboxylic acid (10 g, 44.5 mmol) in 1,4-dioxane (75 ml) and water (75 ml) was added dropwise benzyl chloroformate (6.99 ml, 49.0 mmol). The pH was kept between 7 and 8 by adding saturated aqueous sodium carbonate. After stirring for two hours the reaction mixture was concentrated in vacuo till half volume, 1M sodium hydroxide (aq) was added till pH=9 and the mixture was extracted with diethylether. 2M Hydrochloric acid was added till pH=1 was the mixture was extracted twice with ethyl acetate. The combined organic layers were washed with brine, dried (Na$_2$SO$_4$) and concentrated to yield (trans)-4-((benzyloxycarbonylamino)methyl)cyclohexanecarboxylic acid (12.03 g)

A mixture of (3-chloropyrazin-2-yl)methanamine hydrochloride (5 g, 21.38 mmol), (trans)-4-((benzyloxycarbonylamino)methyl)cyclohexanecarboxylic acid (6.23 g, 21.38 mmol), 1-ethyl-3-(3-dimethylaminopropyl)carbodiimide) hydrochloride (4.51 g, 23.52 mmol), 1-hydroxy-7-azabenzotriazole (1.455 g, 10.69 mmol), and triethyl amine (4.76 ml, 34.2 mmol) in dichloromethane (60 ml) was stirred at room temperature overnight. The mixture was concentrated and the residue was purified by column chromatography (silica gel, dichloromethane with gradient 0.5 to 5% of methanol) to yield benzyl((trans)-4-((3-chloropyrazin-2-yl)methylcarbamoyl)cyclohexyl)methylcarbamate (8.79 g).

To benzyl((trans)-4-((3-chloropyrazin-2-yl)methylcarbamoyl)cyclohexyl)methylcarbamate (8.79 g, 18.98 mmol) in acetonitrile (anhydrous) (90 ml) were added phosphorus oxychloride (5.31 ml, 56.9 mmol) and N,N-dimethylformamide (a drop) and the mixture was stirred at 60° C. overnight. Then the mixture was concentrated, the residue was dissolved in dichloromethane and quenched with an excess of 7M ammonia in methanol. This mixture was concentrated again and the residue was purified by column chromatography (silica gel, dichloromethane with gradient 0 to 5% of methanol) to yield benzyl((trans)-4-(8-chloroimidazo[1,5-a]pyrazin-3-yl)cyclohexyl)methylcarbamate (6.58 g).

To a suspension of benzyl((trans)-4-(8-chloroimidazo[1,5-a]pyrazin-3-yl)cyclohexyl)methylcarbamate (6.58 g, 16.50 mmol) and potassium carbonate (3.42 g, 24.74 mmol) in 1,4-dioxan (200 ml) was added (after flushing with nitrogen) trimethylboroxine (13.84 ml, 49.5 mmol) and 1,1'-bis(diphenylphosphino)ferrocenepalladium(II) dichloride (1.217 g, 1.650 mmol). The reaction was stirred at 100° C. overnight. The reaction mixture was cooled to room temperature, filtered over Celite and Celite washed with ethyl acetate. The filtrate was concentrated and the residue was purified by column chromatography (silica gel, ethyl acetate with gradient of 0 to 10% of methanol) to yield benzyl((trans)-4-(8-methylimidazo[1,5-a]pyrazin-3-yl)cyclohexyl)methylcarbamate (3.52 g)

To benzyl((trans)-4-(8-methylimidazo[1,5-a]pyrazin-3-yl)cyclohexyl)methylcarbamate (3.52 g, 9.05 mmol) in N,N-dimethylformamide (35 ml) was added N-bromosuccinimide (1.611 g, 9.05 mmol) and the mixture was stirred at room temperature for four hours. The reaction was quenched with saturated aqueous sodium hydrogencarbonate and subsequently extracted three times with dichloromethane. The combined organic layers were washed with brine, dried (Na$_2$SO$_4$) and concentrated in vacuo. The residue was purified by column chromatography (silica gel, dichloromethane with gradient 0 to 5% of methanol) to yield benzyl ((trans)-4-(1-bromo-8-methylimidazo[1,5-a]pyrazin-3-yl)cyclohexyl)methylcarbamate (3.01 g).

Benzyl((trans)-4-(1-bromo-8-methylimidazo[1,5-a]pyrazin-3-yl)cyclohexyl)methylcarbamate (1.5 g, 3.28 mmol) was dissolved in hydrobromic acid 33% in acetic acid (15 mL, 3.28 mmol) and the resulting mixture was stirred at room temperature. After eight hours the reaction mixture was concentrated in vacuo and dried in a vacuum oven (40° C.) for three days to yield ((trans)-4-(1-bromo-8-methylimidazo[1,5-a]pyrazin-3-yl)cyclohexyl)methanamine hydrobromide (1.77 g).

Using the procedure described in example 4 step 4c and purification by column chromatography (silica gel; dichloromethane with gradient 0 to 20% methanol) ((trans)-4-(1-bromo-8-methylimidazo[1,5-a]pyrazin-3-yl)cyclohexyl)methanamine hydrobromide (30 mg) and (S)-pentan-2-yl 2-methoxy-4-(4,4,5,5-tetramethyl-1,3,2-dioxaborolan-2-yl)phenylcarbamate (34 mg) yielded (S)-pentan-2-yl 4-(3-

((trans)-4-(aminomethyl)cyclohexyl)-8-methylimidazo[1,5-a]pyrazin-1-yl)-2-methoxyphenylcarbamate (13 mg).

UPLC: Method 0_60: Rt=2.33 min, (M+H)+=480.

Example 61

1-Methyl-N-(4-(8-methyl-3-((trans)-4-(4-methylpiperazin-1-yl)cyclohexyl)imidazo[1,5-a]pyrazin-1-yl)phenyl)-1H-indole-2-carboxamide

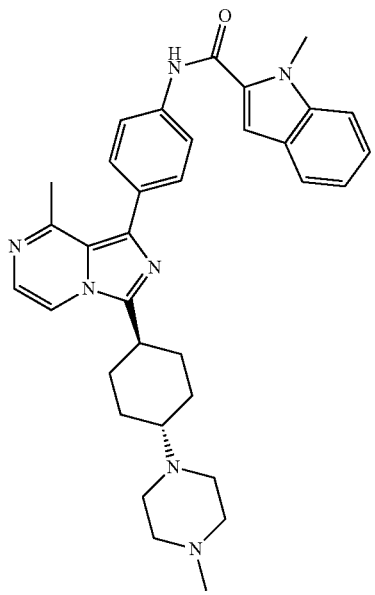 [SMILES: Cc1nccn2c1c(-c1ccc(NC(=O)c3cc4ccccc4n3C)cc1)nc2[C@H]1CC[C@H](N2CCN(C)CC2)CC1]

Reaction of 1-methyl-N-(4-(4,4,5,5-tetramethyl-1,3,2-dioxaborolan-2-yl)phenyl)-1H-indole-2-carboxamide (29 mg), prepared from 1-methyl-1H-indole-2-carboxylic acid which was transformed into its acid chloride first and then reacted with 4-(4,4,5,5-tetramethyl-1,3,2-dioxaborolan-2-yl)aniline, and 1-bromo-8-methyl-3-((trans)-4-(4-methylpiperazin-1-yl)cyclohexyl)imidazo[1,5-a]pyrazine (30 mg) according to the procedure described in example 4 step 4c and purification by column chromatography (silica gel; dichloromethane with gradient 0 to 20% of methanol) gave 1-methyl-N-(4-(8-methyl-3-((trans)-4-(4-methylpiperazin-1-yl)cyclohexyl)imidazo[1,5-a]pyrazin-1-yl)phenyl)-1H-indole-2-carboxamide (12 mg)

UPLC: Method 0_60: Rt=2.00 min, (M+H)+=562

Example 62

N-(2-hydroxy-4-(8-methyl-3-((trans)-4-(4-methylpiperazin-1-yl)cyclohexyl)imidazo[1,5-a]pyrazin-1-yl)phenyl)-4-methoxy-1-methyl-1H-indole-2-carboxamide

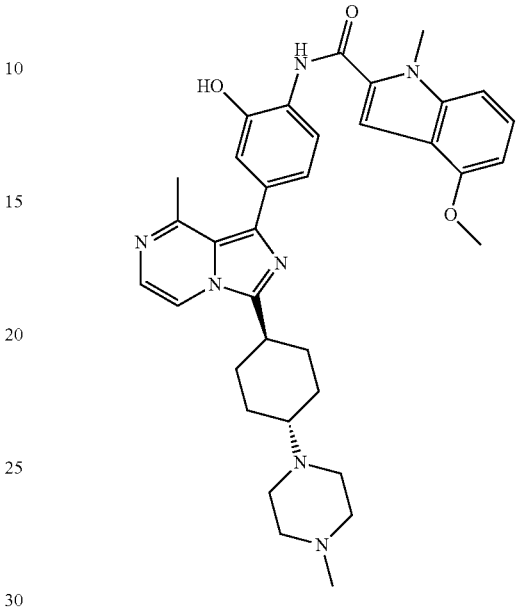

To a suspension of 1-bromo-8-methyl-3-((trans)-4-(4-methylpiperazin-1-yl)cyclohexyl)imidazo[1,5-a]pyrazine (0.714 mmol, 280 mg) and 2-methoxy-4-(4,4,5,5-tetramethyl-1,3,2-dioxaborolan-2-yl)aniline (0.714 mmol, 178 mg) in dioxane (5 mL) was added aqueous 2M potassium carbonate (3.57 mmol, 1.78 mL). The mixture was degassed and put under a nitrogen atmosphere. Then 1,1'-bis(diphenylphosphino)ferrocene palladium (II) chloride complex with dichloromethane (0.050 mmol, 40.4 mg) was added and the reaction mixture was heated to 89° C. After three hours the reaction mixture was diluted with acetonitrile (9 ml) and filtered over decalite. The filtrate was concentrated in vacuo and the residue was purified by column chromatography (silica gel; gradient of dichloromethane to dichloromethane/methanol 5/1) to give 2-methoxy-4-(8-methyl-3-((trans)-4-(4-methylpiperazin-1-yl)cyclohexyl)imidazo[1,5-a]pyrazin-1-yl)aniline (115 mg).

To 2-methoxy-4-(8-methyl-3-((trans)-4-(4-methylpiperazin-1-yl)cyclohexyl)imidazo[1,5-a]pyrazin-1-yl)aniline (0.152 mmol, 66 mg) in dichloromethane (1.4 ml) at 0-5° C. was added boron tribromide (0.758 mmol, 73 µl) under a nitrogen atmosphere. Then the reaction mixture was stirred for three hours at room temperature. Then additional boron tribromide (0.758 mmol, 73 µl) was added. After 30 minutes the reaction mixture was quenched with methanol and stirred during the night. The solid formed was removed by filtration and the filtrate was concentrated in vacuo. Water was added and the mixture was coevaporated with toluene twice. The crude product was dissolved in methanol; sillica gel added, concentrated in vacuo and the residue charged on a silica gel column for purification (gradient of dichloromethane to dichloromethane/methanol 5/1) to give impure 2-amino-5-(8-methyl-3-((trans)-4-(4-methylpiperazin-1-yl)cyclohexyl)imidazo[1,5-a]pyrazin-1-yl)phenol (116 mg content approximately 20%) which was used without further purification.

Under a nitrogen atmosphere 4-methoxy-1-methyl-1H-indole-2-carbonyl chloride (described in example 2g) (0.048 mmol, 10.64 mg) was added to a solution of 2-amino-5-(8-methyl-3-((trans)-4-(4-methylpiperazin-1-yl)cyclohexyl)imidazo[1,5-a]pyrazin-1-yl)phenol (116 mg impure material) and N,N-diisopropylethylamine (0.145 mmol, 24 µl) in dichloromethane at 0° C. The mixture was stirred at room temperature for one hour. Purification by column chromatography (silica gel; gradient of dichloromethane to dichloromethane/methanol 5/1) followed by purification with HPLC (column: X-bridge; eluens acetonitrile/methanol/water with constant 0.003M trifluoroacetic acid). Proper fractions were collected and basified with aqueous sodium carbonate, extracted with dichloromethane, organic layer dried (Na$_2$SO$_4$) and concentrated in vacuo to give N-(2-hydroxy-4-(8-methyl-3-((trans)-4-(4-methylpiperazin-1-yl)cyclohexyl)imidazo[1,5-a]pyrazin-1-yl)phenyl)-4-methoxy-1-methyl-1H-indole-2-carboxamide (7 mg)

UPLC: Method 0_60: Rt=1.92 min, (M+H)$^+$=608

Example 63

4-Methoxy-N-(2-methoxy-4-(8-methyl-3-((trans)-4-((methylamino)methyl)cyclohexyl)imidazo[1,5-a]pyrazin-1-yl)phenyl)-1-methyl-1H-indole-2-carboxamide

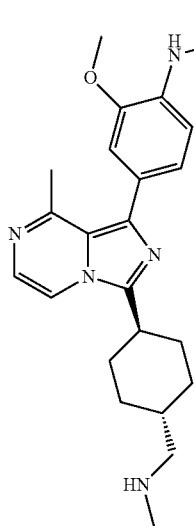

To benzyl((trans)-4-(1-bromo-8-methylimidazo[1,5-a]pyrazin-3-yl)cyclohexyl)-methylcarbamate (0.656 mmol, 300 mg) in N,N-dimethylformamide (6 ml) was added sodium hydride (60 w/w % in mineral oil, 0.656 mmol, 26.2 mg). After being stirred for five minutes iodomethane (0.659 mmol, 41 µl) was added and the reaction mixture was stirred for 18 hours at room temperature. Then the reaction mixture was added dropwise to ice water, ethyl acetate was added and layers were separated. The organic layer was dried (Na$_2$SO$_4$) and concentrated in vacuo. The residue was purified by column chromatography (silica gel; gradient of heptane to ethyl acetate) to give the product (141 mg) as a mixture of desired benzyl((trans)-4-(1-bromo-8-methylimidazo[1,5-a]pyrazin-3-yl)cyclohexyl)methyl(methyl)carbamate and starting material.

The impure benzyl((trans)-4-(1-bromo-8-methylimidazo[1,5-a]pyrazin-3-yl)cyclohexyl)methyl(methyl)carbamate (0.299 mmol, 141 mg) in 37% hydrochloric acid (20.94 mmol, 1.745 ml) was stirred for 18 hours at room temperature and one hour at 40° C. The reaction mixture was concentrated in vacuo. The residue dissolved in water and washed with diethyl ether twice. The aqueous layer basified with 2 N aqueous sodium hydroxide and extracted with dichloromethane twice. The combined organic extracts were dried (Na$_2$SO$_4$) and concentrated in vacuo to give impure 1-((trans)-4-(1-bromo-8-methylimidazo[1,5-a]pyrazin-3-yl)cyclohexyl)-N-methylmethanamine (91 mg).

Reaction of the impure 1-((trans)-4-(1-bromo-8-methylimidazo[1,5-a]pyrazin-3-yl)cyclohexyl)-N-methylmethanamine (20 mg) and 4-methoxy-N-(2-methoxy-4-(4,4,5,5-tetramethyl-1,3,2-dioxaborolan-2-yl)phenyl)-1-methyl-1H-indole-2-carboxamide (26 mg) according to the procedure described in example 4 step 4c and purification by column chromatography (silica gel; dichloromethane with gradient 0 to 20% of methanol (containing 0.1% ammonium hydroxide)) gave 4-methoxy-N-(2-methoxy-4-(8-methyl-3-((trans)-4-((methylamino)methyl)cyclohexyl)imidazo[1,5-a]pyrazin-1-yl)phenyl)-1-methyl-1H-indole-2-carboxamide (5.6 mg)

UPLC: Method 0_60: Rt=2.26 min, (M+H)$^+$=567.

Example 64

N-(4-(3-((trans)-4-((dimethylamino)methyl)cyclohexyl)-8-methylimidazo[1,5-a]pyrazin-1-yl)-2-methoxyphenyl)-4-methoxy-1-methyl-1H-indole-2-carboxamide

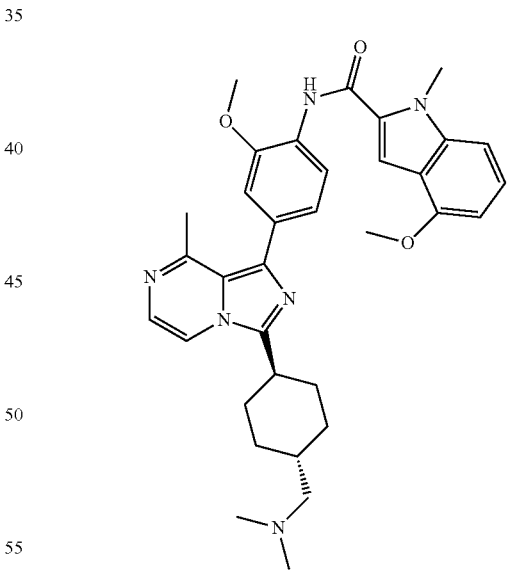

To a stirred mixture of 1-((trans)-4-(1-bromo-8-methylimidazo[1,5-a]pyrazin-3-yl)cyclohexyl)-N-methylmethanamine (0.148 mmol, 50 mg) and a 37% aqueous formaldehyde solution (0.445 mmol, 33.4 µL) was added sodium cyanoborohydride (0.163 mmol, 10.25 mg). After stirring for 30 minutes, acetic acid was added to adjust the pH of the reaction mixture to neutral. Stirring was continued for an additional hour during which time the pH was maintained neutral by addition of acetic acid. The reaction mixture was concentrated in vacuo. To the residue dichloromethane and 2N sodium hydroxide (aq) solution were added and the organic layer was separated. The aqueous layer was washed twice with dichloromethane. The combined organic layers were dried (Na2SO4) and concentrated in vacuo to give 1-((trans)-4-(1-bromo-8-methylimidazo[1,5-a]pyrazin-3-yl)cyclohexyl)-N,N-dimethylmethanamine (57 mg).

1-((Trans)-4-(1-bromo-8-methylimidazo[1,5-a]pyrazin-3-yl)cyclohexyl)-N,N-dimethylmethanamine (26 mg) and 4-methoxy-N-(2-methoxy-4-(4,4,5,5-tetramethyl-1,3,2-dioxaborolan-2-yl)phenyl)-1-methyl-1H-indole-2-carboxamide (32 mg) were used according to the procedure described in example 4 step 4c and the crude product was purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried ($Na_2SO_4$) and concentrated in vacuo to give N-(4-(3-((trans)-4-((dimethylamino)methyl)cyclohexyl)-8-methylimidazo[1,5-a]pyrazin-1-yl)-2-methoxyphenyl)-4-methoxy-1-methyl-1H-indole-2-carboxamide (12 mg).

UPLC: Method 0_60: Rt=2.24 min, $(M+H)^+=581$.

Example 65

(S)-Pentan-2-yl 4-(3-((trans)-4-((dimethylamino)methyl)cyclohexyl)-8-methylimidazo[1,5-a]pyrazin-1-yl)-2-methoxyphenylcarbamate

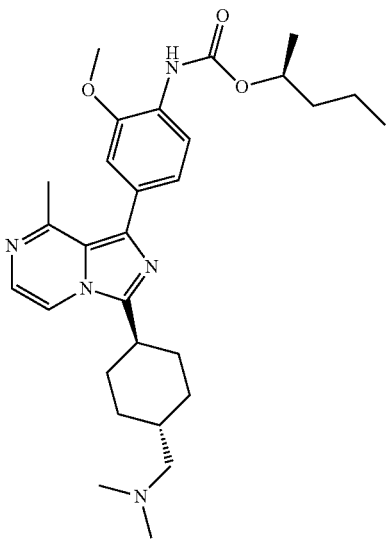 [SMILES: CCC[C@H](C)OC(=O)Nc1ccc(-c2nc([C@H]3CC[C@H](CN(C)C)CC3)n3ccnc(C)c23)cc1OC]

1-((Trans)-4-(1-bromo-8-methylimidazo[1,5-a]pyrazin-3-yl)cyclohexyl)-N,N-dimethylmethanamine (26 mg) and (S)-pentan-2-yl 2-methoxy-4-(4,4,5,5-tetramethyl-1,3,2-dioxaborolan-2-yl)phenylcarbamate (27 mg) were used according to the procedure described in example 4 step 4c and the crude product was purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried ($Na_2SO_4$) and concentrated in vacuo to give (S)-pentan-2-yl 4-(3-((trans)-4-((dimethylamino)methyl)cyclohexyl)-8-methylimidazo[1,5-a]pyrazin-1-yl)-2-methoxyphenylcarbamate (9 mg).

UPLC: Method 0_60: Rt=2.20 min, $(M+H)^+=508$.

Example 66

6-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indazole-3-carboxamide

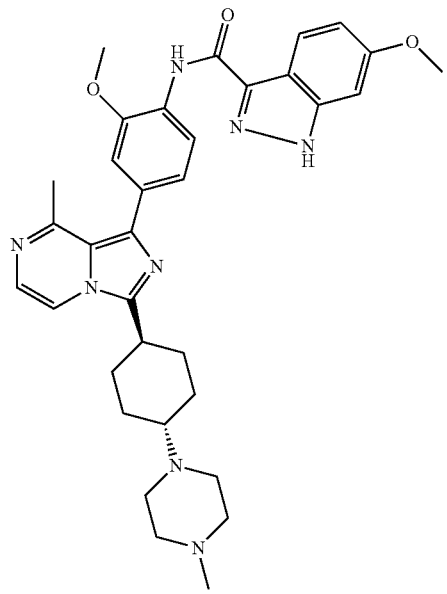 [SMILES: COc1ccc2c(C(=O)Nc3ccc(-c4nc([C@H]5CC[C@H](N6CCN(C)CC6)CC5)n5ccnc(C)c45)cc3OC)n[nH]c2c1]

To ethyl 6-methoxy-1H-indazole-3-carboxylate (0.415 mmol) in methanol (5 ml) was added 4N sodium hydroxide (aq) (8 mL, 32.0 mmol). After two hours stirring, reaction was still not finished and 6 ml of 4N NaOH was added. Upon completion of the reaction, the methanol was removed by evaporation and the water layer was washed with ethyl acetate. Subsequently the water layer was acidified and extracted with ethyl acetate twice. The latter organic layers were combined, dried ($Na_2SO_4$) and concentrated in vacuo to give 6-methoxy-1H-indazole-3-carboxylic acid (64 mg) as a brown solid.

To 6-methoxy-1H-indazole-3-carboxylic acid (64 mg, 0.333 mmol) in dichloromethane (10 ml) was added 2-methoxy-4-(4,4,5,5-tetramethyl-1,3,2-dioxaborolan-2-yl)aniline (166 mg, 0.666 mmol), O-(7-azabenzotriazol-1-yl)1,1,3,3-tetramethyluronium hexafluorophosphate (190 mg, 0.500 mmol) and N,N-diisopropylethylamine (0.174 ml, 0.999 mmol). The reaction mixture was stirred overnight at room temperature. Then the reaction mixture was concentrated in vacuo and the residue was purified by column chromatograpy (silica gel; dichloromethane/methanol 99/1) and thereafter by column chromatograpy (silica gel; heptane/ethyl acetate 2/1) to give 6-methoxy-N-(2-methoxy-4-(4,4,5,5-tetramethyl-1,3,2-dioxaborolan-2-yl)phenyl)-1H-indazole-3-carboxamide (54 mg).

6-Methoxy-N-(2-methoxy-4-(4,4,5,5-tetramethyl-1,3,2-dioxaborolan-2-yl)phenyl)-1H-indazole-3-carboxamide (28 mg) and 1-bromo-8-methyl-3-((trans)-4-(4-methylpiperazin-1-yl)cyclohexyl)imidazo[1,5-a]pyrazine (26 mg) were reacted according to the procedure described in example 4 step 4c and purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried ($Na_2SO_4$) and concentrated in vacuo to give 6-methoxy-N-(2-methoxy-4-(8-methyl-3-((trans)-4-(4-methylpiperazin-1-yl)cyclohexyl)imidazo[1,5-a]pyrazin-1-yl)phenyl)-1H-indazole-3-carboxamide (7.5 mg).

UPLC: Method 0_60: Rt=1.61 min, (M+H)⁺=609.

Example 67

5-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-b]pyridine-2-carboxamide

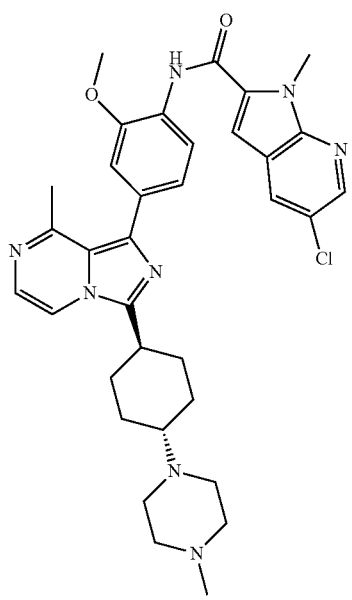 [SMILES: COc1cc(-c2nc([C@H]3CC[C@H](N4CCN(C)CC4)CC3)n3ccnc(C)c23)ccc1NC(=O)c1cc2cc(Cl)cnc2n1C]

To a stirred solution of methyl 5-chloro-1H-pyrrolo[2,3-b]pyridine-2-carboxylate (0.986 g, 4.68 mmol) N,N-dimethylformamide (20 ml) at room temperature under a nitrogen atmosphere was added potassium carbonate (0.647 g, 4.68 mmol). After 30 minutes iodomethane (0.321 ml, 5.15 mmol) was added and the resulting mixture was stirred at room temperature overnight. Brine was added and the mixture was extracted with ethyl acetate three times. The combined organic layers were washed with brine, dried (Na2SO4) and concentrated in vacuo. The residue was coated onto hydromatrix and purified by column chromatography (silica gel; heptane/ethyl acetate 4/1) to give methyl 5-chloro-1-methyl-1H-pyrrolo[2,3-b]pyridine-2-carboxylate (0.89 g).

To 2-methoxy-4-(4,4,5,5-tetramethyl-1,3,2-dioxaborolan-2-yl)aniline (2.073 g, 8.32 mmol) in tetrahydrofuran (dry) (20 ml) under a nitrogen atmosphere was added 2-Methylmagnesium chloride in tetrahydrofuran (4.16 ml, 8.32 mmol) and the mixture was heated at reflux for one hour. To the warm reaction mixture was added methyl 5-chloro-1-methyl-1H-pyrrolo[2,3-b]pyridine-2-carboxylate (0.89 g, 3.96 mmol) in tetrahydrofuran (10 ml) and the resulting mixture was heated overnight. Then the reaction was cooled to room temperature and the solvent was evaporated. The residue was taken up in ethyl acetate and washed four times with 0.5 N hydrochloric acid. The organic layer was washed with brine, dried (Na₂SO₄) and concentrated in vacuo. The residue was purified by column chromatography (silica gel; gradient of heptane to heptane/ethyl acetate 1/1) to give 5-chloro-N-(2-methoxy-4-(4,4,5,5-tetramethyl-1,3,2-dioxaborolan-2-yl)phenyl)-1-methyl-1H-pyrrolo[2,3-b]pyridine-2-carboxamide (1.47 g).

5-Chloro-N-(2-methoxy-4-(4,4,5,5-tetramethyl-1,3,2-dioxaborolan-2-yl)phenyl)-1-methyl-1H-pyrrolo[2,3-b]pyridine-2-carboxamide (34 mg) and 1-bromo-8-methyl-3-((trans)-4-(4-methylpiperazin-1-yl)cyclohexyl)imidazo[1,5-a]pyrazine (30 mg) were reacted according to the procedure described in example 4 step 4c and purified by column chromatography (silica gel; dichloromethane with gradient 0 to 20% of methanol (containing 0.1% ammonium hydroxide)) to give 5-chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-b]pyridine-2-carboxamide (27 mg).

UPLC: Method 0_60: Rt=1.98 min, (M+H)⁺=627.

Example 68

N-(4-(3-((trans)-4-(acetamidomethyl)cyclohexyl)-8-methylimidazo[1,5-a]pyrazin-1-yl)-2-methoxyphenyl)-4-methoxy-1-methyl-1H-indole-2-carboxamide

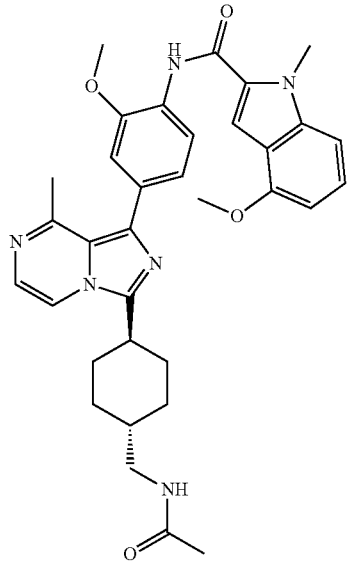 [SMILES: COc1cc(-c2nc([C@H]3CC[C@H](CNC(C)=O)CC3)n3ccnc(C)c23)ccc1NC(=O)c1cc2c(OC)cccc2n1C]

To ((trans)-4-(1-bromo-8-methylimidazo[1,5-a]pyrazin-3-yl)cyclohexyl)methanamine (0.464 mmol, 150 mg) in dichloromethane (5 ml) at 0° C. were added triethylamine (0.466 mmol, 65 µl) and acetyl chloride (0.510 mmol, 36.4 µl). After stirring at room temperature for one hour water was added. The organic layer separated, dried (Na₂SO₄) and concentrated in vacuo to give N-(((trans)-4-(1-bromo-8-methylimidazo[1,5-a]pyrazin-3-yl)cyclohexyl)methyl)acetamide (96 mg)

6-Methoxy-N-(2-methoxy-4-(4,4,5,5-tetramethyl-1,3,2-dioxaborolan-2-yl)phenyl)-1H-indazole-3-carboxamide (24 mg) and N-(((trans)-4-(1-bromo-8-methylimidazo[1,5-a]pyrazin-3-yl)cyclohexyl)methyl)acetamide (20 mg) were reacted according to the procedure described in example 4 step 4c and purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried (Na$_2$SO$_4$) and concentrated in vacuo to give N-(4-(3-((trans)-4-(acetamidomethyl)cyclohexyl)-8-methylimidazo[1,5-a]pyrazin-1-yl)-2-methoxyphenyl)-4-methoxy-1-methyl-1H-indole-2-carboxamide (15 mg).

UPLC: Method 40_80: Rt=0.79 min, (M+H)$^+$=595.

Example 69

(S)-pentan-2-yl 4-(3-((trans)-4-(acetamidomethyl)cyclohexyl)-8-methylimidazo[1,5-a]pyrazin-1-yl)-2-methoxyphenylcarbamate

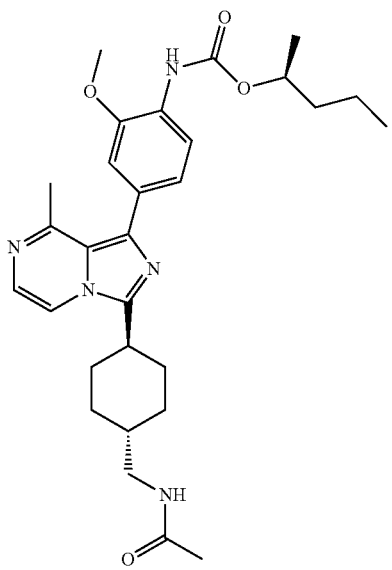 [SMILES: CCC[C@H](C)OC(=O)Nc1ccc(-c2nc([C@H]3CC[C@H](CNC(C)=O)CC3)n3ccnc(C)c23)cc1OC]

(S)-Pentan-2-yl 2-methoxy-4-(4,4,5,5-tetramethyl-1,3,2-dioxaborolan-2-yl)phenyl-carbamate (20 mg) and N-(((trans)-4-(1-bromo-8-methylimidazo[1,5-a]pyrazin-3-yl)cyclohexyl)methyl)acetamide (20 mg) were reacted according to the procedure described in example 4 step 4c and purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried (Na$_2$SO$_4$) and concentrated in vacuo to give (S)-pentan-2-yl 4-(3-((trans)-4-(acetamidomethyl)cyclohexyl)-8-methylimidazo[1,5-a]pyrazin-1-yl)-2-methoxyphenylcarbamate (16 mg).

UPLC: Method 40_80: Rt=0.81 min, (M+H)$^+$=522.

Example 70

(S)-pentan-2-yl 4-(3-((trans)-4-(methoxycarbonylmethyl)cyclohexyl)-8-methylimidazo[1,5-a]pyrazin-1-yl)-2-methoxyphenylcarbamate

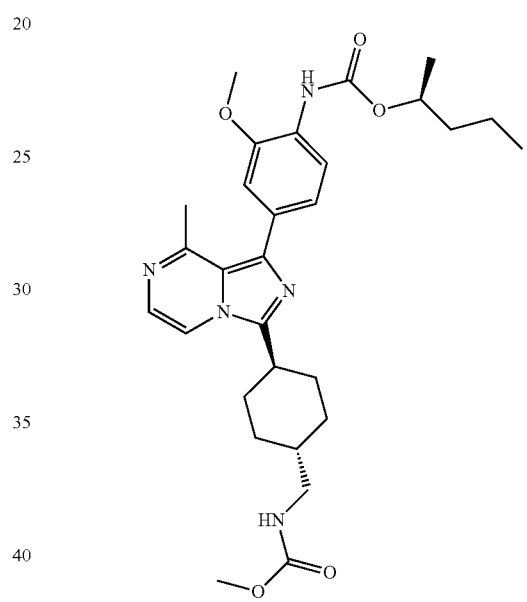

To ((trans)-4-(1-bromo-8-methylimidazo[1,5-a]pyrazin-3-yl)cyclohexyl)methanamine (0.464 mmol, 150 mg) in dichloromethane (5 ml) at 0° C. were added triethylamine (0.464 mmol, 64.7 µl) and methyl carbonochloridate (0.505 mmol, 39 µl). After stirring at room temperature for one hour water was added. The organic layer separated, dried (Na$_2$SO$_4$) and concentrated in vacuo to give methyl((trans)-4-(1-bromo-8-methylimidazo[1,5-a]pyrazin-3-yl)cyclohexyl)methylcarbamate (97 mg).

(S)-Pentan-2-yl 2-methoxy-4-(4,4,5,5-tetramethyl-1,3,2-dioxaborolan-2-yl)phenylcarbamate (19 mg) and methyl ((trans)-4-(1-bromo-8-methylimidazo[1,5-a]pyrazin-3-yl)cyclohexyl)methylcarbamate (20 mg) were reacted according to the procedure described in example 4 step 4c and purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried (Na$_2$SO$_4$) and concentrated in vacuo to give (S)-pentan-2-yl 4-(3-((trans)-4-(methoxycarbonylmethyl)cyclohexyl)-8-methylimidazo[1,5-a]pyrazin-1-yl)-2-methoxyphenylcarbamate (16 mg).

UPLC: Method 40_80: Rt=1.08 min, (M+H)$^+$=0.538

Example 71

4-Methoxy-N-(2-methoxy-4-(8-methyl-3-(4-oxocyclohexyl)imidazo[1,5-a]pyrazin-1-yl)phenyl)-1-methyl-1H-indole-2-carboxamide

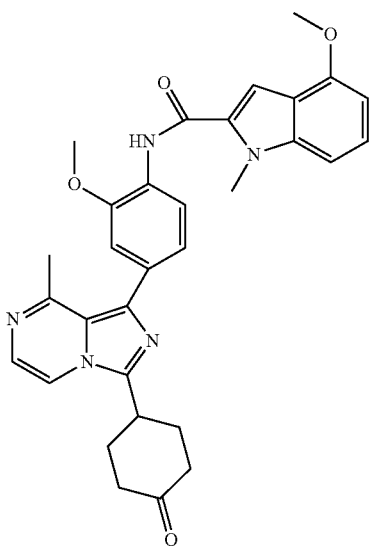 [SMILES: COc1cc(-c2nc(C3CCC(=O)CC3)n3ccnc(C)c23)ccc1NC(=O)c1cc2c(OC)cccc2n1C]

To 2-aminomethyl-3-chloropyrazine hydrochloride (content 76%, 69.4 mmol, 16.43 g), cis-4-hydroxycyclohexanecarboxylic acid (69.4 mmol, 10 g), 1-(3-dimethylaminopropyl)-3-ethylcarbodiimide hydrochloride (104 mmol, 19.95 g), 4-dimethylaminopyridine (6.94 mmol, 0.847 g) in dichloromethane (200 ml) was added N,N-diisopropylethylamine (173 mmol, 30.3 ml, 22.41 g) until pH became eight and the reaction mixture was stirred at room temperature for 18 hours. Then it was concentrated in vacuo, ethyl acetate and water were added and the organic layer separated. The water layer was extracted with ethyl acetate twice. The combined organic layers were washed with brine, dried (MgSO$_4$) and concentrated in vacuo. The residue was purified by column chromatography (silica gel; dichloromethane with gradient of 0% to 7% methanol). All fractions that contained product were combined and concentrated in vacuo. The residue was dissolved in dichloromethane (400 ml) and washed with 2 M sodium hydroxide (aq) (three times 100 ml), washed with brine, dried (MgSO$_4$) and concentrated in vacuo to give (cis)-N-((3-chloropyrazin-2-yl)methyl)-4-hydroxycyclohexanecarboxamide (15.47 g)

To (cis)-N-((3-chloropyrazin-2-yl)methyl)-4-hydroxycyclohexanecarboxamide (57.4 mmol, 15.47 g) and 4-dimethylaminopyridine (5.74 mmol, 0.701 g) in pyridine (125 ml) at 0° C. was added dropwise acetic anhydride (60.2 mmol, 5.69 ml) and the mixture was stirred at room temperature for one hour. Then the reaction was quenched with 4 N hydrochloric acid to a pH of four and extracted with ethyl acetate three times. The combined organic layers were dried (MgSO$_4$) and concentrated in vacuo. The residue was taken up in toluene and concentrated in vacuo again. The residue was dissolved in dichloromethane (100 ml) and washed with 1 M hydrochloric acid (100 ml). The organic layer was washed with brine, dried (MgSO$_4$) and concentrated in vacuo to give (cis)-4-((3-chloropyrazin-2-yl)methylcarbamoyl)cyclohexyl acetate (16.5 g)

To (cis)-4-((3-chloropyrazin-2-yl)methylcarbamoyl)cyclohexyl acetate (52.9 mmol, 16.5 g) in acetonitrile (150 ml) were added dropwise subsequently phosphorus oxychloride (159 mmol, 14.80 ml) and N,N-dimethylformamide (2.65 mmol, 0.206 ml). After addition the reaction mixture was stirred at 70° C. for one hour. The reaction mixture was cooled to room temperature and added dropwise to a mixture of 25% ammonium hydroxide (125 ml) and crushed ice (350 ml). This mixture was stirred for 30 minutes at room temperature and the off white solid was isolated by filteration and rinsed with water. The solids were dissolved in dichloromethane (200 ml) and washed with water (50 ml) and brine, dried (MgSO$_4$), and concentrated in vacuo to give (cis)-4-(8-chloroimidazo[1,5-a]pyrazin-3-yl)cyclohexyl acetate (10.9 g). A second crop of material was obtained by extraction of the filtrate twice using dichloromethane/methanol (10/1, 275 mL). The organic layers were combined and washed with brine, dried (MgSO$_4$) and concentrated in vacuo to give an additional amount of (cis)-4-(8-chloroimidazo[1,5-a]pyrazin-3-yl)cyclohexyl acetate (3.2 g).

To (cis)-4-(8-chloroimidazo[1,5-a]pyrazin-3-yl)cyclohexyl acetate (48.0 mmol, 14.09 g) in dry dioxane (275 ml) under a nitrogen atmosphere were added dry potassium carbonate (71.9 mmol, 9.94 g), trimethylboroxine (144 mmol, 20.03 ml, 50 wt % solution in tetrahydrofuran) and 1,1'-bis (diphenylphosphino)ferrocene palladium (II) chloride complex with dichloromethane (4.80 mmol, 3.88 g) and the reaction mixture was stirred at 95° C. for one hour. The reaction mixture was cooled to room temperature, filtered over decalite, the filter rinsed with dioxane and the filtrate concentrated in vacuo. The residue was purified by column chromatography (silica gel; dichloromethane with gradient 0 to 6% of methanol) to give (cis)-4-(8-methylimidazo[1,5-a]pyrazin-3-yl)cyclohexyl acetate (12.8 g).

To (cis)-4-(8-methylimidazo[1,5-a]pyrazin-3-yl)cyclohexyl acetate (46.8 mmol, 12.8 g) in N,N-dimethylformamide (100 ml) was added N-bromosuccinimide (46.8 mmol, 8.33 g). After stirring at room temperature for one hour the reaction mixture was poured into water and extracted with dichloromethane twice. The combined organic layers were washed with water twice, washed with brine, dried (MgSO$_4$) and concentrated in vacuo. The residue was purified by column chromatography (silica gel; dichloromethane with gradient 0 to 3% of methanol) to give (cis)-4-(1-bromo-8-methylimidazo[1,5-a]pyrazin-3-yl)cyclohexyl acetate (15.34 g).

A solution of (cis)-4-(1-bromo-8-methylimidazo[1,5-a]pyrazin-3-yl)cyclohexyl acetate (43.6 mmol, 15.34 g) in acetonitrile (40 ml) was added potassium hydroxide (218 mmol, 12.22 g) in water (40 ml) and the mixture was stirred at 100° C. overnight. Then the reaction mixture was cooled to room temperature, acidified with 2N hydrochloric acid and extracted with dichloromethane twice. The combined organic layers were washed with brine, dried (MgSO$_4$) and concentrated in vacuo to give (cis)-4-(1-bromo-8-methylimidazo[1,5-a]pyrazin-3-yl)cyclohexanol (9.37 g).

To (cis)-4-(1-bromo-8-methylimidazo[1,5-a]pyrazin-3-yl)cyclohexanol (16.12 mmol, 5 g) and 4-methylmorpholine N-oxide (32.2 mmol, 3.78 g) in acetone (60 ml) was added tetra-N-propylammonium perruthenate(VII) (0.806 mmol, 0.283 g) and the reaction mixture was stirred at room temperature for one night. Then the reaction mixture was filtered over decalite, the filter washed with ethyl acetate and the filtrate concentrated in vacuo. To the residue were subsequently added acetone (40 ml), 4-methylmorpholine N-oxide (32.2 mmol, 3.78 g) and tetra-N-propylammonium perruthenate(VII) (0.806 mmol, 0.283 g) and the reaction mixture was stirred at room temperature for two hours. Then the reaction mixture was filtered over decalite, the filter washed with ethyl acetate and the filtrate concentrated in vacuo. Column chromatography (silica gel; dichloromethane with gradient 0 to 4% of methanol) of the residue gave impure material (3.53 g) which became solid after one night. This solid was triturated with diethylether (8 ml) and the solids were collected and dried in vacuo to give 4-(1-bromo-8-methylimidazo[1,5-a]pyrazin-3-yl)cyclohexanone (2.7 g).

6-Methoxy-N-(2-methoxy-4-(4,4,5,5-tetramethyl-1,3,2-dioxaborolan-2-yl)phenyl)-1H-indazole-3-carboxamide (111 mg) and 4-(1-bromo-8-methylimidazo[1,5-a]pyrazin-3-yl)cyclohexanone (75 mg) were reacted according to the procedure described in example 4 step 4c and purified by column chromatography (silica gel; dichloromethane with gradient 0 to 4% of methanol) to give impure material. Additional purification by column chromatography (silica gel; gradient of heptane/ethyl acetate 3/7 to ethyl acetate, followed by dichloromethane with gradient 0 to 10% of methanol) gave 4-methoxy-N-(2-methoxy-4-(8-methyl-3-(4-oxocyclohexyl)imidazo[1,5-a]pyrazin-1-yl)phenyl)-1-methyl-1H-indole-2-carboxamide (12 mg).

UPLC: Method 0_60: Rt=2.73 min, (M+H)$^+$=538.

Example 72

N-(4-(3-((trans)-4-hydroxy-4-((methylamino)methyl)cyclohexyl)-8-methylimidazo[1,5-a]pyrazin-1-yl)-2-methoxyphenyl)-4-methoxy-1-methyl-1H-indole-2-carboxamide

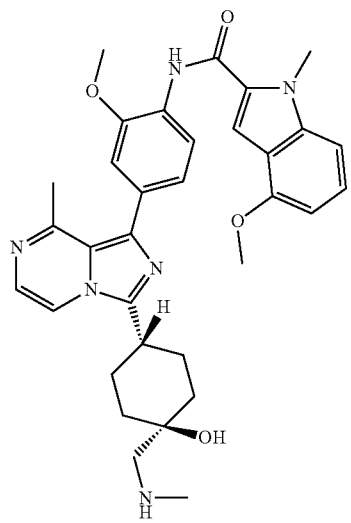 [SMILES: CNC[C@]1(O)CC[C@H](c2nc(-c3ccc(NC(=O)c4cc5c(OC)cccc5n4C)c(OC)c3)c3c(C)nccn32)CC1]

To trimethylsulfoxonium iodide (0.243 mmol, 53.6 mg) in dry dimethylsulfoxide (0.5 ml) under a nitrogen atmosphere at room temperature was added potassium tert-butoxide (0.243 mmol, 27.3 mg). After being stirred for 30 minutes 4-(1-bromo-8-methylimidazo[1,5-a]pyrazin-3-yl)cyclohexanone (0.162 mmol, 50 mg) was added as a solid. After one hour water (5 mL) was added and the mixture extracted five times with dichloromethane. The combined organic extracts were dried (Na2SO4) and concentrated in vacuo. Column chromatography (silica gel; dichloromethane/methanol 10/1) yielded 1-bromo-8-methyl-3-((trans)-1-oxaspiro[2.5]octan-6-yl)imidazo[1,5-a]pyrazine (47 mg).

1-Bromo-8-methyl-3-((trans)-1-oxaspiro[2.5]octan-6-yl)imidazo[1,5-a]pyrazine (22 mg) was dissolved in 33% methylamine in ethanol (32.1 mmol, 4 ml). After 16 hours at room temperature the reaction mixture was concentrated in vacuo to yield crude (trans)-4-(1-bromo-8-methylimidazo[1,5-a]pyrazin-3-yl)-1-((methylamino)methyl)cyclohexanol (26 mg).

6-Methoxy-N-(2-methoxy-4-(4,4,5,5-tetramethyl-1,3,2-dioxaborolan-2-yl)phenyl)-1H-indazole-3-carboxamide (33 mg) and (trans)-4-(1-bromo-8-methylimidazo[1,5-a]pyrazin-3-yl)-1-((methylamino)methyl)cyclohexanol (22 mg) were reacted according to the procedure described in example 4 step 4c and purified by column chromatography (silica gel; dichloromethane with gradient 0 to 20% of methanol) to give impure material. To this sample acetonitril (5 ml) was added and the solids removed by filtration. The filtrate was concentrated in vacuo, rinsed with a few ml of heptanes and dried in vacuo to give N-(4-(3-((trans)-4-hydroxy-4-((methylamino)methyl)cyclohexyl)-8-methylimidazo[1,5-a]pyrazin-1-yl)-2-methoxyphenyl)-4-methoxy-1-methyl-1H-indole-2-carboxamide (23 mg).

UPLC: Method 0_60: Rt=2.17 min, (M+H)$^+$=583.

Example 73

4-Methoxy-N-(2-methoxy-4-(8-methyl-3-(1-methyl-5-oxopyrrolidin-3-yl)imidazo[1,5-a]pyrazin-1-yl)phenyl)-1-methyl-1H-indole-2-carboxamide

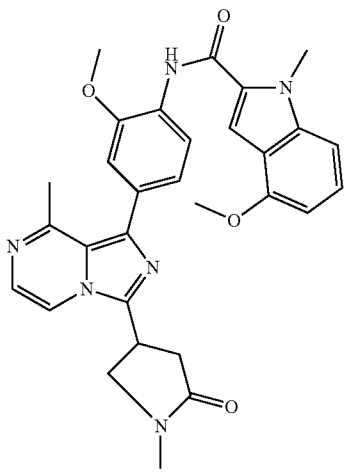 [SMILES: COc1cc(-c2nc(C3CC(=O)N(C)C3)n3ccnc(C)c23)ccc1NC(=O)c1cc2c(OC)cccc2n1C]

(3-Chloropyrazin-2-yl)methanamine hydrochloride (content 77%, 1.634 g, 6.99 mmol) and 1-methyl-5-oxopyrrolidine-3-carboxylic acid (1.000 g, 6.99 mmol) were suspended in dichloromethane (20 ml) and the reaction mixture was cooled to 0° C. under an argon atmosphere. N,N-diisopropylethylamine (3.05 ml, 17.48 mmol), 1-ethyl-3-(3-dimethylaminopropyl)carbodiimide) hydrochloride (1.474 g, 7.69 mmol) and 1-hydroxy-7-azabenzotriazole (0.476 g, 3.50 mmol) were added and the reaction mixture was stirred at room temperature overnight. Reaction was worked up by evaporting the solvents and a dark brown oil was obtained. This crude product was submitted to column chromatography (silica gel; dichloromethane/methanol 96/4) to yield impure material that was further purified by column chromatography (silica gel; dichloromethane/methanol 99/1) to give N-((3-chloropyrazin-2-yl)methyl)-1-methyl-5-oxopyrrolidine-3-carboxamide (1.24 g).

To a stirred suspension of N-((3-chloropyrazin-2-yl)methyl)-1-methyl-5-oxopyrrolidine-3-carboxamide (700 mg, 2.61 mmol) and potassium carbonate (540 mg, 3.91 mmol) in 1,4-dioxan (10 ml) under a nitrogen atmosphere was added trimethylboroxine (981 mg, 7.82 mmol) and 1,1'-bis-(diphenylphosphino)-ferrocene) palladium dichloride (214 mg, 0.261 mmol). The reaction was heated at 100° C. for one hour. Then the reaction mixture was filtered over celite and the celite was rinsed three times with ethyl acetate. Subsequently, the combined filtrates were concentrated in vacuo and the crude product was purified by column chromatography (silica gel; dichloromethane/methanol 96/5) to give 1-methyl-N-((3-methylpyrazin-2-yl)methyl)-5-oxopyrrolidine-3-carboxamide (440 mg).

1-Methyl-N-((3-methylpyrazin-2-yl)methyl)-5-oxopyrrolidine-3-carboxamide (330 mg, 1.329 mmol) was dissolved in Eaton's reagent (2 ml) and the reaction mixture was stirred at 60° C. for 18 hour. Then the reaction mixture was poured into an ice-bath and basified with 7N ammonia in methanol (20 ml). The resulting mixture was extrated with chloroform/iso-propanol (9/1) five times. The combined organic extracts were dried (Na$_2$SO$_4$) and concentrated in vacuo. The residue (280 mg) was stripped with toluene twice and with dichloromethane twice. An additional crop (53 mg) was obtained by extraction of the water layer with chloroform/iso-propanol (9/1) twice and drying and concentrating as described before. In total 333 mg of crude 1-methyl-4-(8-methylimidazo[1,5-a]pyrazin-3-yl)pyrrolidin-2-one was obtained which was used in the next reaction without further purification.

1-Methyl-4-(8-methylimidazo[1,5-a]pyrazin-3-yl)pyrrolidin-2-one (293 mg, 1.27 mmol) was dissolved N,N-dimethylformamide (12 ml) and N-bromosuccinimide (227 mg, 1.27 mmol) was added and reation mixture was stirred at room temperature overnight. Then water was added to the reaction mixture and extracted with chloroform/iso-propanol (9/1) three times. The combined organic layers were dried (Na$_2$SO$_4$) and concentrated in vacuo and a brown oil was obtained. The residue was purified by column chromatography (silica gel; dichloromethane/methanol/heptane=9/1/4) to give 4-(1-bromo-8-methylimidazo[1,5-a]pyrazin-3-yl)-1-methylpyrrolidin-2-one (200 mg).

6-Methoxy-N-(2-methoxy-4-(4,4,5,5-tetramethyl-1,3,2-dioxaborolan-2-yl)phenyl)-1H-indazole-3-carboxamide (28 mg) and 4-(1-bromo-8-methylimidazo[1,5-a]pyrazin-3-yl)-1-methylpyrrolidin-2-one (20 mg) were reacted according to the procedure described in example 4 step 4c and purified by prep-HPLC (column Luna C18(2); gradient acetonitrile/water with constant 0.003M trifluoroacetic acid). Proper fractions were collected and made basic with aqueous sodium hydrogencarbonate, extracted with dichloromethane, organic layer dried (Na$_2$SO$_4$) and concentrated in vacuo to give 4-methoxy-N-(2-methoxy-4-(8-methyl-3-(1-methyl-5-oxopyrrolidin-3-yl)imidazo[1,5-a]pyrazin-1-yl)phenyl)-1-methyl-1H-indole-2-carboxamide (15 mg).

UPLC: Method 0_60: Rt=2.45 min, (M+H)$^+$=539.

Example 74

4-Methoxy-N-(2-methoxy-4-(8-methyl-3-((trans)-4-(4-methyl-3-oxopiperazin-1-yl)cyclohexyl)imidazo[1,5-a]pyrazin-1-yl)phenyl)-1-methyl-1H-indole-2-carboxamide

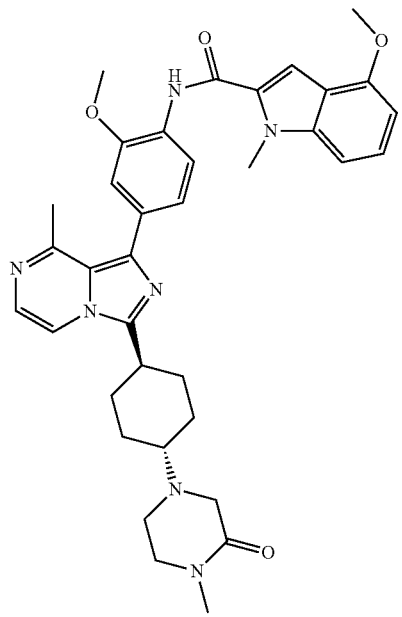 [SMILES: COc1cc(-c2nc([C@H]3CC[C@H](N4CCN(C)C(=O)C4)CC3)n3ccnc(C)c23)ccc1NC(=O)c1cc2c(OC)cccc2n1C]

1-Methyl-piperazin-2-one hydrochloride (0.844 mmol, 127 mg) in dichloromethane was put on a column of Si-Carbonate (Silicycle, 1 g) and eluation with dichloromethane gave the free base 1-methyl-piperazin-2-one. To this compound in 2-propanol (1 ml) were subsequently added 4-(1-bromo-8-methylimidazo[1,5-a]pyrazin-3-yl)cyclohexanone (0.649 mmol, 200 mg) and aluminium isopropoxide (1.469 mmol, 300 mg) and the mixture was stirred at 60° C. for one hour. Sodium triacetoxyborohydride (1.298 mmol, 275 mg) was added and the mixture was stirred at 60° C. overnight. Then the reaction mixture was diluted with dichloromethane and water, the dichloromethane layer isolated by a phase separation filter and concentrated in vacuo. The crude product was purified by column chromatography (silica gel; gradient of dichloromethane to dichloromethane/methanol 92/8) to give 4-((trans)-4-(1-bromo-8-methylimidazo[1,5-a]pyrazin-3-yl)cyclohexyl)-1-methylpiperazin-2-one (50 mg).

6-Methoxy-N-(2-methoxy-4-(4,4,5,5-tetramethyl-1,3,2-dioxaborolan-2-yl)phenyl)-1H-indazole-3-carboxamide (54 mg) and 4-((trans)-4-(1-bromo-8-methylimidazo[1,5-a]pyrazin-3-yl)cyclohexyl)-1-methylpiperazin-2-one (20 mg) were reacted according to the procedure described in example 4 step 4c and purified by column chromatography (silica gel; dichloromethane with gradient 0 to 5% of methanol) to give impure material. Additional purification by prep-HPLC (column Luna C18(2); gradient acetonitrile/water with constant 0.003M trifluoroacetic acid) gave 4-methoxy-N-(2-methoxy-4-(8-methyl-3-((trans)-4-(4-methyl-3-oxopiperazin-1-yl)cyclohexyl)imidazo[1,5-a]pyrazin-1-yl)phenyl)-1-methyl-1H-indole-2-carboxamide (11 mg).

UPLC: Method 0_60: Rt=2.19 min, (M+H)$^+$=636.

Example 75

5-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-c]pyridine-2-carboxamide

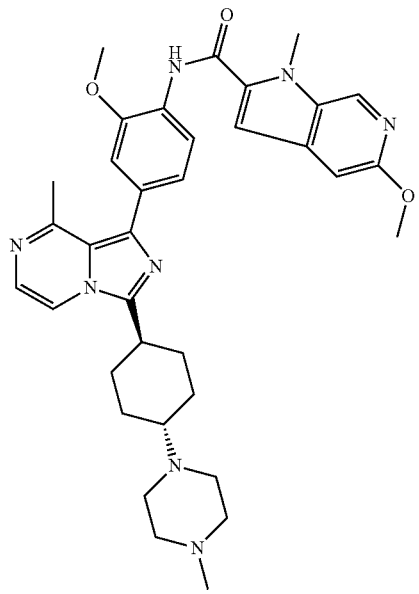 [SMILES: COc1cc2cc(C(=O)Nc3ccc(-c4nc([C@H]5CC[C@H](N6CCN(C)CC6)CC5)n5ccnc(C)c45)cc3OC)n(C)c2cn1]

To 5-methoxy-1H-pyrrolo[2,3-c]pyridine-2-carboxylic acid (1 g, 5.20 mmol) in methanol (100 ml) was added sulfuric acid (0.014 ml, 0.260 mmol). The resulting solution was heated to reflux and stirred at this temperature overnight. Then extra sulfuric acid (0.277 ml, 5.20 mmol) was added and heated at reflux for five days. The heating was stopped and the reaction mixture was concentrated to a smaller volume. The resulting suspension was diluted with ethyl acetate and washed with an aqueous saturated sodium hydrogen carbonate solution. The aqueous layer was extracted twice with ethyl acetate. The combined organic layers were washed with brine, dried (Na$_2$SO$_4$) and concentrated in vacuo to give methyl 5-methoxy-1H-pyrrolo[2,3-c]pyridine-2-carboxylate (910 mg).

To a stirred solution of methyl 5-methoxy-1H-pyrrolo[2,3-c]pyridine-2-carboxylate (910 mg, 4.41 mmol) in N,N-dimethylformamide (35 ml) at room temperature under a nitrogen atmosphere was added slowly sodium hydride (60 w/w % in mineral oil, 177 mg, 4.41 mmol). After 30 minutes iodomethane (0.302 ml, 4.85 mmol) was added and the reaction mixture was stirred at room temperature for 1.5 hours. Then the reaction was quenched in water and extracted with ethyl acetate three times. The combined organic layers were washed with brine, dried (Na$_2$SO$_4$) and concentrated in vacuo. The residue was purified by flash chromatography (gradient of heptane to heptane/ethyl acetate 1/1) to give methyl 5-methoxy-1-methyl-1H-pyrrolo[2,3-c]pyridine-2-carboxylate (878 mg).

To 2-methoxy-4-(4,4,5,5-tetramethyl-1,3,2-dioxaborolan-2-yl)aniline (2.09 g, 8.37 mmol) in tetrahydrofuran (20 ml) under a nitrogen atmosphere was added ethylmagnesium chloride, 2.0 M in tetrahydrofuran (4.19 ml, 8.37 mmol) and the mixture was heated at reflux for one hour. To the warm reaction was added methyl 5-methoxy-1-methyl-1H-pyrrolo[2,3-c]pyridine-2-carboxylate (878 mg, 3.99 mmol) in tetrahydrofuran (10 ml) and the resulting mixture was heated overnight. Then the reaction mixture was cooled to room temperature and concentrated. The residue was taken up in ethyl acetate and washed with water. The aqueous layer was extracted with ethyl acetate twice. The combined organic layers were washed with brine, dried (Na$_2$SO$_4$) and concentrated in vacuo. The residue was coated on hydromatrix and purified by flash chromatography (gradient of heptane to heptane/ethyl acetate 1/1) to give 5-methoxy-N-(2-methoxy-4-(4,4,5,5-tetramethyl-1,3,2-dioxaborolan-2-yl)phenyl)-1-methyl-1H-pyrrolo[2,3-c]pyridine-2-carboxamide (1.05 g).

5-Methoxy-N-(2-methoxy-4-(4,4,5,5-tetramethyl-1,3,2-dioxaborolan-2-yl)phenyl)-1-methyl-1H-pyrrolo[2,3-c]pyridine-2-carboxamide (22 mg) and 1-bromo-8-methyl-3-((trans)-4-(4-methylpiperazin-1-yl)cyclohexyl)imidazo[1,5-a]pyrazine (20 mg) were reacted according to the procedure described in example 4 step 4c and purified by column chromatography (silica gel; dichloromethane with gradient 0 to 20% of methanol) to give 5-methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-c]pyridine-2-carboxamide (19 mg).

UPLC: Method 0_60: Rt=1.08 min, (M+H)$^+$=623.

Example 76
Using the procedures described before the following compounds can be prepared:
| | | |
|---|---|---|
| a | 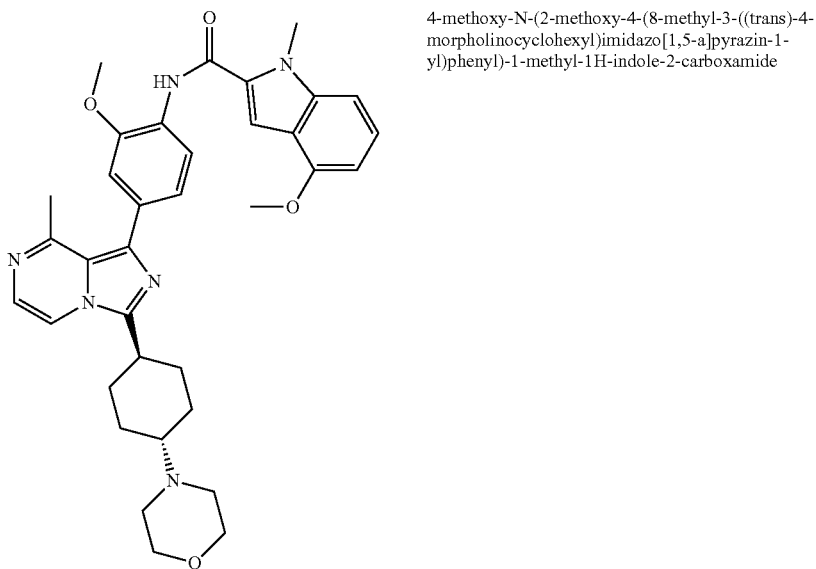 | 4-methoxy-N-(2-methoxy-4-(8-methyl-3-((trans)-4-morpholinocyclohexyl)imidazo[1,5-a]pyrazin-1-yl)phenyl)-1-methyl-1H-indole-2-carboxamide |
| b | 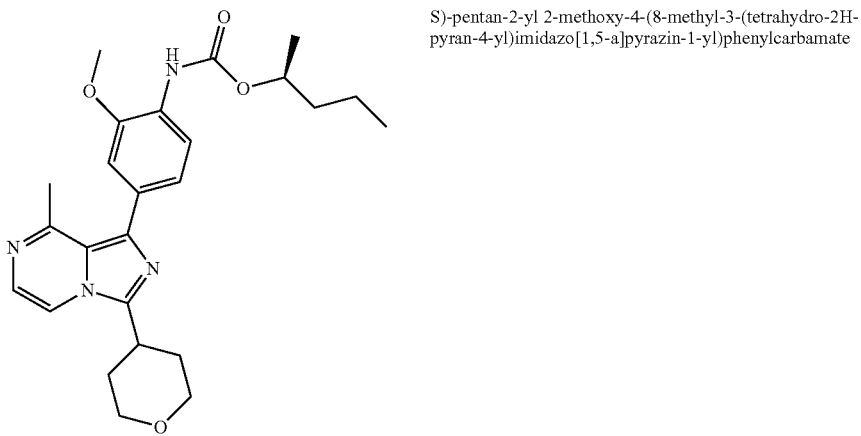 | S)-pentan-2-yl 2-methoxy-4-(8-methyl-3-(tetrahydro-2H-pyran-4-yl)imidazo[1,5-a]pyrazin-1-yl)phenylcarbamate |

| | | |
|---|---|---|
| c | 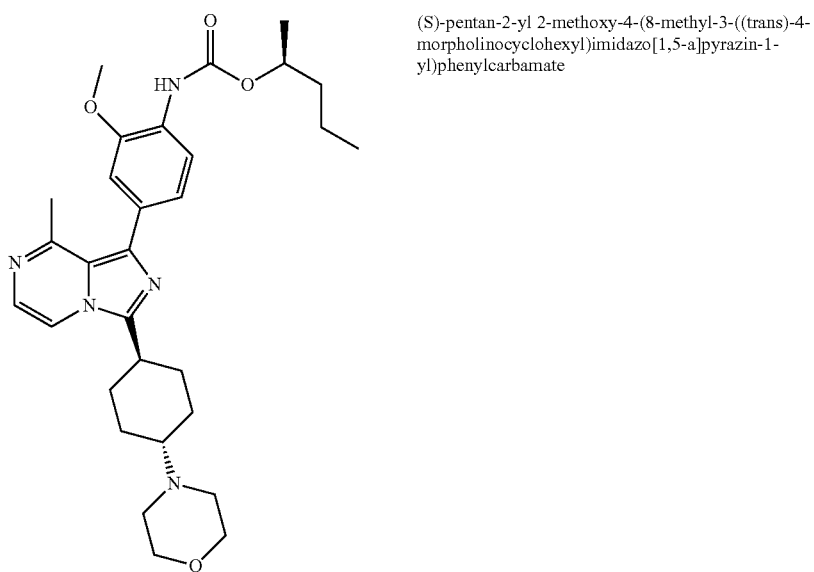 | (S)-pentan-2-yl 2-methoxy-4-(8-methyl-3-((trans)-4-morpholinocyclohexyl)imidazo[1,5-a]pyrazin-1-yl)phenylcarbamate |
| d | 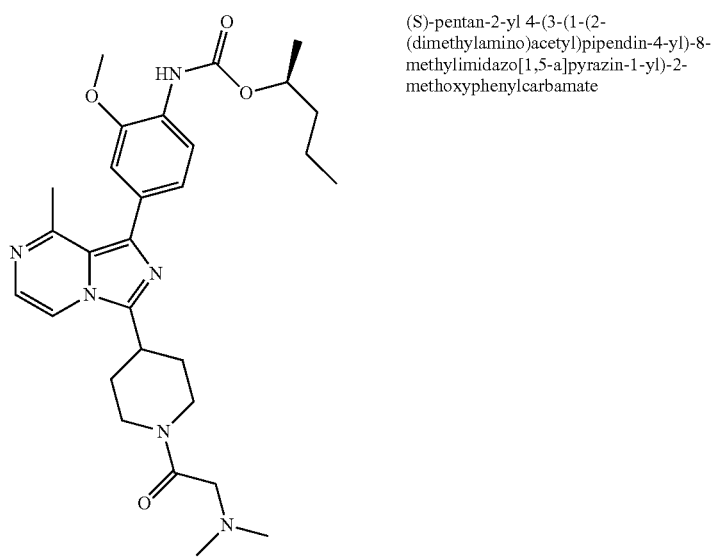 | (S)-pentan-2-yl 4-(3-(1-(2-(dimethylamino)acetyl)pipendin-4-yl)-8-methylimidazo[1,5-a]pyrazin-1-yl)-2-methoxyphenylcarbamate |

| | | |
|---|---|---|
| e | 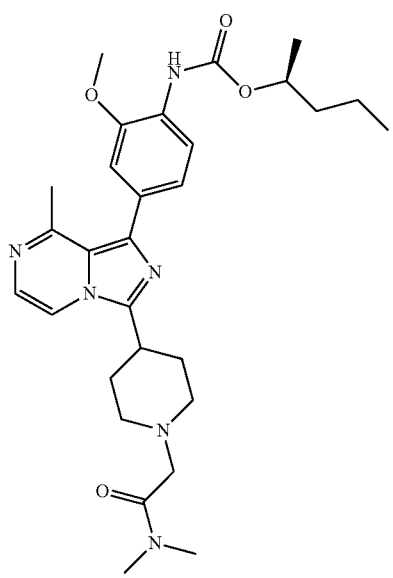 [SMILES: CCC[C@H](C)OC(=O)Nc1ccc(-c2nc(C3CCN(CC(=O)N(C)C)CC3)n3ccnc(C)c23)cc1OC] | (S)-pentan-2-yl 4-(3-(1-(2-(dimethylamino)-2-oxoethyl)pipendin-4-yl)-8-methylimidazo[1,5-a]pyrazin-1-yl)-2-methoxyphenylcarbamate |
| f | 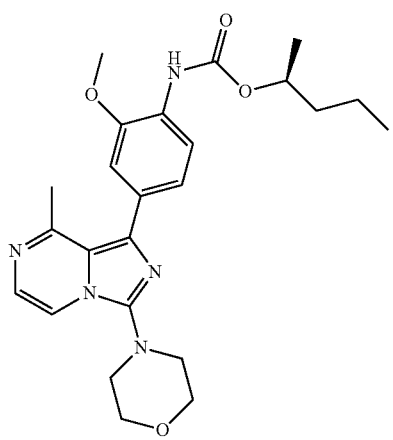 [SMILES: CCC[C@H](C)OC(=O)Nc1ccc(-c2nc(N3CCOCC3)n3ccnc(C)c23)cc1OC] | (S)-pentan-2-yl 2-methoxy-4-(8-methyl-3-morpholinoimidazo[1,5-a]pyrazin-1-yl)phenylcarbamate |
| g | 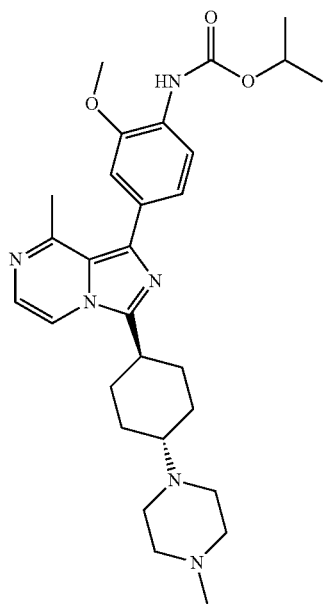 [SMILES: COc1cc(-c2nc([C@H]3CC[C@H](N4CCN(C)CC4)CC3)n3ccnc(C)c23)ccc1NC(=O)OC(C)C] | isopropyl 2-methoxy-4-(8-methyl-3-((trans)-4-(4-methylpiperazin-1-yl)cyclohexyl)imidazo[1,5-a]pyrazin-1-yl)phenylcarbamate |

| | | |
|---|---|---|
| h | 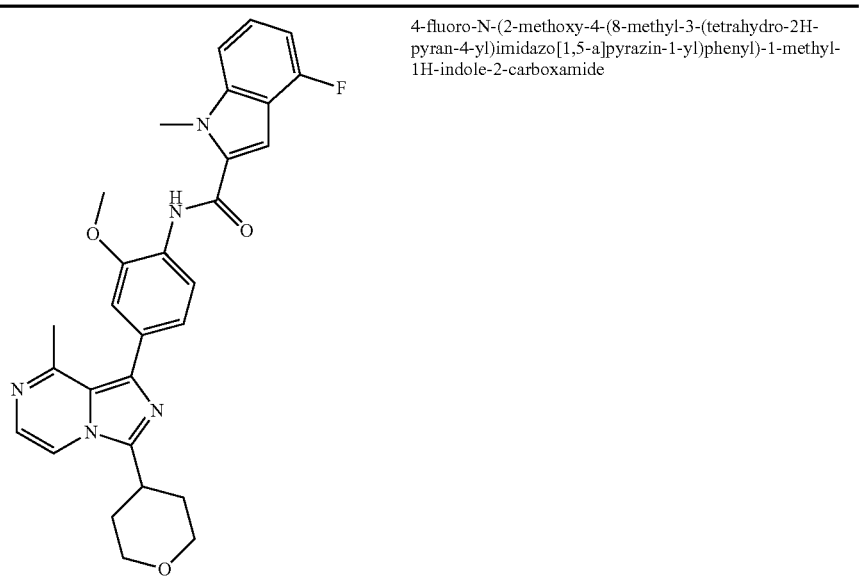 | 4-fluoro-N-(2-methoxy-4-(8-methyl-3-(tetrahydro-2H-pyran-4-yl)imidazo[1,5-a]pyrazin-1-yl)phenyl)-1-methyl-1H-indole-2-carboxamide |
| i | 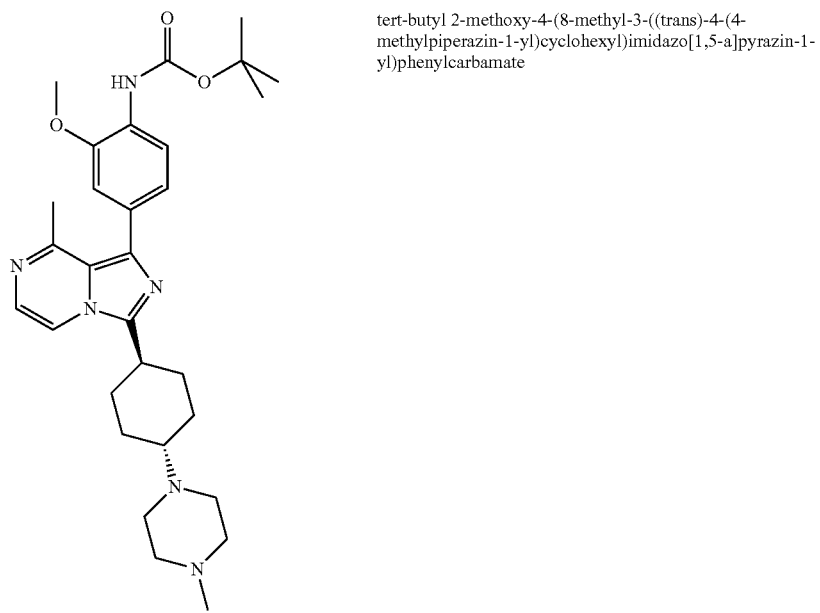 | tert-butyl 2-methoxy-4-(8-methyl-3-((trans)-4-(4-methylpiperazin-1-yl)cyclohexyl)imidazo[1,5-a]pyrazin-1-yl)phenylcarbamate |

| | | |
|---|---|---|
| j | 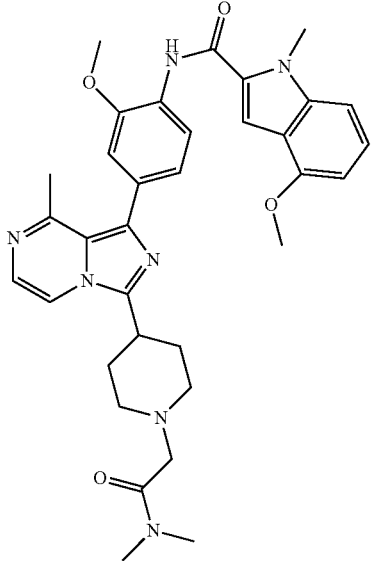 [SMILES: COc1cc(-c2nc(C3CCN(CC(=O)N(C)C)CC3)n3ccnc(C)c23)ccc1NC(=O)c1cc2c(OC)cccc2n1C] | N-(4-(3-(1-(2-(dimethylamino)-2-oxoethyl)piperidin-4-yl)-8-methylimidazo[1,5-a]pyrazin-1-yl)-2-methoxyphenyl)-4-methoxy-1-methyl-1H-indole-2-carboxamide |
| k | 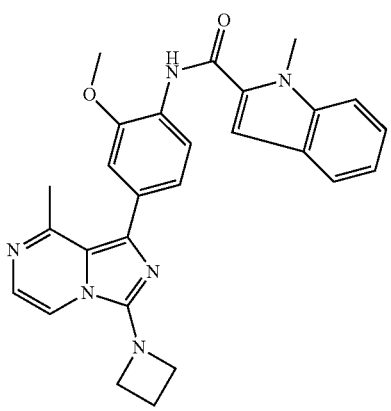 [SMILES: COc1cc(-c2nc(N3CCC3)n3ccnc(C)c23)ccc1NC(=O)c1cc2ccccc2n1C] | N-(4-(3-(azetidin-1-yl)-8-methylimidazo[1,5-a]pyrazin-1-yl)-2-methoxyphenyl)-1-methyl-1H-indole-2-carboxamide |
| l | 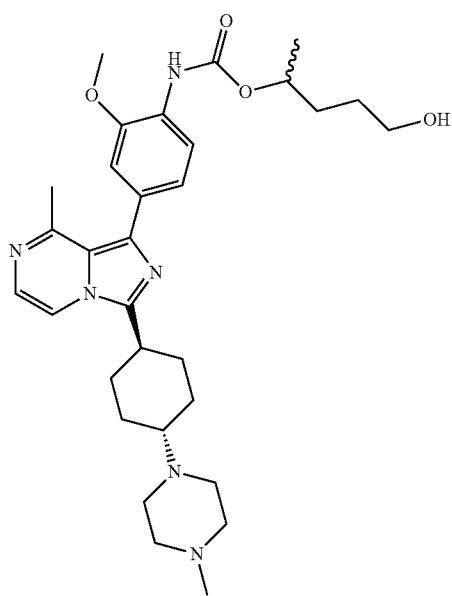 [SMILES: COc1cc(-c2nc([C@H]3CC[C@H](N4CCN(C)CC4)CC3)n3ccnc(C)c23)ccc1NC(=O)OC(C)CCCO] | 5-hydroxypentan-2-yl 2-methoxy-4-(8-methyl-3-((trans)-4-(4-methylpiperazin-1-yl)cyclohexyl)imidazo[1,5-a]pyrazin-1-yl)phenylcarbamate |

| | | |
|---|---|---|
| m | 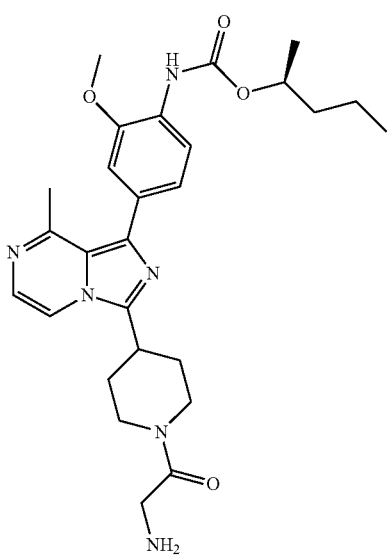 [SMILES: CCC[C@H](C)OC(=O)Nc1ccc(-c2nc(C3CCN(C(=O)CN)CC3)n3ccnc(C)c23)cc1OC] | (S)-pentan-2-yl 4-(3-(1-(2-aminoacetyl)piperidin-4-yl)-8-methylimidazo[1,5-a]pyrazin-1-yl)-2-methoxyphenylcarbamate |
| n | 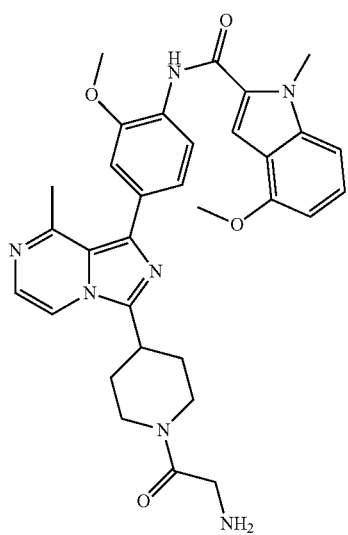 [SMILES: COc1cc(-c2nc(C3CCN(C(=O)CN)CC3)n3ccnc(C)c23)ccc1NC(=O)c1cc2c(OC)cccc2n1C] | N-(4-(3-(1-(2-aminoacetyl)piperidin-4-yl)-8-methylimidazo[1,5-a]pyrazin-1-yl)-2-methoxyphenyl)-4-methoxy-1-methyl-1H-indole-2-carboxamide |
| o | 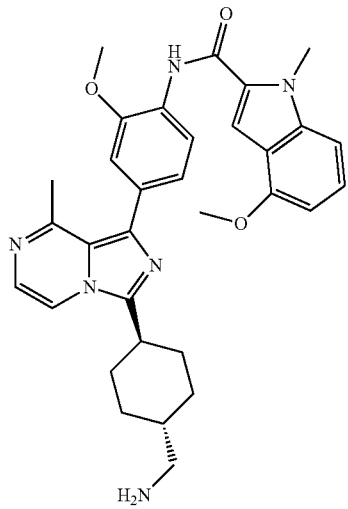 [SMILES: COc1cc(-c2nc([C@H]3CC[C@H](CN)CC3)n3ccnc(C)c23)ccc1NC(=O)c1cc2c(OC)cccc2n1C] | N-(4-(3-((trans)-4-(aminomethyl)cyclohexyl)-8-methylimidazo[1,5-a]pyrazin-1-yl)-2-methoxyphenyl)-4-methoxy-1-methyl-1H-indole-2-carboxamide | p 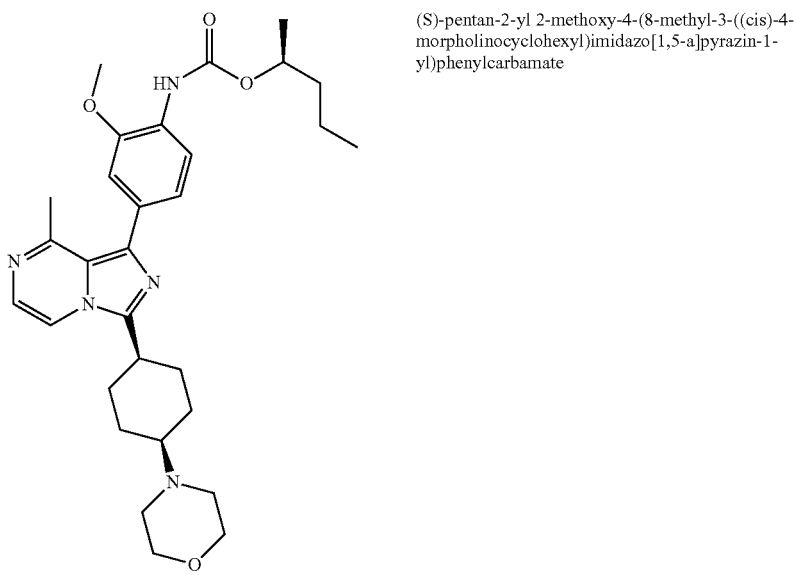
(S)-pentan-2-yl 2-methoxy-4-(8-methyl-3-((cis)-4-morpholinocyclohexyl)imidazo[1,5-a]pyrazin-1-yl)phenylcarbamate
q 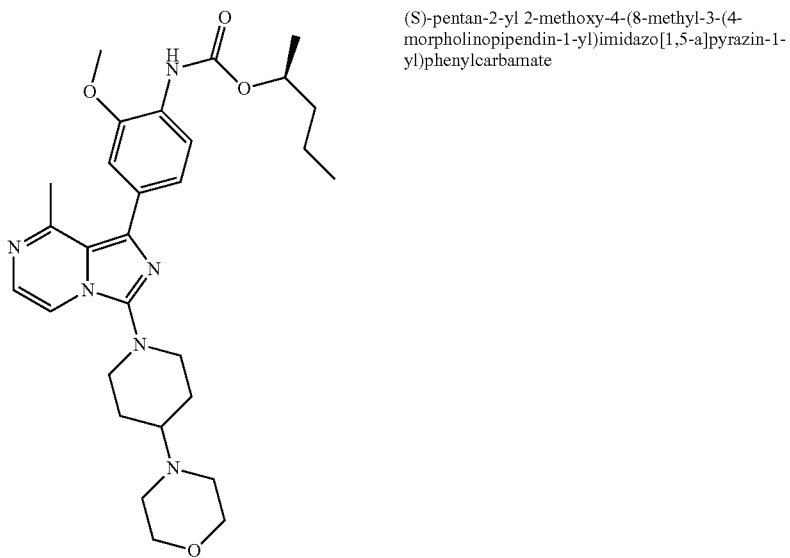
(S)-pentan-2-yl 2-methoxy-4-(8-methyl-3-(4-morpholinopipendin-1-yl)imidazo[1,5-a]pyrazin-1-yl)phenylcarbamate

| r | 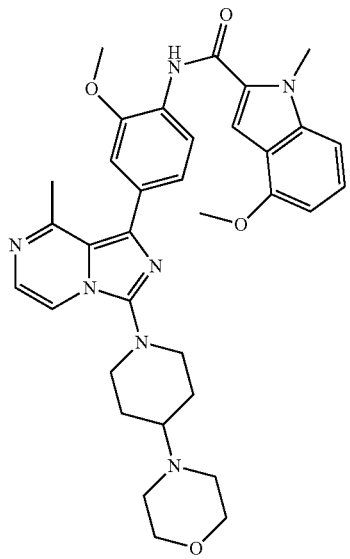 [SMILES: COc1cc(-c2nc(N3CCC(N4CCOCC4)CC3)n3ccnc(C)c23)ccc1NC(=O)c1cc2c(OC)cccc2n1C] | 4-methoxy-N-(2-methoxy-4-(8-methyl-3-(4-morpholinopiperidin-1-yl)imidazo[1,5-a]pyrazin-1-yl)phenyl)-1-methyl-1H-indole-2-carboxamide |
| s | 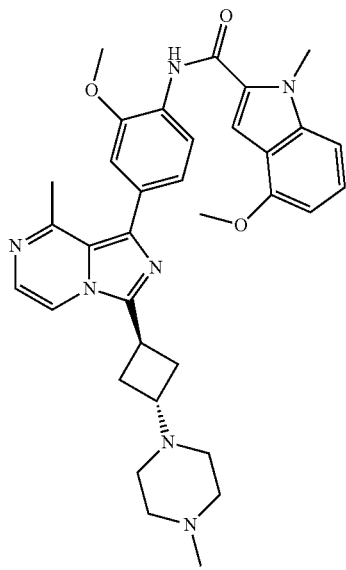 [SMILES: COc1cc(-c2nc([C@H]3C[C@H](N4CCN(C)CC4)C3)n3ccnc(C)c23)ccc1NC(=O)c1cc2c(OC)cccc2n1C] | 4-methoxy-N-(2-methoxy-4-(8-methyl-3-((trans)-3-(4-methylpiperazin-1-yl)cyclobutyl)imidazo[1,5-a]pyrazin-1-yl)phenyl)-1-methyl-1H-indole-2-carboxamide |

| | | |
|---|---|---|
| t | 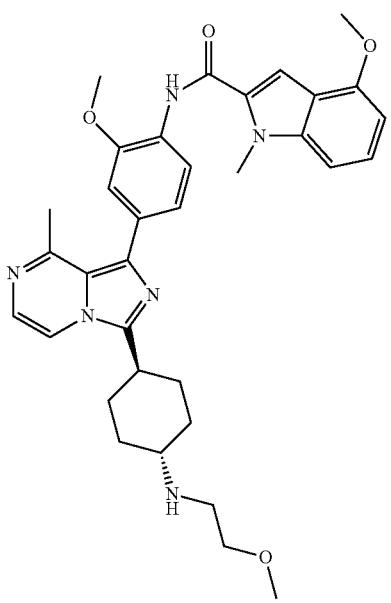 [SMILES: COCCN[C@H]1CC[C@H](c2nc(-c3ccc(NC(=O)c4cc5c(OC)cccc5n4C)c(OC)c3)c3c(C)nccn32)CC1] | 4-methoxy-N-(2-methoxy-4-(3-((trans)-4-(2-methoxyethylamino)cyclohexyl)-8-methylimidazo[1,5-a]pyrazin-1-yl)phenyl)-1-methyl-1H-indole-2-carboxamide |
| u | 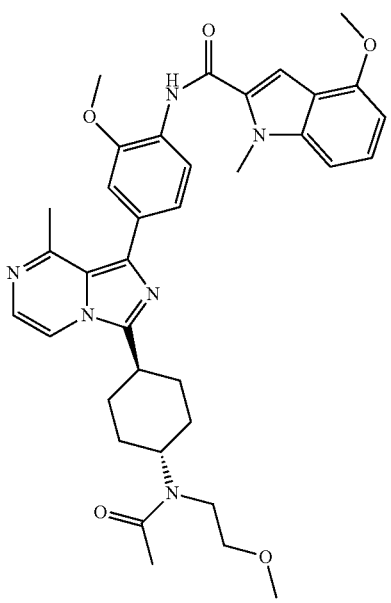 [SMILES: COCCN(C(C)=O)[C@H]1CC[C@H](c2nc(-c3ccc(NC(=O)c4cc5c(OC)cccc5n4C)c(OC)c3)c3c(C)nccn32)CC1] | 4-methoxy-N-(2-methoxy-4-(3-((trans)-4-(N-(2-methoxyethyl)acetamido)cyclohexyl)-8-methylimidazo[1,5-a]pyrazin-1-yl)phenyl)-1-methyl-1H-indole-2-carboxamide |
| v | 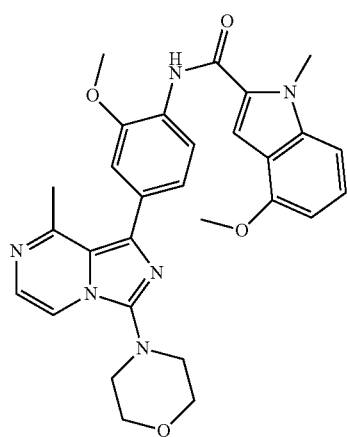 [SMILES: COc1cc(-c2nc(N3CCOCC3)n3ccnc(C)c23)ccc1NC(=O)c1cc2c(OC)cccc2n1C] | 4-methoxy-N-(2-methoxy-4-(8-methyl-3-morpholinoimidazo[1,5-a]pyrazin-1-yl)phenyl)-1-methyl-1H-indole-2-carboxamide |

| | | |
|---|---|---|
| w | 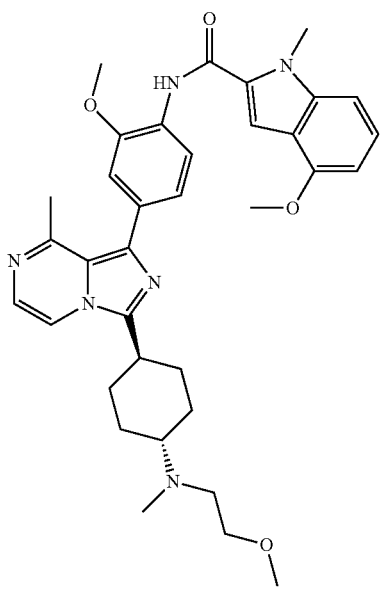 [SMILES: COCCN(C)[C@H]1CC[C@H](c2nc(-c3ccc(NC(=O)c4cc5c(OC)cccc5n4C)c(OC)c3)c3c(C)nccn32)CC1] | 4-methoxy-N-(2-methoxy-4-(3-((trans)-4-((2-methoxyethyl)(methyl)amino)cyclohexyl)-8-methylimidazo[1,5-a]pyrazin-1-yl)phenyl)-1-methyl-1H-indole-2-carboxamide |
| x | 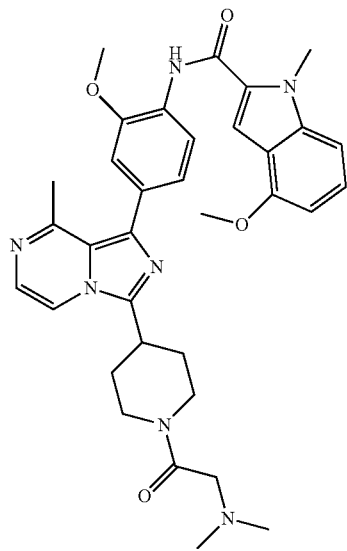 [SMILES: COc1cc(-c2nc(C3CCN(C(=O)CN(C)C)CC3)n3ccnc(C)c23)ccc1NC(=O)c1cc2c(OC)cccc2n1C] | N-(4-(3-(1-(2-(dimethylamino)acetyl)pipendin-4-yl)-8-methylimidazo[1,5-a]pyrazin-1-yl)-2-methoxyphenyl)-4-methoxy-1-methyl-1H-indole-2-carboxamide |

| | | |
|---|---|---|
| y | 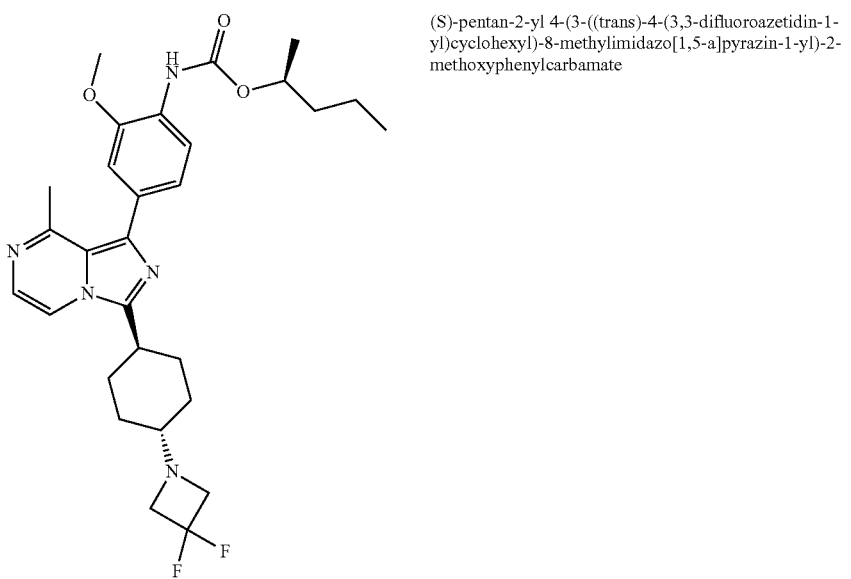 | (S)-pentan-2-yl 4-(3-((trans)-4-(3,3-difluoroazetidin-1-yl)cyclohexyl)-8-methylimidazo[1,5-a]pyrazin-1-yl)-2-methoxyphenylcarbamate |
| z | 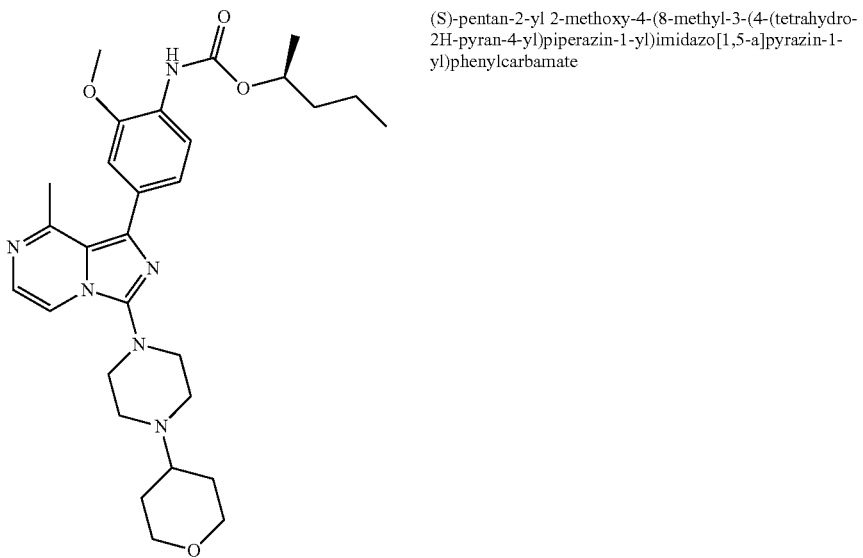 | (S)-pentan-2-yl 2-methoxy-4-(8-methyl-3-(4-(tetrahydro-2H-pyran-4-yl)piperazin-1-yl)imidazo[1,5-a]pyrazin-1-yl)phenylcarbamate |

| | | |
|---|---|---|
| aa | 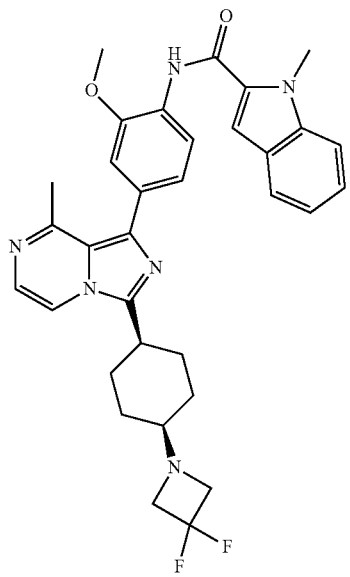 [SMILES: COc1cc(-c2nc([C@H]3CC[C@@H](N4CC(F)(F)C4)CC3)n3ccnc(C)c23)ccc1NC(=O)c1cc2ccccc2n1C] | N-(4-(3-((trans)-4-(3,3-difluoroazetidin-1-yl)cyclohexyl)-8-methylimidazo[1,5-a]pyrazin-1-yl)-2-methoxyphenyl)-1-methyl-1H-indole-2-carboxamide |

Example 77

Lck IMAP assay

Enzyme used was N-terminal His6-tagged recombinant full-length human Lck from Millipore. Phosphorylation substrate was a fluorescein-labeled peptide (5FAM-KVEKIGEGTYGVV—NH2) derived from p34cdc2 from Molecular Devices. Enzymes, substrate and ATP were diluted in Kinase Reaction buffer (10 mM Tris-HCl, 10 mM MgCl2, 0.01% Tween-20, 0.05% NaN3 pH 7.2, 1 mM DTT (dithiotreitol). The final volume at the kinase reaction step of the assay in the 384-well plate was 20 μl. Final amount of enzyme in the reaction was 0.1 U/ml. Enzyme was pre-incubated with compounds diluted in 1% DMSO (dimethylsulfoxide) for 60 minutes at room temperature in the dark. Subsequently, peptide substrate to a final concentration of 100 nM, and ATP to a final concentration of 6 μM were added and the mix was incubated for 120 minutes at room temperature in the dark. IMAP progressive binding buffer (75% 1× buffer A, 25% 1× buffer B with 1:600 Progressive Binding Reagent; Molecular Devices) was added, followed by an incubation step of 60 minutes at room temperature in the dark. Finally, the FP signal was read on an Envision Multilabel reader (Perkin Elmer).

All biochemical assays were run at $K_{M,ATP}$ of the enzyme using non-saturated conditions, meaning that during the incubation time it was assured that the signal increase was linear with time. For all biochemical assays a reference standard was used on each plate. Newly purchased enzyme batches were tested in serial dilutions with the reference standard to assure that comparable compound $pIC_{50}$s were obtained in all assays run over time using different enzyme batches.

Ten point serial dilutions using a √10 dilution factor were used for dose response testing of compounds. Starting concentration was 10-6M for Lck IMAP assays. Dose-response curves were run as two experiments on duplicate plates (N=1; n=2). All data was normalized to percentage effect based on maximum (Max) and minimum (Min) control values. On every 384 assay plate 16 wells were used as minimum wells (wells with ATP, 0% effect) and 16 wells were used as maximum wells (wells without ATP, 100% effect). 16 wells were used for measuring the background signal, obtained from a kinase reaction containing all constituents except the labeled peptide substrate. Percentage effect was plotted against log dilution concentration of compound to obtain sigmoid dose response curves. pIC50 values were calculated using ActivityBase.

Values obtained are given in Table 1.

TABLE 1

| pIC50 | Example |
|---|---|
| ≥6, <7 | 15, 41, 47 |
| ≥7, <8 | 3, 14, 16, 25, 33g, 35, 36, 37, 42, 44, 45, 51, 52 |
| ≥8 | 1, 2, 4, 5, 6, 7, 8, 9, 10, 11, 12, 13, 17, 18, 19, 20, 21, 22, 23, 24, 26a, 26b, 26c, 26d, 26e, 26f, 26g, 27, 28, 29, 30, 31, 32, 33a, 33b, 33c, 33d, 33e, 33f, 34, 38, 39, 40, 43, 46, 48, 49, 50, 53, 54, 55, 56, 57, 58, 59, 60, 61, 62, 63, 64, 65, 66, 67, 68, 69, 70, 71, 72, 73, 74, 75, 76a-aa |

The invention claimed is:

1. A compound according to formula I

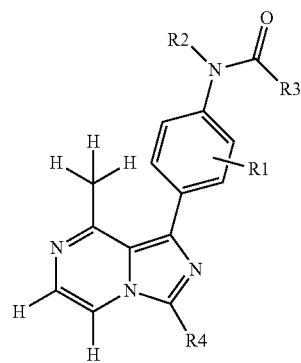

Formula I or a pharmaceutically acceptable salt thereof wherein
R1 is one or two groups independently selected from hydrogen, hydroxy, (1-6C)alkoxy, (1-6C)alkyl, halogen or cyano;
R2 is H or (1-6C)alkyl;
R3 is
(R31)(R32)CH—O; or
R3 is (3-7C)cycloalkoxy which is optionally substituted with one or more substituents selected from fluoro or hydroxy; or
R3 is heteroaryl, which is optionally substituted with one or more substituents selected from R34, R35, R36, halogen, hydroxy or cyano;
R31 is H or (1-5C)alkyl optionally substituted with one or more fluoro, hydroxy or (1-6C)alkoxy;
R32 is (1-5C)alkyl optionally substituted with one or more fluoro;
R34 is (1-6C)alkyl optionally substituted with one or more fluoro;
R35 is (1-6C)alkoxy optionally substituted with one or more fluoro;
R36 is hydrogen or (1-6C)alkyl optionally substituted with one or more fluoro;

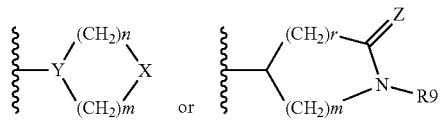

or
R4 is (1-4C)alkyl, optionally substituted independently by one or more substituents selected from R8, fluoro or hydroxy;
wherein
m is 1, 2 or 3;
n is 1, 2 or 3;
r is 1 or 2;
Y is CR5 or N;
X is O, CHR6, C(R66)(R67), NR7 or C=O;
Z is O or
Z forms with R9 a 5 or 6 membered heterocyclyl optionally substituted by R91;
R5 is H or (1-6C)alkyl optionally substituted with one or more fluoro;
R6 is R61, R62, R63, R65, H, hydroxy or fluoro;
R7 is R71, R72, R73, R74 or H;
R8 is heteroaryl, optionally substituted with one or more groups selected from (1-4C)alkyl, hydroxy, (1-6C)alkoxy, amino, (di)[(1-4C)alkyl]amino, [(1-4C)alkyl]amino or halogen;
R9 is H or (1-6C)alkyl optionally substituted with one or more fluoro;
R61 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl or [(1-4C)alkyl][(1-4C)alkoxycarbonyl]amino(1-4C)alkyl, all of the alkyl groups of R61 are optionally substituted with one or more fluoro;
R62 is (1-6C)alkoxy, hydroxy(1-6-C)alkoxy, (1-3C)alkoxy(2-4C)alkoxy, R621-(2-4C)alkoxy, (1-4C)alkylcarbonyloxy, (1-4C)alkylaminocarbonyloxy or (3-6C)cycloalkylaminocarbonyloxy, all of the alkyl groups of R62 are optionally substituted with one or more fluoro;
R63 is amino, [(1-6C)alkyl]amino, (di)[(1-6C)alkyl]amino, [hydroxy(2-6C)alkyl]amino, [(1-6C)alkyl][hydroxy(2-6C)alkyl]amino, (1-6C)alkoxycarbonylamino, (1-6C)alkylaminocarbonylamino, [(1-6C)alkoxy(2-6C)alkyl]amino, [(1-6C)alkyl][(1-6C)alkoxy(2-6C)alkyl]amino, (1-6C)alkylcarbonylamino or [(1-6C)alkylcarbonyl][(1-6C)alkoxy(2-6C)alkyl]amino, all of the alkyl groups of R63 are optionally substituted with one or more fluoro;
R65 is N-attached heterocyclyl which is optionally substituted with one or more oxo, fluoro or one or more R651;
R66 is (1-6C)alkyl, (3-6C)cycloalkyl, (3-6C)cycloalkyl(1-3C)alkyl, amino(1-4C)alkyl, [(1-6C)alkyl]amino(1-4C)alkyl, (di)[(1-6C)alkyl]amino(1-4C)alkyl, [(1-4C)alkylcarbonyl]amino(1-4C)alkyl, [(1-4C)alkyl][(1-4C)alkylcarbonyl]amino(1-4C)alkyl, [(1-4C)alkoxycarbonyl]amino(1-4C)alkyl, [(1-4C)alkyl][(1-4C)alkoxycarbonyl]amino(1-4C)alkyl, all of the alkyl groups of R66 are optionally substituted with one or more fluoro;
R67 is hydroxy, (1-4C)alkoxy or fluoro;
R71 is (1-6C)alkyl, (3-6C)cycloalkyl or (3-6C)cycloalkyl(1-3C)alkyl, any of which is optionally substituted with one or more fluoro;
R72 is (1-4C)alkyl, which is substituted with one group selected from R721, R722, R724 and R725;
R73 is R732-carbonyl, R733-carbonyl, or R735-carbonyl;
R74 is heterocyclyl which is optionally substituted with one or more groups independently selected from fluoro or R741;
R91 is (1-6C)alkyl optionally substituted with one or more fluoro;
R621 is amino, [(1-6C)alkyl]amino, (di)[(1-6C)alkyl]amino, any of the alkyl groups is optionally substituted with one or more fluoro; or
R621 is N-attached heterocyclyl, optionally substituted with one or more fluoro;
R651 is (1-4C)alkyl, (3-6C)cycloalkyl, (3-6C)cycloalkyl(1-3C)alkyl or (1-4C)alkylcarbonyl, all of the alkyl groups of R651 are optionally substituted with one or more groups independently selected from fluoro or hydroxy;
R721 is (1-6C)alkoxy, (3-6C)cycloalkoxy, (1-6C)alkoxy-(3-6C)cycloalkyl, (1-3C)alkoxy(2-4C)alkoxy, amino(2-4C)alkoxy, [(1-6C)alkyl]amino(2-4C)alkoxy, (di)[(1-6C)alkyl]amino(2-4C)alkoxy, [hydroxy(2-6C)alkyl]amino(2-4C)alkoxy, [(1-6C)alkyl][hydroxy(2-6C)alkyl]amino(2-4C)alkoxy, [(1-6C)alkoxy(2-6C)alkyl]amino(2-4C)alkoxy, [(1-6C)alkyl][(1-6C)alkoxy(2-6C)alkyl]amino(2-4C)alkoxy, (cyclyl-N)-(2-4C)alkoxy, [(1-6C)alkylcarbonyl]amino(1-6C)alkoxy, [(1-6C)alkyl][(1-6C)alkylcarbonyl]amino(1-6C)alkoxy, [(3-6C)cycloalkylcarbonyl]amino(1-6C)alkoxy, [(1-6C)alkyl][(3-6C)cycloalkylcarbonyl]amino(1-6C)alkoxy, aminocarbonyl(1-6C)alkoxy, [(1-6C)alkyl]aminocarbonyl(1-6C)alkoxy, (di)[(1-6C)alkyl]aminocarbonyl(1-6C)alkoxy, [hydroxy(1-6C)alkyl]aminocarbonyl(1-6C)alkoxy or (cyclyl-N)carbonyl(1-6C)alkoxy, all of the alkyl groups of R721 are optionally substituted with one or more groups independently selected from fluoro or hydroxy;
R722 is amino, [(1-6C)alkyl]amino, (di)[(1-6C)alkyl]amino, [hydroxy(2-6C)alkyl]amino, [(1-6C)alkyl][hydroxy(2-6C)alkyl]amino, [(1-6C)alkoxy(2-6C)alkyl]amino, [(1-6C)alkyl][(1-6C)alkoxy(2-6C)alkyl]amino or cyclyl-N, all of the alkyl groups of R722 are optionally substituted with one or more fluoro;

R724 is (1-6C)alkoxycarbonylamino, [(1-6C)alkoxycarbonyl(1-6C)alkyl]amino, (1-6C)alkylaminocarbonylamino, (cyclyl-N)carbonylamino;

R725 is aminocarbonyl, [(1-6C)alkyl]aminocarbonyl, (di)[(1-6C)alkyl]aminocarbonyl, [hydroxy(2-6C)alkyl]aminocarbonyl, [(1-6C)alkyl][hydroxy(2-6C)alkyl]aminocarbonyl, [(1-6C)alkoxy(2-6C)alkyl]aminocarbonyl, [(1-6C)alkyl][(1-6C)alkoxy(2-6C)alkyl]aminocarbonyl, (cyclyl-N)carbonyl, amino(2-4C)alkoxycarbonyl or [(1-6C)alkyl]amino(2-4C)alkoxycarbonyl, all of the alkyl groups of R725 are optionally substituted with one or more fluoro;

R732 is (1-4C)alkyl, amino(1-4C)alkyl, [(1-6C)alkyl]amino(1-4C)alkyl, (di)[(1-6C)alkyl]amino(1-4C)alkyl, [hydroxy(2-6C)alkyl]amino(1-4C)alkyl, [(1-6C)alkyl][hydroxy(2-6C)alkyl]amino(1-4C)alkyl, [(1-6C)alkoxy(2-6C)alkyl]amino(1-4C)alkyl, [(1-6C)alkyl][(1-6C)alkoxy(2-6C)alkyl]amino(1-4C)alkyl, (cyclyl-N)(1-4C)alkyl, [(1-6C)alkylcarbonyl]amino(1-4C)alkyl, [(1-6C)alkyl][(1-6C)alkylcarbonyl]amino(1-4C)alkyl, hydroxy(1-4C)alkyl, (1-6C)alkoxy(1-4C)alkyl, (3-6C)cycloalkoxy(1-4C)alkyl, aminocarbonyl(1-4C)alkyl, [(1-6C)alkyl]aminocarbonyl(1-4C)alkyl, (di) [(1-6C)alkyl]aminocarbonyl(1-4C)alkyl, [hydroxy(1-6C)alkyl]aminocarbonyl(1-4C)alkyl, [(1-6C)alkyl][hydroxy(1-6C)alkyl]aminocarbonyl(1-4C)alkyl or [(1-6C)alkoxy(2-6C)alkyl]aminocarbonyl(1-4C)alkyl, all of the alkyl groups of R732 are optionally substituted with one or more fluoro;

R733 is (1-6C)alkoxy;

R735 is amino, [(1-6C)alkyl]amino, (di)[(1-6C)alkyl]amino or cyclyl-N, all of the alkyl groups of R735 are optionally substituted with one or more fluoro;

R741 is (1-4C)alkyl, (3-6C)cycloalkyl, (3-6C)cycloalkyl(1-3C)alkyl, (1-6C)alkoxy or (1-4C)alkylcarbonyl all, of the alkyl groups of R741 are optionally substituted with one or more fluoro or hydroxy.

2. The compound according to claim 1 wherein R1 is one or two groups independently selected from hydrogen, hydroxy, (1-3C)alkoxy or halogen.

3. The compound according to claim 2 wherein
R3 is (R31)(R32)CH—O;
R31 is (1-5C)alkyl optionally substituted with hydroxy; and
R32 is (1-5C)alkyl.

4. The compound according to claim 2 wherein
R3 is heteroaryl, which is optionally substituted with one or more groups selected from R34, R35, R36, fluoro, chloro or hydroxy;
R34 is (1-6C)alkyl;
R35 is (1-6C)alkoxy; and
R36 is hydrogen or (1-6C)alkyl.

5. The compound according to claim 4 wherein the heteroaryl group in R3 is

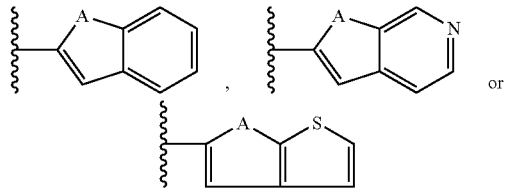

wherein
A is O or NR36 and wherein each C is optionally substituted with one group selected from R34, R35 and fluoro;
R34 is (1-6C)alkyl;
R35 is (1-6C)alkoxy; and
R36 is hydrogen or (1-6C)alkyl.

6. The compound according to claim 5 wherein
R4 is

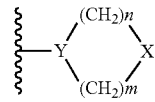

wherein
R62, when present, is (1-6C)alkoxy, hydroxy(1-6C)alkoxy, (1-3C)alkoxy(2-4C)alkoxy, (1-4C)alkylcarbonyloxy, (1-4C)alkylaminocarbonyloxy, or (3-6C)cycloalkylaminocarbonyloxy, all of the alkyl groups of R62 are optionally substituted with one or more fluoro;
R72, when present, is (1-4C)alkyl, which is substituted with R725; and
R725, when present, is aminocarbonyl, [(1-6C)alkyl]aminocarbonyl, (di)[(1-6C)alkyl]aminocarbonyl, [hydroxy(2-6C)alkyl]aminocarbonyl, [(1-6C)alkyl][hydroxy(2-6C)alkyl]aminocarbonyl, [(1-6C)alkoxy(2-6C)alkyl]aminocarbonyl, [(1-6C)alkyl][(1-6C)alkoxy(2-6C)alkyl]aminocarbonyl, (cyclyl-N)carbonyl, amino(2-4C)alkoxycarbonyl, or [(1-6C)alkyl]amino(2-4C)alkoxycarbonyl, all of the alkyl groups of R725 are optionally substituted with one or more fluoro.

7. The compound according to claim 6 wherein
R4 is

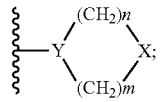

wherein
m is 1 or 2;
n is 1 or 2;
Y is CR5;
X is O, CHR6 or NR7;
R5 is H;
R6 is R61, R63 or R65;
R7 is R71, R72, R73, R74 or H;
R61 is amino(1-3C)alkyl, [(1-3C)alkyl]amino(1-3C)alkyl, (di)[(1-3C)alkyl]amino(1-3C)alkyl, [(1-3C)alkylcarbonyl]amino(1-3C)alkyl, or [(1-3C)alkoxycarbonyl]amino(1-3C)alkyl;
R63 is amino, [(1-3C)alkyl]amino, (di)[(1-3C)alkyl]amino, [(1-3C)alkoxy(2-3C)alkyl]amino, [(1-3C)alkyl][(1-3C)alkoxy(2-3C)alkyl]amino, or [(1-3C)alkylcarbonyl][(1-3C)alkoxy(2-3C)alkyl]amino, all of the alkyl groups of R63 are optionally substituted with one or more fluoro;
R65 is azetidine, pyrrolidine, piperidine, piperazine or morpholine which is optionally substituted with one or more oxo, fluoro or one or more R651;
R71 is (1-3C)alkyl;
R72 is (1-4C)alkyl, which is substituted with R725;
R73 is R732-carbonyl, R733-carbonyl, or R735-carbonyl;
R74 is pyran or piperidine optionally substituted with one or more groups independently selected from fluoro or R741;

R651 is (1-3C)alkyl, or (1-3C)alkylcarbonyl;
R725 is (di)[(1-3C)alkyl]aminocarbonyl;
R732 is (1-4C)alkyl, amino(1-4C)alkyl, (di)[(1-6C)alkyl]amino(1-4C)alkyl, [hydroxy(2-6C)alkyl]amino(1-4C)alkyl, hydroxy(1-4C)alkyl, or (1-6C)alkoxy(1-4C)alkyl;
R733 is (1-6C)alkoxy;
R735 is amino; and
R741 is (1-4C)alkylcarbonyl.

8. The compound according to claim 5 wherein R4 is

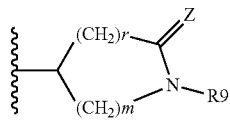

wherein
m is 1, 2 or 3;
r is 1 or 2;
Z is O or
Z forms with R9a 5 or 6 membered heterocyclyl optionally substituted by R91;
R9 is H or (1-6C)alkyl optionally substituted with one or more fluoro; and
R91 is (1-6C)alkyl optionally substituted with one or more fluoro.

9. The compound according to claim 8 wherein R4 is

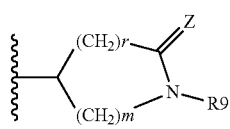

wherein
m is 1 or 2;
r is 1 or 2;
Z is O; and
R9 is H or (1-3C)alkyl.

10. The compound according to claim 5 wherein R4 is (1-4C)alkyl, optionally substituted independently by one or more substituents from R8, or hydroxy, wherein R8 is heteroaryl.

11. The Compound according to claim 1 selected from the group consisting of
N-[2-Methoxy-4-[8-methyl-3-(tetrahydro-2H-pyran-4-yl)imidazo[1,5-a]pyrazine]phenyl]-1-methyl-1H-indole-2-carboxamide,
N-(4-(3-((Trans)-4-(4-acetylpiperazin-1-yl)cyclohexyl)-8-methylimidazo[1,5-a]pyrazin-1-yl)-2-methoxyphenyl)-4-methoxy-1-methyl-1H-indole-2-carboxamide,
(S)-pentan-2-yl 4-(3-(azetidin-1-yl)-8-methylimidazo[1,5-a]pyrazin-1-yl)-2-methoxyphenylcarbamate,
(S)-pentan-2-yl 4-(3-((R)-1-(2-(dimethylamino)acetyl)pyrrolidin-3-yl)-8-methylimidazo[1,5-a]pyrazin-1-yl)-2-methoxyphenylcarbamate,
(Trans)-4-(1-(3-methoxy-4-(4-methoxy-1-methyl-1H-indole-2-carboxamido)phenyl)-8-methylimidazo[1,5-a]pyrazin-3-yl)cyclohexyl acetate,
N-(4-(3-((trans)-4-hydroxycyclohexyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide,
4-Methoxy-N-(2-methoxy-4-(8-methyl-3-((cis)-4-(4-methylpiperazin-1-yl)cyclohexyl)imidazo[1,5-a]pyrazin-1-yl)phenyl)-1-methyl-1H-indole-2-carboxamide,
N-(4-(3-((trans)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide,
N-(4-(3-((cis)-4-(3,3-difluoroazetidin-1-yl)cyclohexyl)-8-methylimidazo[1,5-a]pyrazin-1-yl)-2-methoxyphenyl)-4-methoxy-1-methyl-1H-indole-2-carboxamide,
(S)-Pentan-2-yl 2-methoxy-4-(3-((trans)-4-(2-methoxyethylamino)cyclohexyl)-8-methyl-imidazo[1,5-a]pyrazin-1-yl)phenylcarbamate, N-(2-methoxy-4-(8-methyl-3-((trans)-4-morpholinocyclohexyl)imidazo[1,5-a]pyrazin-1-yl)phenyl)-1-methyl-1H-indole-2-carboxamide,
4-Methoxy-N-(2-methoxy-4-(8-methyl-3-(3-methyloxetan-3-yl)imidazo[1,5-a]pyrazin-1-yl)phenyl)-1-methyl-1H-indole-2-carboxamide,
N-(4-(3-(hydroxymethyl)-8-methylimidazo[1,5-a]pyrazin-1-yl)-2-methoxyphenyl)-4-methoxy-1-methyl-1H-indole-2-carboxamide,
N-(4-(3-((1H-imidazol-1-yl)methyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(8-methyl-3-(1-(tetrahydro-2H-pyran-4-yl)azetidin-3-yl)imidazo[1,5-a]pyrazin-1-yl)phenyl)-1-methyl-1H-indole-2-carboxamide,
4-Methoxy-N-(2-methoxy-4-(8-methyl-3-(piperidin-4-yl)imidazo[1,5-a]pyrazin-1-yl)phenyl)-1-methyl-1H-indole-2-carboxamide,
N-(4-(3-(1-(2-(dimethylamino)-2-oxoethyl)piperidin-4-yl)-8-methylimidazo[1,5-a]pyrazin-1-yl)-2-methoxyphenyl)-1-methyl-1H-indole-2-carboxamide,
N-(4-(3-(1-(2-(dimethylamino)acetyl)piperidin-4-yl)-8-methylimidazo[1,5-a]pyrazin-1-yl)-2-methoxyphenyl)-1-methyl-1H-indole-2-carboxamide,
N-(4-(3-(1-(2-Aminoacetyl)piperidin-4-yl)-8-methylimidazo[1,5-a]pyrazin-1-yl)-2-methoxyphenyl)-1-methyl-1H-indole-2-carboxamide,
N-(4-(3-(1-carbamoylpiperidin-4-yl)-8-methylimidazo[1,5-a]pyrazin-1-yl)-2-methoxyphenyl)-4-methoxy-1-methyl-1H-indole-2-carboxamide,
Methyl 4-(1-(3-methoxy-4-(4-methoxy-1-methyl-1H-indole-2-carboxamido)phenyl)-8-methylimidazo[1,5-a]pyrazin-3-yl)piperidine-1-carboxylate,
N-(2-methoxy-4-(8-methyl-3-(4-methylpiperazin-1-yl)imidazo[1,5-a]pyrazin-1-yl)phenyl)-1-methyl-1H-indole-2-carboxamide,
N-(2-methoxy-4-(8-methyl-3-(morholin-4-yl) imidazo[1,5-a]pyrazin-1-yl)phenyl)-1-methyl-1H-indole-2-carboxamide,
Isopropyl 2-methoxy-4-(8-methyl-3-(4-morpholinopiperidin-1-yl)imidazo[1,5-a]pyrazin-1-yl)phenylcarbamate,
(S)-Pentan-2-yl 2-methoxy-4-(3-((trans)-4-((2-methoxyethyl)(methyl)amino)cyclohexyl)-8-methylimidazo[1,5-a]pyrazin-1-yl)phenylcarbamate,
N-(4-(3-((Trans)-4-(dimethylamino)cyclohexyl)-8-methylimidazo[1,5-a]pyrazin-1-yl)-2-methoxyphenyl)-4-methoxy-1-methyl-1H-indole-2-carboxamide,
4-Methoxy-N-(2-methoxy-4-(3-((cis)-4-((2-methoxyethyl)(methyl)amino)cyclohexyl)-8-methylimidazo[1, 5-a]pyrazin-1-yl)phenyl)-1-methyl-1H-indole-2-carboxamide, 4-Methoxy-N-(2-methoxy-4-(8-methyl-3-((cis)-4-morpholinocyclohexyl)imidazo[1,5-a]pyrazin-1-yl)phenyl)-1-methyl-1H-indole-2-carboxamide, N-(4-(3-((Cis)-4-(dimethylamino)cyclohexyl)-8-methylimidazo[1,5-a]pyrazin-1-yl)-2-methoxyphenyl)-4-methoxy-1-methyl-1H-indole-2-carboxamide, (S)-Pentan-2-yl 4-(3-((cis)-4-(4-acetylpiperazin-1-yl)cyclohexyl)-8-methylimidazo[1,5-a]pyrazin-1-yl)-2-methoxyphenylcarbamate, (S)-Pentan-2-yl 4-(3-((cis)-4-(3,3-difluoroazetidin-1-yl)cyclohexyl)-8-methylimidazo[1,5-a]pyrazin-1-yl)-2-methoxyphenylcarbamate, (S)-Pentan-2-yl 2-methoxy-4-(8-methyl-3-((1r,3r)-3-(4-methylpiperazin-1-yl)cyclobutyl)imidazo[1,5-a]pyrazin-1-yl)phenylcarbamate, (S)-Pentan-2-yl 2-methoxy-4-(8-methyl-3-(4-methylpiperazin-1-yl)cyclopentyl)imidazo[1,5-a]pyrazin-1-yl)phenylcarbamate, (S)-Pentan-2-yl 2-methoxy-4-(3-((trans)-4-(N-(2-methoxyethyl)acetamido)cyclohexyl)-8-methylimidazo[1,5-a]pyrazin-1-yl)phenylcarbamate, 4-Methoxy-N-(2-methoxy-4-(8-methyl-3-(1-(tetrahydro-2H-pyran-4-yl)piperidin-4-yl)imidazo[1,5-a]pyrazin-1-yl)phenyl)-1-methyl-1H-indole-2-carboxamide, (S)-Pentan-2-yl 4-(3-(4-acetylpiperazin-1-yl)-8-methylimidazo[1,5-a]pyrazin-1-yl)-2-methoxyphenylcarbamate, N-(4-(3-(4-(1-Acetylpiperidin-4-yl)piperazin-1-yl)-8-methylimidazo[1,5-a]pyrazin-1-yl)-2-methoxyphenyl)-4-methoxy-1-methyl-1H-indole-2-carboxamide, (S)-Pentan-2-yl 2-methoxy-4-(8-methyl-3-((trans)-4-(4-methylpiperazin-1-yl)cyclohexyl)imidazo[1,5-a]pyrazin-1-yl)phenylcarbamate, N-(2-Methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide 2,2,2-trifluoroacetate, N-(4-(3-((Trans)-4-(4-acetylpiperazin-1-yl)cyclohexyl)-8-methylimidazo[1,5-a]pyrazin-1-yl)-2-methoxyphenyl)-1-methyl-1H-indole-2-carboxamide, (S)-Pentan-2-yl 4-(3-((trans)-4-(4-acetylpiperazin-1-yl)cyclohexyl)-8-methylimidazo[1,5-a]pyrazin-1-yl)-2-methoxyphenylcarbamate, (R)—N-(4-(3-(1-(2-(Dimethylamino)acetyl)pyrrolidin-3-yl)-8-methylimidazo[1,5-a]pyrazin-1-yl)-2-methoxyphenyl)-4-methoxy-1-methyl-1H-indole-2-carboxamide, (S)-Pentan-2-yl 2-methoxy-4-(8-methyl-3-((cis)-4-(4-methylpiperazin-1-yl)cyclohexyl) imidazo[1,5-a]pyrazin-1-yl)phenylcarbamate, N-(4-(3-(4-Acetylpiperazin-1-yl)-8-methylimidazo[1,5-a]pyrazin-1-yl)-2-methoxyphenyl)-4-methoxy-1-methyl-1H-indole-2-carboxamide, 4-Methoxy-N-(2-methoxy-4-(8-methyl-3-(4-(tetrahydro-2H-pyran-4-yl)piperazin-1-yl)imidazo[1,5-a]pyrazin-1-yl)phenyl)-1-methyl-1H-indole-2-carboxamide, (R)-4-methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide, (S)-4-Methoxy-N-(2-methoxy-4-(8-methyl-3-(1-(tetrahydro-2H-pyran-4-yl)pyrrolidin-3-yl)imidazo[1,5-a]pyrazin-1-yl)phenyl)-1-methyl-1H-indole-2-carboxamide, 4-Methoxy-N-(2-methoxy-4-(8-methyl-3-(3-(trifluoromethyl)-5,6-dihydro-[1,2,4]triazolo[4,3-a]pyrazin-7(8H)-yl)imidazo[1,5-a]pyrazin-1-yl)phenyl)-1-methyl-1H-indole-2-carboxamide, 4-Methoxy-N-(2-methoxy-4-(8-methyl-3-(1-methyl-2-oxopiperidin-4-yl)imidazo[1,5-a]pyrazin-1-yl)phenyl)-1-methyl-1H-indole-2-carboxamide, N-(4-(3-((trans)-4-aminocyclohexyl)-8-methylimidazo[1,5-a]pyrazin-1-yl)-2-methoxyphenyl)-4-methoxy-1-methyl-1H-indole-2-carboxamide, N-(4-(3-((trans)-4-(2,2-Difluoroethylamino)cyclohexyl)-8-methylimidazo[1,5-a]pyrazin-1-yl)-2-methoxyphenyl)-4-methoxy-1-methyl-1H-indole-2-carboxamide, Isopropyl 4-(3-((trans)-4-(3,3-difluoroazetidin-1-yl)cyclohexyl)-8-methylimidazo[1,5-a]pyrazin-1-yl)-2-methoxyphenyl(methyl)carbamate, 5-Methoxy-N-(2-methoxy-4-(8-methyl-3-(tetrahydro-2H-pyran-4-yl)imidazo[1,5-a]pyrazin-1-yl)phenyl)-1H-pyrrolo[3,2-b]pyridine-2-carboxamide, N-(2-Methoxy-4-(8-methyl-3-(1-methylpiperidin-4-yl)imidazo[1,5-a]pyrazin-1-yl)phenyl)-1-methyl-1H-indole-2-carboxamide, (S)-4-Hydroxybutan-2-yl 2-methoxy-4-(8-methyl-3-(tetrahydro-2H-pyran-4-yl)imidazo[1,5-a]pyrazin-1-yl) phenylcarbamate, 4-Fluoro-N-(2-methoxy-4-(8-methyl-3-(1-methylpiperidin-4-yl)imidazo[1,5-a]pyrazin-1-yl)phenyl)-1-methyl-1H-indole-2-carboxamide, N-(5-Fluoro-2-methoxy-4-(8-methyl-3-(tetrahydro-2H-pyran-4-yl)imidazo[1,5-a]pyrazin-1-yl)phenyl)-4-methoxy-1-methyl-1H-indole-2-carboxamide, 5-Hydroxypentan-2-yl 5-fluoro-2-methoxy-4-(8-methyl-3-(tetrahydro-2h-pyran-4-yl)imidazo[1,5-a]pyrazin-1-yl)phenylcarbamate, (S)-sec-Butyl 2-methoxy-4-(8-methyl-3-((trans)-4-(4-methylpiperazin-1-yl)cyclohexyl)imidazo[1,5-a]pyrazin-1-yl)phenylcarbamate, N-(4-(3-(1'-acetyl-1,4'-bipiperidin-4-yl)-8-methylimidazo[1,5-a]pyrazin-1-yl)-2-methoxyphenyl)-4-methoxy-1-methyl-1H-indole-2-carboxamide, (S)-pentan-2-yl 2-methoxy-4-(3-((S)-1-(2-methoxyacetyl)pyrrolidin-3-yl)-8-methylimidazo[1,5-a]pyrazin-1-yl)phenylcarbamate, (trans)-4-(1-(3-Methoxy-4-(4-methoxy-1-methyl-1H-indole-2-carboxamido)phenyl)-8-methylimidazo[1,5-a]pyrazin-3-yl)cyclohexyl cyclopentylcarbamate, (R)—N-(4-(3-(1-(2-(dimethylamino)-2-oxoethyl)pyrrolidin-3-yl)-8-methylimidazo[1,5-a]pyrazin-1-yl)-2-methoxyphenyl)-4-methoxy-1-methyl-1H-indole-2-carboxamide, (R)—N-(4-(3-(1-(2-hydroxyacetyl)pyrrolidin-3-yl)-8-methylimidazo[1,5-a]pyrazin-1-yl)-2-methoxyphenyl)-4-methoxy-1-methyl-1H-indole-2-carboxamide, 4-Methoxy-N-(2-methoxy-4-(8-methyl-3-((trans)-4-(piperazin-1-yl)cyclohexyl)imidazo[1,5-a]pyrazin-1-yl) phenyl)-1-methyl-1H-indole-2-carboxamide, 4-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrole-2-carboxamide, N-(2-methoxy-4-(8-methyl-3-((trans)-4-(4-methylpiperazin-1-yl)cyclohexyl)imidazo[1,5-a]pyrazin-1-yl)phenyl)-6-methyl-6H-thieno[2,3-b]pyrrole-5-carboxamide, N-(2-Methoxy-4-(8-methyl-3-((trans)-4-(4-methylpiperazin-1-yl)cyclohexyl)imidazo[1,5-a]pyrazin-1-yl)phenyl)-6H-thieno[2,3-b]pyrrole-5-carboxamide, 4-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indole-2-carboxamide, 4-Hydroxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-indole-2-carboxamide, (S)-Pentan-2-yl 4-(3-((trans)-4-(aminomethyl)cyclohexyl)-8-methylimidazo[1,5-a]pyrazin-1-yl)-2-methoxyphenylcarbamate, 1-Methyl-N-(4-(8-methyl-3-((trans)-4-(4-methylpiperazin-1-yl)cyclohexyl)imidazo[1,5-a]pyrazin-1-yl)phenyl)-1H-indole-2-carboxamide, N-(2-hydroxy-4-(8-methyl-3-((trans)-4-(4-methylpiperazin-1-yl)cyclohexyl)imidazo[1,5-a]pyrazin-1-yl)phenyl)-4-methoxy-1-methyl-1H-indole-2-carboxamide, 4-Methoxy-N-(2-methoxy-4-(8-methyl-3-((trans)-4-((methylamino)methyl)cyclohexyl)imidazo[1,5-a]pyrazin-1-yl)phenyl)-1-methyl-1H-indole-2-carboxamide, N-(4-(3-((trans)-4-((dimethylamino)methyl)cyclohexyl)-8-methylimidazo[1,5-a]pyrazin-1-yl)-2-methoxyphenyl)-4-methoxy-1-methyl-1H-indole-2-carboxamide, (S)-Pentan-2-yl 4-(3-((trans)-4-((dimethylamino)methyl)cyclohexyl)-8-methylimidazo[1,5-a]pyrazin-1-yl)-2-methoxyphenylcarbamate, 6-Methoxy-N-(2-methoxy-4-(8-methyl-3-((trans)-4-(4-methylpiperazin-1-yl)cyclohexyl)imidazo[1,5-a]pyrazin-1-yl)phenyl)-1H-indazole-3-carboxamide, 5-Chloro-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-b]pyridine-2-carboxamide, N-(4-(3-((trans)-4-(acetamidomethyl)cyclohexyl)-8-methylimidazo[1,5-a]pyrazin-1-yl)-2-methoxyphenyl)-4-methoxy-1-methyl-1H-indole-2-carboxamide, (S)-pentan-2-yl 4-(3-((trans)-4-(acetamidomethyl)cyclohexyl)-8-methylimidazo[1,5-a]pyrazin-1-yl)-2-methoxyphenylcarbamate, (S)-pentan-2-yl 4-(3-((trans)-4-(methoxycarbonylmethyl)cyclohexyl)-8-methylimidazo[1,5-a]pyrazin-1-yl)-2-methoxyphenylcarbamate, 4-Methoxy-N-(2-methoxy-4-(8-methyl-3-(4-oxocyclohexyl)imidazo[1,5-a]pyrazin-1-yl)phenyl)-1-methyl-1H-indole-2-carboxamide, N-(4-(3-((trans)-4-hydroxy-4-((methylamino)methyl)cyclohexyl)-8-methylimidazo[1,5-a]pyrazin-1-yl)-2-methoxyphenyl)-4-methoxy-1-methyl-1H-indole-2-carboxamide, 4-Methoxy-N-(2-methoxy-4-(8-methyl-3-(1-methyl-5-oxopyrrolidin-3-yl)imidazo[1,5-a]pyrazin-1-yl)phenyl)-1-methyl-1H-indole-2-carboxamide, 4-Methoxy-N-(2-methoxy-4-(8-methyl-3-((trans)-4-(4-methyl-3-oxopiperazin-1-yl)cyclohexyl)imidazo[1,5-a]pyrazin-1-yl)phenyl)-1-methyl-1H-indole-2-carboxamide, 5-Methoxy-N-(2-methoxy-4-(8-methyl-3-((trans)-4-(4-methylpiperazin-1-yl)cyclohexyl)imidazo[1,5-a]pyrazin-1-yl)phenyl)-1-methyl-1H-pyrrolo[2,3-c]pyridine-2-carboxamide, 4-methoxy-N-(2-methoxy-4-(8-methyl-3-((trans)-4-morpholinocyclohexyl)imidazo[1,5-a]pyrazin-1-yl)phenyl)-1-methyl-1H-indole-2-carboxamide, (S)-pentan-2-yl 2-methoxy-4-(8-methyl-3-(tetrahydro-2H-pyran-4-yl)imidazo[1,5-a]pyrazin-1-yl)phenylcarbamate, (S)-pentan-2-yl 2-methoxy-4-(8-methyl-3-((trans)-4-morpholinocyclohexyl)imidazo[1,5-a]pyrazin-1-yl)phenylcarbamate, (S)-pentan-2-yl 4-(3-(1-(2-(dimethylamino)acetyl)piperidin-4-yl)-8-methylimidazo[1,5-a]pyrazin-1-yl)-2-methoxyphenylcarbamate, (S)-pentan-2-yl 4-(3-(1-(2-(dimethylamino)-2-oxoethyl)piperidin-4-yl)-8-methylimidazo[1,5-a]pyrazin-1-yl)-2-methoxyphenylcarbamate, (S)-pentan-2-yl 2-methoxy-4-(8-methyl-3-morpholinoimidazo[1,5-a]pyrazin-1-yl)phenylcarbamate, isopropyl 2-methoxy-4-(8-methyl-3-((trans)-4-(4-methylpiperazin-1-yl)cyclohexyl)imidazo[1,5-a]pyrazin-1-yl)phenylcarbamate, 4-fluoro-N-(2-methoxy-4-(8-methyl-3-(tetrahydro-2H-pyran-4-yl)imidazo[1,5-a]pyrazin-1-yl)phenyl)-1-methyl-1H-indole-2-carboxamide, tert-butyl 2-methoxy-4-(8-methyl-3-((trans)-4-(4-methylpiperazin-1-yl)cyclohexyl)imidazo[1,5-a]pyrazin-1-yl)phenylcarbamate, N-(4-(3-(1-(2-(dimethylamino)-2-oxoethyl)piperidin-4-yl)-8-methylimidazo[1,5-a]pyrazin-1-yl)-2-methoxyphenyl)-4-methoxy-1-methyl-1H-indole-2-carboxamide, N-(4-(3-(azetidin-1-yl)-8-methylimidazo[1,5-a]pyrazin-1-yl)-2-methoxyphenyl)-1-methyl-1H-indole-2-carboxamide, 5-hydroxypentan-2-yl 2-methoxy-4-(8-methyl-3-((trans)-4-(4-methylpiperazin-1-yl)cyclohexyl)imidazo[1,5-a]pyrazin-1-yl)phenylcarbamate, (S)-pentan-2-yl 4-(3-(1-(2-aminoacetyl)piperidin-4-yl)-8-methylimidazo[1,5-a]pyrazin-1-yl)-2-methoxyphenylcarbamate, N-(4-(3-(1-(2-aminoacetyl)piperidin-4-yl)-8-methylimidazo[1,5-a]pyrazin-1-yl)-2-methoxyphenyl)-4-methoxy-1-methyl-1H-indole-2-carboxamide, N-(4-(3-((trans)-4-(aminomethyl)cyclohexyl)-8-methylimidazo[1,5-a]pyrazin-1-yl)-2-methoxyphenyl)-4-methoxy-1-methyl-1H-indole-2-carboxamide, (S)-pentan-2-yl 2-methoxy-4-(8-methyl-3-((cis)-4-morpholinocyclohexyl)imidazo[1,5-a]pyrazin-1-yl)phenylcarbamate, (S)-pentan-2-yl 2-methoxy-4-(8-methyl-3-(4-morpholinopiperidin-1-yl)imidazo[1,5-a]pyrazin-1-yl)phenylcarbamate, 4-methoxy-N-(2-methoxy-4-(8-methyl-3-(4-morpholinopiperidin-1-yl)imidazo[1,5-a]pyrazin-1-yl)phenyl)-1-methyl-1H-indole-2-carboxamide, 4-methoxy-N-(2-methoxy-4-(8-methyl-3-((trans)-3-(4-methylpiperazin-1-yl)cyclobutyl)imidazo[1,5-a]pyrazin-1-yl)phenyl)-1-methyl-1H-indole-2-carboxamide, 4-methoxy-N-(2-methoxy-4-(3-((trans)-4-(2-methoxyethylamino)cyclohexyl)-8-methylimidazo[1,5-a]pyrazin-1-yl)phenyl)-1-methyl-1H-indole-2-carboxamide, 4-methoxy-N-(2-methoxy-4-(3-((trans)-4-(N-(2-methoxyethyl)acetamido)cyclohexyl)-8-methylimidazo[1,5-a]pyrazin-1-yl)phenyl)-1-methyl-1H-indole-2-carboxamide, 4-methoxy-N-(2-methoxy-4-(8-methyl-3-morpholinoimidazo[1,5-a]pyrazin-1-yl)phenyl)-1-methyl-1H-indole-2-carboxamide, 4-methoxy-N-(2-methoxy-4-(3-((trans)-4-((2-methoxyethyl)(methyl)amino)cyclohexyl)-8-methylimidazo[1,5-a]pyrazin-1-yl)phenyl)-1-methyl-1H-indole-2-carboxamide, N-(4-(3-(1-(2-(dimethylamino)acetyl)piperidin-4-yl)-8-methylimidazo[1,5-a]pyrazin-1-yl)-2-methoxyphenyl)-4-methoxy-1-methyl-1H-indole-2-carboxamide, (S)-pentan-2-yl 4-(3-((trans)-4-(3,3-difluoroazetidin-1-yl)cyclohexyl)-8-methylimidazo[1,5-a]pyrazin-1-yl)-2-methoxyphenylcarbamate, (S)-pentan-2-yl 2-methoxy-4-(8-methyl-3-(4-(tetrahydro-2H-pyran-4-yl)piperazin-1-yl)imidazo[1,5-a]pyrazin-1-yl)phenylcarbamate, and N-(4-(3-((trans)-4-(3,3-difluoroazetidin-1-ypcyclohexyl)-8-methylimidazo[1,5-a]pyrazin-1-yl)-2-methoxyphenyl)-1-methyl-1H-indole-2-carboxamide.

12. A method of modulating lymphocite specific kinase activity in a subject comprising administering to the subject an amount of a compound of claim 1.

\* \* \* \* \*